United States Patent
Cai et al.

(10) Patent No.: US 8,003,785 B2
(45) Date of Patent: Aug. 23, 2011

(54) HALO-SUBSTITUTED PYRIMIDODIAZEPINES

(75) Inventors: Jianping Cai, West Caldwell, NJ (US); Shaoqing Chen, Bridgewater, NJ (US); Xin-Jie Chu, Livingston, NJ (US); Kin-Chun Luk, North Caldwell, NJ (US); Steven Gregory Mischke, Florham Park, NJ (US); Hongmao Sun, Ramsey, NJ (US); Peter Michael Wovkulich, Nutley, NJ (US)

(73) Assignee: Takeda Pharmaceutical Company Limited, San Diego, CA (US)

( * ) Notice: Subject to any disclaimer, the term of this patent is extended or adjusted under 35 U.S.C. 154(b) by 0 days.

(21) Appl. No.: 12/485,108

(22) Filed: Jun. 16, 2009

(65) Prior Publication Data
US 2009/0318408 A1    Dec. 24, 2009

Related U.S. Application Data

(60) Provisional application No. 61/073,388, filed on Jun. 18, 2008.

(51) Int. Cl.
*C07D 487/04*    (2006.01)
(52) U.S. Cl. ...................................... 540/501
(58) Field of Classification Search ................... 540/501; 514/221
See application file for complete search history.

(56) References Cited

U.S. PATENT DOCUMENTS

| | | | |
|---|---|---|---|
| 6,806,272 | B2 | 10/2004 | Bauer et al. |
| 7,517,873 | B2 | 4/2009 | Chen |
| 2004/0029885 | A1 | 2/2004 | Bauer et al. |
| 2004/0147524 | A1 | 7/2004 | Bauer et al. |
| 2008/0009482 | A1 | 1/2008 | Halsall et al. |

FOREIGN PATENT DOCUMENTS

| | | |
|---|---|---|
| WO | WO 01/19828 | 3/2001 |
| WO | WO 03/020722 | 3/2003 |
| WO | WO 2007/095188 | 8/2007 |
| WO | WO 2008/003958 | 1/2008 |
| WO | WO 2008/113711 | 9/2008 |
| WO | WO 2009/042711 | 4/2009 |
| WO | WO 2009/042806 | 4/2009 |

OTHER PUBLICATIONS

Haugwitz et al., J. Med. Chem., 25, pp. 969-974 (1982).

*Primary Examiner* — Bruck Kifle
(74) *Attorney, Agent, or Firm* — David M. Stemerick

(57) ABSTRACT

The present invention provides PLK1 inhibitor compounds of formula I:

(I)

useful in the treatment or control of cell proliferative disorders, particularly oncological disorders. These compounds and formulations containing such compounds may be useful in the treatment or control of solid tumors, such as, for example, breast, colon, lung and prostate tumors and other oncological diseases such as non-Hodgkin's lymphomas. Also provided are intermediate compounds useful in the synthesis of compounds of formula I.

3 Claims, No Drawings

HALO-SUBSTITUTED PYRIMIDODIAZEPINES

PRIORITY TO RELATED APPLICATIONS

This application claims the benefit of U.S. Provisional Application No. 61/073,388, filed Jun. 18, 2008, which is hereby incorporated by reference in its entirety.

BACKGROUND OF THE INVENTION

PLK1 is a member of the Polo-like kinase family. Polo-like kinases are highly conserved from yeast to humans and play a variety of roles in the G2/M phase transition and in the passage through mitotic phase of the cell cycle. Four Polo-like kinases, PLK1, PLK2 (Snk), PLK3 (Fnk), and PLK4 have been identified in humans. These proteins share extensive homologies across their kinase domains, in C-terminal "Polo" boxes. Using neutralizing antibodies, anti-sense oligos, and dominant-negative protein, PLK1 was shown to be essential for mitosis in vitro cultured cells. Furthermore, down regulation of PLK1 appears to have differential effects in tumor versus "normal" cells in that ablation of PLK1 induced mitotic catastrophe and eventual cell death in tumor cells, but G2 arrest in "normal" cells. One plausible explanation is that tumor cells are defective in checkpoint controls and unable to arrest and thus undergo mitotic catastrophe. The roles of PLK2, PLK3, and PLK4 remain elusive.

The expression of PLK1 is restricted to proliferative tissues. Overexpression of PLK1 was detected in solid tumors of various origins (breast, lung, colon, stomach, ovary, smooth muscle, and esophagus) and in non-Hodgkin lymphomas. Furthermore PLK1 has transforming activity; constitutive expression of PLK1 in NIH3T3 cells causes oncogenic focus formation, transformed cells grow in soft agar and form tumors in nude mice. Therefore, blocking PLK1 kinase activity by a small molecule inhibitor represents a novel approach to target mitosis and may be clearly differentiated from other mitosis-targeting agents on the market such as tubulin binders.

Other therapies which involve the disruption of microtubule formation and degradation through the use of taxanes and vinca alkaloids have become successful ways of treating cancer. Some cancerous cells are able to evade the G2/M cell cycle arrest effect of taxanes and vinca alkaloids. PLK1 inhibition provides a means to target those cells which are able to evade the G2/M cell cycle arresting effect of taxanes and vinca alkaloids.

DETAILED DESCRIPTION OF THE INVENTION

According to a first aspect of the invention, there is provided a compound of formula I that inhibits PLK1:

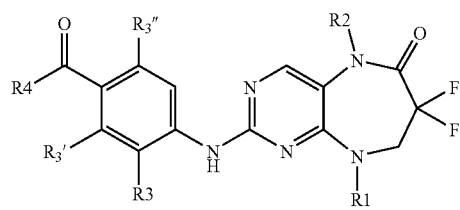
(I)

where
R1 is hydrogen, C1 to C5 straight or branched chain alkyl, C3 to C6 cycloalkyl, —(CH$_2$)$_n$-aryl, phenoxyethyl, methoxybenzyl, or phenylcyclopropyl;
R2 is hydrogen, methyl, or ethyl;
each of R3, R3', and R3" is independently hydrogen, chloro, fluoro, C1 to C5 straight or branched chain alkyl, trifluoromethyl, methoxy, ethoxy, trifluoromethoxy, or trifluoroethoxy;
R4 is hydroxyl, amino, methoxy, R5-NH—, or

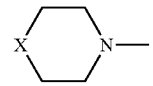

where X is CH$_2$, O, or NH, where if X is CH$_2$ or NH, X may be optionally substituted by amino or C1 to C5 straight or branched chain alkyl;
R5 is

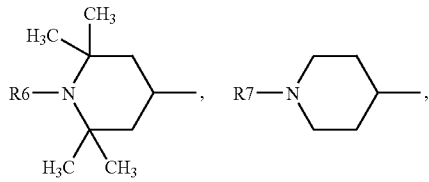

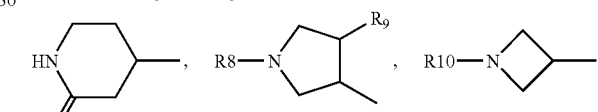

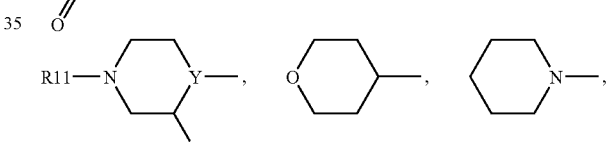

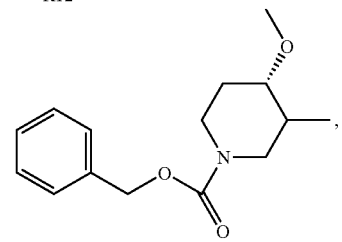

phenyl, pyridyl, 8-methyl-8-aza-bicyclo[2.2.1]oct-3-yl, N-1-aza-bicyclo[2.2.2]oct-3-yl, C3 to C6 cycloalkyl optionally substituted by hydroxyl, amino, carbamoyl, —NHC(O)Ot-Bu, or -cyclopropylmethylpiperazine, R13-(CH$_2$)n-,

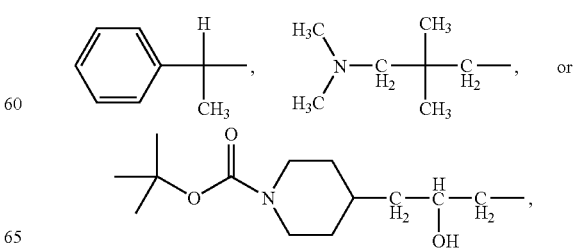

where Y is C or N, n is an integer from 0 to 4,

R6 is H or C1 to C5 straight or branched chain alkyl,

R7 is hydrogen, pyridyl, C1 to C5 straight or branched chain alkyl, C1 to C3 fluoroalkyl, benzyl, C3 to C6 cycloalkyl, $CH_3(CH_2)_pSO_2$—, hydroxyloweralkyl, $NH_2C(CH_3)_2C(O)$—, $CH_3C(O)$—, or —C(O)Ot-Bu, p is an integer from 0 to 3

R8 is hydrogen, benzyl, or —C(O)Ot-Bu,

R9 is hydrogen or hydroxyl,

R10 is C1 to C5 straight or branched chain alkyl or —C(O)Ot-Bu,

R11 is hydrogen, —C(O)Ot-Bu, —C(O)OBn, or —C(O)OFm,

R12 is hydroxy or methoxy,

R13 is R14R15N—, lower alkoxy, hydroxy, trifluoromethyl, C3 to C6 cycloalkyl, phenyl mono or di-substituted by halogen, alkyl, or C1 to C3 haloalkyl, heteroaryl, benzodioxolyl, C4 to C6 heterocyclyl optionally substituted with oxo, C1 to C5 straight or branched chain alkyl, hydroxyl, or hydroxyloweralkyl,

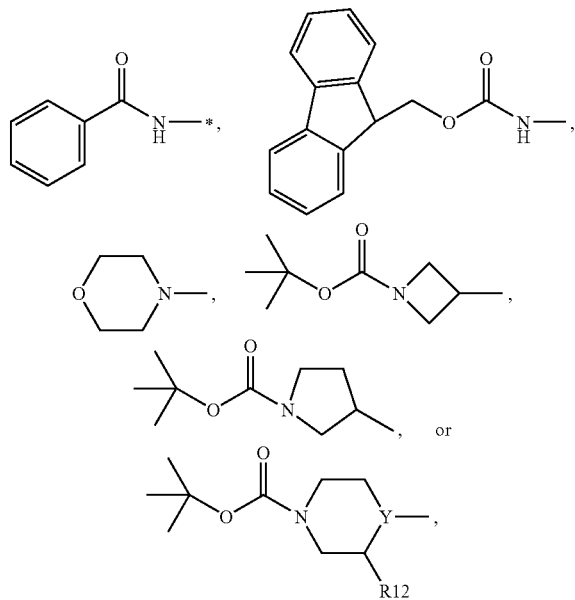

R14 and R15 are independently hydrogen, C1 to C5 straight or branched chain alkyl, C3 to C6 cycloalkyl, or phenyl;

where the compound is not

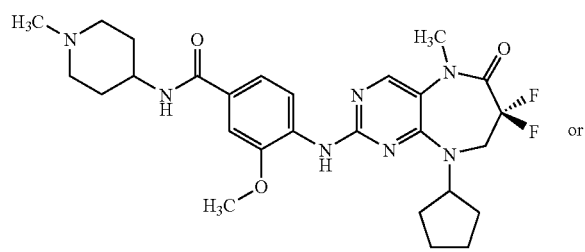

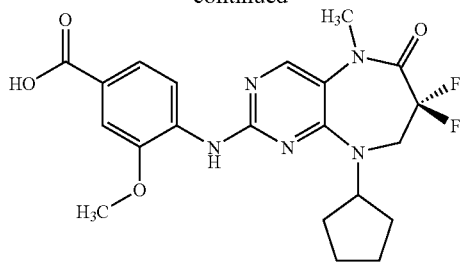

and pharmaceutically acceptable salts thereof.

In another aspect, the invention is directed to compounds of Formula I where R2 is methyl.

In another aspect, the invention is directed to compounds of Formula I where R1 is isopropyl, cyclobutyl, cyclopentyl or cyclohexyl, R2 is methyl, and each of R3, R3', and R3" is independently hydrogen, methyl, ethyl, methoxy, ethoxy, or fluoro.

In another aspect, the invention is directed to compounds of Formula I where R1 is isopropyl, cyclobutyl, cyclopentyl or cyclohexyl, R2 is methyl, R3' is hydrogen, and R3 and R3" are independently hydrogen, methyl, ethyl, methoxy, ethoxy, or fluoro.

In another aspect, the invention is directed to compounds of Formula I where R1 is isopropyl, cyclobutyl, cyclopentyl or cyclohexyl, R2 is methyl, R3' and R3" are hydrogen, and R3 is methyl, ethyl, methoxy, ethoxy, or fluoro.

In another aspect, the invention is directed to compounds of Formula I where R1 is isopropyl, cyclobutyl, cyclopentyl or cyclohexyl, R2 is methyl, R3 is methoxy, R3' is hydrogen and R3" is fluoro.

In another aspect, the invention is directed to compounds of Formula I where R1 is isopropyl, cyclobutyl, cyclopentyl or cyclohexyl, R2 is methyl, R3 is fluoro, R3' is fluoro, and R3" is hydrogen.

In another aspect, the invention is directed to compounds of Formula I where R1 is hydrogen.

In another aspect, the invention is directed to compounds of Formula I where R1 is C1 to C5 straight or branched chain alkyl, —$(CH_2)_n$-aryl, phenoxyethyl, or methoxybenzyl.

In another aspect, the invention is directed to compounds of Formula I where R1 is C3 to C6 cycloalkyl or phenylcyclopropyl.

In another aspect, the invention is directed to intermediate compounds of formula II:

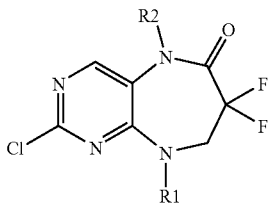

where

R1 is hydrogen, C1 to C5 straight or branched chain alkyl, C3 to C6 cycloalkyl, —$(CH_2)_n$-aryl, phenoxyethyl, methoxybenzyl, or phenylcyclopropyl; and R2 is hydrogen, methyl, or ethyl. These compounds are useful as intermediate compounds in the synthesis of compounds of formula I, above.

In another aspect, the invention is directed to compounds of formula II where R1 is C1 to C5 straight or branched chain alkyl, —(CH$_2$)$_n$-aryl, phenoxyethyl, or methoxybenzyl.

In another aspect, the invention is directed to compounds of formula II where R1 is C3 to C6 cycloalkyl or phenylcyclopropyl.

"Alkyl" denotes a straight-chained, branched or cyclic saturated aliphatic hydrocarbon. Alkyl includes C1-C5 straight or branched chain alkyl, i.e., a C1-C6 alkyl group and includes methyl, ethyl, propyl, isopropyl, butyl, t-butyl, 2-butyl, pentyl, hexyl, and the like. Preferable C1-C5 straight or branched chain alkyl groups are C1-C4 alkyl, and more preferable C1-C5 straight or branched chain alkyl groups are C1-C3 alkyl. Examples of cycloalkyl groups are moieties having 3 to 10, preferably 3 to 7 carbon atoms including cyclopropyl, cyclobutyl, cyclopentyl and cyclohexyl groups.

"Aryl" means a monovalent, monocyclic or bicyclic, aromatic carbocyclic or heterocyclic radical, preferably a 5 to 10 member aromatic ring system. Aromatic heterocyclic radicals are sometimes referred to herein as "heteroaryl". Preferred aryl groups include, but are not limited to, phenyl, naphthyl, tolyl, xylyl, thienyl, furyl, indolyl, pyrrolyl, pyridinyl, oxy-pyridinyl, pyrazinyl, oxazolyl, thiaxolyl, quinolinyl, pyrimidinyl, imidazolyl and tetrazolyl. When indicated, aryl groups can be optionally mono-, di- or tri-substituted by, for example, C1 to C5 straight or branched chain alkyl, cycloalkyl, e.g., cyclopropyl, trihalo-C1 to C5 straight or branched chain alkyl, e.g., trifluoromethyl or trifluoroethyl, hydroxyl, alkoxy, especially lower alkoxy, mono or dihydroxyl-substituted alkoxy, acetamido, methoxyacetamido, dimethylaminoacetamido, halogen, e.g., fluoro, chloro, or bromo, aniline derivatives, amide derivatives of the aniline derivatives and methanesulfonyl. When two or more substituents are present on an aryl or heteroaryl ring they may also be present in the form of a fused ring. Such fused rings include, but are not limited to, 3,4-methylenedioxyphenyl and 3,4-ethylenedioxyphenyl.

"Heteroatom" means an atom selected from N, O and S, unless otherwise specified.

"Heterocyclyl" means a cyclic group having four to six carbon atoms and at least one heteroatom.

"Alkoxy or lower alkoxy" refers to any of the above C1-C5 straight or branched chain alkyl groups attached to an oxygen atom. Typical lower alkoxy groups include methoxy, ethoxy, isopropoxy or propoxy, butyloxy, cyclopropyl methoxy, and the like.

"Bn" refers to a benzyl radical.

"tBu" refers to a tertiary butyl radical.

"Fm" refers to a methyl fluorenyl radical.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds.

"Pharmaceutically acceptable," such as pharmaceutically acceptable carrier, excipient, etc., means pharmacologically acceptable and substantially non-toxic to the subject to which the particular compound is administered.

"Substituted," as in substituted aryl or heteroaryl, means that the substitution can occur at one or more positions and, unless otherwise indicated, that the substituents at each substitution site are independently selected from the specified options.

"Therapeutically effective amount or effective amount" means an amount of at least one designated compound that significantly inhibits proliferation and/or prevents differentiation of a human tumor cell, including human tumor cell lines.

The compounds of the present invention are useful in the treatment or control of cell proliferative disorders, particularly oncological disorders. These compounds and formulations containing said compounds may be useful in the treatment or control of solid tumors, such as, for example, breast, colon, lung and prostate tumors and other oncological diseases such as non-Hodgkin's lymphomas.

The compounds of formula I as well as their salts may have at least one asymmetric carbon atom and therefore may be present as mixtures of different stereoisomers. The various isomers can be isolated by known separation methods, e.g., chromatography.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

The compounds of formula (I) and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, water, polyols, saccharose, invert sugar, glucose, etc. Suitable adjuvants for injection solutions are, for example, water, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

General methods for the preparation of compounds of Formula Ia, below, are given in scheme 1. Other halogens, and especially chlorine, can be used in place of the fluorine atoms in the structures of the schemes below. Briefly, the process involves the formation of 4-substituted-2-chloro-5-nitropyrimidine (IV) by the coupling of a substituted beta-amino acid ester (III) with 2,4-dichloro-5-nitropyrimidine, which is then reduced to the corresponding amino derivative (V) using standard reduction conditions for the conversion of a nitro group to an amine, such as iron powder in acetic acid, tin (II) chloride in acetic acid or hydrogen over a supported catalyst, such as palladium or Raney nickel, and then cyclized to the pyrimidodiazepinone (VI) in the presence or absence of acid catalysts such as acetic acid or mineral acids, such as hydrochloric or sulfuric acid. Pyrimidodiazepinone (VI) is then alkylated with standard alkylating reagents such alkyl halides in the presence of a base, to form pyrimidodiazepinone (VII). The reaction of substituted amines with pyrimidodiazepinone (VII) provides the compounds of formula Ia. Further modification of the Ra group in Ia can be carried out to provide additional derivatives of formula Ia.

A) Preparation of Halo Substituted-Diazepines

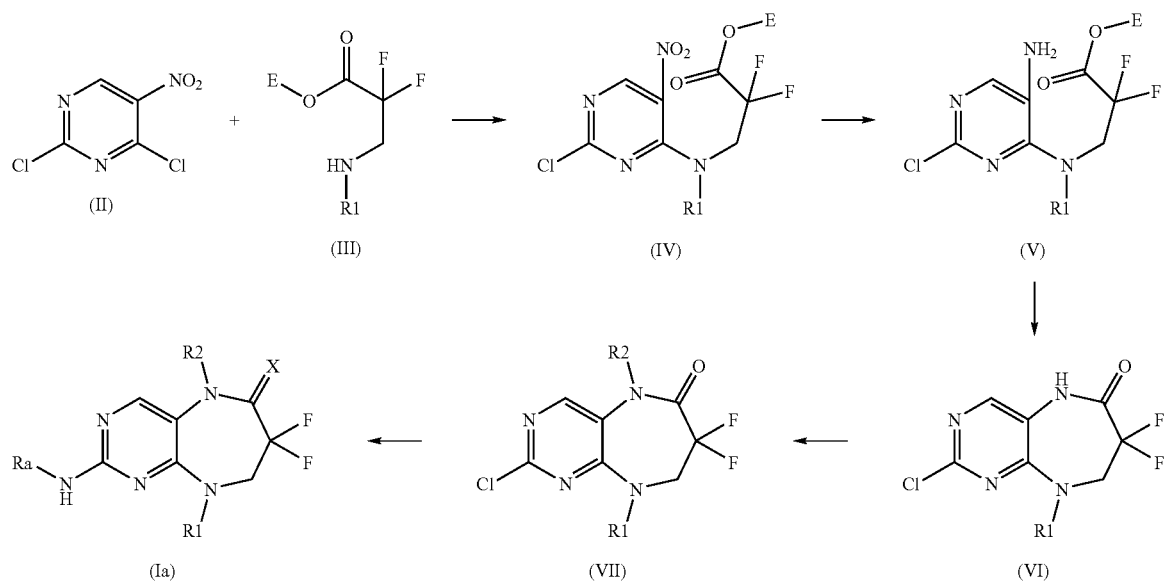

B) Preparation of Beta-Amino Acid Ester Intermediates

The beta-amino acid ester intermediates (III) which are not commercially available or have not been previously described in the literature were prepared by previously disclosed methods which are outlined below.

Method 1: reaction of benzotriazole-1-methanamines with nucleophiles

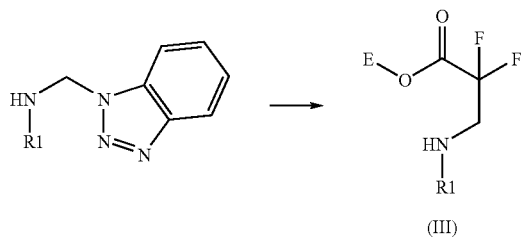

In the examples described, temperatures are indicated in degrees Celsius. For mass spectral data, values are given as the $MH^+/Z$ ion obtained in the positive mode, electrospray measured on a Micromass Platform II mass spectrometer. Unless indicated otherwise, reactions were generally run under an inert atmosphere (argon or nitrogen). Unless indicated otherwise, chromatographic separations were carried using silica gel, solvent mixtures, where indicated are provided as ratio of volumes. Chiral separations were carried out using supercritical fluid chromatography (Berger Instrument Multi-gram II) using a 3.0×25 cm Daicel Chiralpak OD column, eluting with carbon dioxide plus modifier solvent (indicated in parentheses).

Preparation of Intermediates:
Beta-Amino Acid Esters (III)
Method 1 scheme 2

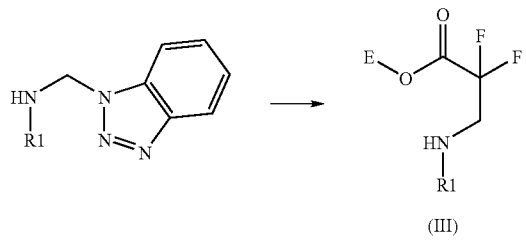

Method 1

3-cyclobutylamino-2,2-difluoropropionic acid ethyl ester

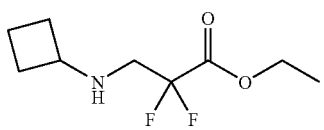

Part a

To a mixture of 28.6 g (0.24 mole) benzotriazole and 17.6 g (0.24 mole) of cyclopentylamine in 1000 mL of ether was added dropwise, 19.5 mL (0.24 mole) of 37% aqueous formaldehyde. The reaction mixture was stirred at room temperature under for 18 hours. The mixture was dried over calcium chloride, filtered and concentrated under reduced pressure. Hexanes was added to the residue, concentrated under reduced pressure to give the crude benzotriazol-1-ylmethyl-cyclobutyl-amine as an oil, which was used in the next without further purification.

Part b

To a mixture of 18.8 g (0.29 g-atom) of zinc powder (325 mesh) and 200 mL of anhydrous tetrahydrofuran was added 27.6 mL (0.22 mole) of chlorotrimethylsilane in one portion. After stirring for 5 minutes, a solution of 25 mL (0.19 mole) of ethyl bromodifluoroacetate in 50 mL of tetrahydrofuran was added dropwise at a rate to keep the internal temperature below 35 degrees. The mixture was stirred for 30 minutes and then cooled to −10 to 0 degrees.

A solution of 55 g (0.272 mole) of benzotriazol-1-ylmethyl-cyclobutyl-amine in 400 mL of anhydrous tetrahydrofuran was added at a rate to keep the internal temperature at −10 to 0 degrees. After 10 minutes, the reaction mixture was warmed to room temperature and stirred for another 3 hours. The mixture was recooled and quenched by the dropwise addition of saturated aqueous sodium bicarbonate at a rate to keep the internal temperature at −10 to 0 degrees. The mixture was stirred for another 20 minutes at room temperature and then filtered through Celite, rinsing with ether. The filtrate was extracted twice with ether, dried over anhydrous sodium sulfate, filtered and concentrated under reduced pressure. The residue was treated with hexane-ether (80:20), filtered to remove solids and the filtrate concentrated under reduced pressure. The residue was distilled (bp. 70-80 degrees at 1 mm Hg) to give 22.2 g of 3-cyclobutylamino-2,2-difluoropropionic acid ethyl ester.

3-cyclopentylamino-2,2-difluoropropionic acid ethyl ester

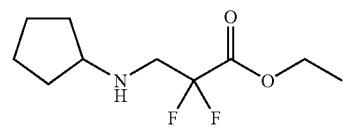

Step a

To the mixture of 36 g (0.3 mole) benzotriazole and 30 mL (0.3 mole) of cyclopentylamine in 1400 mL of ether was added dropwise 22 mL (0.3 mole) of 37% aqueous formaldehyde. The reaction mixture was stirred at room temperature overnight. The solution was dried over calcium chloride, filtered and concentrated under pressure. Hexane was added to the residue cooled in an ice bath and the resulting solid was collected by filtration washing with hexane and then dried to give 58.6 g of benzotriazol-1-ylmethyl-cyclopentylamine as a white solid.

Step b

To a mixture of 12.1 g (0.185 g-atom) of zinc powder (−325 mesh) and 160 mL of anhydrous tetrahydrofuran was added 17.6 mL (0.14 mole) of chlorotrimethylsilane in one portion. After stirring for 20 minutes, a solution of 17.8 mL (0.14 mole) of ethyl bromodifluoroacetate in 20 mL of tetrahydrofuran was added dropwise at a rate to keep the internal temperature below 35 degrees. The mixture was stirred for 20 minutes and then cooled to −10 to 0 degrees. A solution of 20 g (0.093 mole) of benzotriazol-1-ylmethyl-cyclopentylamine in 80 mL of tetrahydrofuran was added dropwise at a rate to keep the internal temperature at −10 to 0 degrees. After 10 minutes the reaction mixture was warmed to room temperature and stirred for 3 hours at room temperature. The solution was cooled to −10 to 0 degrees and quenched by the addition of saturated aqueous sodium bicarbonate at a rate to maintain the internal temperature −10 to 0 degrees. Ether was added, the mixture was stirred for 15 minutes at room temperature and then filtered through Celite, washing with ether. The filtrate was extracted 3 times with ether. The combined organic layers were dried over anhydrous sodium sulfate, filtered, and concentrated under reduced pressure. Ether and hexane were added to the residue, the solids were removed by filtration and the filtrate was concentrated under reduced pressure. The residue was then distilled under vacuum to give 12.4 g of 3-cyclopentylamino-2,2-difluoropropionic acid ethyl ester as a colorless oil. bp 75-82 degrees at 1 mm Hg.

3-cyclohexylamino-2,2-difluoropropionic acid ethyl ester

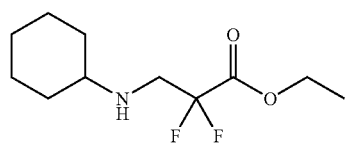

Part a

To a mixture of 54 g (0.45 mole) benzotriazole and 51.5 mL (0.45 mole) of cyclohexylamine in 2000 mL of ether was added dropwise 36.5 mL (0.45 mole) of 37% aqueous formaldehyde. The reaction mixture was stirred at room temperature for 18 hours. The mixture was dried over calcium chloride, filtered and concentrated under reduced pressure. 200 mL of hexanes was added to the residue and the resulting solid collected by filtration, washed with 300 mL of hexane to give 90.0 g of benzotriazol-1-ylmethyl-cyclohexylamine as a white solid.

Part b

To a mixture of 13.7 g (0.21 g-atom) of zinc powder (325 mesh) and 200 mL of anhydrous tetrahydrofuran was added 20 mL (0.156 mole) of chlorotrimethylsilane in one portion. After stirring for 5 minutes, a solution of 20.4 mL (0.156 mole) of ethyl bromodifluoroacetate in 50 mL of tetrahydrofuran was added dropwise at a rate to maintain the internal temperature below 35 degrees. The mixture was stirred for 30 minutes and then cooled to −10 to 0 degrees. A solution of 40 g (0.174 mole) of benzotriazol-1-ylmethyl-cyclohexylamine in 400 mL of tetrahydrofuran was added dropwise at a rate to maintain the internal temperature at −10 to 0 degrees. After 10 minutes, the reaction mixture was warmed to room temperature, stirred for another 3 hours and then cooled to −10 to 0 degrees. The reaction was quenched by the addition of 200 mL of saturated aqueous sodium bicarbonate, added at a rate to maintain the internal temperature at −10 to 0. The mixture was stirred at room temperature for 10 minutes, then filtered through Celite, washing with 200 mL of ether. The filtrate was extracted twice with 200 mL of ether. The combined organic layers were dried over anhydrous sodium sulfate, filtered, and concentrated under reduced pressure. 200 mL of hexanes-ether (80:20) was added to the residue, the resulting solid was removed by filtration and the filtrated concentrated under reduced pressure. The residue was distilled under vacuum to give 12.9 g of 3-cyclohexylamino-2,2-difluoropropionic acid ethyl ester as a colorless oil. bp. 85-90 degrees at 1 mm Hg.

2,2-difluoro-3-(4-methoxy-benzylamino)-propionic acid ethyl ester

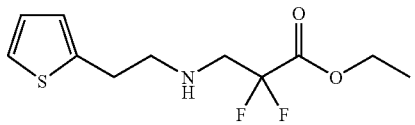

Step a

To the mixture of 18 g (0.15 mole) benzotriazole and 19.6 mL (0.15 mole) of 4-methoxy-benzylamine in 700 mL of ether was added dropwise 11.1 mL (0.15 mole) of 37% aqueous formaldehyde. The reaction mixture was stirred at room temperature overnight. The solution was dried over calcium chloride, filtered and concentrated under pressure. Hexane was added under ice-cooled bath and the resulting solid was collected by filtration and washed with hexane dried to give 31 g of benzotriazol-1-ylmethyl-(4-methoxy-benzylamine)-amine as an oil.

To a mixture of 3.0 g (0.046 g-atom) of zinc powder (−325 mesh) and 40 mL of anhydrous tetrahydrofuran was added 4.4 mL (0.035 mole) of chlorotrimethylsilane in one portion. After stirring for 20 minutes, a solution of 4.5 mL (0.035 mole) of ethyl bromodifluoroacetate in 5 mL of tetrahydrofuran was added dropwise at a rate to keep the internal temperature below 35 degrees. The mixture was stirred for 20 minutes and then cooled to −10 to 0 degrees. A solution of 7 g (0.027 mole) of benzotriazol-1-ylmethyl-(4-methoxy-benzylamine)-amine in 20 mL of tetrahydrofuran was added dropwise at a rate to keep the internal temperature at −10 to 0 degrees. After 10 minutes the reaction mixture was warmed to room temperature and stirred for 3 hours at room temperature. The solution was cooled to −10 to 0 degrees and quenched by the addition of saturated aqueous sodium bicarbonate at a rate to maintain the internal temperature −10 to 0 degrees. Ether was added, the mixture was stirred for 15 minutes at room temperature and then filtered through Celite, washing with ether. The filtrate was extracted 3 times with ether. The combined organic layers were dried over anhydrous sodium sulfate, filtered, and concentrated under reduced pressure. Ether and hexane were added to the residue, the solids were removed by filtration and the filtrate was concentrated under reduced pressure. The residue was purified by silica gel chromatography, eluting with hexane-ethyl acetate (gradient, 100:0-80:20) to give 1.2 g of 2,2-difluoro-3-(4-methoxy-benzylamino)-propionic acid ethyl ester as a oil.

2,2-difluoro-3-(2-thiophen-2-yl-ethylamino)-propionic acid ethyl ester

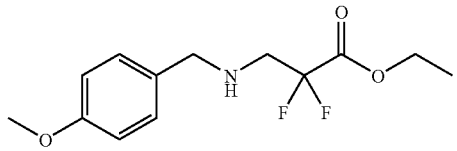

Step a

To a mixture of 12 g (0.1 mole) benzotriazole and 13 g (0.1 mole) of 2-thiophen-2-yl-ethylamine in 500 mL of ether was added dropwise 7.4 mL (0.1 mole) of 37% aqueous formaldehyde. The reaction mixture was stirred at room temperature overnight. The solution was dried over calcium chloride, filtered and concentrated under pressure. Hexane was added to the residue cooled in an ice bath and the resulting solid was collected by filtration, washing with hexane and then dried to give 26.0 g of benzotriazol-1-ylmethyl-(2-thiophen-2-yl-ethyl)-amine as a light yellow oil (100%).

Step b

To a mixture of 3.5 g (0.054 g-atom) of zinc powder (−325 mesh) and 60 mL of anhydrous tetrahydrofuran was added 5.1 mL (0.041 mole) of chlorotrimethylsilane in one portion. After stirring for 20 minutes, a solution of 5.2 mL (0.041 mole) of ethyl bromodifluoroacetate in 5 mL of tetrahydrofuran was added dropwise at a rate to keep the internal temperature below 35 degrees. The mixture was stirred for 20 minutes and then cooled to −10 to 0 degrees. A solution of 7 g (0.027 mole) of benzotriazol-1-ylmethyl-(2-thiophen-2-yl-ethyl)-amine in 20 mL of tetrahydrofuran was added dropwise at a rate to keep the internal temperature at −10 to 0 degrees. After 10 minutes the reaction mixture was warmed to room temperature and stirred for 3 hours at room temperature. The solution was cooled to −10 to 0 degrees and quenched by the addition of saturated aqueous sodium bicarbonate at a rate to maintain the internal temperature −10 to 0 degrees. Ether was added, the mixture was stirred for 15 minutes at room temperature and then filtered through Celite, washing with ether. The filtrate was extracted 3 times with ether. The combined organic layers were dried over anhydrous sodium sulfate, filtered, and concentrated under reduced pressure. Ether and hexane were added to the residue, the solids were removed by filtration and the filtrate was concentrated under reduced pressure. The residue was purified by silica gel chromatography, eluting with hexane-ethyl acetate (gradient, 100:

0-80:20) to give 2 g of 2,2-difluoro-3-(2-thiophen-2-yl-ethylamino)-propionic acid ethyl ester as a oil.

2,2-difluoro-3-phenethylamino-propionic acid ethyl ester

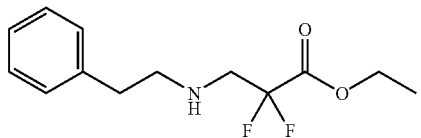

Step a

To a mixture of 17.7 g (0.149 mole) benzotriazole and 18 g (0.149 mole) of phenethylamine in 700 mL of ether was added dropwise 12 mL (0.149 mole) of 37% aqueous formaldehyde. The reaction mixture was stirred at room temperature overnight. The solution was dried over calcium chloride, filtered and concentrated under pressure. Hexane was added under ice-cooled bath and the resulting solid was collected by filtration and washed with hexane dried to give 38.0 g of benzotriazol-1-ylmethyl-phenethyl-amine as a light yellow oil).

Step b

To a mixture of 3.63 g (0.056 g-atom) of zinc powder (–325 mesh) and 60 mL of anhydrous tetrahydrofuran was added 5.3 mL (0.042 mole) of chlorotrimethylsilane in one portion. After stirring for 20 minutes, a solution of 5.4 mL (0.042 mole) of ethyl bromodifluoroacetate in 5 mL of tetrahydrofuran was added dropwise at a rate to keep the internal temperature below 35 degrees. The mixture was stirred for 20 minutes and then cooled to –10 to 0 degrees. A solution of 7 g (0.028 mole) of benzotriazol-1-ylmethyl-phenethyl-amine in 30 mL of tetrahydrofuran was added dropwise at a rate to keep the internal temperature at –10 to 0 degrees. After 10 minutes the reaction mixture was warmed to room temperature and stirred for 3 hours at room temperature. The solution was cooled to –10 to 0 degrees and quenched by the addition of saturated aqueous sodium bicarbonate at a rate to maintain the internal temperature –10 to 0 degrees. Ether was added, the mixture was stirred for 15 minutes at room temperature and then filtered through Celite, washing with ether. The filtrate was extracted 3 times with ether. The combined organic layers were dried over anhydrous sodium sulfate, filtered, and concentrated under reduced pressure. Ether and hexane were added to the residue, the solids were removed by filtration and the filtrate was concentrated under reduced pressure. The residue was purified by silica gel chromatography, eluting with hexane-ethyl acetate (gradient, 100:0-80:20) to give 0.8 g of 2,2-difluoro-3-phenethylamino-propionic acid ethyl ester as a oil.

2,2-difluoro-3-(3-phenyl-propylamino)-propionic acid ethyl ester

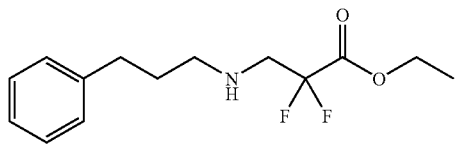

Step a

To the mixture of 8.8 g (0.74 mole) benzotriazole and 10 g (0.74 mole) of phenylpropylamine in 200 mL of dichloromethane was added dropwise 6.0 mL (0.74 mole) of 37% aqueous formaldehyde. The reaction mixture was stirred at room temperature overnight. The solution was dried over calcium chloride, filtered and concentrated under pressure. Hexane was added under ice-cooled bath and the resulting solid was collected by filtration and washed with hexane dried to give 21.0 g of benzotriazol-1-ylmethyl-(3-phenyl-propyl)-amine as an oil.

Step b

To a mixture of 3.44 g (0.056 g-atom) of zinc powder (–325 mesh) and 60 mL of anhydrous tetrahydrofuran was added 5.0 mL (0.039 mole) of chlorotrimethylsilane in one portion. After stirring for 20 minutes, a solution of 5.1 mL (0.039 mole) of ethyl bromodifluoroacetate in 5 mL of tetrahydrofuran was added dropwise at a rate to keep the internal temperature below 35 degrees. The mixture was stirred for 20 minutes and then cooled to –10 to 0 degrees. A solution of 7 g (0.026 mole) of benzotriazol-1-ylmethyl-(3-phenyl-propyl)-amine in 30 mL of tetrahydrofuran was added dropwise at a rate to keep the internal temperature at –10 to 0 degrees. After 10 minutes the reaction mixture was warmed to room temperature and stirred for 3 hours at room temperature. The solution was cooled to –10 to 0 degrees and quenched by the addition of saturated aqueous sodium bicarbonate at a rate to maintain the internal temperature –10 to 0 degrees. Ether was added, the mixture was stirred for 15 minutes at room temperature and then filtered through Celite, washing with ether. The filtrate was extracted 3 times with ether. The combined organic layers were dried over anhydrous sodium sulfate, filtered, and concentrated under reduced pressure. Ether and hexane were added to the residue, the solids were removed by filtration and the filtrate was concentrated under reduced pressure. The residue was purified by silica gel chromatography, eluting with hexane-ethyl acetate (gradient, 100:0-80:20) to give 1.1 g of 2,2-difluoro-3-(3-phenyl-propylamino)-propionic acid ethyl ester as a oil.

2,2-difluoro-3-(trans-2-phenyl-cyclopropylamino)-propionic acid ethyl ester

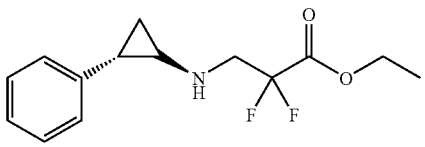

Step a

To the mixture of 6.7 g (0.056 mole) benzotriazole and 7.4 g (0.056 mole) of trans-2-phenyl-cyclopropylamine in 150 mL of ether was added dropwise 4.5 mL (0.056 mole) of 37% aqueous formaldehyde. The reaction mixture was stirred at room temperature overnight. The solution was dried over calcium chloride, filtered and concentrated under pressure. Hexane was added under ice-cooled bath and the resulting solid was collected by filtration and washed with hexane dried to give 15 g of benzotriazol-1-ylmethyl-(trans-2-phenyl-cyclopropyl)-amine as an oil.

Step b

To a mixture of 7.3 g (0.112 g-atom) of zinc powder (–325 mesh) and 120 mL of anhydrous tetrahydrofuran was added 10.7 mL (0.084 mole) of chlorotrimethylsilane in one portion.

After stirring for 20 minutes, a solution of 10.8 mL (0.084 mole) of ethyl bromodifluoroacetate in 10 mL of tetrahydrofuran was added dropwise at a rate to keep the internal temperature below 35 degrees. The mixture was stirred for 20 minutes and then cooled to −10 to 0 degrees. A solution of 14.8 g (0.056 mole) of benzotriazol-1-ylmethyl-(trans-2-phenyl-cyclopropyl)-amine in 60 mL of tetrahydrofuran was added dropwise at a rate to keep the internal temperature at −10 to 0 degrees. After 10 minutes the reaction mixture was warmed to room temperature and stirred for 3 hours at room temperature. The solution was cooled to −10 to 0 degrees and quenched by the addition of saturated aqueous sodium bicarbonate at a rate to maintain the internal temperature −10 to 0 degrees. Ether was added, the mixture was stirred for 15 minutes at room temperature and then filtered through Celite, washing with ether. The filtrate was extracted 3 times with ether. The combined organic layers were dried over anhydrous sodium sulfate, filtered, and concentrated under reduced pressure. Ether and hexane were added to the residue, the solids were removed by filtration and the filtrate was concentrated under reduced pressure. The residue was purified by silica gel chromatography, eluting with hexane-ethyl acetate (gradient, 100:0-80:20) to give 1.7 g of 2,2-difluoro-3-(trans-2-phenyl-cyclopropylamino)-propionic acid ethyl ester as a oil.

2,2-dichloro-3-cyclopentylamino-propionic acid methyl ester

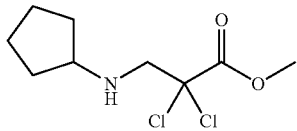

Step a

To the mixture of 36 g (0.3 mole) of benzotriazole and 30 mL (0.3 mole) of cyclopentylamine in 1400 mL of ether was added dropwise 22 mL (0.3 mole) of 37% aqueous formaldehyde. The reaction mixture was stirred at room temperature overnight. The solution was dried over calcium chloride, filtered and concentrated under pressure. Hexane was added under ice-cooled bath and the resulting solid was collected by filtration and washed with hexane dried to give 58.6 g of benzotriazol-1-ylmethyl-cyclopentyl-amine as a white solid.

Step b

To a suspension of 5.9 g (0.091 g-atom) of zinc powder (−325 mesh) in 40 mL of tetrahydrofuran was added 0.2 mL of 1,2-dibromoethane. The mixture was heated at gentle reflux for 30 minutes. The mixture was cooled to room temperature and 7.1 mL (0.06 mole) of methyl trichloroacetate was added dropwise, followed by 9.1 mL (0.097 mole) of trimethylsilyl chloride at rate such the internal temperature was below 50 degrees. The mixture was stirred at room temperature for 1 hour and then diluted with hexane. The resulting solid was removed by filtration, and the filtrate concentrated under reduced pressure. Solids were removed by filtration, washing with hexane. The filtrated was concentrated under reduced pressure and the residue was then distilled under vacuum to give 8.0 g of (2,2-dichloro-1-methoxy-vinyloxy)-trimethyl-silane as a colorless oil. Bp 45-48 degrees at 1 mm Hg.

Step c

To a solution of 4.3 g (0.02 mole) of benzotriazol-1-ylmethyl-cyclopentyl-amine and 6.4 g (0.030 mole) of (2,2-dichloro-1-methoxy-vinyloxy)-trimethyl-silane in 140 ml of anhydrous dichloromethane was added dropwise 3.7 ml (0.030 mole) of boron trifluride diethyl etherate at 0 degrees. The reaction was stirred at 0 degrees for 1 hour and then at room temperature for 24 hours. The reaction was quenched by the addition of 10% aqueous sodium carbonate and extracted with dichloromethane. The organic layer was washed with saturated sodium carbonate, brine, dried over sodium sulfate, filtered and concentrated under reduced pressure. Purification by silica gel chromatography, eluting with hexane-ethyl acetate (gradient, 100:0-85:15) gave 2.4 g of 2,2-dichloro-3-cyclopentylamino-propionic acid methyl ester as a colorless oil.

Preparation of Anilines 4-amino-N-(tetrahydro-pyran-4-yl)-benzamide

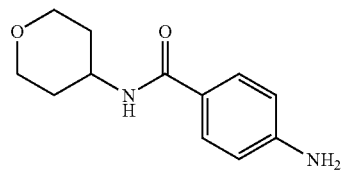

To a mixture of 1.1441 g (4.5 mmole) of 4-amino-benzoic acid benzotriazol-1-yl ester and 8 mL of dry dimethylformamide was added 0.6575 g (6.5 mmole) of 4-amino-pyran followed by 0.4554 g (0.45 mmole) of triethylamine. The mixture stirred at room temperature for 90 minutes. Volatiles were removed under reduced pressure and the residue taken up in ethyl acetate, and the organic layer washed once with 100 mL of 0.5 M sodium carbonate, twice with 75 mL water, and then 75 mL brine, dried over anhydrous sodium sulfate and concentrated under reduced pressure to give 0.5378 g 4-amino-N-(tetrahydro-pyran-4-yl)-benzamide, which was used without further purification.

4-amino-N-(2-dimethylamino-ethyl)-3-methoxy-benzamide

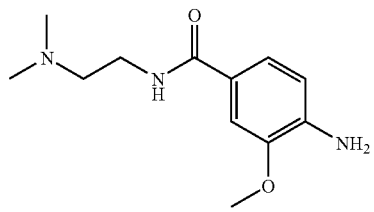

To a mixture of 1.2793 g (4.5 mmole) of 4-amino-3-methoxy-benzoic acid benzotriazol-1-yl ester and 8 mL of dry tetrahydrofuran at 0 degrees was added 0.5950 g (6.75 mmole) of 2-N,N-dimethylamino-ethanamine followed by 1.1384 g (11.25 mmole) of triethylamine. The cooling bath was removed and the mixture stirred at room temperature for 35 minutes. Volatiles were removed under reduced pressure and the residue taken up in ethyl acetate, and the organic layer washed twice with 50 mL of 0.5 M sodium carbonate, 50 mL water, and then 50 mL brine, dried over anhydrous sodium sulfate and concentrated under reduced pressure to give 0.8798 g 4-amino-N-(2-dimethylamino-ethyl)-3-methoxy-benzamide, which was used without further purification.

4-amino-N-(3-dimethylamino-propyl)-3-methoxy-benzamide

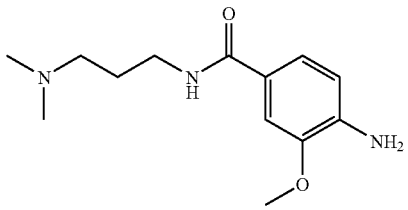

To a mixture of 1.1371 g (4.0 mmole) of 4-amino-3-methoxy-benzoic acid benzotriazol-1-yl ester and 8 mL of dry tetrahydrofuran at 0 degrees was added 0.6131 g (6.0 mmole) of 3-dimethylamino-propylamine followed by 1.0119 g (10 mmole) of triethylamine. The cooling bath was removed and the mixture stirred at room temperature for 65 minutes. Volatiles were removed under reduced pressure and the residue taken up in ethyl acetate, and the organic layer washed twice with 50 mL of 0.5 M sodium carbonate, 50 mL water, and then 50 mL brine, dried over anhydrous sodium sulfate and concentrated under reduced pressure to give 0.8587 g 4-amino-N-(3-dimethylamino-propyl)-3-methoxy-benzamide, which was used without further purification.

4-amino-N-(1-ethyl-piperidin-4-yl)-3-methoxy-benzamide

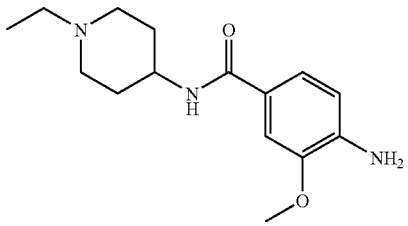

To a mixture of 1.1371 g (4.0 mmole) of 4-amino-3-methoxy-benzoic acid benzotriazol-1-yl ester and 8 mL of dry tetrahydrofuran at 0 degrees was added 0.5129 g (4.0 mmole) of 4-amino-1-ethylpiperidine followed by 1.0119 g (10 mmole) of triethylamine. The cooling bath was removed and the mixture stirred at room temperature for 65 minutes. Volatiles were removed under reduced pressure and the residue taken up in ethyl acetate, and the organic layer washed twice with 50 mL of 0.5 M sodium carbonate, 50 mL water, and then 50 mL brine, dried over anhydrous sodium sulfate and concentrated under reduced pressure to give 1.0056 g 4-amino-N-(1-ethyl-piperidin-4-yl)-3-methoxy-benzamide, which was used without further purification.

4-amino-N-[1-(2-fluoro-ethyl)-piperidin-4-yl]-3-methoxy-benzamide

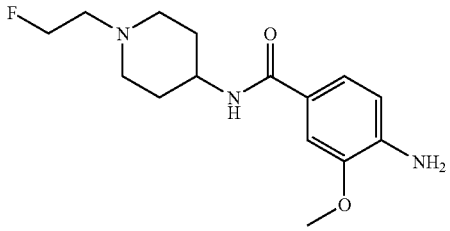

To a mixture of 0.5432 g (1.91 mmole) of 4-amino-3-methoxy-benzoic acid benzotriazol-1-yl ester, 0.4187 g (1.91 mmole) of 1-(2-fluoro-ethyl)-piperidin-4-ylamine dihydrochloride and 8 mL of dimethylformamide was added 1.3316 mL of triethylamine. The mixture was stirred for 25 hours, then taken up in ethyl acetate and twice with 50 mL 0.5 M sodium carbonate, once with 50 mL water, once with 50 mL brine, dried over anhydrous sodium sulfate, filtered and concentrated under reduced pressure. The residue was purified by silica gel chromatography, eluting with acetonitrile-methanol-triethylamine (90:10:0.8), to give 0.4159 g 4-amino-N-[1-(2-fluoro-ethyl)-piperidin-4-yl]-3-methoxy-benzamide.

4-amino-N-[1-(2,2-difluoro-ethyl)-piperidin-4-yl]-3-methoxy-benzamide

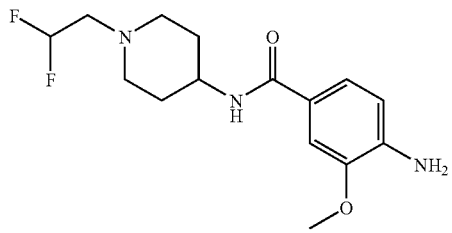

A mixture of 2.0028 g (0.010 mole) of 4-Boc-aminopiperidine, 2.585 g (0.020 mole) of ethyldiisopropylamine, 15 mL of tetrahydrofuran and 2.3034 g (0.012 mole) of 2,2-difluroethyl iodide was heated 55 degrees for 91 hours, then cooled and concentrated under reduced pressure. The residue was taken up in 300 mL of ethyl acetate, washed with 100 mL of 0.5 M sodium carbonate, 75 mL brine, dried over anhydrous sodium sulfate, filtered and concentrated under reduced pressure. Purification by silica gel chromatography gave 1.2104 g of [1-(2,2-difluoro-ethyl)-piperidin-4-yl]-carbamic acid tert-butyl ester.

To a cooled (0 degrees) mixture of 1.21 g (4.58 mmole) of [1-(2,2-difluoro-ethyl)-piperidin-4-yl]-carbamic acid tert-butyl ester and 20 mL of dioxane, was added 5.7 mL of 4M HCl in dioxane. The mixture was stirred at room temperature overnight, and the solid collected by filtration to give 0.90 g of 1-(2,2-difluoro-ethyl)-piperidin-4-ylamine dihydrochloride.

To a mixture of 1.07 g (3.78 mmole) of 4-amino-3-methoxy-benzoic acid benzotriazol-1-yl ester, 0.90 g (3.78 mmole) of 1-(2,2-difluoro-ethyl)-piperidin-4-ylamine dihydrochloride and 5 mL of dimethylformamide was added 2.63 mL of triethylamine. The mixture was stirred for 20 hours, then taken up in dichloromethane and washed twice with 100 mL of saturated aqueous sodium bicarbonate, once with 50 mL water, once with 50 mL brine, dried over anhydrous sodium sulfate, filtered and concentrated under reduced pressure. The residue was purified by silica gel chromatography, eluting with dichloromethane-methanol (gradient, 100:0-90:10) to give 1.05 g of 4-amino-N-[1-(2,2-difluoro-ethyl)-piperidin-4-yl]-3-methoxy-benzamide.

4-amino-N-[1-(2-hydroxy-ethyl)-piperidin-4-yl]-3-methoxy-benzamide

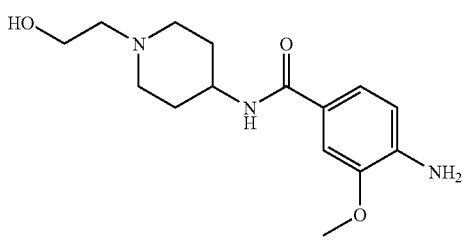

To a mixture of 0.70 g (3.23 mmole) of 2-(4-amino-piperidin-1-yl)-ethanol, 0.92 g of 4-amino-3-methoxy-benzoic acid benzotriazol-1-yl ester, and 5 mL of dimethylformamide was added 1.63 g (16.1 mmole) of triethylamine. The mixture was stirred overnight, then taken up in 150 mL of dichloromethane and washed twice with saturated aqueous sodium bicarbonate, once with water, once with brine, dried over anhydrous sodium sulfate, filtered and concentrated under reduced pressure. The residue was purified by silica gel chromatography, eluting with dichloromethane-methanol (gradient, 100:0-80:20) to give 0.35 g of 4-amino-N-[1-(2-hydroxy-ethyl)-piperidin-4-yl]-3-methoxy-benzamide.

4-amino-N-(1-methanesulfonyl-piperidin-4-yl)-3-methoxy-benzamide

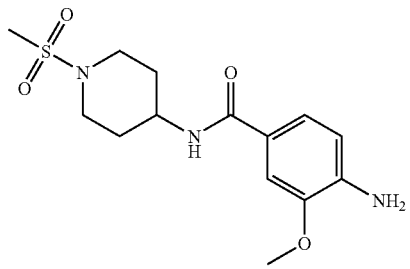

To a mixture of 0.8813 g (3.1 mmole) of 4-amino-3-methoxy-benzoic acid benzotriazol-1-yl ester and 8 mL of dry tetrahydrofuran at 0 degrees was added 0.6995 g (3.1 mmole) of 1-methanesulfonyl-piperidin-4-ylamine followed by 0.7842 g (7.75 mmole) of triethylamine. The cooling bath was removed and the mixture stirred at room temperature for 90 hours. Volatiles were removed under reduced pressure and the residue taken up in ethyl acetate, and the organic layer washed twice with 50 mL of 0.5 M sodium carbonate, 50 mL water, and then 50 mL brine, dried over anhydrous sodium sulfate and concentrated under reduced pressure to give 1.0056 g 4-amino-N-(1-ethyl-piperidin-4-yl)-3-methoxy-benzamide.

Recrystallization from acetonitrile gave 0.1641 g of 4-amino-N-(1-methanesulfonyl-piperidin-4-yl)-3-methoxy-benzamide.

4-amino-N-(1-ethyl-piperidin-4-yl)-benzamide

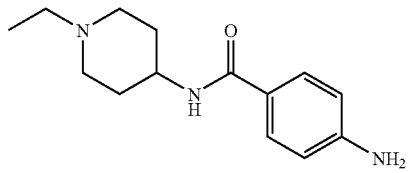

To a mixture of 1.0424 g (4.1 mmole) of 4-amino-benzoic acid benzotriazol-1-yl ester and 8 mL of dry tetrahydrofuran at 0 degrees was added 0.5257 g (4.1 mmole) of 4-amino-1-ethylpiperidine followed by 1.0372 g (10.3 mmole) of triethylamine. The cooling bath was removed and the mixture stirred at room temperature for 65 minutes. Volatiles were removed under reduced pressure and the residue taken up in ethyl acetate, and the organic layer washed twice with 50 mL of 0.5 M sodium carbonate, 50 mL water, and then 50 mL brine, dried over anhydrous sodium sulfate and concentrated under reduced pressure to give 0.8522 g 4-amino-N-(1-ethyl-piperidin-4-yl)-benzamide, as a white solid which was used without further purification.

4-amino-N-[1-(3-methanesulfonyl-propyl)-piperidin-4-yl]-3-methoxy-benzamide

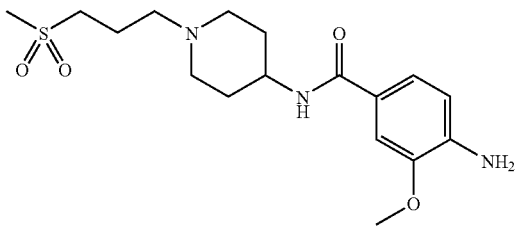

To a cooled (0 degrees) mixture of 3.7 g (0.019 mole) of piperidin-4-yl-carbamic acid tert-butyl ester in 60 mL of dichloromethane, was added 2.1 g (0.020 mole) of triethylamine, followed by 4.2 g (0.017 mole) of 3-(methylsulfonyl)-1-propanol-1-methanesulfonate. The mixture was stirred at room temperature for 18 hours, then diluted with water and the organic layer washed twice with 40 mL of water, once with 40 mL of brine, dried over anhydrous sodium sulfate, filtered and concentrated under reduced pressure. The residue was purified by silica gel chromatography, eluting with dichloromethane-methanol (gradient, 100:0-90:10) to give 3.6 g of [1-(3-methanesulfonyl-propyl)-piperidin-4-yl]-carbamic acid tert-butyl ester.

To a cooled (0 degrees) mixture of 3.6 g (0.0113 mole) of [1-(3-methanesulfonyl-propyl)-piperidin-4-yl]-carbamic acid tert-butyl ester and 30 mL of dioxane, was added 14.1 mL of 4M HCl in dioxane. The mixture was stirred 18 hours at room temperature, and the solid collected by filtration to give 2.3 g of 1-(3-methanesulfonyl-propyl)-piperidin-4-ylamine dihydrochloride.

To a mixture of 2.3 g of 1-(3-methanesulfonyl-propyl)-piperidin-4-ylamine dihydrochloride, 2.7 g (0.0095 mole) of 4-amino-3-methoxy-benzoic acid benzotriazol-1-yl ester and 15 mL of dimethylformamide was added 4.0 g (0.0395 mole) of triethylamine. The mixture was stirred at room temperature for 20 hours, then diluted with 150 mL of dichloromethane. The mixture was washed twice with 100 mL of sodium bicarbonate, once with 50 mL of water, once with 50 mL of brine, dried over anhydrous sodium sulfate, filtered, and concentrated under reduced pressure. The residue was purified by silica gel chromatography, eluting with dichloromethane-methanol (gradient, 100:0-80:20) to give 2.0 g of 4-amino-N-[1-(3-methanesulfonyl-propyl)-piperidin-4-yl]-3-methoxy-benzamide.

4-amino-2-fluoro-5-methoxy-benzoic acid methyl ester

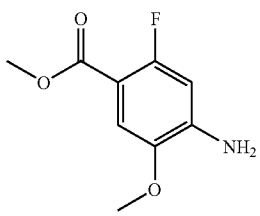

To a mixture 0.30 g (7.55 mmole) of sodium hydride (60% in mineral oil) and 30 mL of methanol was added 1.49 g (6.86 mmole) of 2,5-difluoro-4-nitro-benzoic acid methyl ester. The mixture was heated at reflux for 18 hours and then quenched by the addition of water, and then concentrated under reduced pressure. The residue was diluted with ethyl acetate, washed with brine, dried over anhydrous magnesium sulfate, filtered and concentrated under reduced pressure. The residue was purified by silica gel chromatography eluting with dichloromethane-hexanes (1:1) to give 0.92 g of 2-fluoro-5-methoxy-4-nitro-benzoic acid methyl ester.

To a solution of 0.92 g (4.01 mmole) of 2-fluoro-5-methoxy-4-nitro-benzoic acid methyl ester and 30 mL of ethanol was added 0.10 g of 10% Pd/C. The mixture was hydrogenated in a Parr hydrogenator at 50 Psi for 1 day. The catalyst was removed by filtration and the solution was concentrated under reduced pressure to give 0.78 g of 4-amino-2-fluoro-5-methoxy-benzoic acid methyl ester.

4-amino-3-chloro-N-(1-methyl-piperidin-4-yl)-benzamide

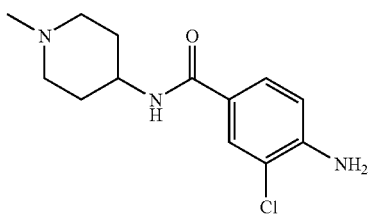

To a solution of 1.0 g (5.9 mole) of 4-amino-3-chlorobenzoic acid, 0.8 g (7.0 mole) of 4-amino-1-methyl-piperidine and 4.14 mL (23 mmole) of ethyldiisopropyl amine in 20 mL of dimethylformamide was added a solution of 2.4 g (6.4 mole) of 1-(di-1-pyrrolidinylmethylene)-1H-benzotriazolium 3-oxide hexafluorophosphate in 5 mL of dimethylformamide. The mixture was stirred at room temperature for 2 hours, then diluted with ice water and saturated sodium carbonate. The mixture was extracted with ethyl acetate twice. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-60:40) gave 1.41 g of 4-amino-3-chloro-N-(1-methyl-piperidin-4-yl)-benzamide as a solid.

4-amino-3-isopropoxy-N-(1-methyl-piperidin-4-yl)-benzamide

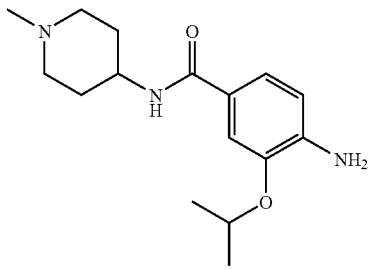

A mixture of 2.0 g (10 mmole) of 3-hydroxy-4-nitro-benzoic acid methyl ester, 1.32 mL (13 mmole) of 2-iodopropane, 6.6 g (20 mole) of cesium carbonate and 60 mL of dimethylformamide was heated at 85 degrees overnight. The mixture was cooled, diluted with water and extracted twice with ethyl acetate. The combined organic layers were washed three times with sodium carbonate, three times with brine, dried over anhydrous sodium sulfate, filtered and concentrated under reduced pressure. Purification by silica gel chromatography, eluting with ethyl acetate-hexane (gradient, 100: 0-70:30) gave 1.62 g of 3-isopropoxy-4-nitro-benzoic acid methyl ester as a yellow liquid.

To a solution of 1.0 g (4.2 mole) of 3-isopropoxy-4-nitro-benzoic acid methyl ester in 20 mL of methanol was added 8.4 mL (8.4 mole) of 1M lithium hydroxide. The mixture was stirred at room temperature for 2 hours. The mixture was partially concentrated under reduced pressure and then acidified to by addition of 1 M of hydrochloric acid. The solid, which formed, was collected by filtration, washed with water and dried under vacuum to give 0.93 g of 3-isopropoxy-4-nitro-benzoic acid as a white solid.

To a mixture of 0.88 g (3.9 mmole) of 3-isopropoxy-4-nitro-benzoic acid, 2.8 mL (16 mmole) of ethyldiisopropyl amine, 0.54 g (4.7 mmole) of 4-amino-1-methyl-piperidine and 18 mL of dimethylformamide was added 1.63 g (4.3 mmole) of 1-[bis(dimethylamino)methylene]-1H-benzotriazolium 3-oxide hexafluorophosphate. The mixture was stirred at room temperature for 2 hours, then diluted with ice water and saturated sodium carbonate. The mixture was extracted with ethyl acetate 3 times. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-40:60) gave 1.2 g of 3-isopropoxy-N-(1-methyl-piperidin-4-yl)-4-nitro-benzamide as a yellow solid.

To a solution of 1.2 g (3.6 mmole) of 3-isopropoxy-N-(1-methyl-piperidin-4-yl)-4-nitro-benzamide in 25 mL of methanol was added 0.12 g of 10% palladium on carbon. The hydrogenation reaction was carried out under 50 psi of hydrogen for 2 hours. The mixture was filtered, concentrated under reduced pressure and triturated with ether. The solid was collected by filtration, washed with ether and dried under vacuum to give 1.0 g of 4-amino-3-isopropoxy-N-(1-methyl-piperidin-4-yl)-benzamide as a white solid.

4-amino-N-(1-methyl-piperidin-4-yl)-3-trifluoromethoxy-benzamide

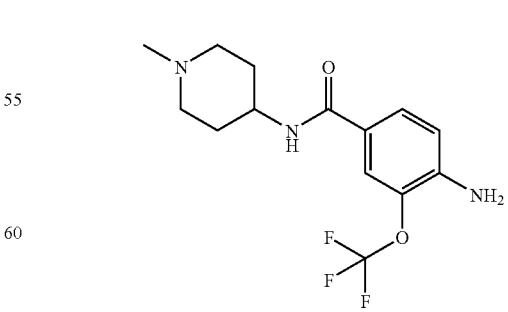

To a solution of 0.5 g (2.3 mmole) of 4-amino-3-trifluoromethoxy-benzoic acid, 0.31 g (2.8 mmole) of 4-amino-1-methyl-piperidine, 1.2 mL (69 mmole) of ethyldiisopropyl amine and 4 mL of dimethylformamide was added the solution of 1.2 g (2.8 mmole) of 1-(di-1-pyrrolidinylmethylene)-1H-benzotriazolium 3-oxide hexafluorophosphate in 2 mL of dimethylformamide. The mixture was stirred at room temperature for 2 hour, then diluted with ice water and saturated sodium carbonate. The mixture was extracted with dichloromethane twice. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-60:40) gave 0.7 g of 4-amino-N-(1-methyl-piperidin-4-yl)-3-trifluoromethoxy-benzamide as a white solid.

EXAMPLES

Example 1

4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoic acid (I-1)

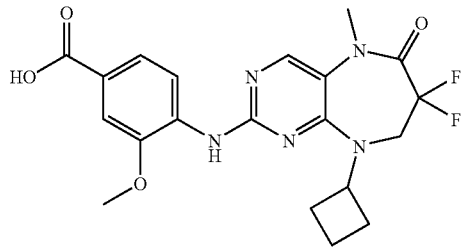

Step a

A solution of 17.76 g (0.086 mole) 3-cyclobutylamino-2,2-difluoropropionic acid ethyl ester in 10 mL of ethyl acetate was added dropwise to a mixture of 16.6 g (0.086 mole) of 2,4-dichloro-5-nitro-pyrimidine, 28.9 g (0.344 mole) of sodium bicarbonate and 100 mL of ethyl acetate at 0 degrees. The cooling bath was removed and the reaction was stirred at room temperature for 18 h. Activated charcoal was added, and the mixture was filtered through a pad of Celite, washing the filter pad with ethyl acetate. The filtrate was concentrated under reduced pressure and the residue purified by silica gel chromatography (elution with hexanes-ethyl acetate, gradient 100:0-50:50), to give 11.6 g of 3-[(2-chloro-5-nitro-pyrimidin-4-yl)-cyclobutyl-amino]-2,2-difluoro-prop ionic acid ethyl ester (IV-1).

Step b

To a solution of 11.6 g (0.032 mole) of 3-[(2-chloro-5-nitro-pyrimidin-4-yl)-cyclobutyl-amino]-2,2-difluoro-propionic acid ethyl ester in 100 mL of acetic acid was added 15.5 g (0.191 g-atom) of iron powder. The mixture was heated to 80 degrees for 2 hours and then filtered while hot. Water and ethyl acetate were added to the filtrate and mixture was stirred for 10 minutes and then filtered. The organic layer was washed with ammonium hydroxide and water, dried over anhydrous sodium sulfate, filtered and concentrated under reduced pressure. The solid residue was washed with 50 mL of hexanes-ethyl acetate (90:10) and then air dried to give 6.8 g of 2-chloro-9-cyclobutyl-7,7-difluoro-5,7,8,9-tetrahydro-pyrimido[4,5-b][1,4]diazepin-6-one (VI-1).

Step c

To a mixture of 5.5 g (0.0191 mole) of 2-chloro-9-cyclobutyl-7,7-difluoro-5,7,8,9-tetrahydro-pyrimido[4,5-b][1,4]diazepin-6-one (VI-1), 25 mL of dimethylformamide and 9.4 g (0.0287 mole) of cesium carbonate was added 10.9 g (0.0764 mole) of iodomethane. The mixture was stirred for 3 hours, then 80 mL of water was added and the solid collected by suction filtration to give 4.8 g of 2-chloro-9-cyclobutyl-7,7-difluoro-5-methyl-5,7,8,9-tetrahydro-pyrimido[4,5-b][1,4]diazepin-6-one (VII-1).

Step d

A mixture of 2.00 g (0.0066 mole) of 2-chloro-9-cyclobutyl-7,7-difluoro-5-methyl-5,7,8,9-tetrahydro-pyrimido[4,5-b][1,4]diazepin-6-one (VII-1), 1.655 g (0.0099 mole) of 4-amino-3-methoxybenzoic acid and 200 mL of ethanol-water-hydrochloric acid (20:80:1) was refluxed for 18 hours, then concentrated under reduced pressure. The solid was washed with water and then purified by silica gel chromatography, eluting with dichloromethane-methanol-ammonium hydroxide (92:8:0.3) to give 1.500 g of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoic acid (I-1).

Example 2

4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzamide (I-2)

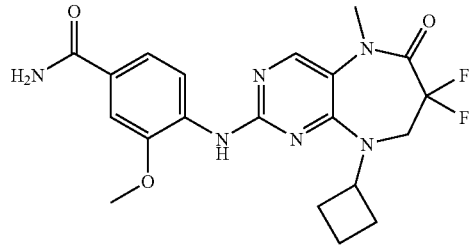

A mixture of 0.115 g (0.26 mmole) of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoic acid (I-1), 0.105 g (1.04 mmole) of triethylamine, 0.148 g (0.39 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes, then 0.045 g (0.84 mmole) of ammonium chloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.075 g of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzamide (I-2).

Example 3

4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-methyl-benzamide (I-3)

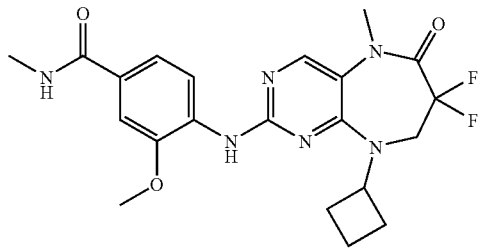

A mixture of 0.100 g (0.23 mmole) of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoic acid (I-1), 0.092 g (0.92 mmole) of triethylamine, 0.148 g (0.39 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes and then 0.023 g (0.35 mmole) of methylamine hydrochloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.052 g of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-methyl-benzamide (I-3).

Example 4

4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-4)

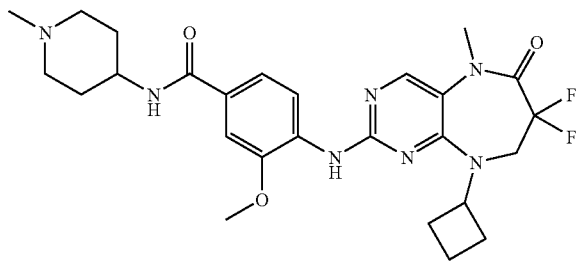

A mixture of 0.100 g (0.23 mmole) of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoic acid (I-1), 0.093 g (0.92 mmole) of triethylamine, 0.148 g (0.39 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes and then 0.040 g (0.35 mmole) of 4-amino-1-methyl-piperidine was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.056 g of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-4).

Example 5

4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-piperidin-4-yl-benzamide (I-5)

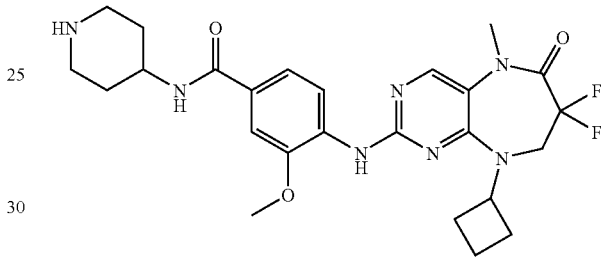

A mixture of 0.095 g (0.22 mmole) of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoic acid (I-1), 0.089 g (0.88 mmole) of triethylamine, 0.125 g (0.33 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes and then 0.066 g (0.33 mmole) of 4-amino-1-piperidinecarboxylic acid 1,1-dimethylethyl ester was added. The mixture was stirred for 3 hours, then taken up in 50 mL of dichloromethane and washed twice with 100 mL of water and then 100 mL of brine. The organic layer was dried over anhydrous sodium sulfate, filtered and concentrated under reduced pressure. The residue was purified by silica gel chromatography, eluting with hexane-ethyl acetate (gradient 50:50-0:100) to give 0.078 g of 4-[4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester. A mixture of 0.078 g (0.013 mmole) of 4-[4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester 1 mL of trifluoroacetic acid and 5 mL of dichloromethane was stirred for 1 hour and then concentrated under reduced pressure. The residue was taken up in 30 mL of ethyl acetate, washed twice with 30 mL of saturated aqueous sodium bicarbonate and then brine. The organic layer was dried over anhydrous sodium sulfate, filtered and concentrated under reduced pressure. The residue was triturated with ether, to give 0.055 g of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-piperidin-4-yl-benzamide (I-5).

Example 6

2-[4-(4-amino-piperidine-1-carbonyl)-2-methoxy-phenylamino]-9-cyclobutyl-7,7-difluoro-5-methyl-5,7,8,9-tetrahydro-pyrimido[4,5-b][1,4]diazepin-6-one (I-6)

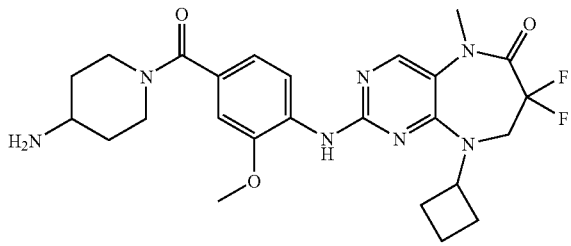

A mixture of 0.200 g (0.46 mmole) of 4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoic acid (I-1), 0.186 g (1.84 mmole) of triethylamine, 0.220 g (0.51 mmole) of N-[(dimethylamino)(3H-1,2,3-triazolo[4,5-b]pyridin-3-yloxy)methylene]-N-methyl-methanaminium, hexafluorophosphate(1-) (1:1) and 5 mL of dimethylformamide was stirred for 15 minutes and then 0.182 g (0.51 mmole) of 4-piperidinyl-carbamic acid 9H-fluoren-9-ylmethyl ester monohydrochloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with hexane-ethyl acetate (gradient 50:50-0:100) to give 0.210 g of {1-[4-(9-Cyclobutyl-7,7-difluoro-5-methyl-6-oxo-6,7,8,9-tetrahydro-5H-pyrimido[4,5-b][1,4]diazepin-2-ylamino)-3-methoxy-benzoyl]-piperidin-4-yl}-carbamic acid 9H-fluoren-9-ylmethyl ester.

A mixture of 0.150 g (0.20 mmole) of {1-[4-(9-Cyclobutyl-7,7-difluoro-5-methyl-6-oxo-6,7,8,9-tetrahydro-5H-pyrimido[4,5-b][1,4]diazepin-2-ylamino)-3-methoxy-benzoyl]-piperidin-4-yl}-carbamic acid 9H-fluoren-9-ylmethyl ester, 1 mL of piperidine and 5 mL of dichloromethane was stirred for 1 hour and then concentrated under reduced pressure. The residue was purified by silica gel chromatography, eluting with dichloromethane-methanol-ammonium hydroxide (gradient 100:0:0-92:8:0.3) to give 0.025 g of 2-[4-(4-amino-piperidine-1-carbonyl)-2-methoxy-phenylamino]-9-cyclobutyl-7,7-difluoro-5-methyl-5,7,8,9-tetrahydro-pyrimido[4,5-b][1,4]diazepin-6-one (I-6).

Example 7

4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-(tetrahydro-pyran-4-yl)-benzamide (I-7)

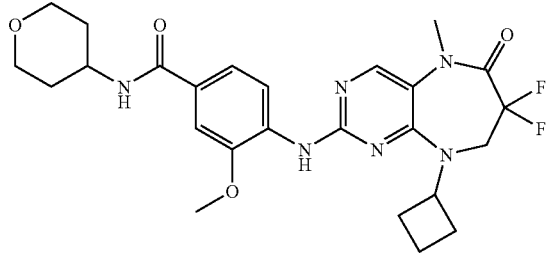

A mixture of 0.0605 g (0.20 mmole) 2-chloro-9-cyclobutyl-7,7-difluoro-5-methyl-5,7,8,9-tetrahydro-pyrimido[4,5-b][1,4]diazepin-6-one (VII-1), 0.0571 g (0.30 mmole) of toluenesulfonic acid monohydrate, 0.0501 g (0.20 mmole) of 4-amino-3-methoxy-N-(tetrahydro-2H-pyran-4-yl) benzamide and 1 mL of isopropanol was heated in a sealed vessel at 140 degrees for 19.5 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was recrystallized from acetonitrile-methanol to give 0.0452 g 4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-(tetrahydro-pyran-4-yl)-benzamide (I-7).

Example 8

4-(9-cyclobutyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methoxy-benzamide (I-8)

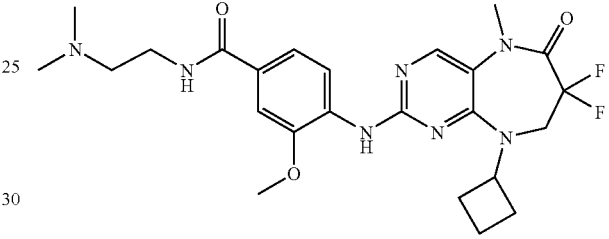

A mixture of 0.0663 g (0.219 mmole) 2-chloro-9-cyclobutyl-7,7-difluoro-5-methyl-5,7,8,9-tetrahydro-pyrimido[4,5-b][1,4]diazepin-6-one (VII-1), 0.0625 g (0.33 mmole) of toluenesulfonic acid monohydrate, 0.052 g (0.219 mmole) of 4-amino-N-(2-dimethylamino-ethyl)-3-methoxy-benzamide and 1 mL of isopropanol was heated in a sealed vessel at 140 degrees for 19.5 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (85:15:1) and then recrystallization from acetonitrile to give 0.0434 g of 4-(9-cyclobutyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methoxy-benzamide (I-8) as a white solid.

Example 9

4-(9-cyclobutyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methoxy-benzamide (I-9)

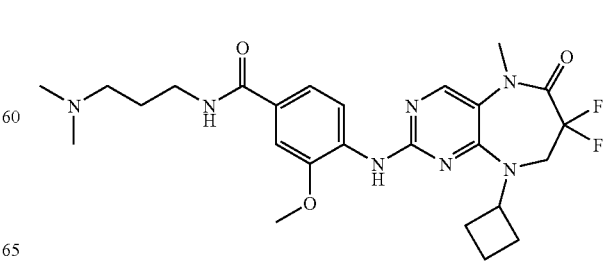

A mixture of 0.0638 g (0.211 mmole) 2-chloro-9-cyclobutyl-7,7-difluoro-5-methyl-5,7,8,9-tetrahydro-pyrimido[4,5-b][1,4]diazepin-6-one (VII-1), 0.0601 g (0.32 mmole) of toluenesulfonic acid monohydrate, 0.053 g (0.211 mmole) of 4-amino-N-(2-dimethylamino-ethyl)-3-methoxy-benzamide and 1 mL of isopropanol was heated in a sealed vessel at 140 degrees for 20 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (85:15:1) and then recrystallization from acetonitrile to give 0.0363 g of 4-(9-cyclobutyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methoxy-benzamide (I-9) as a white solid.

Example 10

4-(9-cyclobutyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide (I-10)

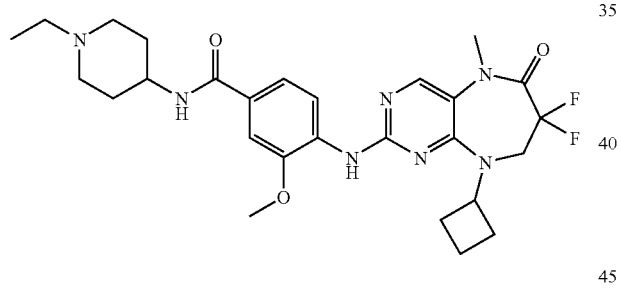

A mixture of 0.0605 g (0.20 mmole) 2-chloro-9-cyclobutyl-7,7-difluoro-5-methyl-5,7,8,9-tetrahydro-pyrimido[4,5-b][1,4]diazepin-6-one (VII-1), 0.0571 g (0.30 mmole) of toluenesulfonic acid monohydrate, 0.0555 g (0.20 mmole) of 4-amino-N-(1-ethyl-piperidin-4-yl)-3-methoxy-benzamide and 1 mL of isopropanol was heated in a sealed vessel at 140 degrees for 25 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (90:10:1) and then recrystallization from acetonitrile to give 0.0452 g of 4-(9-cyclobutyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide (I-10) as a white solid.

Example 11

4-(9-cyclobutyl-7,7-difluoro-5-methyl-6-oxo-6,7,8,9-tetrahydro-5H-pyrimido[4,5-b][1,4]diazepin-2-ylamino)-benzoic acid (I-11)

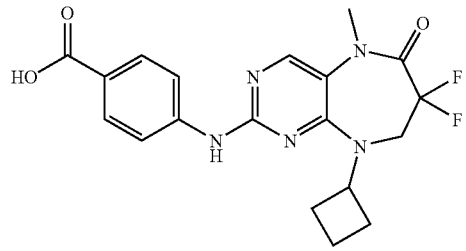

A mixture of 2.00 g (6.6 mmole) of 2-chloro-9-cyclobutyl-7,7-difluoro-5-methyl-5,7,8,9-tetrahydro-pyrimido[4,5-b][1,4]diazepin-6-one (VII-1), 1.655 g (12.08 mmole) of 4-amino-benzoic acid and 200 mL of ethanol-water-hydrochloric acid (20:80:1) was refluxed for 18 hours, then concentrated under reduced pressure. The solid was washed with water and then purified by silica gel chromatography, eluting with dichloromethane-methanol-ammonium hydroxide (92:8:0.3) to give 1.600 g of 4-(9-cyclobutyl-7,7-difluoro-5-methyl-6-oxo-6,7,8,9-tetrahydro-5H-pyrimido[4,5-b][1,4]diazepin-2-ylamino)-benzoic acid (I-11).

Example 12

4-(9-cyclobutyl-7,7-difluoro-5-methyl-6-oxo-6,7,8,9-tetrahydro-5H-pyrimido[4,5-b][1,4]diazepin-2-ylamino)-benzamide (I-12)

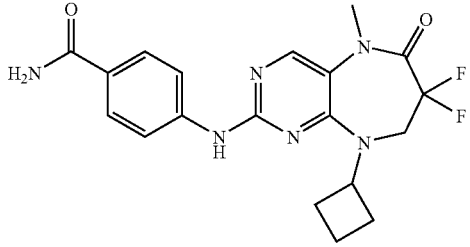

A mixture of 0.104 g (0.26 mmole) of 4-(9-cyclobutyl-7,7-difluoro-5-methyl-6-oxo-6,7,8,9-tetrahydro-5H-pyrimido[4,5-b][1,4]diazepin-2-ylamino)-benzoic acid (I-11), 0.105 g (1.04 mmole) of triethylamine, 0.148 g (0.39 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes, then 0.045 g (0.84 mmole) of ammonium chloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.060 g of 4-(9-cyclobutyl-7,7-difluoro-5-methyl-6-oxo-6,7,8,9-tetrahydro-5H-pyrimido[4,5-b][1,4]diazepin-2-ylamino)-benzamide (I-12).

Example 13

4-(9-cyclobutyl-7,7-difluoro-5-methyl-6-oxo-6,7,8,9-tetrahydro-5H-pyrimido[4,5-b][1,4]diazepin-2-ylamino)-N-methyl-benzamide (I-13)

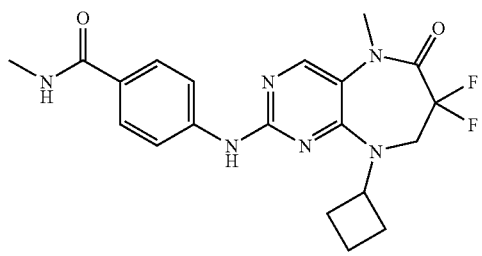

A mixture of 0.089 g (0.22 mmole) of 4-(9-cyclobutyl-7,7-difluoro-5-methyl-6-oxo-6,7,8,9-tetrahydro-5H-pyrimido[4,5-b][1,4]diazepin-2-ylamino)-benzoic acid (I-11), 0.089 g (0.88 mmole) of triethylamine, 0.125 g (0.33 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes, then 0.022 g (0.33 mmole) of methylamine hydrochloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.056 g of 4-(9-cyclobutyl-7,7-difluoro-5-methyl-6-oxo-6,7,8,9-tetrahydro-5H-pyrimido[4,5-b][1,4]diazepin-2-ylamino)-N-methyl-benzamide (I-13).

Example 14

4-(9-cyclobutyl-7,7-difluoro-5-methyl-6-oxo-6,7,8,9-tetrahydro-5H-pyrimido[4,5-b][1,4]diazepin-2-ylamino)-N-piperidin-4-yl-benzamide (I-14)

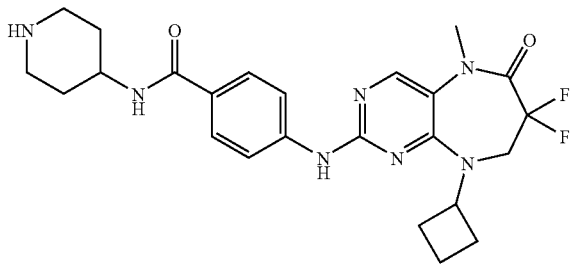

A mixture of 0.093 g (0.23 mmole) of 4-(9-cyclobutyl-7,7-difluoro-5-methyl-6-oxo-6,7,8,9-tetrahydro-5H-pyrimido[4,5-b][1,4]diazepin-2-ylamino)-benzoic acid (I-11), 0.093 g (0.92 mmole) of triethylamine, 0.133 g (0.35 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes and then 0.070 g (0.35 mmole) of 4-amino-1-piperidinecarboxylic acid 1,1-dimethylethyl ester was added. The mixture was stirred for 3 hours, then taken up in 50 mL of dichloromethane and washed twice with 100 mL of water and then 100 mL of brine. The organic layer was dried over anhydrous sodium sulfate, filtered and concentrated under reduced pressure. The residue was purified by silica gel chromatography, eluting with hexane-ethyl acetate (gradient 50:50-0:100) to give 0.075 g of 4-[4-(9-cyclobutyl-7,7-difluoro-5-methyl-6-oxo-6,7,8,9-tetrahydro-5H-pyrimido[4,5-b][1,4]diazepin-2-ylamino)-benzoylamino]-piperidine-1-carboxylic acid tert-butyl ester.

A mixture of 0.075 g (0.013 mmole) of 4-[4-(9-cyclobutyl-7,7-difluoro-5-methyl-6-oxo-6,7,8,9-tetrahydro-5H-pyrimido[4,5-b][1,4]diazepin-2-ylamino)-benzoylamino]-piperidine-1-carboxylic acid tert-butyl ester 1 mL of trifluoroacetic acid and 5 mL of dichloromethane was stirred for 1 hour and then concentrated under reduced pressure. The residue was taken up in 30 mL of ethyl acetate, washed twice with 30 mL of saturated aqueous sodium bicarbonate and then brine. The organic layer was dried over anhydrous sodium sulfate, filtered and concentrated under reduced pressure. The residue was triturated with ether, to give 0.048 g of 4-(9-cyclobutyl-7,7-difluoro-5-methyl-6-oxo-6,7,8,9-tetrahydro-5H-pyrimido[4,5-b][1,4]diazepin-2-ylamino)-N-piperidin-4-yl-benzamide (I-14).

Example 15

2-[4-(4-amino-piperidine-1-carbonyl)-phenylamino]-9-cyclobutyl-7,7-difluoro-5-methyl-5,7,8,9-tetrahydro-pyrimido[4,5-b][1,4]diazepin-6-one (I-15)

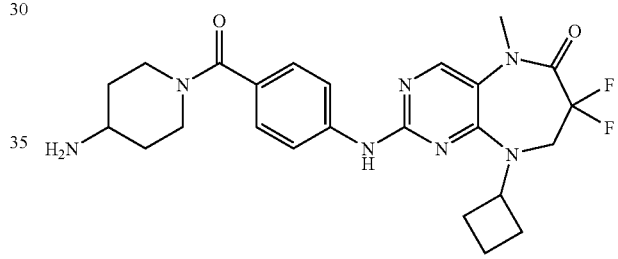

A mixture of 0.250 g (0.62 mmole) of 4-(9-cyclobutyl-7,7-difluoro-5-methyl-6-oxo-6,7,8,9-tetrahydro-5H-pyrimido[4,5-b][1,4]diazepin-2-ylamino)-benzoic acid (I-11), 0.250 g (2.48 mmole) of triethylamine, 0.319 g (0.74 mmole) of N-[(dimethylamino)(3H-1,2,3-triazolo[4,5-b]pyridin-3-yloxy)methylene]-N-methyl-methanaminium, hexafluorophosphate(1-) (1:1) and 5 mL of dimethylformamide was stirred for 15 minutes and then 0.267 g (0.74 mmole) of 4-piperidinyl-carbamic acid 9H-fluoren-9-ylmethyl ester monohydrochloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with hexane-ethyl acetate (gradient 50:50-0:100) to give 0.220 g of {1-[4-(9-cyclobutyl-7,7-difluoro-5-methyl-6-oxo-6,7,8,9-tetrahydro-5H-pyrimido[4,5-b][1,4]diazepin-2-ylamino)-benzoyl]-piperidin-4-yl}-carbamic acid 9H-fluoren-9-ylmethyl ester.

A mixture of 0.220 g (0.31 mmole) of {1-[4-(9-cyclobutyl-7,7-difluoro-5-methyl-6-oxo-6,7,8,9-tetrahydro-5H-pyrimido[4,5-b][1,4]diazepin-2-ylamino)-benzoyl]-piperidin-4-yl}-carbamic acid 9H-fluoren-9-ylmethyl ester, 1 mL of piperidine and 5 mL of dichloromethane was stirred for 1 hour and then concentrated under reduced pressure. The residue was purified by silica gel chromatography, eluting with dichloromethane-methanol-ammonium hydroxide (92:8:0.3)

to give 0.038 g of 2-[4-(4-amino-piperidine-1-carbonyl)-phenylamino]-9-cyclobutyl-7,7-difluoro-5-methyl-5,7,8,9-tetrahydro-pyrimido[4,5-b][1,4]diazepin-6-one (I-15).

Example 16

4-(9-cyclobutyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide (I-16)

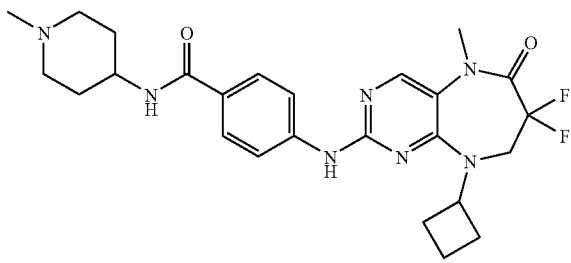

A mixture of 0.0605 g (0.20 mmole) 2-chloro-9-cyclobutyl-7,7-difluoro-5-methyl-5,7,8,9-tetrahydro-pyrimido[4,5-b][1,4]diazepin-6-one (VII-1), 0.0571 g (0.30 mmole) of toluenesulfonic acid monohydrate, 0.0467 g (0.20 mmole) of 4-amino-N-(1-methyl-piperidin-4-yl)-benzamide and 1 mL of isopropanol was heated in a sealed vessel at 140 degrees for 19.5 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was recrystallized from acetonitrile-methanol to give 0.0637 g of 4-(9-cyclobutyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide (I-16) as a white solid.

Example 17

4-(9-cyclobutyl-7,7-difluoro-5-methyl-6-oxo-6,7,8,9-tetrahydro-5H-pyrimido[4,5-b][1,4]diazepin-2-ylamino)-N-(tetrahydro-pyran-4-yl)-benzamide (I-17)

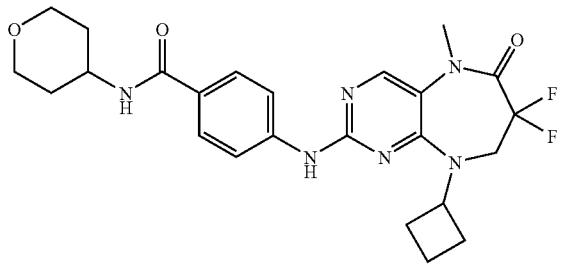

A mixture of 0.0636 g (0.21 mmole) 2-chloro-9-cyclobutyl-7,7-difluoro-5-methyl-5,7,8,9-tetrahydro-pyrimido[4,5-b][1,4]diazepin-6-one (VII-1), 0.0609 g (0.32 mmole) of toluenesulfonic acid monohydrate, 0.0463 g (0.21 mmole) of 4-amino-N-(tetrahydro-pyran-4-yl)-benzamide and 1 mL of isopropanol was heated in a sealed vessel at 140 degrees for 19.5 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was recrystallized from acetonitrile-methanol to give 0.0661 g of 4-(9-cyclobutyl-7,7-difluoro-5-methyl-6-oxo-6,7,8,9-tetrahydro-5H-pyrimido[4,5-b][1,4]diazepin-2-ylamino)-N-(tetrahydro-pyran-4-yl)-benzamide (I-17) as a white solid.

Example 18

4-(9-cyclobutyl-7,7-difluoro-5-methyl-6-oxo-6,7,8,9-tetrahydro-5H-pyrimido[4,5-b][1,4]diazepin-2-ylamino)-N-(2-dimethylamino-ethyl)-benzamide (I-18)

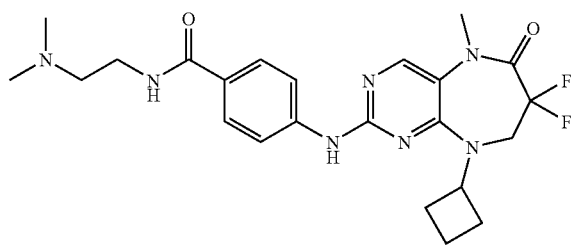

A mixture of 0.0666 g (0.22 mmole) 2-chloro-9-cyclobutyl-7,7-difluoro-5-methyl-5,7,8,9-tetrahydro-pyrimido[4,5-b][1,4]diazepin-6-one (VII-1), 0.0628 g (0.33 mmole) of toluenesulfonic acid monohydrate, 0.0456 g (0.22 mmole) of 4-amino-N-(2-dimethylamino-ethyl)-benzamide and 1 mL of isopropanol was heated in a sealed vessel at 140 degrees for 20 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (85:15:1) to give 0.0938 g of 4-(9-cyclobutyl-7,7-difluoro-5-methyl-6-oxo-6,7,8,9-tetrahydro-5H-pyrimido[4,5-b][1,4]diazepin-2-ylamino)-N-(2-dimethylamino-ethyl)-benzamide (I-18)

Example 19

4-(9-cyclobutyl-7,7-difluoro-5-methyl-6-oxo-6,7,8,9-tetrahydro-5H-pyrimido[4,5-b][1,4]diazepin-2-ylamino)-N-(3-dimethylamino-propyl)-benzamide (I-19)

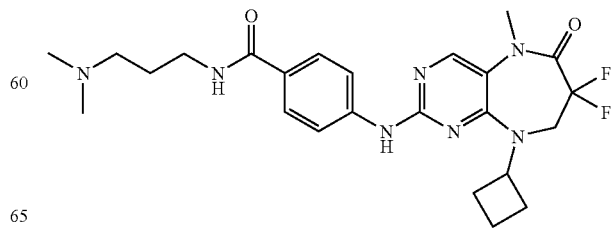

A mixture of 0.0673 g (0.22 mmole) 2-chloro-9-cyclobutyl-7,7-difluoro-5-methyl-5,7,8,9-tetrahydro-pyrimido[4,5-b][1,4]diazepin-6-one (VII-1), 0.0634 g (0.33 mmole) of toluenesulfonic acid monohydrate, 0.0492 g (0.22 mmole) of 4-amino-N-(3-dimethylamino-propyl)-benzamide and 1 mL of isopropanol was heated in a sealed vessel at 140 degrees for 22 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (85:15:1) to give 0.0938 g of 4-(9-cyclobutyl-7,7-difluoro-5-methyl-6-oxo-6,7,8,9-tetrahydro-5H-pyrimido[4,5-b][1,4]diazepin-2-ylamino)-N-(3-dimethylamino-propyl)-benzamide (I-19)

Example 20

4-(9-cyclopentyl-7,7-difluoro-5-methyl-6-oxo-6,7,8,9-tetrahydro-5H-pyrimido[4,5-b][1,4]diazepin-2-ylamino)-benzoic acid (I-20)

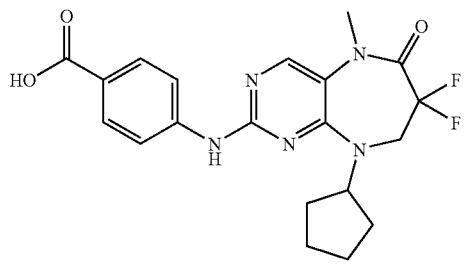

Step a

A solution of 3.6 g (0.016 mole) of 3-cyclopentylamino-2,2-difluoro-propanoic acid ethyl ester in 3 mL of ethyl acetate was added over 5 minutes to a cooled (0 degrees) mixture of 3.2 g (0.016 mole) of 2,4-dichloro-5-nitro-pyrimidine, 5.47 g (0.064 mole) of sodium bicarbonate and 36 mL of ethyl acetate. The cooling bath was removed and the mixture stirred for 17 hours at room temperature. Activated charcoal was added and after stirring briefly, the mixture was filtered through a pad of Celite, washing the filter pad with ethyl acetate. The filtrate was concentrated under reduced pressure to give 6.29 g of 3-[(2-chloro-5-nitro-pyrimidin-4-yl)-cyclopentyl-amino]-2,2-difluoro-propanoic acid ethyl ester (IV-20) as a yellow thick oil, which contained a small portion of a regioisomer. This material was used directly in the next step without further purification.

Step b

To a solution of 6.16 g (0.016 mole) of 3-[(2-chloro-5-nitro-pyrimidin-4-yl)-cyclopentyl-amino]-2,2-difluoro-propanoic acid ethyl ester (IV-20) in 120 mL of acetic acid was added 6.0 g (0.11 g-atom) of iron powder. The mixture was heated to 80 degrees for 2 hours and then filtered while hot. Water and ethyl acetate were added to the filtrate and the mixture was stirred for 10 minutes and then filtered. The layers were separated. The organic layer was washed successively with ammonium hydroxide and water, dried over anhydrous magnesium sulfate, filtered and concentrated under reduced pressure. Recrystallization of the residue with ethyl acetate and hexane gave 2.94 g of 2-chloro-9-cyclopentyl-7,7-difluoro-5,7,8,9-tetrahydro-pyrimido[4,5-b][1,4]diazepin-6-one (VI-20).

Step c

To a solution of 1.4 g (0.0046 mole) of 2-chloro-9-cyclopentyl-7,7-difluoro-5,7,8,9-tetrahydro-pyrimido[4,5-b][1,4]diazepin-6-one (VI-20) in 30 mL of dimethylformamide was added 2.27 g (0.0069 mole) of cesium carbonate, followed by 0.87 mL (0.014 mole) of iodomethane. After stirring four hours, the mixture filtered and then concentrated under reduced pressure. Ice water was added to the residue to give a precipitate. The solid was collected by filtration, washed with water and dried under vacuum to give 1.37 g of 2-chloro-9-cyclopentyl-7,7-difluoro-5-methyl-5,7,8,9-tetrahydro-pyrimido[4,5-b][1,4]diazepin-6-one (VII-20) as a white solid.

Step d

A mixture of 0.15 g (0.48 mmole) of 2-chloro-9-cyclopentyl-7,7-difluoro-5-methyl-5,7,8,9-tetrahydro-pyrimido[4,5-b][1,4]diazepin-6-one (VII-20) and 0.078 g (0.57 mmole) of 4-amino-benzoic acid in 15 mL of ethanol-water-hydrochloric acid (20:80:1) was refluxed for 18 hours, then cooled and partially concentrated under reduced pressure. The resulting solid was collected by filtration, washed with water and dried to give 0.11 g of 4-(9-cyclopentyl-7,7-difluoro-5-methyl-6-oxo-6,7,8,9-tetrahydro-5H-pyrimido[4,5-b][1,4]diazepin-2-ylamino)-benzoic acid (I-20)

Example 21

4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide (I-21)

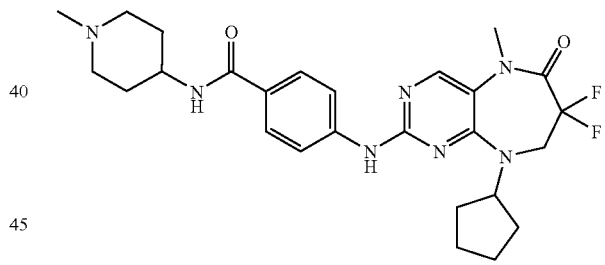

To a mixture of 0.11 g (0.27 mmole) of 4-(9-cyclopentyl-7,7-difluoro-5-methyl-6-oxo-6,7,8,9-tetrahydro-5H-pyrimido[4,5-b][1,4]diazepin-2-ylamino)-benzoic acid (I-20), 0.19 mL (1.1 mmole) of ethyldiisopropyl amine and 0.034 g (0.30 mmole) of 4-amino-1-methyl-piperidine in 3.0 mL of dimethylformamide was added 0.13 g (0.30 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-75:25) gave 0.10 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide (I-21) as a white solid.

Example 22

4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22)

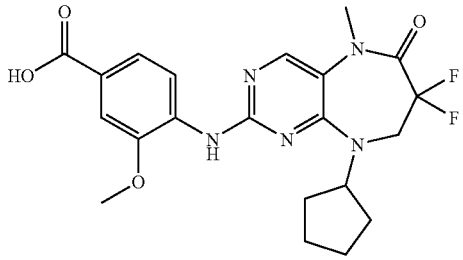

A mixture of 1.0 g (3.2 mmole) of 2-chloro-9-cyclopentyl-7,7-difluoro-5-methyl-5,7,8,9-tetrahydro-pyrimido[4,5-b][1,4]diazepin-6-one (VII-20) and 0.63 g (3.8 mmole) of 4-amino-3-methoxy-benzoic acid in 76 mL of ethanol-water-hydrochloric acid (20:80:1) was refluxed for 18 hours, then cooled and partially concentrated under reduced pressure. The resulting solid was collected by filtration, washed with water and dried to give 0.92 g of crude 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22).

Example 23

4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-23)

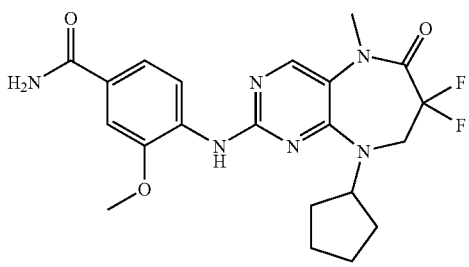

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.011 g (0.20 mmole) of ammonium chloride, 0.075 g (0.20 mmole) of 1-[bis(dimethylamino)methylene]-1H-1,2,3-triazolo[4,5-b]pyridinium-3-oxide hexafluorophosphate, 0.068 mL (0.39 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with dichloromethane-methanol (gradient 100:0-60:40) to give 0.034 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-23) as a white solid.

Example 24

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-methyl-benzamide (I-24)

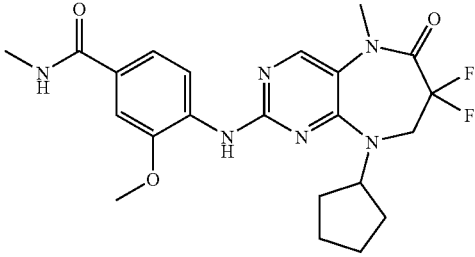

To a mixture of 0.08 g (0.18 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.13 mL (0.72 mmole) of ethyldiisopropyl amine and 0.013 g (0.20 mmole) of methylamine hydrochloride in 2.0 mL of dimethylformamide was added 0.085 g (0.20 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with hexane-ethylactate (gradient, 50:50-0:100) gave 0.062 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-methyl-benzamide (I-24) as a white solid.

Example 25

4-(9-cyclopentyl-7,7-difluoro-5-methyl-6-oxo-6,7,8,9-tetrahydro-5H-pyrimido[4,5-b][1,4]diazepin-2-ylamino)-N-isopropyl-3-methoxy-benzamide (I-25)

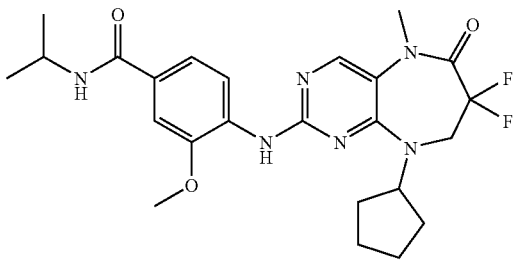

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.30 mmole) of ethyldiisopropyl amine and 1.0 mL of dimethylformamide was stirred for 5 minutes and then 0.009 g (0.15 mmole) isopropylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient a 0:100-80:20) to give 0.044 g of 4-(9-cyclopentyl-7,7-difluoro-5-methyl-6-oxo-6,7,8,9-tetrahydro-5H-pyrimido[4,5-b][1,4]diazepin-2-ylamino)-N-isopropyl-3-methoxy-benzamide (I-25) as a white solid.

Example 26

4-(9-cyclopentyl-7,7-difluoro-5-methyl-6-oxo-6,7,8,9-tetrahydro-5H-pyrimido[4,5-b][1,4]diazepin-2-ylamino)-N-cyclopropyl-3-methoxy-benzamide (I-26)

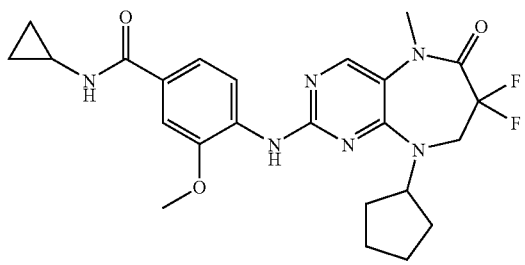

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.013 g (0.23 mmole) of cyclopropylamine, 0.074 g (0.19 mmole) of 1-[bis(dimethylamino)methylene]-1H-1,2,3-triazolo[4,5-b]pyridinium-3-oxide hexafluorophosphate, 0.195 mL (1.1 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with dichloromethate-methanol (gradient 100:0-60:40) to give 0.042 g of 4-(9-cyclopentyl-7,7-difluoro-5-methyl-6-oxo-6,7,8,9-tetrahydro-5H-pyrimido[4,5-b][1,4]diazepin-2-ylamino)-N-cyclopropyl-3-methoxy-benzamide (I-26) as a white solid.

Example 27

N-cyclohexyl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-27)

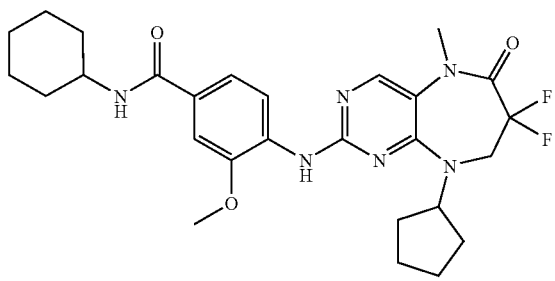

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.033 g (0.33 mmole) of cyclohexylamine, 0.102 g (0.27 mmole) of 1-[bis(dimethylamino)methylene]-1H-1,2,3-triazolo[4,5-b]pyridinium-3-oxide hexafluorophosphate, 0.036 g (0.27 mmole) of 1-hydroxybenzotriazole, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by C18 reverse phase silica gel chromatography, eluting with an acetonitrile-water (gradient, 20:80-100:0) to give 0.013 g of N-cyclohexyl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-27) as a white solid.

Example 28

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-methoxy-ethyl)-benzamide (I-28)

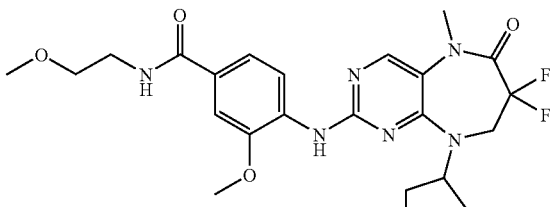

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.102 g (0.27 mmole) of 1-[bis(dimethylamino)methylene]-1H-1,2,3-triazolo[4,5-b]pyridinium-3-oxide hexafluorophosphate, 0.036 g (0.27 mmole) of 1-hydroxybenzotriazole, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by C18 reverse phase silica gel chromatography, eluting with an acetonitrile-water (gradient, 20:80-100:0) to give 0.038 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-methoxy-ethyl)-benzamide (I-28) as a white solid.

Example 29

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-methoxy-propyl)-benzamide (I-29)

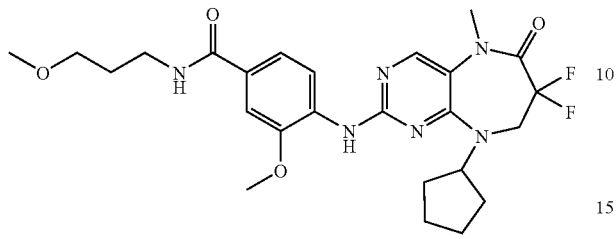

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.034 mL (0.33 mmole) of 3-methoxy-propylamine, 0.102 g (0.27 mmole) of 1-[bis(dimethylamino)methylene]-1H-1,2,3-triazolo[4,5-b]pyridinium-3-oxide hexafluorophosphate, 0.036 g (0.27 mmole) of 1-hydroxybenzotriazole, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by C18 reverse phase silica gel chromatography, eluting with an acetonitrile-water (gradient, 20:80-100:0) to give 0.0084 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-methoxy-propyl)-benzamide (I-29) as a white solid.

Example 30

4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxy-ethyl)-3-methoxy-benzamide (I-30)

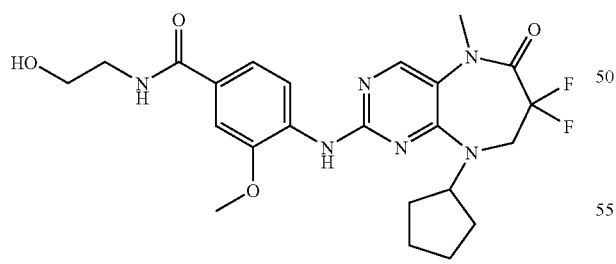

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.021 g (0.33 mmole) of 2-amino-ethanol, 0.102 g (0.27 mmole) of 1-[bis(dimethylamino)methylene]-1H-1,2,3-triazolo[4,5-b]pyridinium-3-oxide hexafluorophosphate, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with dichloromethane-methanol (gradient, 100:0-60:40) to give 0.0065 g of 4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxy-ethyl)-3-methoxy-benzamide (I-30) as a white solid.

Example 31

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2,2,2-trifluoro-ethyl)-benzamide (I-31)

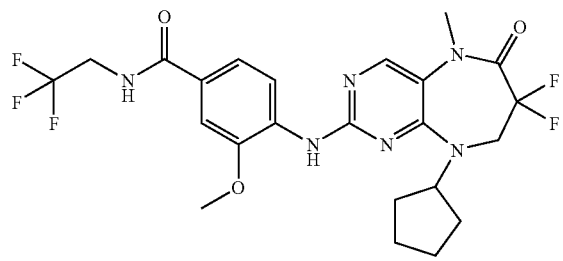

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.027 g (0.19 mmole) of 4-trifluoromethyl-benzylamine, 0.071 g (0.19 mmole) of 1-[bis(dimethylamino)methylene]-1H-1,2,3-triazolo[4,5-b]pyridinium-3-oxide hexafluorophosphate, 0.136 mL (0.78 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 80:20-0:100) to give 0.049 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2,2,2-trifluoro-ethyl)-benzamide (I-31) as a white solid.

Example 32

N-cyclohexylmethyl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-32)

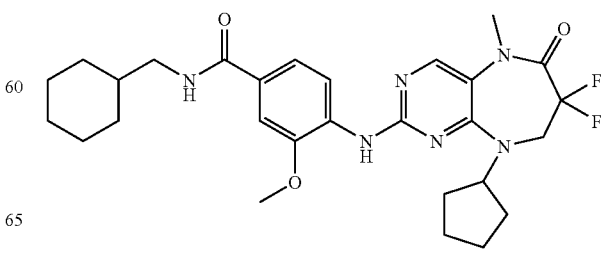

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.017 (0.23 mmole) of cyclohexanemethanamine, 0.071 g (0.19 mmole) of 1-[bis(dimethylamino)methylene]-1H-1,2,3-triazolo[4,5-b]pyridinium-3-oxide hexafluorophosphate, 0.136 mL (0.78 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by C18 reverse phase silica gel chromatography, eluting with an acetonitrile-water (gradient, 20:80-100:0) to give 0.012 g of N-cyclohexylmethyl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-32) as a white solid.

Example 33

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-thiophen-3-ylmethyl-benzamide (I-33)

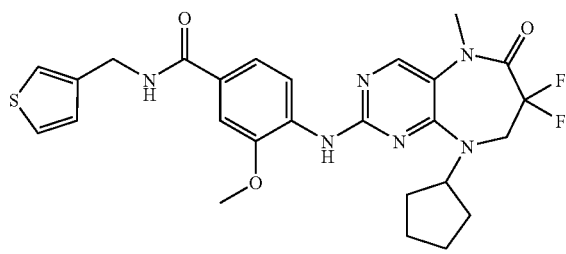

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.035 (0.23 mmole) of 3-thiophenemethanamine 0.071 g (0.19 mmole) of 1-[bis(dimethylamino)methylene]-1H-1,2,3-triazolo[4,5-b]pyridinium-3-oxide hexafluorophosphate, 0.136 mL (0.78 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by C18 reverse phase silica gel chromatography, eluting with an acetonitrile-water (gradient, 20:80-100:0) to give 0.020 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-thiophen-3-ylmethyl-benzamide (I-33) as a light brown solid.

Example 34

4-(9-cyclopentyl-7,7-difluoro-5-methyl-6-oxo-6,7,8,9-tetrahydro-5H-pyrimido[4,5-b][1,4]diazepin-2-ylamino)-N-furan-3-ylmethyl-3-methoxy-benzamide (I-34)

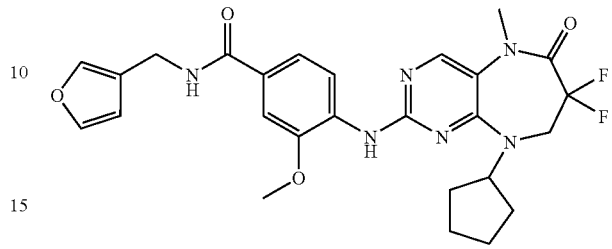

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.031 g (0.32 mmole) of furfurylamine, 0.071 g (0.19 mmole) of 1-[bis(dimethylamino)methylene]-1H-1,2,3-triazolo[4,5-b]pyridinium-3-oxide hexafluorophosphate, 0.136 mL (0.78 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 80:20-0:100) to give 0.036 g of 4-(9-cyclopentyl-7,7-difluoro-5-methyl-6-oxo-6,7,8,9-tetrahydro-5H-pyrimido[4,5-b][1,4]diazepin-2-ylamino)-N-furan-3-ylmethyl-3-methoxy-benzamide (I-34) as a white solid.

Example 35

N-benzyl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-35)

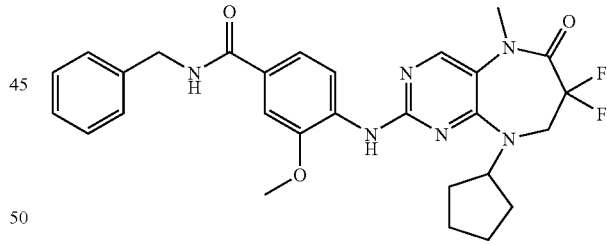

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.016 g (0.15 mmole) benzylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with acetonitrile-water (gradient, 100:0-20:80) to give 0.048 g of N-benzyl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-35) as a white solid.

Example 36

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(4-trifluoromethyl-benzyl)-benzamide (I-35)

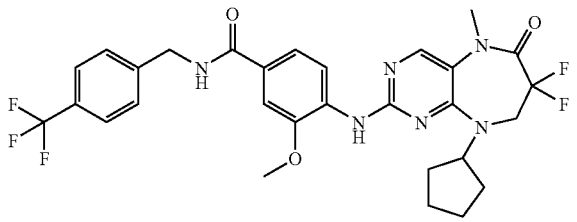

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.027 g (0.19 mmole) of 4-trifluoromethyl-benzylamine, 0.071 g (0.19 mmole) of 1-[bis(dimethylamino)methylene]-1H-1,2,3-triazolo[4,5-b]pyridinium-3-oxide hexafluorophosphate, 0.136 mL (0.78 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 80:20-0:100) to give 0.049 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(4-trifluoromethyl-benzyl)-benzamide (I-36) as a white solid.

Example 37 rac-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-phenyl-ethyl)-benzamide (I-37)

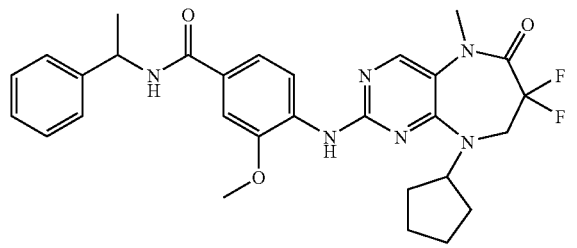

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.30 mmole) of ethyldiisopropyl amine and 1.0 mL of dimethylformamide was stirred for 5 minutes and then 0.018 g (0.15 mmole) 1-phenyl-ethylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with acetonitrile-water (gradient, 100:0-20:80) to give 0.042 g of rac-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-phenyl-ethyl)-benzamide (I-37) as a white solid.

Example 38

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-phenyl-benzamide (I-38)

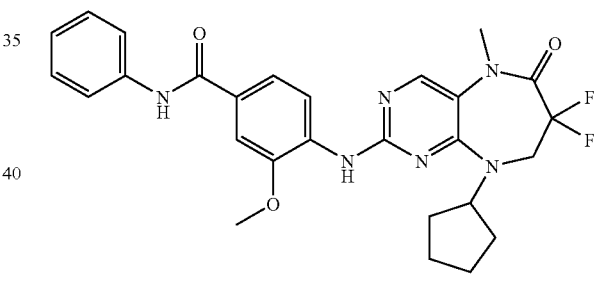

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.30 mmole) of ethyldiisopropyl amine and 1.0 mL of dimethylformamide was stirred for 5 minutes and then 0.011 g (0.12 mmole) of aniline was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with acetonitrile-water (gradient, 100:0-20:80) to give 0.042 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-phenyl-benzamide (I-38) as a white solid.

Example 39

4-(9-cyclopentyl-7,7-difluoro-5-methyl-6-oxo-6,7,8,9-tetrahydro-5H-pyrimido[4,5-b][1,4]diazepin-2-ylamino)-N-(4-hydroxy-butyl)-3-methoxy-benzamide (I-39)

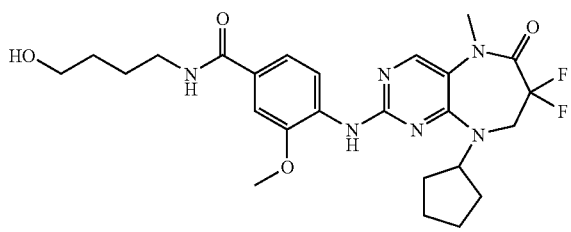

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.30 mmole) of ethyldiisopropyl amine and 1.0 mL of dimethylformamide was stirred for 5 minutes and then 0.013 g (0.15 mmole) 4-Amino-butan-1-ol was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with acetonitrile-water (gradient, 100:0-20:80) to give 0.038 g of 4-(9-cyclopentyl-7,7-difluoro-5-methyl-6-oxo-6,7,8,9-tetrahydro-5H-pyrimido[4,5-b][1,4]diazepin-2-ylamino)-N-(4-hydroxy-butyl)-3-methoxy-benzamide (I-39) as a white solid.

Example 40

4-(9-cyclopentyl-7,7-difluoro-5-methyl-6-oxo-6,7,8,9-tetrahydro-5H-pyrimido[4,5-b][1,4]diazepin-2-ylamino)-N-(2-ethoxy-ethyl)-3-methoxy-benzamide (I-40)

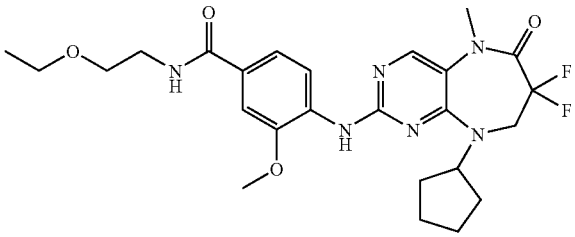

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.30 mmole) of ethyldiisopropyl amine and 1.0 mL of dimethylformamide was stirred for 5 minutes and then 0.013 g (0.15 mmole) 2-Ethoxy-ethylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with acetonitrile-water (gradient, 100:0-20:80) to give 0.040 g of 4-(9-cyclopentyl-7,7-difluoro-5-methyl-6-oxo-6,7,8,9-tetrahydro-5H-pyrimido[4,5-b][1,4]diazepin-2-ylamino)-N-(2-ethoxy-ethyl)-3-methoxy-benzamide (I-40) as a white solid.

Example 41

4-(9-cyclopentyl-7,7-difluoro-5-methyl-6-oxo-6,7,8,9-tetrahydro-5H-pyrimido[4,5-b][1,4]diazepin-2-ylamino)-N-(3-hydroxy-propyl)-3-methoxy-benzamide (I-41)

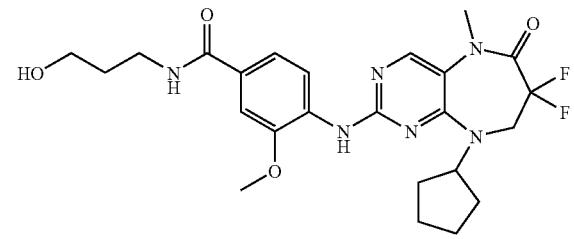

To a mixture of 0.08 g (0.18 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-100), 0.16 mL (0.90 mmole) of ethyldiisopropyl amine and 0.016 mL (0.20 mmole) of 3-amino-propan-1-ol in 2.0 mL of dimethylformamide was added 0.085 g (0.20 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-90:10) gave 0.080 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-hydroxy-propyl)-3-methoxy-benzamide (I-41) as a white solid.

Example 42

4-(9-cyclopentyl-7,7-difluoro-5-methyl-6-oxo-6,7,8,9-tetrahydro-5H-pyrimido[4,5-b][1,4]diazepin-2-ylamino)-N-(3,5-dichloro-benzyl)-3-methoxy-benzamide (I-42)

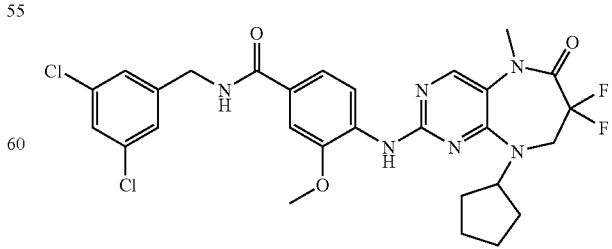

A mixture of 0.100 g (0.22 mmole) of 4-(9-cyclopentyl-7,7-difluoro-5-methyl-6-oxo-6,7,8,9-tetrahydro-5H-pyrimido

[4,5-b][1,4]diazepin-2-ylamino)-3-methoxy-benzoic acid (I-22), 0.059 g (0.33 mmole) of 3,5-dichloro-benzylamine, 0.102 g (0.27 mmole) of 1-[bis(dimethylamino)methylene]-1H-1,2,3-triazolo[4,5-b]pyridinium-3-oxide hexafluorophosphate, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 80:20-0:100) to give 0.078 g of 4-(9-cyclopentyl-7,7-difluoro-5-methyl-6-oxo-6,7,8,9-tetrahydro-5H-pyrimido[4,5-b][1,4]diazepin-2-ylamino)-N-(3,5-dichloro-benzyl)-3-methoxy-benzamide (I-42) as a white solid.

Example 43

N-(2-benzo[1,3]dioxol-5-yl-ethyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-43)

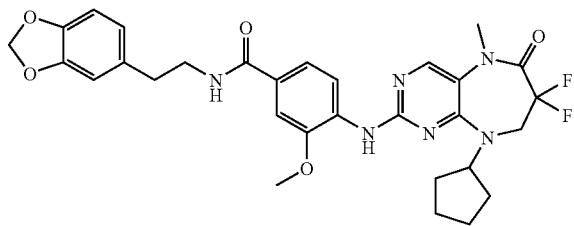

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.069 g (0.42 mmole) of 2-benzo[1,3]dioxol-5-yl-ethylamine, 0.102 g (0.27 mmole) of 1-[bis(dimethylamino)methylene]-1H-1,2,3-triazolo[4,5-b]pyridinium-3-oxide hexafluorophosphate, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 80:20-0:100) to give 0.080 g of N-(2-benzo[1,3]dioxol-5-yl-ethyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-43) as a white solid.

Example 44

N-[(1S,2R)-(2-carbamoyl-cyclopentyl)]-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-44)

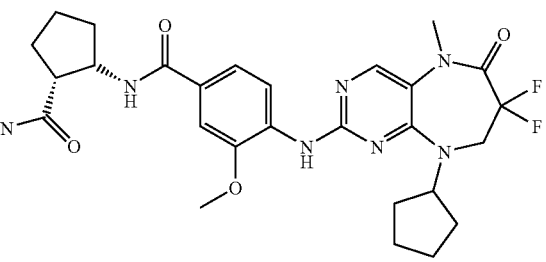

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.030 g (0.19 mmole) of (1R,2S)-2-amino-cyclopentanecarboxylic acid amide, 0.071 g (0.19 mmole) of 1-[bis(dimethylamino)methylene]-1H-1,2,3-triazolo[4,5-b]pyridinium-3-oxide hexafluorophosphate, 0.136 mL (0.78 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 80:20-0:100) to give 0.022 g of N-[(1S,2R)-(2-carbamoyl-cyclopentyl)]-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-44) as a white solid.

Example 45

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-pyrrolidin-1-yl-ethyl)-benzamide (I-45)

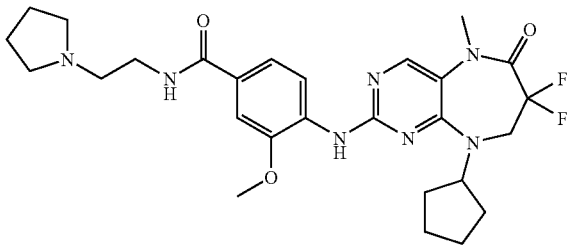

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.026 g (0.33 mmole) of 2-pyrrolidin-1-yl-ethylamine, 0.102 g (0.27 mmole) of 1-[bis(dimethylamino)methylene]-1H-1,2,3-triazolo[4,5-b]pyridinium-3-oxide hexafluorophosphate, 0.036 g (0.27 mmole) of 1-hydroxybenzotriazole, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by C18 reverse phase silica gel chromatography, eluting with acetonitrile-water (gradient, 20:80-100:0) to give 0.012 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-pyrrolidin-1-yl-ethyl)-benzamide (I-45) as a white solid.

Example 46

4-(9-cyclopentyl-7,7-difluoro-5-methyl-6-oxo-6,7,8,9-tetrahydro-5H-pyrimido[4,5-b][1,4]diazepin-2-ylamino)-N-(3-isopropylamino-propyl)-3-methoxy-benzamide (I-46)

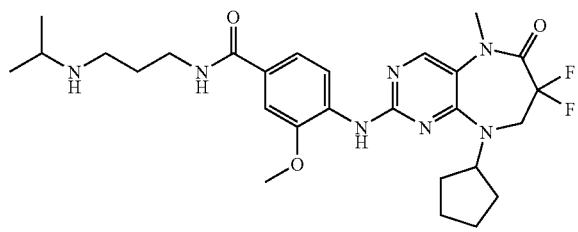

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.039 g (0.33 mmole) of N-isopropyl-1,3-propanediamine, 0.102 g (0.27 mmole) of 1-[bis(dimethylamino)methylene]-1H-1,2,3-triazolo[4,5-b]pyridinium-3-oxide hexafluorophosphate, 0.036 g (0.27 mmole) of 1-hydroxybenzotriazole, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by C18 reverse phase silica gel chromatography, eluting with acetonitrile-water (gradient, 20:80-100:0) to give 0.023 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-isopropylamino-propyl)-3-methoxy-benzamide (I-46) as a white solid.

Example 47

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[2-(4-methyl-piperazin-1-yl)-ethyl]-benzamide (I-47)

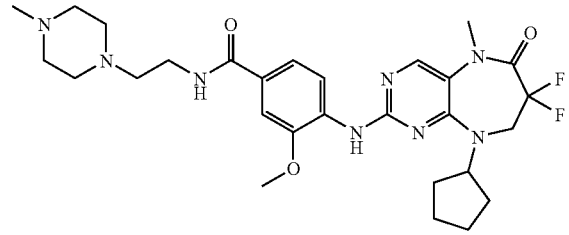

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.039 g (0.33 mmole) of 2-(4-methyl-piperazin-1-yl)-ethylamine, 0.102 g (0.27 mmole) of 1-[bis(dimethylamino)methylene]-1H-1,2,3-triazolo[4,5-b]pyridinium-3-oxide hexafluorophosphate, 0.036 g (0.27 mmole) of 1-hydroxybenzotriazole, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by C18 reverse phase silica gel chromatography, eluting with acetonitrile-water (gradient, 20:80-100:0) to give 0.021 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[2-(4-methyl-piperazin-1-yl)-ethyl]-benzamide (I-47) as a white solid.

Example 48

N-(2-amino-ethyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-48)

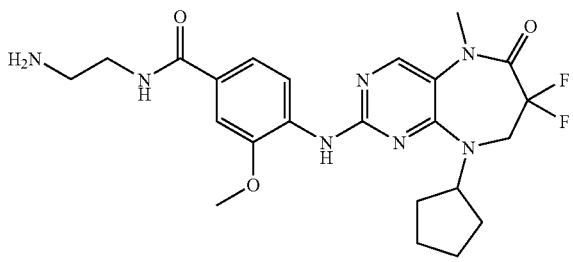

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.054 g (0.33 mmole) of (2-amino-ethyl)-carbamic acid tert-butyl ester, 0.102 g (0.27 mmole) of 1-[bis(dimethylamino)methylene]-1H-1,2,3-triazolo[4,5-b]pyridinium-3-oxide hexafluorophosphate, 0.036 g (0.27 mmole) of 1-hydroxybenzotriazole, 0.195 mL (0.00112 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 100:0-60:40) to give 0.100 g of 2-[4-(9-cyclopentyl-7,7-difluoro-5-methyl-6-oxo-6,7,8,9-tetrahydro-5H-pyrimido-[4,5b][1,4]-diazepin-2-ylamino)-3-methoxy-benzoylamino]-ethyl}-carbamic acid tert-butyl ester as a colorless oil.

A mixture of 0.100 g of 2-[4-(9-cyclopentyl-7,7-difluoro-5-methyl-6-oxo-6,7,8,9-tetrahydro-5H-pyrimido-[4,5b][1,4]-diazepin-2-ylamino)-3-methoxy-benzoylamino]-ethyl}-carbamic acid tert-butyl ester and 2.0 mL of 4.0 M hydrochloric acid in dioxane was stirred at room temperature for 18 h. The mixture was diluted with 10 mL of dichloromethane and treated with saturated aqueous sodium bicarbonate. The aqueous phase was extracted 3 times with 20 mL of dichloromethane. The combined extracts were washed with brine, dried over anhydrous sodium sulfate, filtered and concentrated under reduced pressure. The residue was purified by silica gel chromatography, eluting with dichloromethane-methanol (gradient, 100:0-75:25) to give 0.033 g of N-(2-amino-ethyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-48) as a white solid.

Example 49

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-piperazin-1-yl-ethyl)-benzamide (I-49)

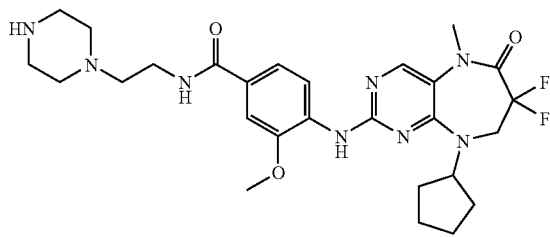

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.077 g (0.33 mmole) of (2-amino-ethyl)-carbamic acid tert-butyl ester, 0.102 g (0.27 mmole) of 1-[bis(dimethylamino)methylene]-1H-1,2,3-triazolo[4,5-b]pyridinium-3-oxide hexafluorophosphate, 0.036 g (0.27 mmole) of 1-hydroxybenzotriazole, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 100:0-60:40) to give 0.14 g of 4-{2-[4-(9-cyclopentyl-7,7-difluoro-5-methyl-6-oxo-6,7,8,9-tetrahydro-5H-pyrimido[4,5b][1,4]diazepin-2-ylamino)-3-methoxy-benzoylamino]-ethyl}-piperazine-1-carboxylic acid tert-butyl ester as a colorless oil.

A mixture of 0.100 g of 4-{2-[4-(9-cyclopentyl-7,7-difluoro-5-methyl-6-oxo-6,7,8,9-tetrahydro-5H-pyrimido[4,5b][1,4]diazepin-2-ylamino)-3-methoxy-benzoylamino]-ethyl}-piperazine-1-carboxylic acid tert-butyl ester and 2.0 mL of 4.0 M hydrochloric acid in dioxane was stirred at room temperature for 18 h. The mixture was diluted with 10 mL of dichloromethane and treated with saturated aqueous sodium bicarbonate. The aqueous phase was extracted 3 times with 20 mL of dichloromethane. The combined extracts were washed with brine, dried over anhydrous sodium sulfate, filtered and concentrated under reduced pressure. The residue was purified by silica gel chromatography, eluting with dichloromethane-methanol (gradient, 100:0-75:25) to give 0.058 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-piperazin-1-yl-ethyl)-benzamide (I-49) as a white solid.

Example 50

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(8-methyl-8-aza-bicyclo[3.2.1]oct-3-yl)-benzamide (I-50)

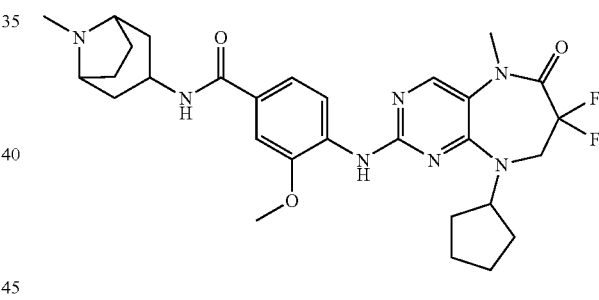

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.031 g (0.22 mmole) of 8-methyl-8-azabicyclo[3.2.1]octan-3-amine, 0.102 g (0.27 mmole) of 1-[bis(dimethylamino)methylene]-1H-1,2,3-triazolo[4,5-b]pyridinium-3-oxide hexafluorophosphate, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with dichloromethane-methanol (gradient, 100:0-60:40) to give 0.034 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(8-methyl-8-azabicyclo[3.2.1]oct-3-yl)-benzamide (I-50) as a white solid.

Example 51

4-(9-cyclopentyl-7,7-difluoro-5-methyl-6-oxo-6,7,8,9-tetrahydro-5H-pyrimido[4,5-b][1,4]diazepin-2-ylamino)-N-[2-(1H-indol-3-yl)-ethyl]-3-methoxy-benzamide (I-51)

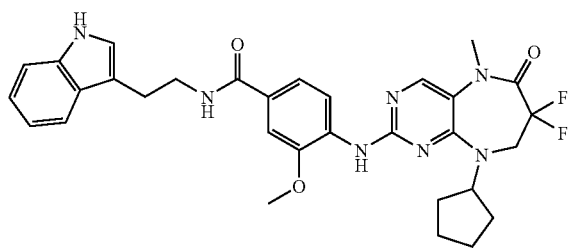

A mixture of 0.100 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.071 g (0.33 mmole) of tryptamine, 0.102 g (0.27 mmole) of 1-[bis(dimethylamino)methylene]-1H-1,2,3-triazolo[4,5-b]pyridinium-3-oxide hexafluorophosphate, 0.195 mL (1.12 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with dichloromethane-methanol (gradient, 100:0-60:40) to give 0.068 g of 4-(9-cyclopentyl-7,7-difluoro-5-methyl-6-oxo-6,7,8,9-tetrahydro-5H-pyrimido[4,5-b][1,4]diazepin-2-ylamino)-N-[2-(1H-indol-3-yl)-ethyl]-3-methoxy-benzamide (I-51) as a white solid.

Example 52

4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methoxy-benzamide (I-52)

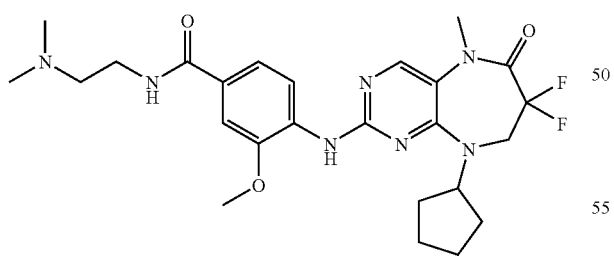

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.021 g (0.23 mmole) of N,N-dimethyl-ethane-1,2-diamine, 0.071 g (0.19 mmole) of 1-[bis(dimethylamino)methylene]-1H-1,2,3-triazolo[4,5-b]pyridinium-3-oxide hexafluorophosphate, 0.136 mL (0.78 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 80:20-0:100) to give 0.028 g of 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methoxy-benzamide (I-52) as a white solid.

Example 53

N-(3-cyclohexylamino-propyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-53)

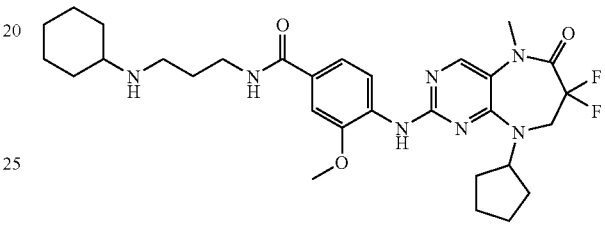

A mixture of 0.070 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.037 (0.23 mmole) of N-1-cyclohexyl-propane-1,3-diamine, 0.071 g (0.19 mmole) of 1-[bis(dimethylamino)methylene]-1H-1,2,3-triazolo[4,5-b]pyridinium-3-oxide hexafluorophosphate, 0.136 mL (0.78 mmole) of diisopropylethyl amine and 2.0 mL of dimethylformamide was stirred for 18 hours. The mixture was diluted with 10 mL of water plus 2 mL of saturated aqueous sodium bicarbonate and then extracted 3 times with 10 mL of ethyl acetate. The combined extracts were washed with brine, dried over anhydrous sodium sulfate, filtered and concentrated under reduced pressure. The residue was purified by silica gel chromatography, eluting with hexanes-ethyl acetate (gradient, 80:20-0:100) to give 0.028 g of N-(3-cyclohexylamino-propyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-53) as a white solid.

Example 54 rac-(3R,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-hydroxy-piperidine-1-carboxylic acid benzyl ester (I-54)

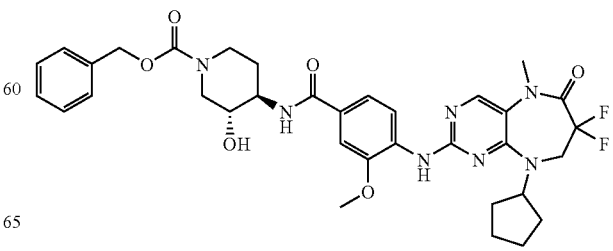

A mixture of 0.067 g (0.15 mmole) of (rac)-(3R,4R)-4-amino-3-hydroxy-piperidine-1-carboxylic acid benzyl ester, 0.042 g (0.17 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.057 g (0.15 mmole) 1-[bis(dimethylamino)methylene]-1H-benzotriazolium-3-oxide hexafluorophosphate, 0.039 g (0.30 mmole) of diisopropylethylamine and 2 mL of dimethylformamide was stirred at room temperature for 1 hour. The mixture was poured into 50 mL of water and extracted three times with 25 mL of ethyl acetate. The combined organic extracts were washed three times with 25 mL of water, once with 25 mL of saturated aqueous ammonium chloride solution, once with 25 mL of saturated aqueous sodium bicarbonate solution, once with 25 mL of brine and dried over anhydrous magnesium sulfate. The mixture was filtered and concentrated under reduced pressure. The residue was purified by silica gel chromatography, eluting with dichloromethane-methanol (96:4) to give 0.061 g of rac-(3R,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-hydroxy-piperidine-1-carboxylic acid benzyl ester (I-54) as a foam. Trituration of the foam with diethyl ether gave a white solid.

Example 55 rac-(3R,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-methoxy-piperidine-1-carboxylic acid benzyl ester (I-55)

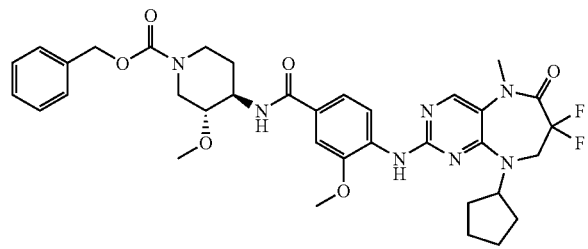

To a mixture of 0.150 g (0.54 mmole) of (rac)-(3R,4R)-4-azido-3-hydroxy-piperidine-1-carboxylic acid benzyl ester in 3.75 mL of tetrahydrofuran-dimethylformamide (4:1) at 0 degrees, was added 0.026 g of sodium hydride (60% mineral oil dispersion). After stirring for 10 minutes, 0.060 mL of iodomethane was added. The mixture was warmed to room temperature, stirred for 2 hours, then cooled in an ice-bath, and 1 mL of saturated aqueous ammonium chloride solution added. The resulting mixture was partitioned between 50 mL of ethyl acetate and 50 mL of saturated aqueous ammonium chloride solution. The organic layer was successively with water, then brine and dried over anhydrous magnesium sulfate. The mixture was filtered and concentrated under reduced pressure. The residue was purified by silica gel chromatoraphy, eluting with hexanes-ethyl acetate (85:15) to give 0.085 g of (rac)-(3R,4R)-4-azido-3-methoxy-piperidine-1-carboxylic acid benzyl ester as a colorless oil.

A mixture of 0.123 g (0.42 mmole) of (rac)-(3R,4R)-4-azido-3-methoxy-piperidine-1-carboxylic acid benzyl ester, 0.105 g (0.39 mg-atom) of zinc, 0.20 g of ammonium chloride and 4 mL of tetrahydrofuran-methanol (1:1) was stirred at room temperature for 2 hours and then filtered through a Celite pad, washing with 25 mL of water and 25 mL of tetrahydrofuran. The combined filtrates were made strongly acidic with hydrochloric acid and extracted twice with 25 mL of ethyl acetate. The aqueous layer was made basic with potassium carbonate and extracted three times with 25 mL of ethyl acetate. The combined organic extracts were dried over anhydrous magnesium sulfate and concentrated under reduced pressure to give 0.069 g of (rac)-(3R,4R)-4-amino-3-methoxy-piperidine-1-carboxylic acid benzyl ester as a colorless oil.

A mixture of 0.058 g (0.22 mmole) of (rac)-(3R,4R)-4-amino-3-methoxy-piperidine-1-carboxylic acid benzyl ester, 0.089 g (0.20 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.083 g (0.22 mmole) 1-[bis(dimethylamino)methylene]-1H-benzotriazolium-3-oxide hexafluorophosphate, 0.057 g (0.44 mmole) of diisopropylethylamine and 2 mL of dimethylformamide was stirred at room temperature for 1 hour. The mixture was poured into 50 mL of water and extracted three times with 25 mL of ethyl acetate. The combined organic extracts were washed three times with 25 mL of water, once with 25 mL of saturated aqueous ammonium chloride solution, once with 25 mL of saturated aqueous sodium bicarbonate solution, once with 25 mL of brine and dried over anhydrous magnesium sulfate. The mixture was filtered and concentrated under reduced pressure. The residue was purified by silica gel chromatography, eluting with dichloromethane-methanol (98:2) to give 0.081 g of rac-(3R,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-methoxy-piperidine-1-carboxylic acid benzyl ester (I-55) as a foam. Trituration of the foam with diethyl ether gave a white solid.

Example 56 rac-(3S,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-methoxy-piperidine-1-carboxylic acid tert-butyl ester (I-56)

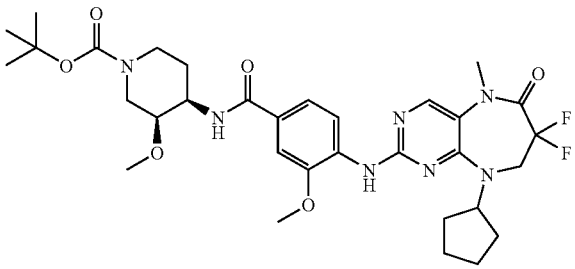

To a mixture of 0.100 g (0.156 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0654 g (0.17 mmole) of 1-[bis(dimethylamino)methylene]-1H-1,2,3-triazolo[4,5-b]pyridinium-3-oxide hexafluorophosphate, 0.13 mL of triethylamine, and 3 mL of dichloromethane was added followed by 0.0395 g (0.17 mmole) of (rac)-cis-4-amino-3-methoxy-piperidine-1-carboxylic acid tert-butyl ester. The mixture was stirred for 1 hour, then diluted with 4 mL of dichloromethane, 4 mL of water and 0.2 mL of 1M sodium hydroxide. The dichloromethane layer was dried over anhydrous magnesium sulfate, filtered and concentrated under reduced pressure. The residue was purified by silica gel chromatography, eluting with hexanes-ethyl acetate (gradient, 100:0-0:100) to give 0.0643 g of rac-(3S,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-methoxy-piperidine-1-carboxylic acid tert-butyl ester (I-56).

Example 57 rac-(3S,4R)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-methoxy-piperidin-4-yl)-benzamide (I-57)

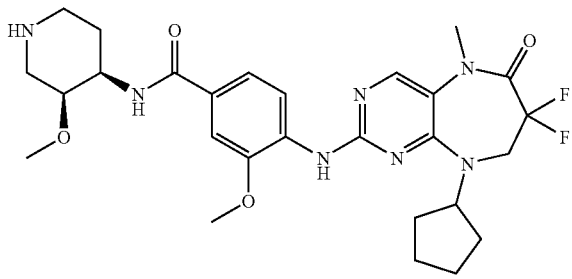

To a mixture of 0.050 g (0.075 mmole) of rac-(3S,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-methoxy-piperidine-1-carboxylic acid tert-butyl ester (I-56) and 1 mL of dichloromethane was added 1 mL of trifluoroacetic acid-dichloromethane (25:75). The mixture was stirred for 1.5 hours, and then concentrated under reduced pressure. The residue was dissolved in methanol, and the mixture neutralized by the addition of 1M sodium hydroxide at 0 degrees. The mixture was purified by reverse phase silica gel chromatography, eluting with acetonitrile-water (gradient, 1:99-90:10) to give 0.0156 g of rac-(3S,4R)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-methoxy-piperidin-4-yl)-benzamide (I-57).

Example 58 rac-(3S,4S)-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-4-methoxy-piperidine-1-carboxylic acid benzyl ester (I-58)

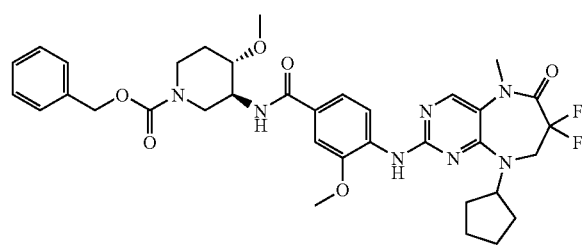

A mixture of 0.078 g (0.30 mmole) of (rac)-(3S,4S)-3-amino-4-hydroxy-piperidine-1-carboxylic acid benzyl ester, 0.113 g (0.25 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.1138 g (0.30 mmole) 1-[bis(dimethylamino)methylene]-1H-benzotriazolium-3-oxide hexafluorophosphate, 0.0776 g (0.60 mmole) of diisopropylethylamine and 2 mL of dimethylformamide was stirred at room temperature for 1 hour. The mixture was poured into 50 mL of water and extracted three times with 25 mL of ethyl acetate. The combined organic extracts were washed three times with 25 mL of water, once with 25 mL of saturated aqueous ammonium chloride solution, once with 25 mL of saturated aqueous sodium bicarbonate solution, once with 25 mL of brine and dried over anhydrous magnesium sulfate. The mixture was filtered and concentrated under reduced pressure. The residue was purified by silica gel chromatography, eluting with dichloromethane-methanol (96:4) to give 0.088 g of rac-(3S,4S)-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-4-methoxy-piperidine-1-carboxylic acid benzyl ester (I-58) as a foam. Trituration of the foam with diethyl ether gave a white solid.

Example 59

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-59)

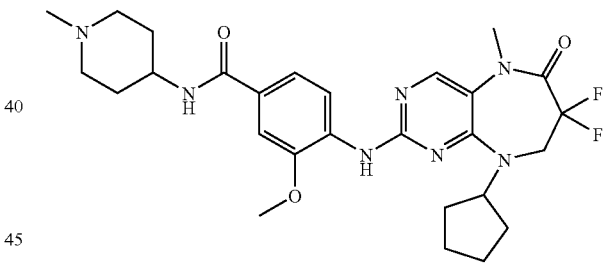

To a mixture of 0.10 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.16 mL (0.90 mmole) of ethyldiisopropyl amine and 0.028 g (0.25 mmole) of 4-amino-1-methyl-piperidine in 3.0 mL of dimethylformamide was added 0.11 g (0.25 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-90:10) gave 0.057 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-59) as a white solid.

Example 60

4-(9-cyclopentyl-7,7-difluoro-5-methyl-6-oxo-6,7,8, 9-tetrahydro-5H-pyrimido[4,5-b][1,4]diazepin-2-ylamino)-N-(3-dimethylamino-2,2-dimethyl-propyl)-3-methoxy-benzamide (I-60)

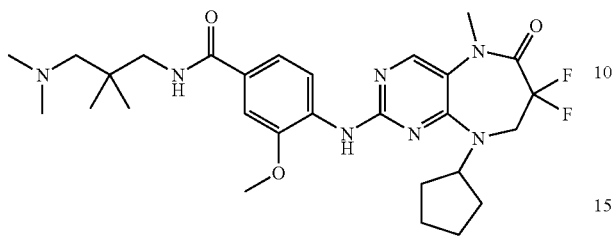

To a mixture of 0.10 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-100), 0.12 mL (0.66 mmole) of ethyldiisopropyl amine and 0.039 mL (0.25 mmole) of N,N,-2,2-tetramethyl-propane-1,3-diamine in 2.0 mL of dimethylformamide was added 0.11 g (0.25 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-90:10) gave 0.080 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-2,2-dimethyl-propyl)-3-methoxy-benzamide (I-60) as a white solid.

Example 61

4-(9-cyclopentyl-7,7-difluoro-5-methyl-6-oxo-6,7,8, 9-tetrahydro-5H-pyrimido[4,5-b][1,4]diazepin-2-ylamino)-N-(3-imidazol-1-yl-propyl)-3-methoxy-benzamide (I-61)

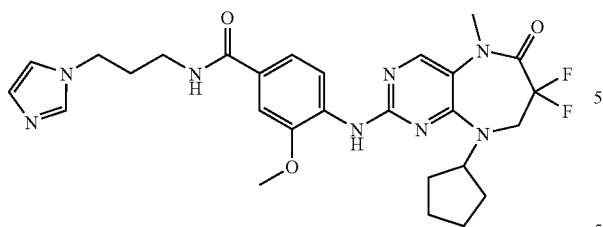

To a mixture of 0.10 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.12 mL (0.66 mmole) of ethyldiisopropyl amine and 0.029 mL (0.25 mmole) of 3-imidazol-1-yl-propylamine in 2.0 mL of dimethylformamide was added 0.11 g (0.25 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-90:10) gave 0.086 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-imidazol-1-yl-propyl)-3-methoxy-benzamide (I-61) as a white solid.

Example 62

4-(9-cyclopentyl-7,7-difluoro-5-methyl-6-oxo-6,7,8, 9-tetrahydro-5H-pyrimido[4,5-b][1,4]diazepin-2-ylamino)-3-methoxy-N-(3,4,5,6-tetrahydro-2H-[1,4'] bipyridinyl-4-yl)-benzamide (I-62)

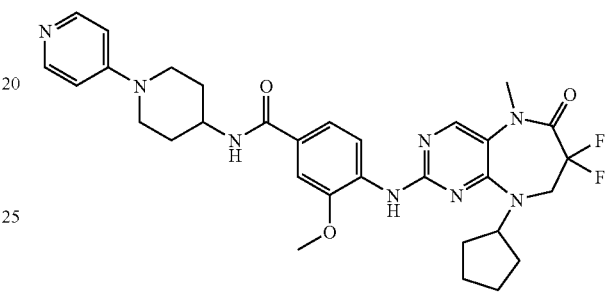

To a mixture of 0.10 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.2 mL (1.1 mmole) of ethyldiisopropyl amine and 0.062 mL (0.25 mmole) of 3,4,5,6-tetrahydro-2H-[1,4'] bipyridinyl-4-ylamine hydrochloride salt in 2.0 mL of dimethylformamide was added 0.11 g (0.25 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-70:30) gave 0.089 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3,4,5,6-tetrahydro-2H-[1,4']bipyridinyl-4-yl)-benzamide (I-62) as a white solid.

Example 63

4-(9-cyclopentyl-7,7-difluoro-5-methyl-6-oxo-6,7,8, 9-tetrahydro-5H-pyrimido[4,5-b][1,4]diazepin-2-ylamino)-N-(1-cyclopentyl-piperidin-4-yl)-3-methoxy-benzamide (I-63)

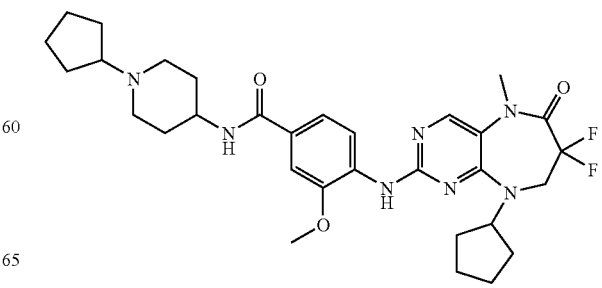

To a mixture of 0.050 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.08 mL (0.44 mmole) of ethyldiisopropyl amine and 0.021 g (0.12 mmole) of 1-cyclopentyl-piperidin-4-ylamine in 1.5 mL of dimethylformamide was added 0.053 g (0.12 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-85:15) gave 0.029 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-cyclopentyl-piperidin-4-yl)-3-methoxy-benzamide (I-63).

Example 64

4-(9-cyclopentyl-7,7-difluoro-5-methyl-6-oxo-6,7,8,9-tetrahydro-5H-pyrimido[4,5-b][1,4]diazepin-2-ylamino)-N-(1-isopropyl-piperidin-4-yl)-3-methoxy-benzamide (I-64)

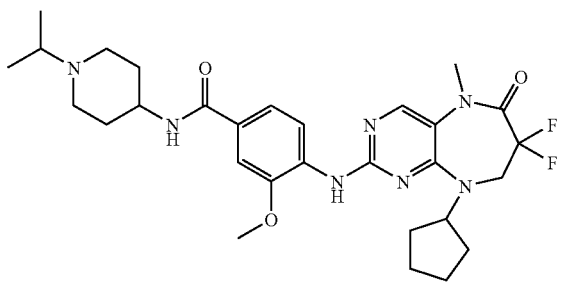

To a mixture of 0.050 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.08 mL (0.44 mmole) of ethyldiisopropyl amine and 0.018 g (0.12 mmole) of 1-isopropyl-piperidin-4-ylamine in 1.5 mL of dimethylformamide was added 0.053 g (0.12 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-85:15) gave 0.010 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-isopropyl-piperidin-4-yl)-3-methoxy-benzamide (I-64) as a white solid.

Example 65

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2,2,6,6-tetramethyl-piperidin-4-yl)-benzamide (I-65)

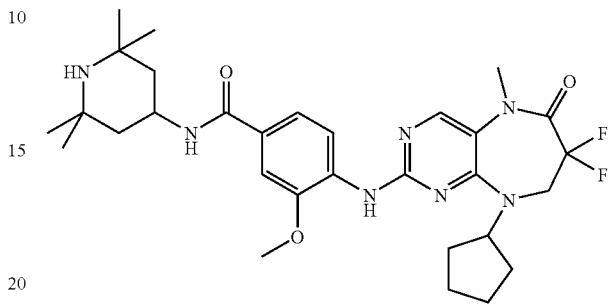

To a mixture of 0.10 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.12 mL (0.66 mmole) of ethyldiisopropyl amine and 0.039 g (0.25 mmole) of 2,2,6,6-tetramethyl-piperidin-4-ylamine in 2.0 mL of dimethylformamide was added 0.11 g (0.25 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-60:40) gave 0.065 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2,2,6,6-tetramethyl-piperidin-4-yl)-benzamide (I-65) as a white solid.

Example 66

4-(9-cyclopentyl-7,7-difluoro-5-methyl-6-oxo-6,7,8,9-tetrahydro-5H-pyrimido[4,5-b][1,4]diazepin-2-ylamino)-N-(1-cyclopropyl-piperidin-4-yl)-3-methoxy-benzamide (I-66)

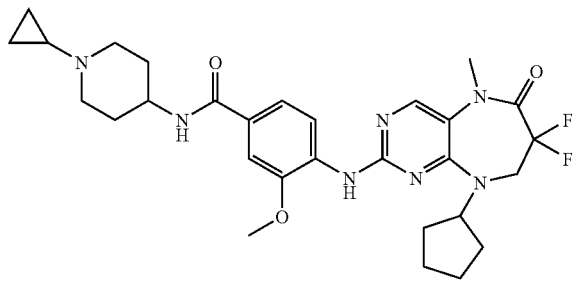

To a mixture of 0.10 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.2 mL (1.1 mmole) of ethyldiisopropyl amine and 0.038 g (0.25 mmole) of 1-cyclopropyl-piperidin-4-ylamine in 4.0 mL of dimethylformamide was added 0.11 g (0.25 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted with three times with dichloromethane. The combined organic layers were washed three times with sodium carbonate and three times with brine, dried over anhydrous sodium sulfate, filtered and concentrated under reduced pressure. Purification by silica gel chromatography, eluting with dichloromethane-methanol (gradient, 100:0-95:5) gave 0.081 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-cyclopropyl-piperidin-4-yl)-3-methoxy-benzamide (I-66) as a white solid.

Example 67

4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide (I-67)

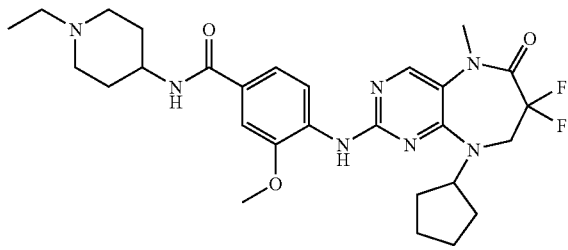

To a mixture of 0.10 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.2 mL (1.1 mmole) of ethyldiisopropyl amine and 0.034 g (0.26 mmole) of 1-ethyl-piperidin-4-ylamine in 4.0 mL of dimethylformamide was added 0.11 g (0.25 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-80:20) gave 0.070 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide (I-67) as a white solid.

Example 68 cis-4-(9-cyclopentyl-7,7-difluoro-5-methyl-6-oxo-6,7,8,9-tetrahydro-5H-pyrimido[4,5-b][1,4]diazepin-2-ylamino)-N-(4-hydroxy-cyclohexyl)-3-methoxy-benzamide (I-68)

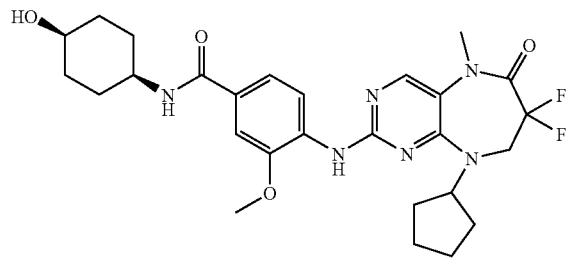

To a mixture of 0.08 g (0.18 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.13 mL (0.72 mmole) of ethyldiisopropyl amine and 0.030 g (0.20 mmole) of cis-4-amino-cyclohexanol hydrochloride in 2.0 mL of dimethylformamide was added 0.085 g (0.2 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-90:10) gave 0.066 g of cis-4-(9-cyclopentyl-7,7-difluoro-5-methyl-6-oxo-6,7,8,9-tetrahydro-5H-pyrimido[4,5-b][1,4]diazepin-2-ylamino)-N-(4-hydroxy-cyclohexyl)-3-methoxy-benzamide (I-68) as a white solid.

Example 69 trans-4-(9-cyclopentyl-7,7-difluoro-5-methyl-6-oxo-6,7,8,9-tetrahydro-5H-pyrimido[4,5-b][1,4]diazepin-2-ylamino)-N-(4-hydroxy-cyclohexyl)-3-methoxy-benzamide (I-69)

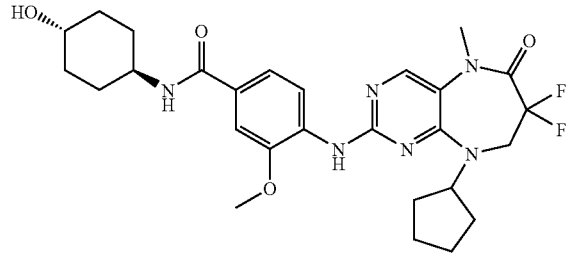

To a mixture of 0.08 g (0.18 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.13 mL (0.72 mmole) of ethyldiisopropyl amine and 0.030 g (0.20 mmole) of trans-4-amino-cyclohexanol hydrochloride in 2.0 mL of dimethylformamide was added 0.085 g (0.2 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-90:10) gave 0.077 g of trans-4-(9-cyclopentyl-7,7-difluoro-5-methyl-6-oxo-6,7,8,9-tetrahydro-5H-pyrimido[4,5-b][1,4]diazepin-2-ylamino)-N-(4-hydroxy-cyclohexyl)-3-methoxy-benzamide (I-69) as a white solid.

Example 70

4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid 9H-fluoren-9-ylmethyl ester (I-70)

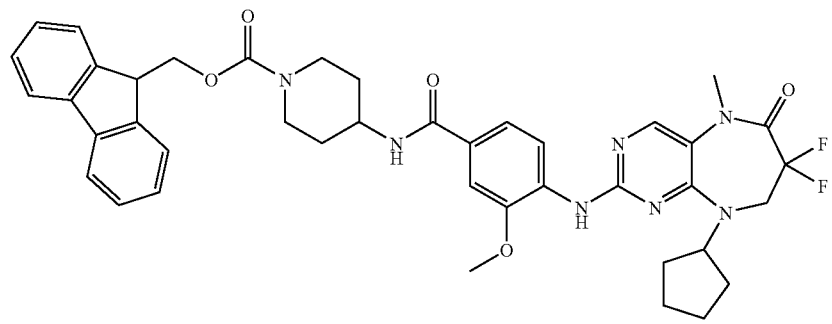

To a mixture of 0.15 g (0.34 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.24 mL (1.3 mmole) of ethyldiisopropyl amine and 0.13 g (0.37 mmole) of 4-amino-1-Fmoc-piperidine hydrochloride in 5.0 mL of dimethylformamide was added 0.16 g (0.37 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum to give 0.25 g of 4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid 9H-fluoren-9-ylmethyl ester (I-70) as a white solid.

Example 71

4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester (I-71)

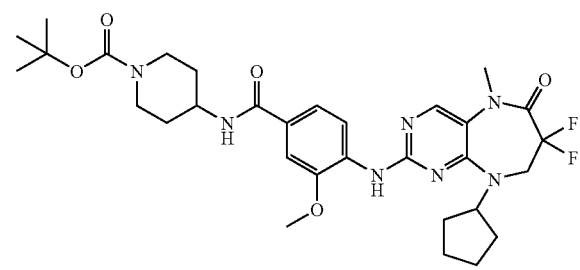

To a mixture of 0.25 g (0.56 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.30 mL (1.7 mmole) of ethyldiisopropyl amine and 0.12 g (0.62 mmole) of 4-amino-1-Boc-piperidine in 4.0 mL of dimethylformamide was added 0.27 g (0.62 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with hexane-ethylacetate (gradient, 70:30-0:100) gave 0.21 g of 4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester (I-71) as a white solid.

Example 72

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-piperidin-4-yl-benzamide (I-72)

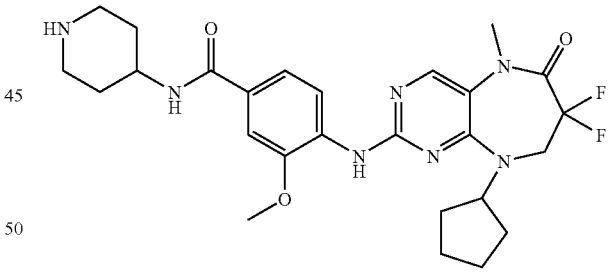

To the solution 0.17 g (0.27 mmole) of 4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester (I-71) in 10 mL of dichloromethane was added 5 mL of trifluoroacetic acid. The mixture was stirred at room temperature for 1 hour. After removal of the solvents under reduced pressure. Then dichloromethane and saturated sodium carbonate were added. The mixture was extracted with dichloromethane three times. The combined organic layers were washed three times with sodium carbonate, three times with water, dried over anhydrous sodium sulfate, filtered and concentrated under reduced pressure. Dichloromethane and ether were added to the residue, followed by hexane to give a precipitate.

The solid was collected by filtration, washing with hexane to give 0.125 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-piperidin-4-yl-benzamide (I-72) as a white solid.

Example 73

{3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-propyl}-carbamic acid 9H-fluoren-9-ylmethyl ester (I-73)

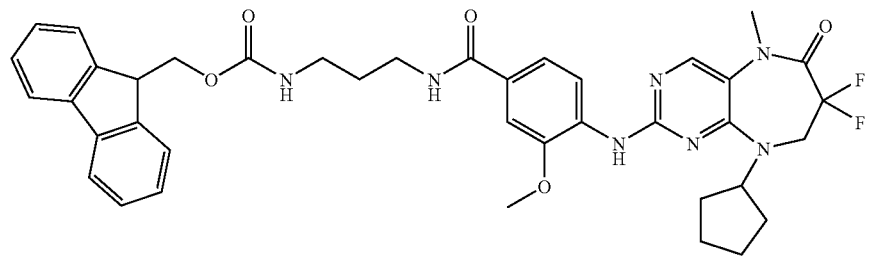

To a mixture of 0.10 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.16 mL (0.88 mmole) of ethyldiisopropyl amine and 0.082 g (0.24 mmole) of N-1-Fmoc-1,3-diaminopropane hydrochloride in 4.0 mL of dimethylformamide was added 0.11 g (0.25 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum to give 0.15 g of {3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-propyl}-carbamic acid 9H-fluoren-9-ylmethyl ester (I-73) as a white solid.

Example 74

N-(3-amino-propyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-74)

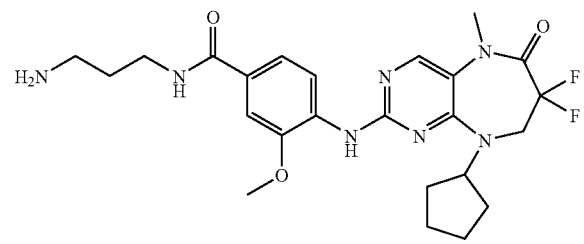

To the suspension 0.12 g (0.16 mmole) of {3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-propyl}-carbamic acid 9H-fluoren-9-ylmethyl ester (I-73) in 2 mL of dichloromethane was added 0.4 mL of piperidine. The mixture was stirred at room temperature for 1 hour, then volatiles were removed under reduced pressure. Purification by silica gel chromatography, eluting with dichloromethane-methanol (gradient, 100:0-0:100) gave 0.027 g of N-(3-amino-propyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-74) as a white solid.

Example 75

4-(9-cyclopentyl-7,7-difluoro-5-methyl-6-oxo-6,7,8,9-tetrahydro-5H-pyrimido[4,5-b][1,4]diazepin-2-ylamino)-N-[1-(2-fluoro-ethyl)-piperidin-4-yl]-3-methoxy-benzamide (I-75)

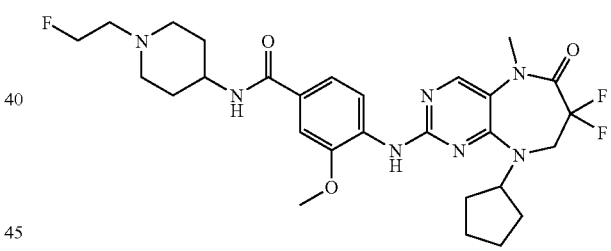

A mixture of 0.08 g (0.25 mmole) of 2-chloro-9-cyclopentyl-7,7-difluoro-5-methyl-5,7,8,9-tetrahydro-pyrimido[4,5-b][1,4]diazepin-6-one (VII-20) and 0.075 g (0.25 mmole) of 4-amino-N-[1-(2-fluoro-ethyl)-piperidin-4-yl]-3-methoxy-benzamide and 0.072 g (0.38 mmole) of p-toluenesulfonic acid monohydrate in 3 mL of isopropanol was stirred in a sealed tube at 140 degrees overnight. The mixture was cooled, and dichloromethane and saturated sodium carbonate were added. The mixture was extracted twice with dichloromethane. The combined organic layers were washed three times with sodium carbonate three times with brine, dried over anhydrous sodium sulfate, filtered and concentrated under reduced pressure. Purification by silica gel chromatography, eluting with dichloromethane-methanol (gradient, 100:0-90:10) gave 0.080 g of 4-(9-cyclopentyl-7,7-difluoro-5-methyl-6-oxo-6,7,8,9-tetrahydro-5H-pyrimido[4,5-b][1,4]diazepin-2-ylamino)-N-[1-(2-fluoro-ethyl)-piperidin-4-yl]-3-methoxy-benzamide (I-75).

Example 76

4-(9-cyclopentyl-7,7-difluoro-5-methyl-6-oxo-6,7,8,9-tetrahydro-5H-pyrimido[4,5-b][1,4]diazepin-2-ylamino)-N-[1-(3-methanesulfonyl-propyl)-piperidin-4-yl]-3-methoxy-benzamide (I-76)

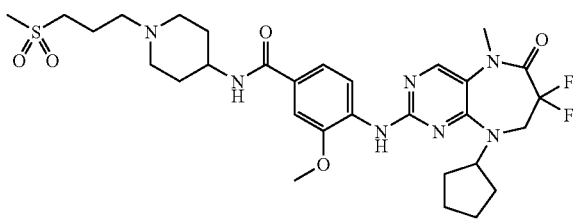

A mixture of 0.08 g (0.25 mmole) of 2-chloro-9-cyclopentyl-7,7-difluoro-5-methyl-5,7,8,9-tetrahydro-pyrimido[4,5-b][1,4]diazepin-6-one (VII-20) and 0.112 g (0.30 mmole) of 4-amino-N-[1-(3-methanesulfonyl-propyl)-piperidin-4-yl]-3-methoxy-benzamide and 0.072 g (0.38 mmole) of p-toluenesulfonic acid monohydrate in 3 mL of isopropanol was stirred in a sealed tube at 140 degrees overnight. After cooling, dichloromethane and saturated sodium carbonate were added. The mixture was extracted twice with dichloromethane. The combined organic layers were washed three times with sodium carbonate solution, three times with brine, dried over anhydrous sodium sulfate, filtered and concentrated under reduced pressure. Purification by silica gel chromatography, eluting with dichloromethane-methanol (gradient, 100:0-85:15) gave 0.11 g of 4-(9-cyclopentyl-7,7-difluoro-5-methyl-6-oxo-6,7,8,9-tetrahydro-5H-pyrimido[4,5-b][1,4]diazepin-2-ylamino)-N-[1-(3-methanesulfonyl-propyl)-piperidin-4-yl]-3-methoxy-benzamide (I-76) as a white solid.

Example 77

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[1-(2,2,2-trifluoro-ethyl)-piperidin-4-yl]-benzamide (I-77)

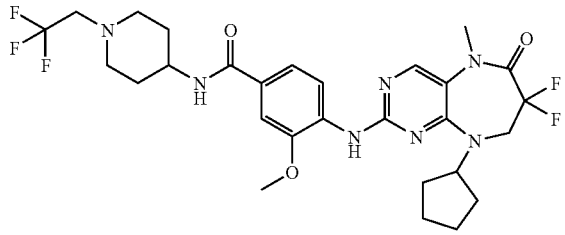

To a suspension of 1.0 g (0.005 mole) of 4-Boc-aminopiperidine and 2.78 mL (0.020 mole) of triethyl amine in 14 mL of tetrahydrofuran was added 1.16 g (0.005 mole) of trifluoromethanesulfonic acid 2,2,2-trifluoro-ethyl ester. After stirring at 75 degrees overnight, the mixture was cooled and saturated sodium carbonate was added. The mixture was extracted three times with dichloromethane. The combined organic layers were washed three times with saturated sodium carbonate, three times with brine, dried over anhydrous sodium sulfate, filtered and concentrated under reduced pressure. Purification by silica gel chromatography, eluting with ethyl acetate-hexane (gradient, 100:0-20:80) gave 1.27 g of [1-(2,2,2-trifluoro-ethyl)-piperidin-4-yl]-carbamic acid tert-butyl ester as a white solid.

A suspension of 1.26 g (0.0045 mole) of [1-(2,2,2-trifluoro-ethyl)-piperidin-4-yl]-carbamic acid tert-butyl ester in 10 mL of 4 M HCl in dioxane solution was stirred at room temperature for 24 hours. Volatiles were removed under reduced pressure, methanol was added to the residue followed by ether. The resulting solid was collected by filtration, washing with ether to give 0.92 g of 1-(2,2,2-trifluoro-ethyl)-piperidin-4-ylamine; hydrochloride as a white solid.

To a mixture of 0.10 g (0.22 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.20 mL (1.1 mmole) of ethyldiisopropyl amine and 0.068 g (0.26 mmole) of 1-(2,2,2-trifluoro-ethyl)-piperidin-4-ylamine; hydrochloride in 4.0 mL of dimethylformamide was added 0.11 g (0.25 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate solution, three times with brine, dried over anhydrous sodium sulfate, filtered and concentrated under reduced pressure. Purification by silica gel chromatography, eluting with hexane-ethylacetate (gradient, 80:20-0:100) gave 0.11 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[1-(2,2,2-trifluoro-ethyl)-piperidin-4-yl]-benzamide (I-77) as a white solid.

Example 78

4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methoxy-benzamide (I-78)

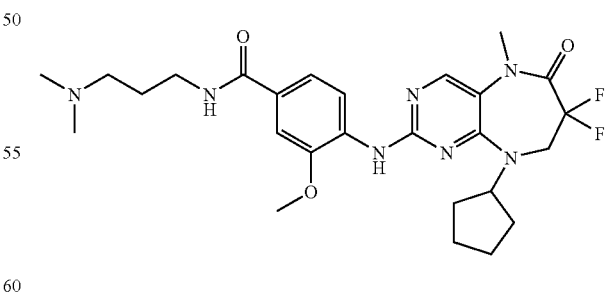

To a mixture of 0.0827 g (0.185 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0773 g (0.20 mmole) of 1-[bis(dimethylamino)methylene]-1H-1,2,3-triazolo[4,5-b]pyridinium-3-oxide hexafluorophosphate, 2 mL of dichloromethane, 0.11 mL of triethylamine was added followed by 0.05 mL of N1,N1- dimethyl-3-propanediamine. After 2 hours, 6 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with ethyl acetate-methanol-ammonium hydroxide (75:25:2) to give 0.0472 g, of 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methoxy-benzamide (I-78).

Example 79

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-morpholin-4-yl-propyl)-benzamide (I-79)

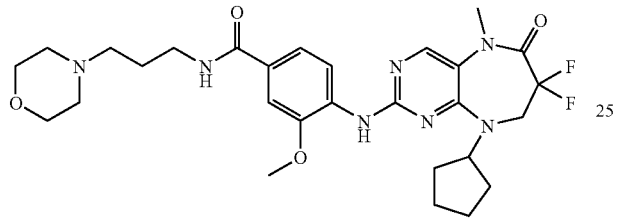

To a mixture of 0.080 g (0.18 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0849 g (0.22 mmole) of 1-[bis(dimethylamino)methylene]-1H-1,2,3-triazolo[4,5-b]pyridinium-3-oxide hexafluorophosphate, 2 mL of dichloromethane, 0.11 mL of triethylamine was added followed by 0.05 mL of 3-morpholin-4-yl-propylamine. After 2 hours, 6 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with ethyl acetate-methanol-ammonium hydroxide (91:9:0.8) to give 0.0608 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-morpholin-4-yl-propyl)-benzamide (I-79).

Example 80

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-pyrrolidin-1-yl-propyl)-benzamide (I-80)

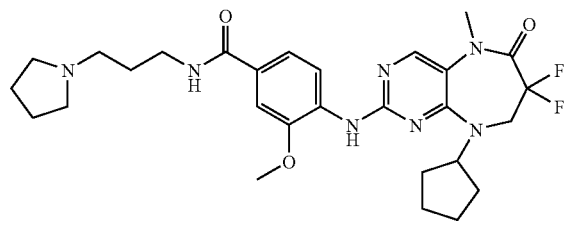

To a mixture of 0.0524 g (0.117 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.049 g (0.13 mmole) of 1-[bis(dimethylamino)methylene]-1H-1,2,3-triazolo[4,5-b]pyridinium-3-oxide hexafluorophosphate, 2 mL of dichloromethane, 0.11 mL of triethylamine was added followed by 0.0174 g of 3-pyrrolidin-1-yl-propylamine. After 2 hours, 6 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with ethyl acetate-methanol-ammonium hydroxide (83:17:1.5) to give 0.0303 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-pyrrolidin-1-yl-propyl)-benzamide (I-80).

Example 81

R-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-pyrrolidine-1-carboxylic acid tert-butyl ester (I-81)

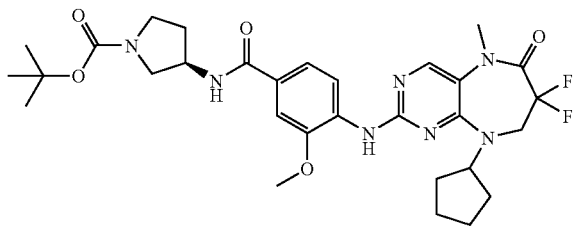

To a mixture of 0.0749 g (0.167 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0636 g (0.167 mmole) of 1-[bis(dimethylamino)methylene]-1H-1,2,3-triazolo[4,5-b]pyridinium-3-oxide hexafluorophosphate, 3 mL of dichloromethane, 0.07 mL of triethylamine was added followed by 0.0373 g (0.20 mmole) of R-3-amino-pyrrolidine-1-carboxylic acid tert-butyl ester. After 2 hours, 6 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with hexanes-ethyl acetate (gradient, 40:60-0:100) to give 0.0414 g of R-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-pyrrolidine-1-carboxylic acid tert-butyl ester (I-81).

Example 82

S-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-pyrrolidine-1-carboxylic acid tert-butyl ester (I-82)

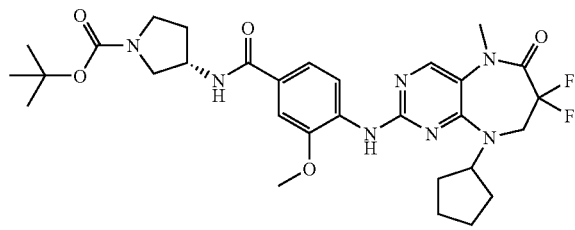

To a mixture of 0.0734 g (0.164 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0623 g (0.164 mmole) of 1-[bis(dimethylamino)methylene]-1H-1,2,3-triazolo[4,5-b]pyridinium-3-oxide hexafluorophosphate, 3 mL of dichloromethane, 0.07 mL of triethylamine was added followed by 0.0373 g (0.20 mmole) of R-3-amino-pyrrolidine-1-carboxylic acid tert-butyl ester. After 2 hours, 6 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with hexanes-ethyl acetate (gradient, 40:60-0:100) to give 0.0506 g of S-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-pyrrolidine-1-carboxylic acid tert-butyl ester (I-82).

Example 83

S-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N—(S)-pyrrolidin-3-yl-benzamide (I-83)

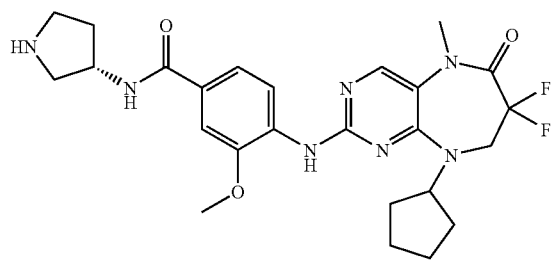

A mixture of 0.027 g (0.044 mmole) of S-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-pyrrolidine-1-carboxylic acid tert-butyl ester 1-82, 2.125 mL of dichloromethane and 0.375 mL of trifluoroacetic acid was stirred overnight and then concentrated under reduced pressure. The residue was diluted with dichloromethane and neutralized with 1.0 M sodium hydroxide at 0 degrees. The dichloromethane layer was dried over anhydrous magnesium sulfate, filtered and concentrated under reduced pressure. The residue was purified by silica gel chromatography, eluting with ethyl acetate-methanol-ammonium hydroxide (83:17:1.5) to give 0.0032 g of S-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N—(S)-pyrrolidin-3-yl-benzamide (I-83).

Example 84

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-piperidin-1-yl-propyl)-benzamide (I-84)

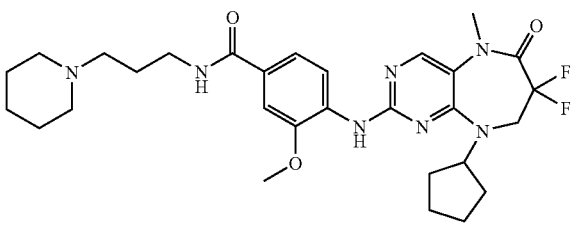

To a mixture of 0.051 g (0.114 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0433 g (0.114 mmole) of 1-[bis(dimethylamino)methylene]-1H-1,2,3-triazolo[4,5-b]pyridinium-3-oxide hexafluorophosphate, 2.5 mL of dichloromethane, 0.05 mL of triethylamine was added followed by 0.0162 g (0.114 mmole) of 3-piperidin-1-yl-propylamine. After 2 hours, 6 mL of dichloromethane, 4 mL of water and 0.2 mL of 1 M sodium hydroxide was added. The dichloromethane layer was dried over anhydrous magnesium sulfate, filtered and concentrated under reduced pressure. The residue was purified by silica gel chromatography, eluting with ethyl acetate-methanol-ammonium hydroxide (91:9:0.75) to give 0.0431 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-piperidin-1-yl-propyl)-benzamide (I-84).

Example 85

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1,2,2,6,6-pentamethyl-piperidin-4-yl)-benzamide (I-85)

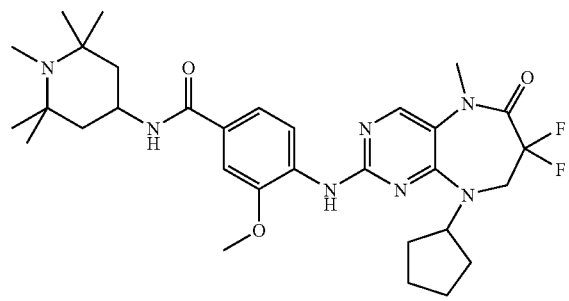

To a mixture of 0.051 g (0.114 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0433 g (0.114 mmole) of 1-[bis(dimethylamino)methylene]-1H-1,2,3-triazolo[4,5-b]pyridinium-3-oxide hexafluorophosphate, 2.5 mL of dichloromethane, 0.05 mL of triethylamine was added followed by 0.0194 g (0.114 mmole) of 1,2,2,6,6-pentamethyl-piperidin-4-ylamine. After 2 hours, 6 mL of dichloromethane, 4 mL of water and 0.2 mL of 1 M sodium hydroxide was added. The dichloromethane layer was dried over anhydrous magnesium sulfate, filtered and concentrated under reduced pressure. The residue was purified by silica gel chromatography, eluting with ethyl acetate-methanol-ammonium hydroxide (83:17:1.5) to give 0.045 g of S-3-[4-(9-cyclopentyl-7,7-difluoro-5-methyl-6-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1,2,2,6,6-pentamethyl-piperidin-4-yl)-benzamide (I-85).

Example 86

3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-azetidine-1-carboxylic acid tert-butyl ester (I-86)

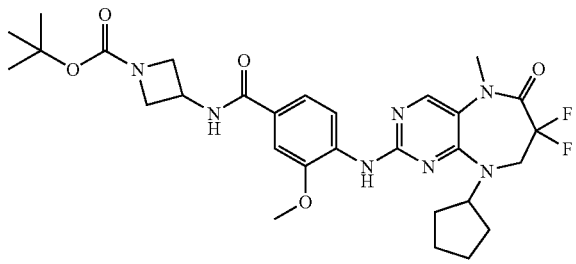

To a mixture of 0.090 g (0.2 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0764 g (0.2 mmole) of 1-[bis(dimethylamino)methylene]-1H-1,2,3-triazolo[4,5-b]pyridinium-3-oxide hexafluorophosphate, 3 mL of dichloromethane, 0.08 mL of triethylamine was added followed by 0.0344 g (0.2 mmole) of 3-amino-azetidine-1-carboxylic acid tert-butyl ester. After 2 hours, 6 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with hexanes-ethyl acetate (gradient, 60:40-0:100) to give 0.0523 g of 3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-azetidine-1-carboxylic acid tert-butyl ester (I-86).

Example 87

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[3-(4-methyl-piperazin-1-yl)-propyl]-benzamide (I-87)

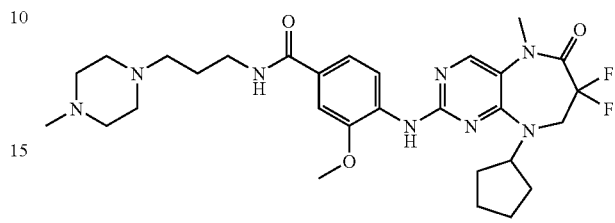

To a mixture of 0.050 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.043 g (0.11 mmole) of 1-[bis(dimethylamino)methylene]-1H-1,2,3-triazolo[4,5-b]pyridinium-3-oxide hexafluorophosphate, 2.5 mL of dichloromethane, 0.05 mL of triethylamine was added followed by 0.0173 g (0.11 mmole) of 3-(4-methyl-piperazin-1-yl)-propylamine. After 2 hours, 6 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with ethyl acetate-methanol-ammonium hydroxide (83:17:1.5) to give 0.0333 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[3-(4-methyl-piperazin-1-yl)-propyl]-benzamide (I-87).

Example 88

N-[1-(2-amino-2-methyl-propionyl)-piperidin-4-yl]-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-88)

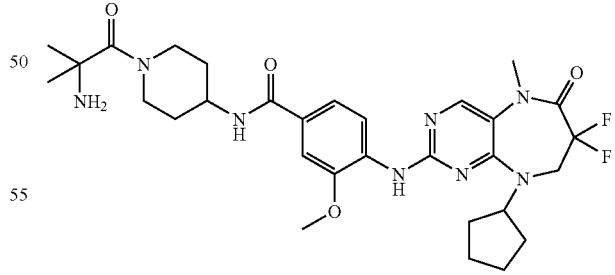

To a mixture of 0.265 g (0.59 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.2256 g (0.59 mmole) of 1-[bis(dimethylamino)methylene]-1H-1,2,3-triazolo[4,5-b]pyridinium-3-oxide hexafluorophosphate, 8 mL of dichloromethane, 0.25 mL of triethylamine was added followed by 0.1181 g (0.59 mmole) of 4-amino-piperidine-1-carboxylic acid tert-butyl ester.

After stirring overnight, 16 mL of dichloromethane, 14 mL of water and 0.8 mL of 1M sodium hydroxide was added. The dichloromethane layer was dried over anhydrous magnesium sulfate, filtered and concentrated under reduced pressure. The residue was purified by silica gel chromatography, eluting with hexanes-ethyl acetate (gradient, 40:60-10:90) to give 0.2278 g of 4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester.

The intermediate was stirred overnight with 8 mL of dichloromethane and 1 mL of trifluoroacetic acid, and then concentrated under reduced pressure. The residue was diluted with water and 1 mL of 3.0 M HCl, and the solid collected by filtration, washing with water. The solid (62.6 mg) was suspended in 4 mL of dichloromethane and 0.0264 g of 2-tert-butoxycarbonylamino-2-methyl-propionic acid was added followed by 0.0494 g of 1-[bis(dimethylamino)methylene]-1H-1,2,3-triazolo[4,5-b]pyridinium-3-oxide hexafluorophosphate and 0.1 mL of triethylamine. After stirring overnight, 8 mL of dichloromethane, 4 mL of water and 0.2 mL of 1M sodium hydroxide was added. The dichloromethane layer was dried over anhydrous magnesium sulfate, filtered and concentrated under reduced pressure. The residue was stirred with 1.375 mL of dichloromethane and 0.125 mL of trifluoroacetic acid for 3 hours and then concentrated under reduced pressure. The residue was diluted with dichloromethane and neutralized with 1.0 M sodium hydroxide at 0 degrees. The dichloromethane layer was dried over anhydrous magnesium sulfate, filtered and concentrated under reduced pressure. The residue was purified by silica gel chromatography, eluting with ethyl acetate-methanol-ammonium hydroxide (91:9:0.5) to give 0.0355 g of N-[1-(2-amino-2-methyl-propionyl)-piperidin-4-yl]-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-88).

Example 89

R-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-oxo-piperidin-4-yl)-benzamide (I-89)

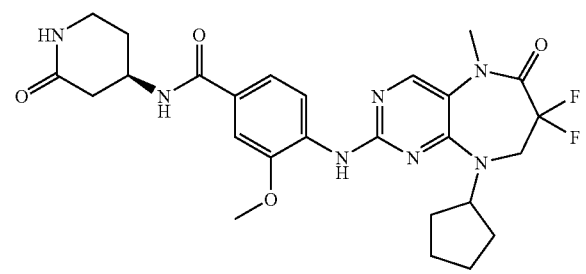

To a mixture of 0.066 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.046 g (0.11 mmole) of 1-[bis(dimethylamino)methylene]-1H-1,2,3-triazolo[4,5-b]pyridinium-3-oxide hexafluorophosphate, 2.5 mL of dichloromethane, 0.07 mL of triethylamine was added followed by 0.0182 g (0.12 mmole) of R-4-amino-piperidin-2-one dihydrochloride. After stirring overnight, the mixture was concentrated under reduced pressure. The residue was purified by silica gel chromatography, eluting with acetonitrile-water (gradient, 5:95-0:100) to give 0.0184 g of R-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-oxo-piperidin-4-yl)-benzamide (I-89).

Example 90

S-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-oxo-piperidin-4-yl)-benzamide (I-90)

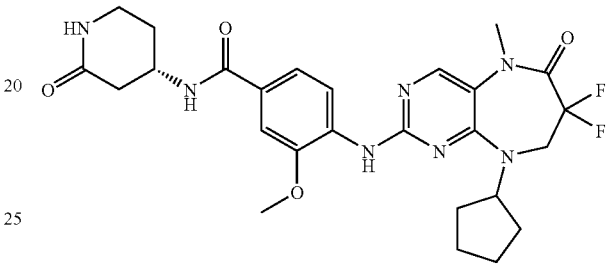

To a mixture of 0.072 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.050 g (0.13 mmole) of 1-[bis(dimethylamino)methylene]-1H-1,2,3-triazolo[4,5-b]pyridinium-3-oxide hexafluorophosphate, 2.5 mL of dichloromethane, 0.07 mL of triethylamine was added followed by 0.0199 g (0.13 mmole) of S-4-amino-piperidin-2-one dihydrochloride. After stirring overnight, the mixture was concentrated under reduced pressure. The residue was purified by silica gel chromatography, eluting with acetonitrile-water (gradient, 5:95-0:100) to give 0.0308 g of S-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-oxo-piperidin-4-yl)-benzamide (I-90).

Example 91

3-{[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-methyl}-azetidine-1-carboxylic acid tert-butyl ester (I-91)

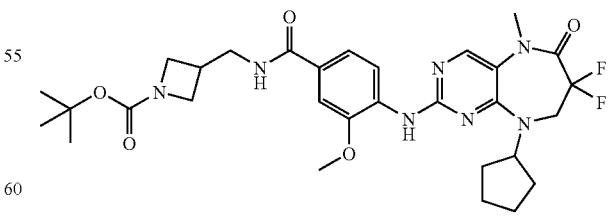

To a mixture of 0.097 g (0.15 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0634 g (0.17 mmole) of 1-[bis(dimethylamino)methylene]-1H-1,2,3-triazolo[4,5-b]pyridinium-3-oxide hexafluorophosphate, 3 mL of dichloromethane, 0.13 mL of triethylamine was added followed by 0.0317 g (0.17 mmole) of 3-aminomethyl-azetidine-1-carboxylic acid tert-butyl ester. After 1 hour, 4 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with hexanes-ethyl acetate (gradient, 100:0-0:100) to give 0.0714 g of 3-{[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-methyl}-azetidine-1-carboxylic acid tert-butyl ester (I-91).

Example 92

3-{[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-methyl}-pyrrolidine-1-carboxylic acid tert-butyl ester (I-92)

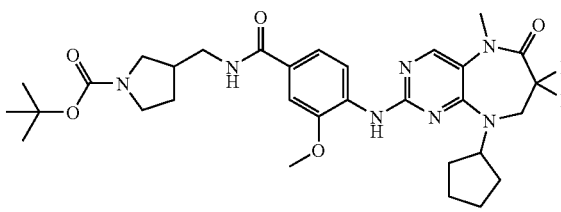

To a mixture of 0.097 g (0.15 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0634 g (0.17 mmole) of 1-[bis(dimethylamino)methylene]-1H-1,2,3-triazolo[4,5-b]pyridinium-3-oxide hexafluorophosphate, 3 mL of dichloromethane, 0.13 mL of triethylamine was added followed by 0.0317 g (0.17 mmole) of 3-aminomethyl-pyrrolidine-1-carboxylic acid tert-butyl ester. After 1 hour, 4 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with hexanes-ethyl acetate (gradient, 100:0-0:100) to give 0.0748 g of 3-{[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-methyl}-pyrrolidine-1-carboxylic acid tert-butyl ester (I-92).

Example 93

4-(9-cyclopentyl-7,7-difluoro-5-methyl-6-oxo-6,7,8,9-tetrahydro-5H-pyrimido[4,5b][1,4]diazepin-2-ylamino)-3-methoxy-N-pyrrolidin-3-ylmethyl-benzamide (I-93)

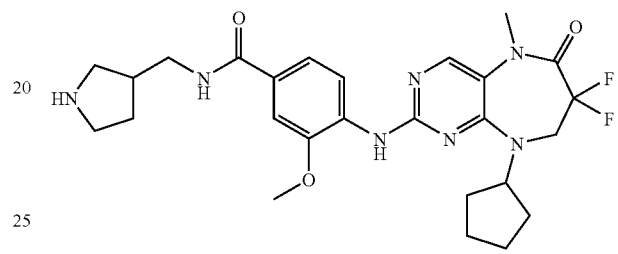

A mixture of 0.050 g (0.079 mmole) of 3-{[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-methyl}-pyrrolidine-1-carboxylic acid tert-butyl ester (I-92), 2.5 mL of chloroform and 0.5 mL of trifluoroacetic acid was 2 hours and then concentrated under reduced pressure. The residue was diluted with dichloromethane and neutralized with 1.0 M sodium hydroxide at 0 degrees. The dichloromethane layer was dried over anhydrous magnesium sulfate, filtered and concentrated under reduced pressure to give 0.0274 g of 4-(9-cyclopentyl-7,7-difluoro-5-methyl-6-oxo-6,7,8,9-tetrahydro-5H-pyrimido[4,5b][1,4]diazepin-2-ylamino)-3-methoxy-N-pyrrolidin-3-ylmethyl-benzamide (I-93).

Example 94

4-{3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-propyl}-piperazine-1-carboxylic acid tert-butyl ester (I-94)

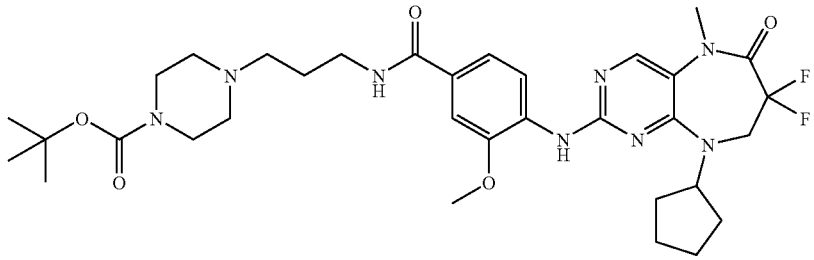

To a mixture of 0.105 g (0.23 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0988 g (0.26 mmole) of 1-[bis(dimethylamino)methylene]-1H-1,2,3-triazolo[4,5-b]pyridinium-3-oxide hexafluorophosphate, 1 mL of dichloromethane, 0.2 mL of triethylamine was added followed by 0.0199 g (0.13 mmole) of 4-(3-amino-propyl)-piperazine-1-carboxylic acid tert-butyl ester. After stirring 1.5 hours, the mixture was concentrated under reduced pressure. The residue was purified by silica gel chromatography, eluting with acetonitrile-water (gradient, 5:95-0:100) to give 0.0609 g of 4-{3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-propyl}-piperazine-1-carboxylic acid tert-butyl ester (I-94).

Example 95

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-piperazin-1-yl-propyl)-benzamide (I-95)

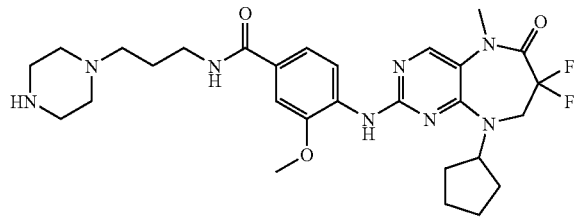

A mixture of 0.0245 g (0.035 mmole) of 4-{3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-propyl}-piperazine-1-carboxylic acid tert-butyl ester (I-94), 2.25 mL of dichloromethane and 0.25 mL of trifluoroacetic acid was stirred for 2 hours and then concentrated under reduced pressure. The residue was diluted with methanol and neutralized with 1.0 M sodium hydroxide at 0 degrees. The methanol solution was purified by reverse phase silica gel chromatography, eluting with acetonitrile-water (gradient, 1:99-90:10) to give 0.0162 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-piperazin-1-yl-propyl)-benzamide (I-95).

Example 96

4-(9-cyclopentyl-7,7-difluoro-5-methyl-6-oxo-6,7,8,9-tetrahydro-5H-pyrimido[4,5-b][1,4]diazepin-2-ylamino)-N-{3-[4-(2-hydroxy-ethyl)-piperazin-1-yl]-propyl}-3-methoxy-benzamide (I-96)

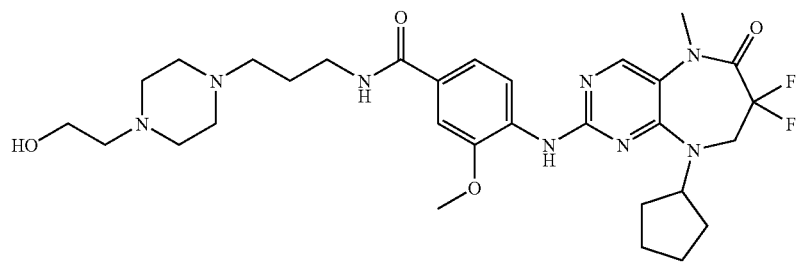

To a mixture of 0.051 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.0494 g (0.13 mmole) of 1-[bis(dimethylamino)methylene]-1H-1,2,3-triazolo[4,5-b]pyridinium-3-oxide hexafluorophosphate, 0.6 mL of dichloromethane, 0.6 mL of dimethylformamide, 0.12 mL of triethylamine was added followed by 0.0235 g (0.13 mmole) of 2-[4-(3-amino-propyl)-piperazin-1-yl]-ethanol. After stirring 1.5 hours, the mixture was concentrated under reduced pressure. The residue was purified by silica gel chromatography, eluting with acetonitrile-water (gradient, 5:95-0:100) to give 0.0054 g of 4-(9-cyclopentyl-7,7-difluoro-5-methyl-6-oxo-6,7,8,9-tetrahydro-5H-pyrimido[4,5-b][1,4]diazepin-2-ylamino)-N-{3-[4-(2-hydroxy-ethyl)-piperazin-1-yl]-propyl}-3-methoxy-benzamide (I-96).

Example 97 cis-{4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-cyclohexyl}-carbamic acid tert-butyl ester (I-97)

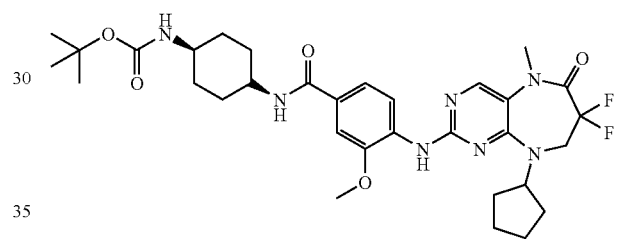

To a mixture of 0.112 g (0.15 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.099 g (0.27 mmole) of 1-[bis(dimethylamino)methylene]-1H-1,2,3-triazolo[4,5-b]pyridinium-3-oxide hexafluorophosphate, 2 mL of dichloromethane, 0.3 mL of triethylamine was added followed by 0.051 g (0.24 mmole) of cis-(4-amino-cyclohexyl)-carbamic acid tert-butyl ester. After 3 hours, 4 mL of dichloromethane, 4 mL of water and 0.2 mL of 1M sodium hydroxide was added. The dichloromethane layer was dried over anhydrous magnesium sulfate, filtered and concentrated under reduced pressure. The residue was purified by silica gel chromatography, eluting with hexanes-ethyl acetate (gradient, 100:0-0:100) to give 0.0673 g of cis-{4-[4-(9-cyclopentyl-7,7-difluoro-5-methyl-6-oxo-6,7,8,9-tetrahydro-5H-pyrimido[4,5-b][1,4]diazepin- 2-ylamino)-3-methoxy-benzoylamino]-cyclohexyl}-carbamic acid tert-butyl ester (I-97).

Example 98 cis-N-(4-amino-cyclohexyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-98)

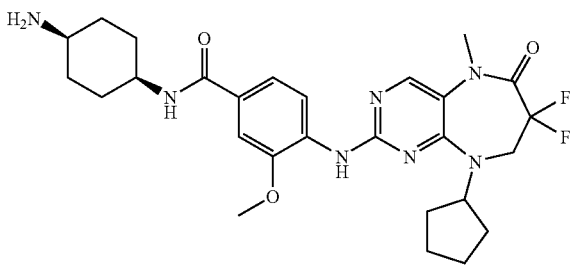

A mixture of 0.046 g (0.07 mmole) of cis-{4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-cyclohexyl}-carbamic acid tert-butyl ester (I-97), 2.25 mL of dichloromethane and 0.25 mL of trifluoroacetic acid was stirred for 1.5 hours and then concentrated under reduced pressure. The residue was diluted with methanol and neutralized with 1.0 M sodium hydroxide at 0 degrees. The methanol solution was purified by reverse phase silica gel chromatography, eluting with acetonitrile-water (gradient, 1:99-90:10) to give 0.0226 g of cis-N-(4-amino-cyclohexyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-98).

Example 99

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-azetidin-3-yl)-benzamide (I-99)

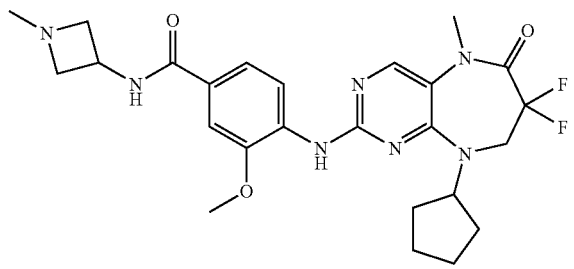

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.01 g (0.12 mmole) of 1-Methyl-azetidin-3-ylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.04 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-azetidin-3-yl)-benzamide (I-99), as a white solid.

Example 100

N—((S)-1-benzyl-pyrrolidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-100)

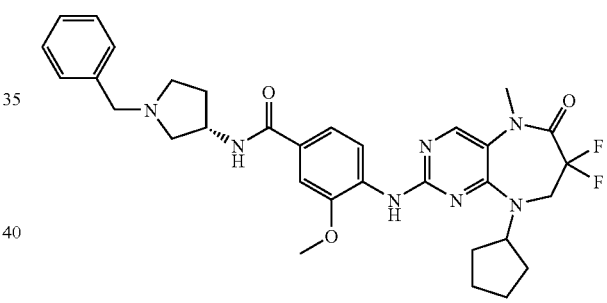

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.021 g (0.12 mmole) of (S)-1-benzyl-pyrrolidin-3-ylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.051 g of N—((S)-1-benzyl-pyrrolidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-100) as a white solid.

Example 101

N—((R)-1-benzyl-pyrrolidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-101)

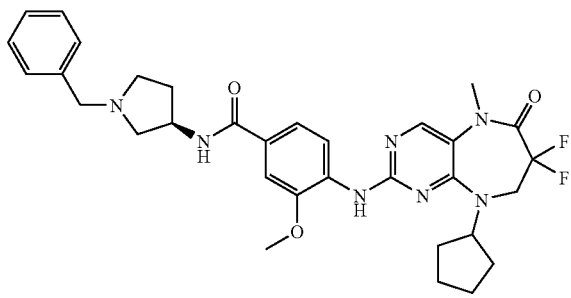

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.021 g (0.12 mmole) of (R)-1-Benzyl-pyrrolidin-3-ylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.052 g of N—((R)-1-benzyl-pyrrolidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide as a white solid.

Example 102

N-(1-acetyl-piperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-102)

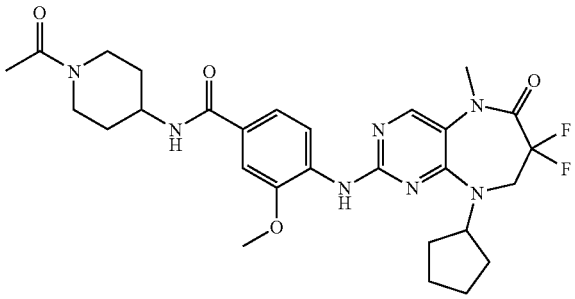

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.017 g (0.12 mmole) of 1-(4-Aminopiperidin-1-yl)-ethanone was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.05 g of N-(1-acetyl-piperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-102) as a white solid.

Example 103

(3R,4R)-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-4-hydroxy-pyrrolidine-1-carboxylic acid tert-butyl ester (I-103)

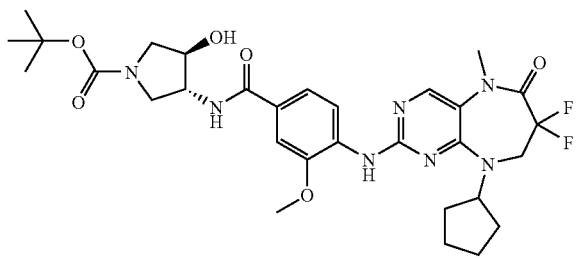

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.024 g (0.12 mmole) of (3R,4R)-3-amino-4-hydroxy-pyrrolidine-1-carboxylic acid tert-butyl ester was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.053 g of (3R,4R)-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-4-hydroxy-pyrrolidine-1-carboxylic acid tert-butyl ester (I-103) as a white solid.

Example 104

4-(9-cyclopentyl-7,7-difluoro-5-methyl-6-oxo-6,7,8,9-tetrahydro-5H-pyrimido[4,5-b][1,4]diazepin-2-ylamino)-N-((3R,4R)-4-hydroxy-pyrrolidin-3-yl)-3-methoxy-benzamide (I-104)

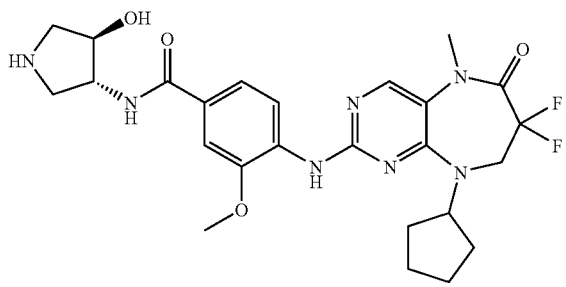

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.012 g (0.12 mmole) (3R,4R)-4-amino-pyrrolidin-3-ol was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.042 g of 4-(9-cyclopentyl-7,7-difluoro-5-methyl-6-oxo-6,7,8,9-tetrahydro-5H-pyrimido[4,5-b][1,4]diazepin-2-ylamino)-N-((3R,4R)-4-hydroxy-pyrrolidin-3-yl)-3-methoxy-benzamide (I-104) as a white solid.

Example 105

4-(9-cyclopentyl-7,7-difluoro-5-methyl-6-oxo-6,7,8,9-tetrahydro-5H-pyrimido[4,5-b][1,4]diazepin-2-ylamino)-N-[3-(4-hydroxy-piperidin-1-yl)-propyl]-3-methoxy-benzamide (I-105)

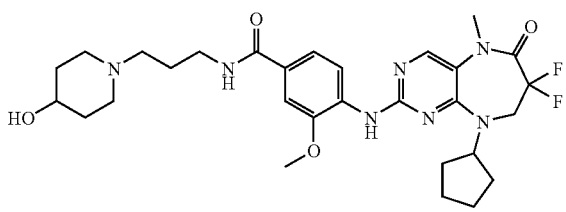

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.019 g (0.12 mmole) 1-(3-Aminopropyl)-piperidin-4-ol was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.049 g of 4-(9-cyclopentyl-7,7-difluoro-5-methyl-6-oxo-6,7,8,9-tetrahydro-5H-pyrimido[4,5-b][1,4]diazepin-2-ylamino)-N-[3-(4-hydroxy-piperidin-1-yl)-propyl]-3-methoxy-benzamide (I-105) as a white solid.

Example 106

N—(R)-1-aza-bicyclo[2.2.2]oct-3-yl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-106)

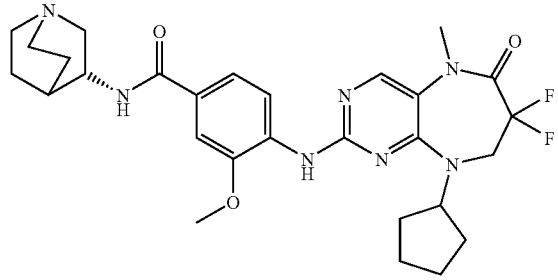

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.015 g (0.12 mmole) (R)-(1-azabicyclo[2.2.2]oct-3-yl)amine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.039 g of N—(R)-1-aza-bicyclo[2.2.2]oct-3-yl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-106) as a white solid.

Example 107

N—(S)-1-aza-bicyclo[2.2.2]oct-3-yl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-107)

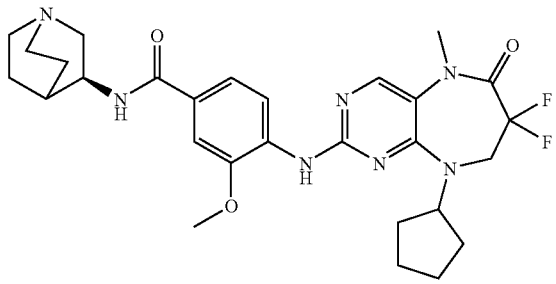

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.015 g (0.12 mmole) (S)-(1-azabicyclo[2.2.2]oct-3-yl)amine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.041 g of N—(S)-1-aza-bicyclo[2.2.2]oct-3-yl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide as a white solid.

Example 108

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3,4,5,6-tetrahydro-2H-[1,2']bipyridinyl-4-yl)-benzamide (I-108)

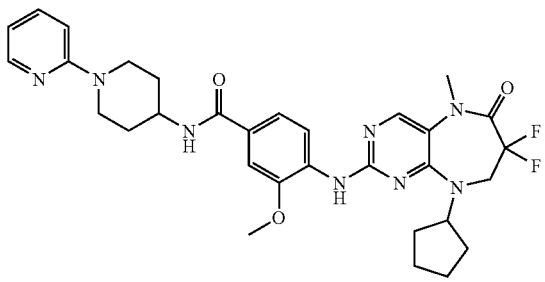

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.021 g (0.12 mmole) 3,4,5,6-tetrahydro-2H-[1,2']bipyridinyl-4-ylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.046 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3,4,5,6-tetrahydro-2H-[1,2']bipyridinyl-4-yl)-benzamide (I-108) as a white solid.

Example 109

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-2-ylmethyl-benzamide (I-109)

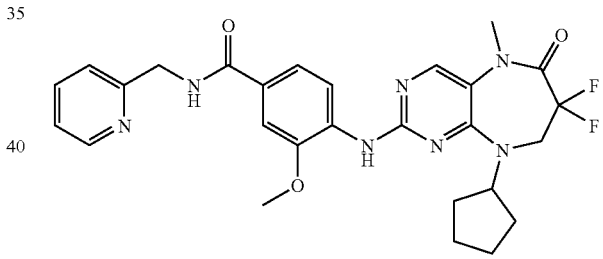

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.013 g (0.12 mmole) 2-pyridinemethanamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.038 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-2-ylmethyl-benzamide (I-109) as a white solid.

Example 110

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[3-(2-methyl-piperidin-1-yl)-propyl]-benzamide (I-110)

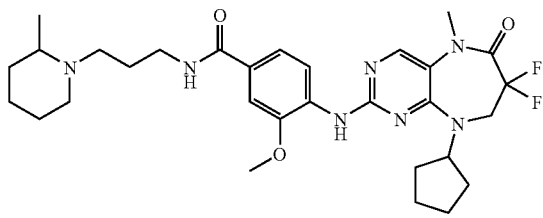

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.019 g (0.12 mmole) 3-(2-Methyl-piperidin-1-yl)-propylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.042 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[3-(2-methyl-piperidin-1-yl)-propyl]-benzamide as a white solid.

Example 111

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-3-yl-methyl benzamide (I-111)

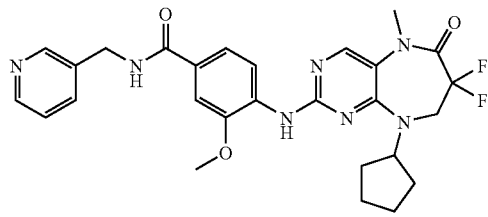

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.013 g (0.12 mmole) C-Pyridin-3-yl-methylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.041 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-3-yl-methyl benzamide (I-111) as a white solid.

Example 112

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[2-(1-methyl-pyrrolidin-2-yl)-ethyl]-benzamide (I-112)

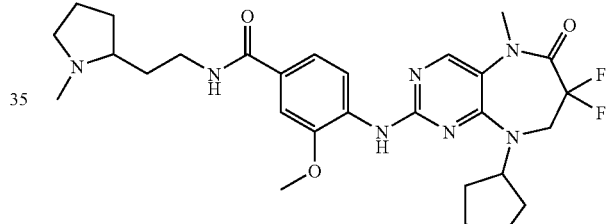

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.015 g (0.12 mmole) 2-(1-methyl-pyrrolidin-2-yl)-ethylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.046 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[2-(1-methyl-pyrrolidin-2-yl)-ethyl]-benzamide (I-112) as a white solid.

Example 113

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[3-(2-oxo-pyrrolidin-1-yl)-propyl]-benzamide (I-113)

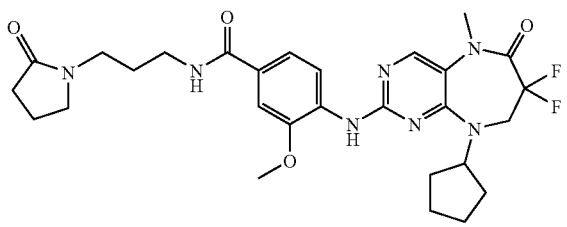

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.017 g (0.12 mmole) 1-(3-aminopropyl)-pyrrolidin-2-one was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.045 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[3-(2-oxo-pyrrolidin-1-yl)-propyl]-benzamide (I-113) as a white solid.

Example 114

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-piperidin-1-yl-ethyl)-benzamide (I-114)

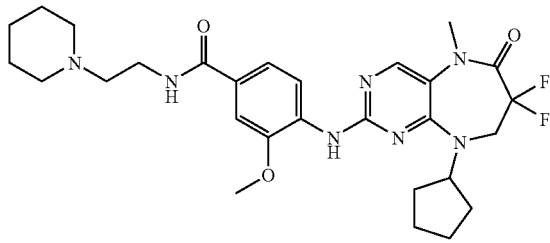

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.015 g (0.12 mmole) 2-Piperidin-1-yl-ethylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.043 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-piperidin-1-yl-ethyl)-benzamide (I-114) as a white solid.

Example 115

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-piperidin-1-yl-benzamide (I-115)

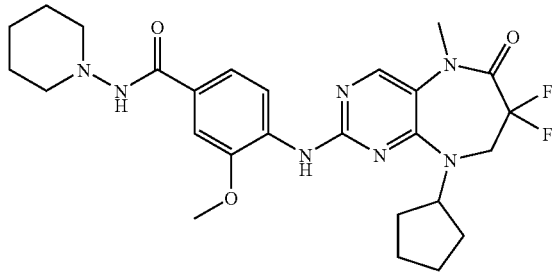

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.012 g (0.12 mmole) piperidin-1-ylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.036 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-piperidin-1-yl-benzamide (I-115) as a white solid.

Example 116

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-pyridin-2-yl-ethyl)-benzamide (I-116)

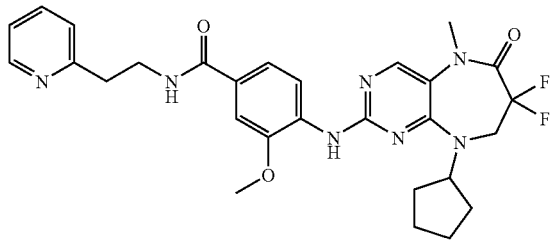

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.015 g (0.12 mmole) 2-pyridin-2-yl-ethylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.044 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-pyridin-2-yl-ethyl)-benzamide (I-116) as a white solid.

Example 117

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-morpholin-4-yl-ethyl)-benzamide (I-117)

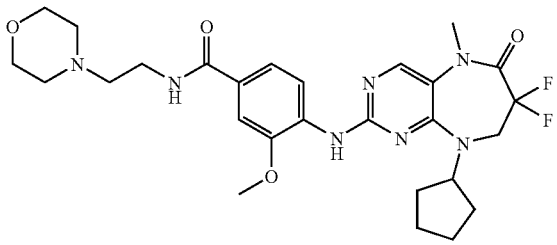

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.016 g (0.12 mmole) 2-morpholin-4-yl-ethylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.036 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-morpholin-4-yl-ethyl)-benzamide (I-117) as a white solid.

Example 118

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(4-methyl-piperazin-1-yl)benzamide (I-118)

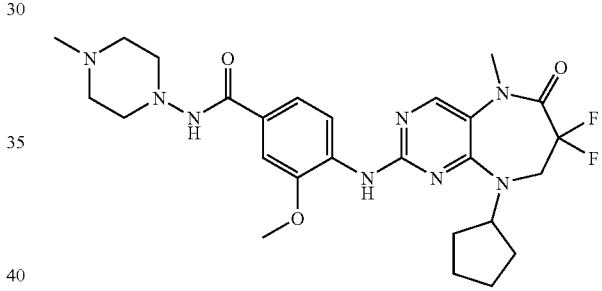

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.014 g (0.12 mmole) 4-methyl-piperazin-1-ylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.034 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(4-methyl-piperazin-1-yl) benzamide (I-118) as a white solid.

Example 119

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-phenylamino-ethyl)-benzamide (I-119)

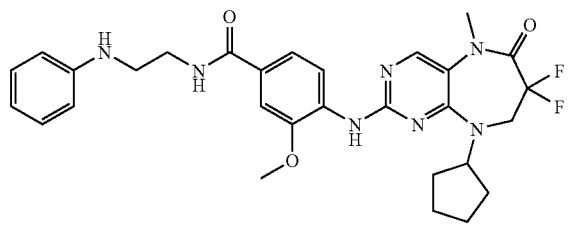

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.016 g (0.12 mmole) N-phenyl-ethane-1,2-diamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.037 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-phenylamino-ethyl)-benzamide (I-119) as a white solid.

Example 120

4-{3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-2-hydroxy-propyl}-piperazine-1-carboxylic acid tert-butyl ester (I-120)

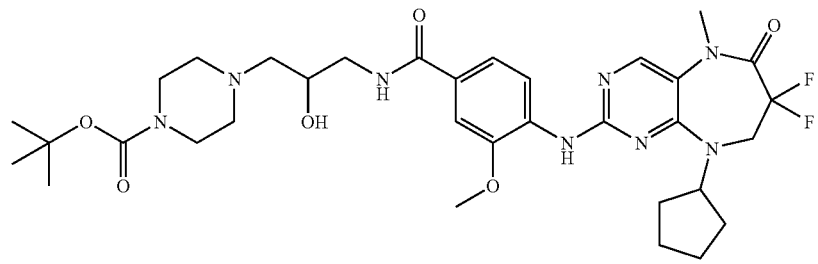

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.031 g (0.12 mmole) 4-(3-amino-2-hydroxy-propyl)-piperazine-1-carboxylic acid tert-butyl ester was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.052 g of 4-{3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-2-hydroxy-propyl}-piperazine-1-carboxylic acid tert-butyl ester (I-120) as a white solid.

Example 121

4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxy-3-piperazin-1-yl-propyl)-3-methoxy-benzamide (I-121)

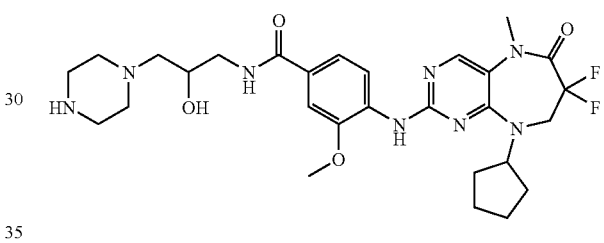

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.019 g (0.12 mmole) 1-amino-3-piperazin-1-yl-propan-2-ol was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.04 g of 4-(9-cyclopentyl-7,7-difluoro-5-methyl-6- oxo-6,7,8,9-tetrahydro-5H-pyrimido[4,5-b][1,4]diazepin-2-ylamino)-N-(2-hydroxy-3-piperazin-1-yl-propyl)-3-methoxy-benzamide (I-121) as a white solid.

Example 122

N-(1-benzyl-piperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-122)

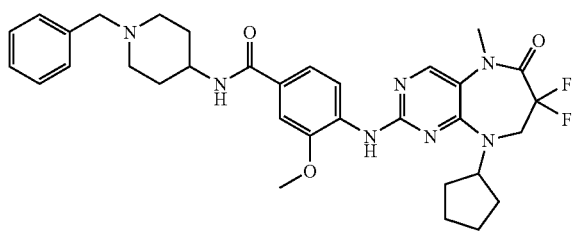

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.029 g (0.15 mmole) 1-benzyl-piperidin-4-ylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.051 g of N-(1-benzyl-piperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide (I-122) as a white solid.

Example 123

4-(9-cyclopentyl-7,7-difluoro-5-methyl-6-oxo-6,7,8,9-tetrahydro-5H-pyrimido[4,5-b][1,4]diazepin-2-ylamino)-N-(3-diethylamino-propyl)-3-methoxy-benzamide (I-123)

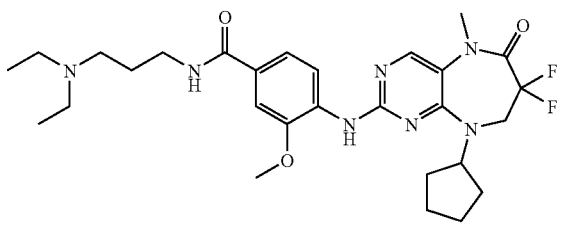

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.02 g (0.15 mmole) N,N-diethylpropane-1,3-diamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.041 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-diethylamino-propyl)-3-methoxy-benzamide (I-123) as a white solid.

Example 124

4-(9-cyclopentyl-7,7-difluoro-5-methyl-6-oxo-3,5,6,7,8,9-hexahydro-2H-pyrimido[4,5-b][1,4]diazepin-2-ylamino)-3-methoxy-N-(tetrahydro-pyran-4-yl)-benzamide (I-124)

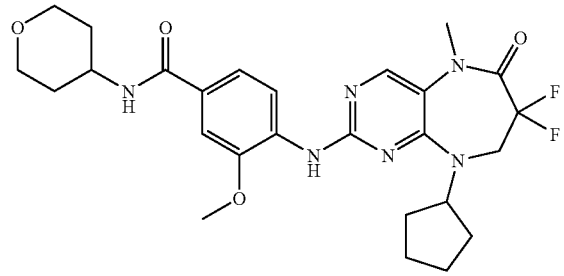

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.015 g (0.15 mmole) tetrahydro-pyran-4-ylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.04 g of 4-(9-cyclopentyl-7,7-difluoro-5-methyl-6-oxo-3,5,6,7,8,9-hexahydro-2H-pyrimido[4,5-b][1,4]diazepin-2-ylamino)-3-methoxy-N-(tetrahydro-pyran-4-yl)-benzamide (I-124) as a white solid.

Example 125

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N,N-dimethyl-benzamide
(I-125)

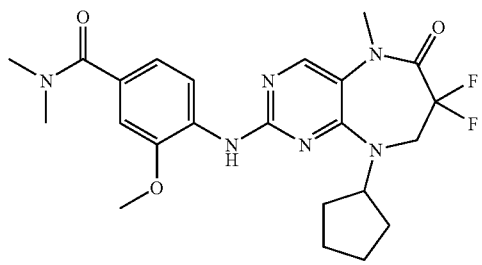

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.007 g (0.15 mmole) dimethylamine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.041 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N,N-dimethyl-benzamide (I-125) as a white solid.

Example 126

9-cyclopentyl-7,7-difluoro-2-[2-methoxy-4-(piperidine-1-carbonyl)-phenylamino]-5-methyl-5,7,8,9-tetrahydro-pyrimido[4,5-b][1,4]diazepin-6-one
(I-126)

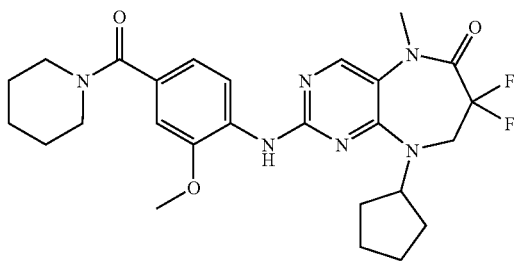

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.013 g (0.15 mmole) piperidine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.042 g of 9-cyclopentyl-7,7-difluoro-2-[2-methoxy-4-(piperidine-1-carbonyl)-phenylamino]-5-methyl-5,7,8,9-tetrahydro-pyrimido[4,5-b][1,4]diazepin-6-one (I-126) as a white solid.

Example 127

9-cyclopentyl-7,7-difluoro-2-[2-methoxy-4-(morpholine-4-carbonyl)-phenylamino]-5-methyl-5,7,8,9-tetrahydro-pyrimido[4,5-b][1,4]diazepin-6-one
(I-127)

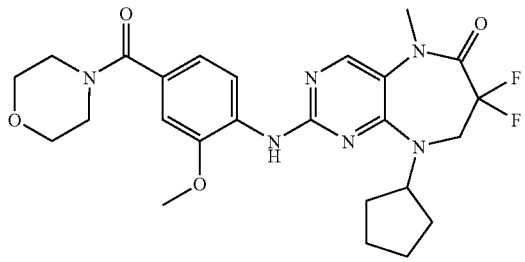

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.013 g (0.15 mmole) morpholine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.045 g of 9-cyclopentyl-7,7-difluoro-2-[2-methoxy-4-(morpholine-4-carbonyl)-phenylamino]-5-methyl-5,7,8,9-tetrahydro-pyrimido[4,5-b][1,4]diazepin-6-one (I-127) as a white solid.

Example 128

9-cyclopentyl-7,7-difluoro-2-[2-methoxy-4-(4-methyl-piperazine-1-carbonyl)-phenylamino]-5-methyl-5,7,8,9-tetrahydro-pyrimido[4,5-b][1,4]diazepin-6-one (I-128)

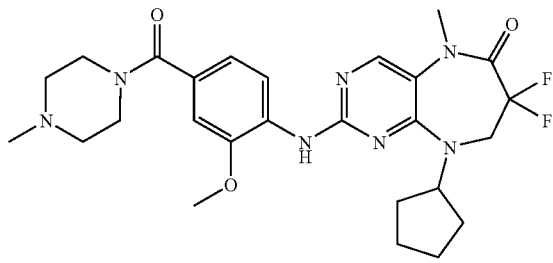

A mixture of 0.045 g (0.1 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxybenzoic acid (I-22), 0.042 g (0.110 mmole) of 1-[bis(dimethylamino)methylene]-1H-1,2,3-triazolo[4,5-b]pyridinium-3-oxide hexafluorophosphate, 0.052 ml (0.300 mmole) of ethyldiisopropyl amine and 1.0 mL of dimethylformamide was stirred for 5 minutes and then 0.015 g (0.15 mmole) 1-methyl-piperazine was added. The mixture was stirred for 3 hours, then diluted with 10 mL of water plus 2 mL of saturated aqueous sodium bicarbonate and then extracted 3 times with 10 mL of ethyl acetate. The combined extracts were washed with brine, dried over anhydrous magnesium sulfate, filtered and concentrated under reduced pressure. The residue was purified by reverse phase silica gel chromatography, eluting with water-acetonitrile (gradient, 0:100-80:20) to give 0.043 g of 9-cyclopentyl-7,7-difluoro-2-[2-methoxy-4-(4-methyl-piperazine-1-carbonyl)-phenylamino]-5-methyl-5,7,8,9-tetrahydro-pyrimido[4,5-b][1,4]diazepin-6-one (I-128) as a white solid.

Example 129

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-4-yl-benzamide (I-129)

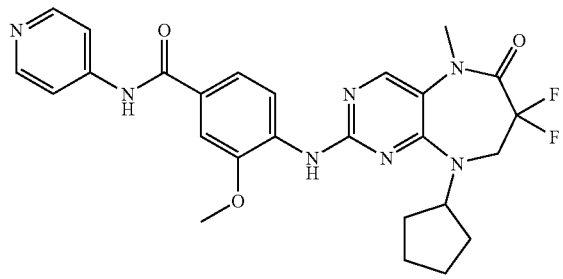

A mixture of 0.050 g (0.11 mmole) of 4-(9-cyclopentyl-7,7-difluoro-5-methyl-6-oxo-6,7,8,9-tetrahydro-5H-pyrimido[4,5-b][1,4]diazepin-2-yl-amino)-3-methoxy-benzoic acid (I-22), 0.048 g (0.12 mmole) of N-[(dimethylamino)-1H-1,2,3-triazolo[4,5-b]pyridine-1-ylmethylene]-N-methylmethanaminiumhexafluorophosphate N-oxide, 0.037 g (0.28 mmole) of ethyldiisopropyl amine, 0.016 g (0.17 mmole) of pyridine-4-ylamine and 0.5 ml of dichloromethane was stirred for 2 hours and then concentrated under reduced pressure. The residue was dissolved in 0.5 ml of methanol, and then precipitated by the addition of water. The residue was washed three times with water and then purified by chromatography on reverse phase silica gel, eluting with acetonitrile-water to give 0.01 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-4-yl-benzamide (I-129).

Example 130

4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-3-yl-benzamide (I-130)

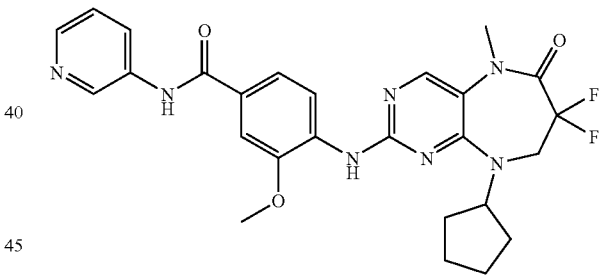

A mixture of 0.050 g (0.11 mmole) of 4-(9-cyclopentyl-7,7-difluoro-5-methyl-6-oxo-6,7,8,9-tetrahydro-5H-pyrimido[4,5-b][1,4]diazepin-2-yl-amino)-3-methoxy-benzoic acid (I-22), 0.048 g (0.12 mmole) of N-[(dimethylamino)-1H-1,2,3-triazolo[4,5-b]pyridine-1-ylmethylene]-N-methylmethanaminiumhexafluorophosphate N-oxide, 0.037 g (0.28 mmole) of ethyldiisopropyl amine, 0.016 g (0.17 mmole) of pyridine-4-ylamine and 0.5 ml of dichloromethane was stirred for 2 hours and then concentrated under reduced pressure. The residue was dissolved in 0.5 ml of methanol, and then precipitated by the addition of water. The residue was washed three times with water and then purified by chromatography on reverse phase silica gel, eluting with acetonitrile-water to give 0.01 g of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-3-yl-benzamide (I-130)

Example 131

4-(9-cyclopentyl-7,7-difluoro-6-oxo-6,7,8,9-tetrahydro-5H-pyrimido[4,5-b][1,4]diazepin-2-ylamino)-benzoic acid (I-131)

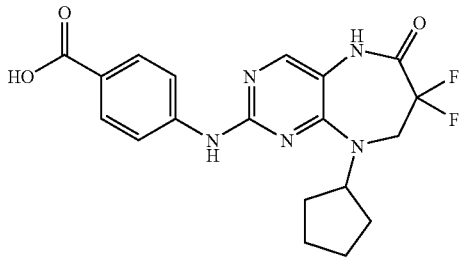

A mixture of 0.20 g (0.66 mmole) of 2-chloro-9-cyclopentyl-7,7-difluoro-5,7,8,9-tetrahydro-pyrimido[4,5-b][1,4]diazepin-6-one (VI-20) and 0.11 g (0.79 mmole) of 4-aminobenzoic acid in a 1:4 mixture of 5 mL of ethanol and 1M hydrochloric acid was heated at 100 degrees for 18 hours. After cooling, the precipitate was collected by filtration, washed with water and dried to give 0.21 g of 4-(9-cyclopentyl-7,7-difluoro-6-oxo-6,7,8,9-tetrahydro-5H-pyrimido[4,5-b][1,4]diazepin-2-ylamino)-benzoic acid (I-131).

Example 132

4-(9-cyclopentyl-7,7-difluoro-6-oxo-6,7,8,9-tetrahydro-5H-pyrimido[4,5-b][1,4]diazepin-2-ylamino)-benzamide (I-132)

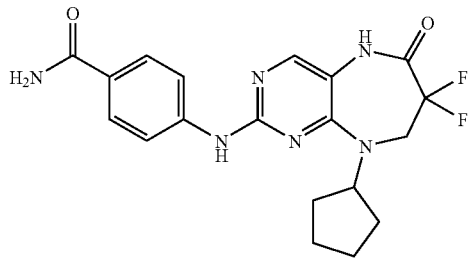

To a mixture of 0.05 g (0.12 mmole) of 4-(9-cyclopentyl-7,7-difluoro-6-oxo-6,7,8,9-tetrahydro-5H-pyrimido[4,5-b][1,4]diazepin-2-ylamino)-benzoic acid (I-131) and 0.06 g (0.15 mmole) of 1-[bis(dimethylamino)methylene]-1H-1,2,3-triazolo[4,5-b]pyridinium-3-oxide hexafluorophosphate and 2 mL of dimethylformamide was added 0.03 mL (0.186 mmole) of diisopropylethylamine. After stirring at room temperature for 30 minutes, 0.01 g (0.186 mmole) of ammonium chloride was then added. The mixture was stirred at room temperature for 18 hours and then diluted with ethyl acetate and water. The aqueous phase was extracted twice with ethyl acetate, and the combined organic layers washed with water, then brine, dried over anhydrous magnesium sulfate, filtered and concentrated under reduced pressure. The residue was triturated with hot methanol to give 0.01 g of 4-(9-cyclopentyl-7,7-difluoro-6-oxo-6,7,8,9-tetrahydro-5H-pyrimido[4,5-b][1,4]diazepin-2-ylamino)-benzamide (I-132).

Example 133

4-(9-cyclopentyl-7,7-difluoro-6-oxo-6,7,8,9-tetrahydro-5H-pyrimido[4,5-b][1,4]diazepin-2-ylamino)-N-methyl-benzamide (I-133)

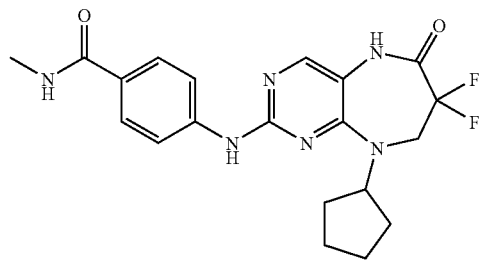

To a mixture of 0.075 g (0.19 mmole) of 4-(9-cyclopentyl-7,7-difluoro-6-oxo-6,7,8,9-tetrahydro-5H-pyrimido[4,5-b][1,4]diazepin-2-ylamino)-benzoic acid (I-131) and 0.09 g (0.24 mmole) of 1-[bis(dimethylamino)methylene]-1H-1,2,3-triazolo[4,5-b]pyridinium-3-oxide hexafluorophosphate and 2 mL of dimethylformamide was added 0.06 mL (0.37 mmole) of diisopropylethylamine. The mixture was stirred for 30 minutes and then 0.14 mL (0.28 mmole) of 2M methylamine in tetrahydrofuran was added. The mixture was stirred at room temperature for 18 hours. The mixture was diluted with ethyl acetate and water and the aqueous phase was extracted twice with ethyl acetate. The combined organic layers were washed with water, then brine, dried over anhydrous magnesium sulfate, filtered and concentrated under reduced pressure. The residue was purified by silica gel chromatography, eluting with ethyl acetate to give 0.015 g of 4-(9-cyclopentyl-7,7-difluoro-6-oxo-6,7,8,9-tetrahydro-5H-pyrimido[4,5-b][1,4]diazepin-2-ylamino)-N-methyl-benzamide (I-133).

Example 134

4-(9-cyclopentyl-7,7-difluoro-6-oxo-6,7,8,9-tetrahydro-5H-pyrimido[4,5-b][1,4]diazepin-2-ylamino)-N-(1-methyl-piperidin-4-yl)-benzamide (I-134)

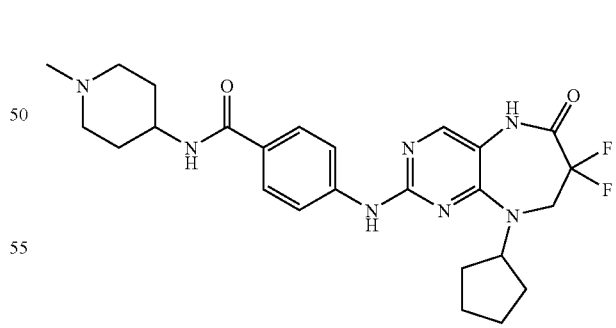

A mixture of 0.05 g (0.17 mmole) of 2-chloro-9-cyclopentyl-7,7-difluoro-5,7,8,9-tetrahydro-pyrimido[4,5-b][1,4]diazepin-6-one (VI-20), 0.05 g (0.20 mmole) of 4-amino-N-(1-methyl-piperidin-4-yl)-benzamide and 0.05 g (0.25 mmole) of p-toluenesulfonic acid monohydrate in 4.0 mL of 2-propanol was heated at 160 degrees for 2 hours in a microwave reactor. The reaction mixture was cooled and then concentrated under reduced pressure. The residue was diluted with dichloromethane and saturated aqueous sodium bicarbonate solution. The precipitate was collected by filtration, washed with water and dried to give 0.030 g of 4-(9-cyclopentyl-7,7-difluoro-6-oxo-6,7,8,9-tetrahydro-5H-pyrimido[4,5-b][1,4]diazepin-2-ylamino)-N-(1-methyl-piperidin-4-yl)-benzamide (I-134).

Example 135

4-(9-cyclopentyl-7,7-difluoro-6-oxo-6,7,8,9-tetrahydro-5H-pyrimido[4,5-b][1,4]diazepin-2-yl-amino)-N-(3-dimethyl-amino-propyl)-benzamide (I-135)

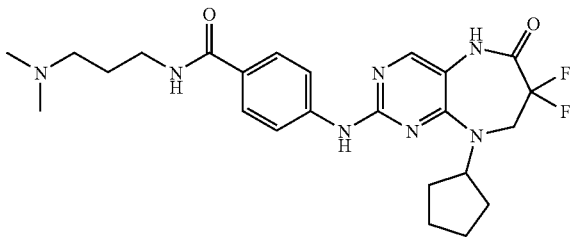

A mixture of 0.05 g (0.17 mmole) of 2-chloro-9-cyclopentyl-7,7-difluoro-5,7,8,9-tetrahydro-pyrimido[4,5-b][1,4]diazepin-6-one (VI-20), 0.04 g (0.20 mmole) of N-(3-dimethylamino-propyl)-4-amino-benzamide and 0.05 g (0.25 mmole) of p-toluenesulfonic acid monohydrate in 4.0 mL of 2-propanol was heated at 160 degrees for 2 hours in microwave. N-(3-dimethylamino-propyl)-4-amino-benzamide (0.02 g) and p-toluenesulfonic acid monohydrate (0.03 g) were added. The reaction mixture was heated at 160 degrees for another 1 hour. The mixture was then concentrated. The residue was diluted with dichloromethane and washed twice with saturated aqueous sodium bicarbonate solution. The aqueous phase was extracted twice with dichloromethane, and the combined organic phases washed with brine, dried over anhydrous magnesium sulfate, filtered and concentrated under reduced pressure. The residue was washed with hot methanol and dried to give 0.012 g of 4-(9-cyclopentyl-7,7-difluoro-6-oxo-6,7,8,9-tetrahydro-5H-pyrimido[4,5-b][1,4]diazepin-2-ylamino)-N-(3-dimethyl-amino-propyl)-benzamide (I-135).

Example 136

4-(9-cyclopentyl-7,7-difluoro-6-oxo-6,7,8,9-tetrahydro-5H-pyrimido[4,5-b][1,4]diazepin-2-ylamino)-N-(tetrahydro-pyran-4-yl)-benzamide (I-136)

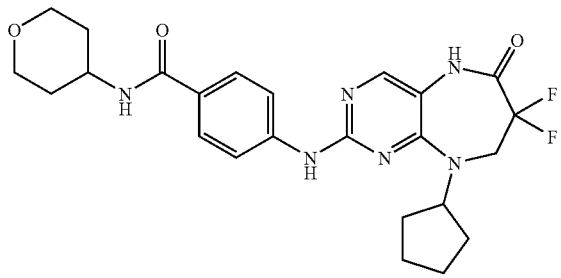

A mixture of 0.05 g (0.17 mmole) of 2-chloro-9-cyclopentyl-7,7-difluoro-5,7,8,9-tetrahydro-pyrimido[4,5-b][1,4]diazepin-6-one (VI-20), 0.04 g (0.20 mmole) of 4-amino-N-(tetrahydro-pyran-4-yl)-benzamide and 0.05 g (0.25 mmole) of p-toluenesulfonic acid monohydrate in 4.0 mL of 2-propanol was heated at 160 degrees for 2 hours in a microwave reactor. The cooled mixture was then concentrated under reduced pressure. The residue was diluted with dichloromethane and washed twice with saturated aqueous sodium bicarbonate solution. The aqueous phase was extracted with dichloromethane, and the combined organic layers washed with brine, dried over anhydrous magnesium sulfate, filtered and concentrated under reduced pressure. The residue was washed with water and dried to give 0.070 g of 4-(9-cyclopentyl-7,7-difluoro-6-oxo-6,7,8,9-tetrahydro-5H-pyrimido[4,5-b][1,4]diazepin-2-ylamino)-N-(tetrahydro-pyran-4-yl)-benzamide (I-136).

Example 137

4-(9-cyclopentyl-7,7-difluoro-6-oxo-6,7,8,9-tetrahydro-5H-pyrimido[4,5-b][1,4]diazepin-2-ylamino)-3-methoxy-N-(1-methyl-piperidin-4-yl)-benzamide (I-137)

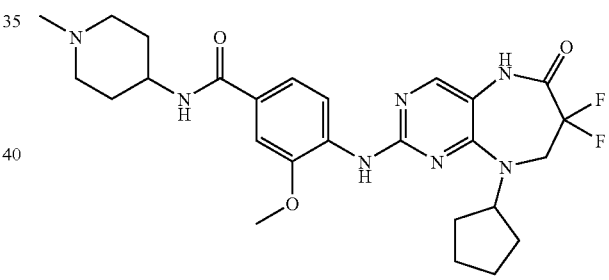

A mixture of 0.040 g (0.1 mmole) of 2-chloro-9-cyclopentyl-7,7-difluoro-5,7,8,9-tetrahydro-pyrimido[4,5-b][1,4]diazepin-6-one (VI-20), 0.029 g (0.11 mmole) of 4-amino-3-methoxy-N-(1-methyl-piperidin-4-yl)-benzamide, 0.030 g (0.15 mmole) of p-toluenesulfonic acid monohydrate and 2 mL of isopropanol was stirred in a pressure tube at 140 degrees overnight. The mixture was cooled, diluted with dichloromethane and saturated sodium carbonate and extracted twice with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (100:0-50:50) gave 0.033 g of give 4-(9-cyclopentyl-7,7-difluoro-6-oxo-6,7,8,9-tetrahydro-5H-pyrimido[4,5-b][1,4]diazepin-2-ylamino)-3-methoxy-N-(1-methyl-piperidin-4-yl)-benzamide (I-137) as a white solid.

Example 138

4-(9-cyclopentyl-5-ethyl-7,7-difluoro-6-oxo-6,7,8,9-tetrahydro-5H-pyrimido[4,5-b][1,4]diazepin-2-ylamino)-benzoic acid (I-138)

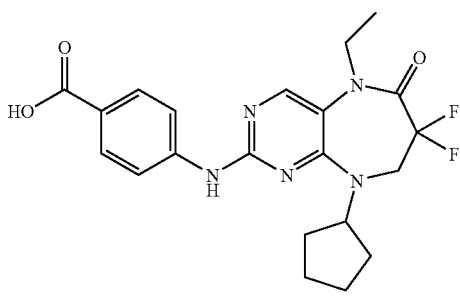

To a stirred solution of 1.0 g (0.0033 mole) of 2-chloro-9-cyclopentyl-7,7-difluoro-5,7,8,9-tetrahydro-pyrimido[4,5-b][1,4]diazepin-6-one (VI-20) in 10 mL of dimethylformamide was added 3.23 g (0.0099 mole) of cesium carbonate followed by 0.8 mL (0.0099 mole) of iodoethane. The mixture was stirred at room temperature for 18 hours, then water was added. After 15 minutes, the mixture was extracted with ethyl acetate. The organic layer was washed with water, 5% aqueous sodium metabisulfite solution and then brine. The aqueous layers were reextracted with ethyl acetate. The combined organic layers were dried over anhydrous magnesium sulfate, filtered, and concentrated under reduced pressure. The residue was recrystallized from hexanes-dichloromethane to give 0.90 g of 2-chloro-9-cyclopentyl-5-ethyl-7,7-difluoro-5,7,8,9-tetrahydro-pyrimido[4,5-b][1,4]diazepin-6-one (VII-138) as white crystals.

A mixture of 0.20 g (0.6 mmole) 2-chloro-9-cyclopentyl-5-ethyl-7,7-difluoro-5,7,8,9-tetrahydro-pyrimido[4,5-b][1,4]diazepin-6-one (VII-138) and 0.12 g (0.91 mmole) of 4-aminobenzoic acid in a 1:4 mixture of 10 mL of ethanol and 1M hydrochloric acid was heated at 100 degrees for 18 hours. After cooling, the precipitate was collected by filtration, washed with water and dried to give 0.19 g of 4-(9-cyclopentyl-5-ethyl-7,7-difluoro-6-oxo-6,7,8,9-tetrahydro-5H-pyrimido[4,5-b][1,4]diazepin-2-ylamino)-benzoic acid (I-138).

Example 139

4-(9-cyclopentyl-5-ethyl-7,7-difluoro-6-oxo-6,7,8,9-tetrahydro-5H-pyrimido[4,5-b][1,4]diazepin-2-ylamino)-benzamide (I-139)

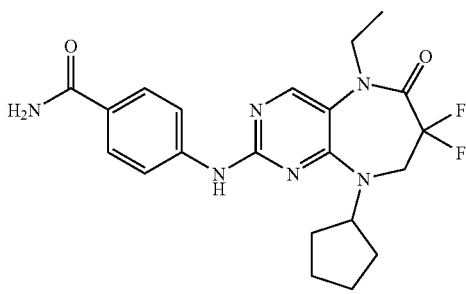

To a mixture of 0.053 g (0.12 mmole) of 4-(9-cyclopentyl-5-ethyl-7,7-difluoro-6-oxo-6,7,8,9-tetrahydro-5H-pyrimido[4,5-b][1,4]diazepin-2-ylamino)-benzoic acid (I-138) and 0.06 g (0.15 mmole) of 1-[bis(dimethylamino)methylene]-1H-1,2,3-triazolo[4,5-b]pyridinium-3-oxide hexafluorophosphate in 2 mL of dimethylformamide was added 0.03 mL (0.186 mmole) of diisopropylethylamine. After stirring at room temperature for 30 minutes 0.01 g (0.186 mmole) of ammonium chloride was added. The mixture was stirred at room temperature for 18 hours and then diluted with ethyl acetate and water. The aqueous phase was extracted twice with ethyl acetate. The combined organic layers were washed with water, brine, dried over anhydrous magnesium sulfate, filtered and concentrated under reduced pressure. The residue was purified by silica gel chromatography eluting with hexanes-ethyl acetate (30:70) to give 0.047 g of 4-(9-cyclopentyl-5-ethyl-7,7-difluoro-6-oxo-6,7,8,9-tetrahydro-5H-pyrimido[4,5-b][1,4]diazepin-2-ylamino)-benzamide (I-139).

Example 140

4-(9-cyclopentyl-5-ethyl-7,7-difluoro-6-oxo-6,7,8,9-tetrahydro-5H-pyrimido[4,5-b][1,4]diazepin-2-ylamino)-N-methyl-benzamide (I-140)

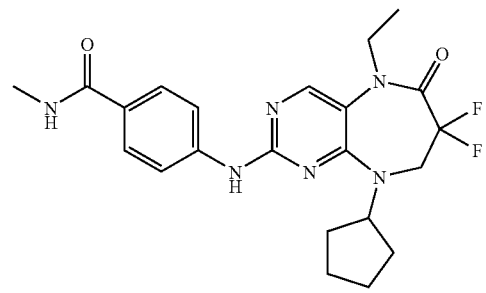

To a mixture of 0.053 g (0.12 mmole) of 4-(9-cyclopentyl-5-ethyl-7,7-difluoro-6-oxo-6,7,8,9-tetrahydro-5H-pyrimido[4,5-b][1,4]diazepin-2-ylamino)-benzoic acid (I-138), 0.06 g (0.15 mmole) of 1-[bis(dimethylamino)methylene]-1H-1,2,3-triazolo[4,5-b]pyridinium-3-oxide hexafluorophosphate and 2 mL of dimethylformamide was added 0.03 mL (0.186 mmole) of diisopropylethylamine. After stirring at room temperature for 30 minutes, a solution of 0.09 mL (0.186 mmole) of 2M methylamine in tetrahydrofuran was added. The mixture was stirred at room temperature for 18 hours and then diluted with ethyl acetate and water. The aqueous phase was extracted twice with ethyl acetate. The combined organic layers were washed with water, brine, dried over anhydrous magnesium sulfate, filtered and concentrated under reduced pressure. The residue was purified by silica gel chromatography eluting with hexanes-ethyl acetate (30:70) to give 0.036 g of 4-(9-cyclopentyl-5-ethyl-7,7-difluoro-6-oxo-6,7,8,9-tetrahydro-5H-pyrimido[4,5-b][1,4]diazepin-2-ylamino)-N-methyl-benzamide (I-140).

Example 141

4-(9-cyclopentyl-5-ethyl-7,7-difluoro-6-oxo-6,7,8,9-tetrahydro-5H-pyrimido[4,5-b][1,4]diazepin-2-ylamino)-N-(1-methyl-piperidin-4-yl)-benzamide (I-141)

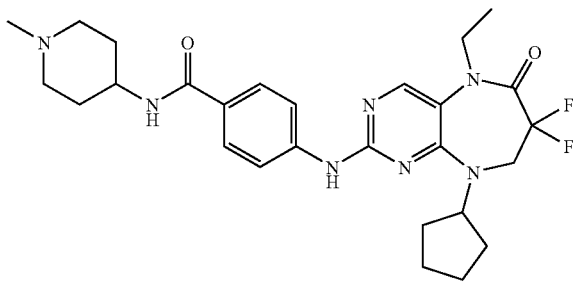

A mixture of 0.05 g (0.15 mmole) of 2-chloro-9-cyclopentyl-5-ethyl-7,7-difluoro-5,7,8,9-tetrahydro-pyrimido[4,5-b][1,4]diazepin-6-one (VII-138), 0.04 g (0.18 mmole) of 4-amino-N-(1-methyl-piperidin-4-yl)-benzamide, 0.04 g (0.23 mmole) of p-toluenesulfonic acid monohydrate and 4.0 mL of 2-propanol was heated at 160 degrees for 2 hours in a microwave reactor. The cooled reaction mixture was concentrated under reduced pressure. The residue was diluted with dichloromethane and washed twice with saturated aqueous sodium bicarbonate solution. The aqueous phases were extracted with dichloromethane, and the combined organic layers washed with brine, dried over anhydrous magnesium sulfate, filtered and concentrated under reduced pressure. The residue was purified by silica gel chromatography eluting with methanol-dichloromethane (gradient, 0:100-25:75) to give 0.041 g of 4-(9-cyclopentyl-5-ethyl-7,7-difluoro-6-oxo-6,7,8,9-tetrahydro-5H-pyrimido[4,5-b][1,4]diazepin-2-ylamino)-N-(1-methyl-piperidin-4-yl)-benzamide (I-141).

Example 142

4-(9-cyclopentyl-5-ethyl-7,7-difluoro-6-oxo-6,7,8,9-tetrahydro-5H-pyrimido[4,5-b][1,4]diazepin-2-ylamino)-N-(3-dimethyl-amino-propyl)-benzamide (I-142)

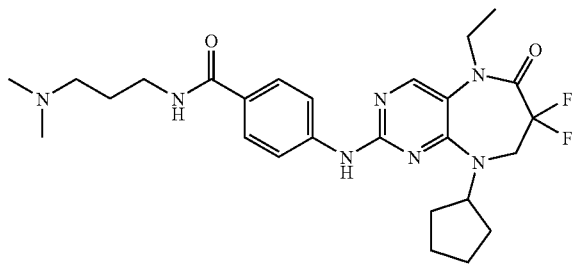

A mixture of 0.05 g (0.15 mmole) of 2-chloro-9-cyclopentyl-5-ethyl-7,7-difluoro-5,7,8,9-tetrahydro-pyrimido[4,5-b][1,4]diazepin-6-one (VII-138), 0.04 g (0.18 mmole) of N-(3-dimethylamino-propyl)-4-amino-benzamide, 0.04 g (0.23 mmole) of p-toluenesulfonic acid monohydrate and 4.0 mL of 2-propanol was heated at 160 degrees for 2 hours in a microwave reactor. The cooled mixture was concentrated under reduced pressure. The residue was diluted with dichloromethane and washed twice with saturated aqueous sodium bicarbonate solution. The aqueous phases were extracted with dichloromethane, and the combined organic layers washed with brine, dried over anhydrous magnesium sulfate, filtered and concentrated under reduced pressure. The residue was purified by silica gel chromatography eluting with methanol-dichloromethane (gradient, 0:100-25:75) to give 0.015 g of 4-(9-cyclopentyl-5-ethyl-7,7-difluoro-6-oxo-6,7,8,9-tetrahydro-5H-pyrimido[4,5-b][1,4]diazepin-2-ylamino)-N-(3-dimethyl-amino-propyl)-benzamide (I-142).

Example 143

4-(9-cyclopentyl-5-ethyl-7,7-difluoro-6-oxo-6,7,8,9-tetrahydro-5H-pyrimido[4,5-b][1,4]diazepin-2-ylamino)-N-(tetrahydro-pyran-4-yl)-benzamide (I-143)

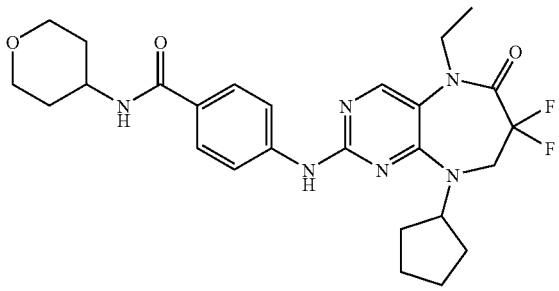

A mixture of 0.05 g (0.15 mmole) of 2-chloro-9-cyclopentyl-5-ethyl-7,7-difluoro-5,7,8,9-tetrahydro-pyrimido[4,5-b][1,4]diazepin-6-one (VII-138), 0.04 g (0.18 mmole) of 4-amino-N-(tetrahydro-pyran-4-yl)-benzamide, 0.04 g (0.23 mmole) of p-toluenesulfonic acid monohydrate and 4.0 mL of 2-propanol was heated at 160 degrees for 2 hours in a microwave reactor. The cooled mixture was concentrated under reduced pressure. The residue was diluted with dichloromethane and washed twice with saturated aqueous sodium bicarbonate solution. The aqueous phases were extracted with dichloromethane, and the combined organic layers washed with brine, dried over anhydrous magnesium sulfate, filtered and concentrated under reduced pressure. The residue was purified by silica gel chromatography eluting with hexanes-ethyl acetate (30:70), followed by recrystallization from ethyl acetate-hexanes-methanol to give 0.036 g of 4-(9-cyclopentyl-5-ethyl-7,7-difluoro-6-oxo-6,7,8,9-tetrahydro-5H-pyrimido[4,5-b][1,4]diazepin-2-ylamino)-N-(tetrahydro-pyran-4-yl)-benzamide (I-143).

Example 144

4-(9-cyclopentyl-7,7-difluoro-6-oxo-5-propyl-6,7,8,9-tetrahydro-5H-pyrimido[4,5-b][1,4]diazepin-2-ylamino)-benzoic acid (I-144)

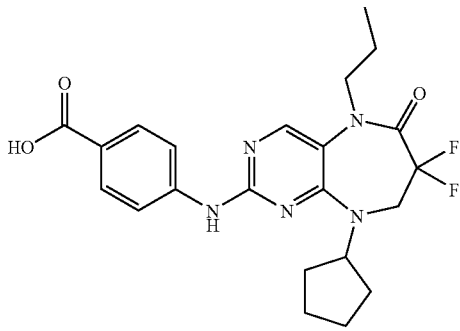

To a stirred solution of 1.0 g (0.0033 mole) of 2-chloro-9-cyclopentyl-7,7-difluoro-5,7,8,9-tetrahydro-pyrimido[4,5-b][1,4]diazepin-6-one (VI-20) and 10 mL of dimethylformamide was added 3.23 g (0.0099 mole) cesium carbonate followed by 0.8 mL (0.0099 mole) of 1-iodopropane. The mixture was stirred at room temperature for 18 hours, then water was added. After 15 minutes, the mixture was extracted with ethyl acetate. The organic layer was washed with water, 5% aqueous sodium metabisulfite solution and then brine. The aqueous layers were reextracted with ethyl acetate. The combined organic layers were dried over anhydrous magnesium sulfate, filtered and concentrated under reduced pressure. The residue was recrystallized from hexanes-dichloromethane to give 1.0 g of 2-Chloro-9-cyclopentyl-7,7-difluoro-5-propyl-5,7,8,9-tetrahydro-pyrimido[4,5-b][1,4]diazepin-6-one (VII-144) as white crystals.

A mixture of 0.20 g (0.58 mmole) of 2-chloro-9-cyclopentyl-7,7-difluoro-5-propyl-5,7,8,9-tetrahydro-pyrimido[4,5-b][1,4]diazepin-6-one (VII-144) and 0.12 g (0.87 mmole) of 4-aminobenzoic acid in a 1:4 mixture of 10 mL of ethanol and 1M hydrochloric acid was heated at 100 degrees for 18 hours. After cooling, the precipitate was collected by filtration, washed with water and dried to give 0.21 g of 4-(9-cyclopentyl-7,7-difluoro-6-oxo-5-propyl-6,7,8,9-tetrahydro-5H-pyrimido[4,5-b][1,4]diazepin-2-ylamino)-benzoic acid (I-144).

Example 145

4-(9-cyclopentyl-7,7-difluoro-6-oxo-5-propyl-6,7,8,9-tetrahydro-5H-pyrimido[4,5-b][1,4]diazepin-2-ylamino)-benzamide (I-145)

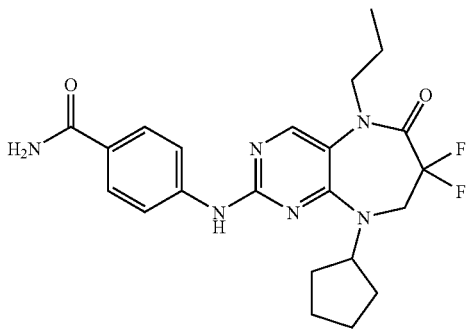

To a mixture of 0.055 g (0.12 mmole) of 4-(9-cyclopentyl-5-7,7-difluoro-6-oxo-5-propyl-6,7,8,9-tetrahydro-5H-pyrimido[4,5-b][1,4]diazepin-2-ylamino)-benzoic acid (I-144), 0.06 g (0.15 mmole) of 1-[bis(dimethylamino)methylene]-1H-1,2,3-triazolo[4,5-b]pyridinium-3-oxide hexafluorophosphate and 2 mL of dimethylformamide was added 0.03 mL (0.186 mmole) of diisopropylethylamine. After stirring at room temperature for 30 minutes, 0.01 g (0.186 mmole) of ammonium chloride was then added. The mixture was stirred at room temperature for 18 hours. The mixture was diluted with ethyl acetate and water. The aqueous phase was extracted twice with ethyl acetate, and the combined organic layers were washed with water, brine, dried over anhydrous magnesium sulfate, filtered and concentrated under reduced pressure. The residue was purified by silica gel chromatography eluting with hexanes-ethyl acetate (30:70) to give 0.040 g of 4-(9-cyclopentyl-7,7-difluoro-6-oxo-5-propyl-6,7,8,9-tetrahydro-5H-pyrimido[4,5-b][1,4]diazepin-2-ylamino)-benzamide (I-145).

Example 146

4-(9-cyclopentyl-7,7-difluoro-6-oxo-5-propyl-6,7,8,9-tetrahydro-5H-pyrimido[4,5-b][1,4]diazepin-2-ylamino)-N-methyl-benzamide (I-146)

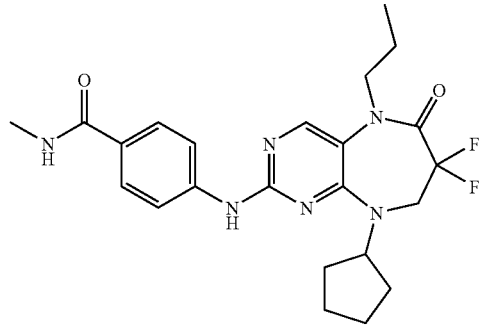

To a mixture of 0.055 g (0.12 mmole) of 4-(9-cyclopentyl-7,7-difluoro-6-oxo-5-propyl-6,7,8,9-tetrahydro-5H-pyrimido[4,5-b][1,4]diazepin-2-ylamino)-benzoic acid (I-144) and 0.06 g (0.15 mmole) of 1-[bis(dimethylamino)methylene]-1H-1,2,3-triazolo[4,5-b]pyridinium-3-oxide hexafluorophosphate and 2 mL of dimethylformamide was added 0.03 mL (0.186 mmole) of diisopropylethylamine. After stirring at room temperature for 30 minutes 0.09 mL (0.186 mmole) of 2M methylamine in tetrahydrofuran was then added. The mixture was stirred at room temperature for 18 hours. The mixture was diluted with ethyl acetate and water. The aqueous phase was twice extracted with ethyl acetate, and the combined organic layers were washed with water, brine, dried anhydrous magnesium sulfate, filtered and concentrated under reduced pressure. The residue was purified by silica gel chromatography eluting with hexanes-ethyl acetate (30:70) to give 0.029 g of 4-(9-cyclopentyl-7,7-difluoro-6-oxo-5-propyl-6,7,8,9-tetrahydro-5H-pyrimido[4,5-b][1,4]diazepin-2-ylamino)-N-methyl-benzamide (I-146).

Example 147

4-(9-cyclopentyl-7,7-difluoro-6-oxo-5-propyl-6,7,8,9-tetrahydro-5H-pyrimido[4,5-b][1,4]diazepin-2-ylamino)-N-(1-methyl-piperidin-4-yl)-benzamide
(I-147)

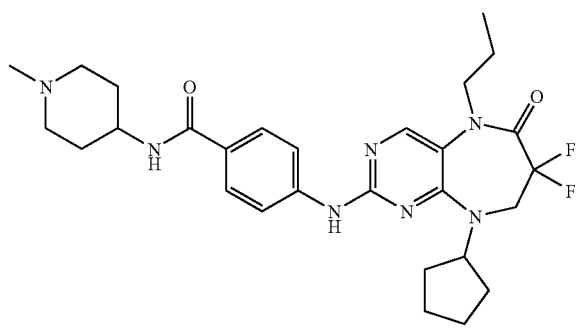

A mixture of 0.05 g (0.15 mmole) of 2-chloro-9-cyclopentyl-7,7-difluoro-5-propyl-5,7,8,9-tetrahydro-pyrimido[4,5-b][1,4]diazepin-6-one (VII-144), 0.05 g (0.17 mmole) of 4-amino-N-(1-methyl-piperidin-4-yl)-benzamide, 0.04 g (0.22 mmole) of p-toluenesulfonic acid monohydrate and 4.0 mL of 2-propanol was heated at 160 degrees for 2 hours in a microwave reactor. The cooled mixture was concentrated under reduced pressure. The residue was diluted with dichloromethane and washed twice with saturated aqueous sodium bicarbonate solution. The aqueous phases were extracted with dichloromethane, and the combined organic layers washed with brine, dried over anhydrous magnesium sulfate, filtered and concentrated under reduced pressure. The residue was purified by silica gel chromatography eluting with methanol-dichloromethane (gradient, 0:100-25:75), to give 0.051 g of 4-(9-cyclopentyl-7,7-difluoro-6-oxo-5-propyl-6,7,8,9-tetrahydro-5H-pyrimido[4,5-b][1,4]diazepin-2-ylamino)-N-(1-methyl-piperidin-4-yl)-benzamide (I-147).

Example 148

4-(9-cyclopentyl-7,7-difluoro-6-oxo-5-propyl-6,7,8,9-tetrahydro-5H-pyrimido[4,5-b][1,4]diazepin-2-ylamino)-N-(3-dimethyl-amino-propyl)-benzamide
(I-148)

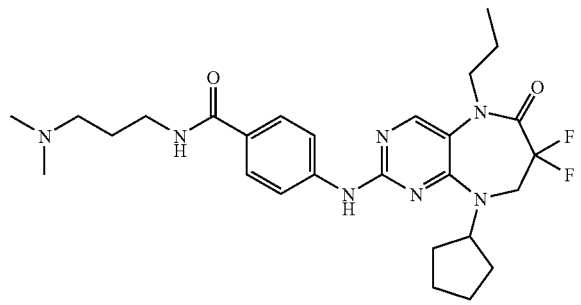

A mixture of 0.05 g (0.15 mmole) of 2-chloro-9-cyclopentyl-7,7-difluoro-5-propyl-5,7,8,9-tetrahydro-pyrimido[4,5-b][1,4]diazepin-6-one (VII-144), 0.04 g (0.17 mmole) of N-(3-dimethylamino-propyl)-4-amino-benzamide, 0.04 g (0.22 mmole) p-toluenesulfonic acid monohydrate and 4.0 mL of 2-propanol was heated at 160 degrees for 2 hours in a microwave reactor. The cooled mixture was concentrated under reduced pressure. The residue was diluted with dichloromethane and washed twice with saturated aqueous sodium bicarbonate solution. The aqueous phases were extracted with dichloromethane, and the combined organic layers washed with brine, dried over anhydrous magnesium sulfate, filtered and concentrated under reduced pressure. The residue was purified by silica gel chromatography eluting with methanol-dichloromethane (gradient, 0:100-25:75), to give 0.020 g of 4-(9-cyclopentyl-7,7-difluoro-6-oxo-5-propyl-6,7,8,9-tetrahydro-5H-pyrimido[4,5-b][1,4]diazepin-2-ylamino)-N-(3-dimethyl-amino-propyl)-benzamide (I-148).

Example 149

4-(9-cyclopentyl-7,7-difluoro-6-oxo-5-propyl-6,7,8,9-tetrahydro-5H-pyrimido[4,5-b][1,4]diazepin-2-ylamino)-N-(tetrahydro-pyran-4-yl)-benzamide
(I-149)

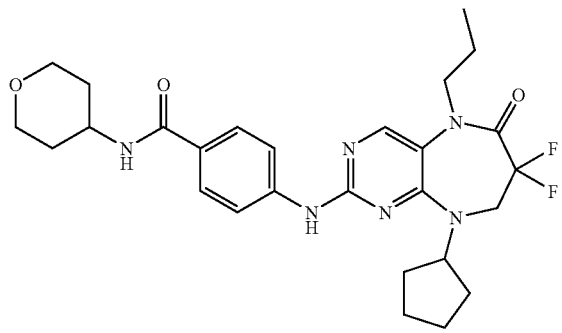

A mixture of 0.05 g (0.15 mmole) of 2-chloro-9-cyclopentyl-7,7-difluoro-5-propyl-5,7,8,9-tetrahydro-pyrimido[4,5-b][1,4]diazepin-6-one (VII-144), 0.04 g (0.17 mmole) of 4-amino-N-(tetrahydro-pyran-4-yl)-benzamide, 0.04 g (0.22 mmole) of p-toluenesulfonic acid monohydrate and 4.0 mL of 2-propanol was heated at 160 degrees for 2 hours in a microwave reactor. The cooled mixture was concentrated under reduced pressure. The residue was diluted with dichloromethane and washed twice with saturated aqueous sodium bicarbonate solution. The aqueous phases were extracted with dichloromethane, and the combined organic layers washed with brine, dried over anhydrous magnesium sulfate, filtered and concentrated under reduced pressure. The residue was purified by silica gel chromatography eluting with methanol-dichloromethane (gradient, 0:100-25:75), to give 0.020 g of 4-(9-cyclopentyl-7,7-difluoro-6-oxo-5-propyl-6,7,8,9-tetrahydro-5H-pyrimido[4,5-b][1,4]diazepin-2-ylamino)-N-(tetrahydro-pyran-4-yl)-benzamide (I-149).

Example 150

4-[9-cyclopentyl-7,7-difluoro-6-oxo-5-(2,2,2-trifluoro-ethyl)-6,7,8,9-tetrahydro-5H-pyrimido[4,5-b][1,4]diazepin-2-ylamino]-3-methoxy-N-(1-methyl-piperidin-4-yl)-benzamide (I-150)

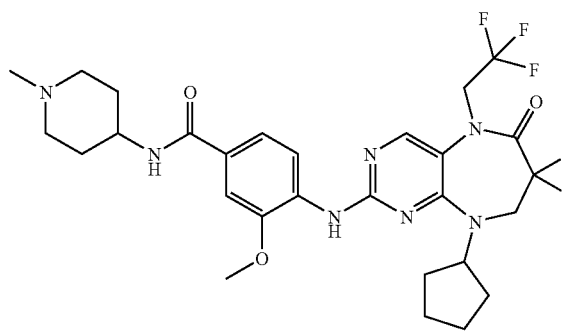

To a suspension of 0.50 g (0.0017 mole) of 2-chloro-9-cyclopentyl-7,7-difluoro-5,7,8,9-tetrahydro-pyrimido[4,5-b][1,4]diazepin-6-one (VI-20), 0.50 g (0.0034 mole) of potassium carbonate and 10 mL of tetrahydrofuran was added 0.46 g (0.0020 mole) of trifluoro-methanesulfonic acid 2,2,2-trifluoro-ethyl ester. After stirring at 75 degrees for four hours, the mixture was cooled and water was added. The mixture was extracted with ethyl acetate twice. The combined organic layers were washed three times with sodium carbonate, three times with brine, dried over anhydrous sodium sulfate, filtered and concentrated under reduced pressure. Purification by silica gel chromatography, eluting with ethyl acetate-hexane (gradient, 100:0-30:70) gave 0.25 g of 2-chloro-9-cyclopentyl-7,7-difluoro-5-(2,2,2-trifluoro-ethyl)-5,7,8,9-tetrahydro-pyrimido[4,5-b][1,4]diazepin-6-one (VII-150)

A mixture of 0.10 g (0.26 mmole) of 2-chloro-9-cyclopentyl-7,7-difluoro-5-(2,2,2-trifluoro-ethyl)-5,7,8,9-tetrahydro-pyrimido[4,5-b][1,4]diazepin-6-one (VII-150), 0.072 g (0.27 mmole) of 4-amino-3-methoxy-N-(1-methyl-piperidin-4-yl)-benzamide, 0.074 g (0.39 mmole) of p-toluenesulfonic acid monohydrate and 4 mL of isopropanol was heated in a pressure tube at 140 degrees overnight. After cooling, dichloromethane and saturated sodium carbonate were added. The mixture was extracted with dichloromethane twice. The combined organic layers were washed three times with sodium carbonate, three times with brine, dried over anhydrous sodium sulfate, filtered and concentrated under reduced pressure. Purification by silica gel chromatography, eluting with dichloromethane-methanol (100:0-70:30) gave 0.075 g of 4-[9-cyclopentyl-7,7-difluoro-6-oxo-5-(2,2,2-trifluoro-ethyl)-6,7,8,9-tetrahydro-5H-pyrimido[4,5-b][1,4]diazepin-2-ylamino]-3-methoxy-N-(1-methyl-piperidin-4-yl)-benzamide (I-150) as a white solid.

Example 151

4-(9-cyclopentyl-7,7-difluoro-6-oxo-6,7,8,9-tetrahydro-5H-pyrimido[4,5-b][1,4]diazepin-2-ylamino)-3-methoxy-benzoic acid (I-151)

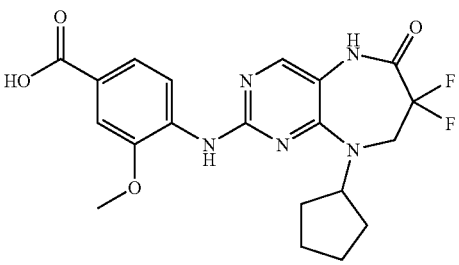

A mixture of 0.30 g (0.99 mmole) of 2-chloro-9-cyclopentyl-7,7-difluoro-5,7,8,9-tetrahydro-pyrimido[4,5-b][1,4]diazepin-6-one (VI-20) and 0.20 g (1.19 mmole) of 4-amino-3-methoxy-benzoic acid in a 1:4 mixture of 5 mL of ethanol and 1M hydrochloric acid was heated at 100 degrees for 18 hours. After cooling, the precipitate was collected by filtration, washed with water and dried to give 0.29 g of 4-(9-cyclopentyl-7,7-difluoro-6-oxo-6,7,8,9-tetrahydro-5H-pyrimido[4,5-b][1,4]diazepin-2-ylamino)-3-methoxy-benzoic acid (I-151).

Example 152

4-(9-cyclopentyl-7,7-difluoro-6-oxo-6,7,8,9-tetrahydro-5H-pyrimido[4,5-b][1,4]diazepin-2-ylamino)-3-methoxy-benzamide (I-152)

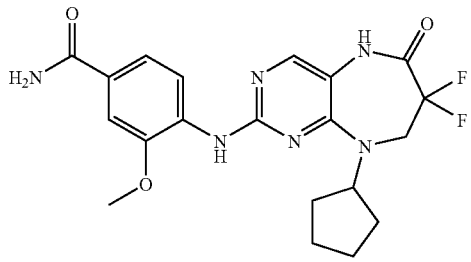

To a mixture of 0.07 g (0.16 mmole) of 4-(9-cyclopentyl-7,7-difluoro-6-oxo-6,7,8,9-tetrahydro-5H-pyrimido[4,5-b][1,4]diazepin-2-ylamino)-3-methoxy-benzoic acid (I-151), 0.07 g (0.19 mmole) of 1-[bis(dimethylamino)methylene]-1H-1,2,3-triazolo[4,5-b]pyridinium-3-oxide hexafluorophosphate and 2 mL of dimethylformamide was added 0.04 mL (0.24 mmole) of diisopropylethylamine. After stirring at room temperature for 30 minutes, 0.013 g (0.24 mmole) of ammonium chloride was added. The mixture was stirred at room temperature for 18 hours. The mixture was diluted with ethyl acetate and water. The aqueous phase was extracted twice with ethyl acetate and the combined organic layers washed with water, then brine, dried over anhydrous magnesium sulfate, filtered and concentrated under reduced pressure. The residue was triturated with hot methanol to give 0.012 g of 4-(9-cyclopentyl-7,7-difluoro-6-oxo-6,7,8,9-tetrahydro-5H-pyrimido[4,5-b][1,4]diazepin-2-ylamino)-3-methoxy-benzamide (I-152).

Example 153

4-(9-cyclopentyl-7,7-difluoro-6-oxo-6,7,8,9-tetrahydro-5H-pyrimido[4,5-b][1,4]diazepin-2-ylamino)-3-methoxy-N-methyl-benzamide (I-153)

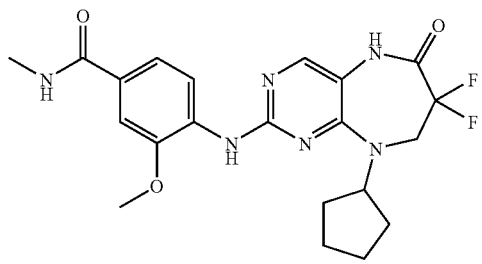

To a mixture of 0.06 g (0.14 mmole) of 4-(9-cyclopentyl-7,7-difluoro-6-oxo-6,7,8,9-tetrahydro-5H-pyrimido[4,5-b][1,4]diazepin-2-ylamino)-3-methoxy-benzoic acid (I-151), 0.08 g (0.21 mmole) of 1-[bis(dimethylamino)methylene]-1H-1,2,3-triazolo[4,5-b]pyridinium-3-oxide hexafluorophosphate and 2 mL of dimethylformamide was added 0.07 mL (0.41 mmole) of diisopropylethylamine. The mixture was stirred at room temperature for 30 minutes. To this was then added 0.21 mL (0.41 mmole) of 2M methylamine in tetrahydrofuran. The mixture was stirred at room temperature for 18 hours and then diluted with ethyl acetate and water. The aqueous phase was extracted twice with ethyl acetate. The combined organic layers were washed with water, then brine, dried over anhydrous magnesium sulfate, filtered and concentrated under reduced pressure. The residue was triturated with hot methanol to give 0.018 g of 4-(9-cyclopentyl-7,7-difluoro-6-oxo-6,7,8,9-tetrahydro-5H-pyrimido[4,5-b][1,4]diazepin-2-ylamino)-3-methoxy-N-methyl-benzamide (I-153).

Example 154

4-(9-cyclopentyl-7,7-difluoro-6-oxo-6,7,8,9-tetrahydro-5H-pyrimido[4,5-b][1,4]diazepin-2-ylamino)-N-(3-dimethylamino-propyl)-3-methoxy-benzamide (I-154)

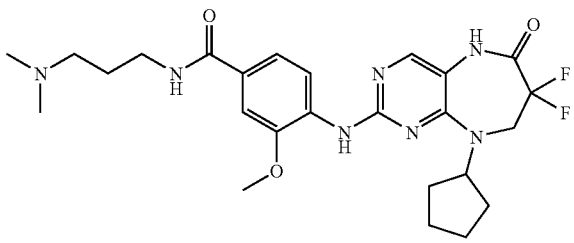

To a mixture of 0.06 g (0.14 mmole) of 4-(9-cyclopentyl-7,7-difluoro-6-oxo-6,7,8,9-tetrahydro-5H-pyrimido[4,5-b][1,4]diazepin-2-ylamino)-3-methoxy-benzoic acid (I-151), 0.08 g (0.21 mmole) of 1-[bis(dimethylamino)methylene]-1H-1,2,3-triazolo[4,5-b]pyridinium-3-oxide hexafluorophosphate and 2 mL of dimethylformamide was added 0.07 mL (0.41 mmole) diisopropylethylamine. After stirring at room temperature for 30 minutes, 0.05 mL (0.41 mmole) of 3-(dimethylamino)-propylamine was then added. The mixture was stirred at room temperature for 18 hours. The mixture was diluted with ethyl acetate and water. The aqueous phase was extracted twice with ethyl acetate. The combined organic layers were washed with water, then brine, dried over anhydrous magnesium sulfate, filtered and concentrated under reduced pressure. The residue was purified by silica gel chromatography eluting with methanol-dichloromethane (gradient 0:100-25:75) to give 0.020 g of 4-(9-cyclopentyl-7,7-difluoro-6-oxo-6,7,8,9-tetrahydro-5H-pyrimido[4,5-b][1,4]diazepin-2-ylamino)-N-(3-dimethylamino-propyl)-3-methoxy-benzamide (I-154).

Example 155

4-(9-cyclopentyl-7,7-difluoro-6-oxo-6,7,8,9-tetrahydro-5H-pyrimido[4,5-b][1,4]diazepin-2-ylamino)-3-methoxy-N-(tetrahydro-pyran-4-yl)-benzamide (I-155)

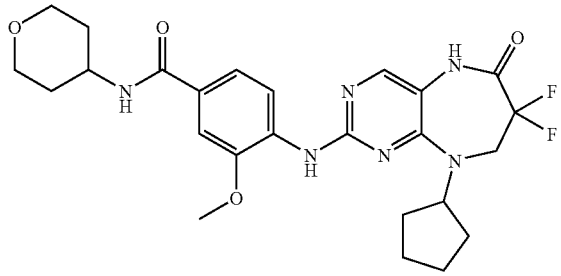

To a mixture of 0.06 g (0.13 mmole) of 4-(9-cyclopentyl-7,7-difluoro-6-oxo-6,7,8,9-tetrahydro-5H-pyrimido[4,5-b][1,4]diazepin-2-ylamino)-3-methoxy-benzoic acid (I-151), 0.08 g (0.21 mmole) of 1-[bis(dimethylamino)methylene]-1H-1,2,3-triazolo[4,5-b]pyridinium-3-oxide hexafluorophosphate and 2 mL of dimethylformamide was added 0.07 mL (0.41 mmole) diisopropylethylamine. After stirring at room temperature for 30 minutes, 0.042 g (0.41 mmole) of 4-amino-tetrahydropyran was then added. The mixture was stirred at room temperature for 18 hours. The mixture was diluted with ethyl acetate and water. The aqueous phase was extracted twice with ethyl acetate. The combined organic layers were washed with water, then brine, dried over anhydrous magnesium sulfate, filtered and concentrated under reduced pressure. The residue was triturated with hot methanol to give 0.014 g of 4-(9-cyclopentyl-7,7-difluoro-6-oxo-6,7,8,9-tetrahydro-5H-pyrimido[4,5-b][1,4]diazepin-2-ylamino)-3-methoxy-N-(tetrahydro-pyran-4-yl)-benzamide (I-155).

Example 156

4-(9-cyclopentyl-5-ethyl-7,7-difluoro-6-oxo-6,7,8,9-tetrahydro-5H-pyrimido[4,5-b][1,4]diazepin-2-ylamino)-3-methoxy-benzoic acid (I-156)

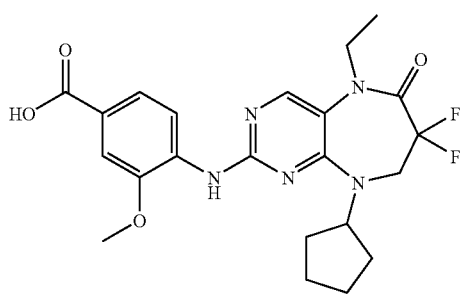

A mixture of 0.30 g (0.91 mmole) 2-chloro-9-cyclopentyl-5-ethyl-7,7-difluoro-5,7,8,9-tetrahydro-pyrimido[4,5-b][1,4]diazepin-6-one (VII-138) and 0.18 g (1.09 mmole) 4-amino-3-methoxy-benzoic acid in a 1:4 mixture of 5 mL of ethanol and 1 M hydrochloric acid was heated at 100 degrees for 18 hours. After cooling, the precipitate was collected by filtration, washed with water and dried to give 0.28 g of 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-benzoic acid (I-156).

Example 157

4-(9-cyclopentyl-5-ethyl-7,7-difluoro-6-oxo-6,7,8,9-tetrahydro-5H-pyrimido[4,5-b][1,4]diazepin-2-ylamino)-3-methoxy-benzamide (I-157)

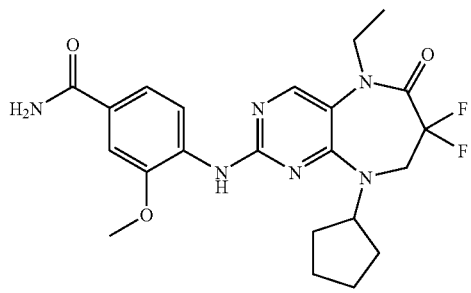

To a mixture of 0.05 g (0.11 mmole) of 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-benzoic acid (I-156), 0.05 g (0.13 mmole) of 1-[bis(dimethylamino)methylene]-1H-1,2,3-triazolo[4,5-b]pyridinium-3-oxide hexafluorophosphate and 2 mL of dimethylformamide was added 0.03 mL (0.16 mmole) of diisopropylethylamine. After stirring at room temperature for 30 minutes, 0.010 g (0.16 mmole) of ammonium chloride was added. The mixture was stirred at room temperature for 18 hours. The mixture was diluted with ethyl acetate and water. The aqueous phase was extracted twice with ethyl acetate. The combined organic layers were washed with water then brine, dried over anhydrous magnesium sulfate, filtered and concentrated under reduced pressure. The residue was purified by silica gel chromatography eluting with ethyl acetate to give 0.012 g of 4-(9-cyclopentyl-5-ethyl-7,7-difluoro-6-oxo-6,7,8,9-tetrahydro-5H-pyrimido[4,5-b][1,4]diazepin-2-yl-amino)-3-methoxy-benzamide (I-157).

Example 158

4-(9-cyclopentyl-5-ethyl-7,7-difluoro-6-oxo-6,7,8,9-tetrahydro-5H-pyrimido[4,5-b][1,4]diazepin-2-ylamino)-3-methoxy-N-methyl-benzamide (I-158)

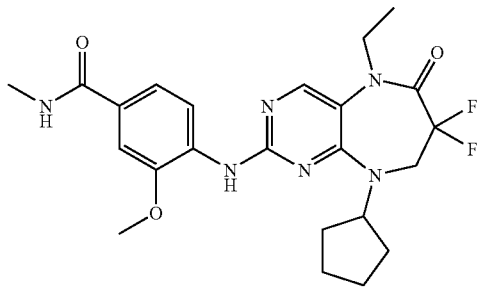

To a mixture of 0.05 g (0.11 mmole) of 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-benzoic acid (I-156), 0.06 g (0.17 mmole) of 1-[bis(dimethylamino)methylene]-1H-1,2,3-triazolo[4,5-b]pyridinium-3-oxide hexafluorophosphate and 2 mL of dimethylformamide was added 0.06 mL (0.33 mmole) of diisopropylethylamine. After stirring at room temperature for 30 minutes 0.17 mL (0.33 mmole) of 2M methylamine in tetrahydrofuran was then added. The mixture was stirred at room temperature for 18 hours. The mixture was diluted with ethyl acetate and water. The aqueous phase was extracted twice with ethyl acetate. The combined organic layers were washed with water then brine, dried over anhydrous magnesium sulfate, filtered and concentrated under reduced pressure. The residue was purified by silica gel chromatography eluting with ethyl acetate-hexanes to give 0.018 g of 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-N-methyl-benzamide (I-158).

Example 159

4-(9-cyclopentyl-5-ethyl-7,7-difluoro-6-oxo-6,7,8,9-tetrahydro-5H-pyrimido[4,5-b][1,4]diazepin-2-ylamino)-3-methoxy-N-(1-methyl-piperidin-4-yl)-benzamide (I-159)

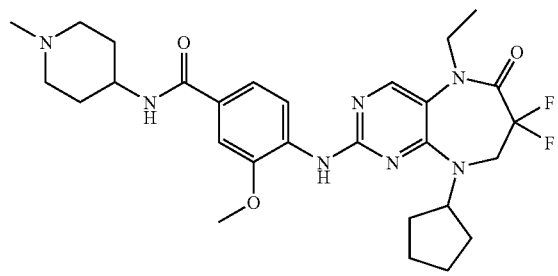

A mixture of 0.05 g (0.15 mmole) of 2-chloro-9-cyclopentyl-5-ethyl-7,7-difluoro-5,7,8,9-tetrahydro-pyrimido[4,5-b][1,4]diazepin-6-one (VII-138), 0.05 g (0.18 mmole) of 4-amino-3-methoxy-N-(1-methyl-piperidin-4-yl)-benzamide, 0.04 g (0.23 mmole) of p-toluenesulfonic acid monohydrate and 4.0 mL of 2-propanol was heated at 160 degrees for 2 hours in a microwave reactor. The cooled reaction mixture was concentrated under reduced pressure. The residue was diluted with dichloromethane and washed twice with saturated aqueous sodium bicarbonate solution. The aqueous phases were extracted with dichloromethane. The combined organic layers were washed with brine, dried, dried over anhydrous magnesium sulfate, filtered and concentrated under reduced pressure. The residue was purified by silica gel chromatography eluting with methanol-dichloromethane (gradient, 0:100-25:75) to give 0.040 g of 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-N-(1-methyl-piperidin-4-yl)-benzamide (I-159).

Example 160

4-(9-cyclopentyl-5-ethyl-7,7-difluoro-6-oxo-6,7,8,9-tetra-hydro-5H-pyrimido[4,5-b][1,4]diazepin-2-ylamino)-N-(3-dimethylamino-propyl)-3-methoxy-benzamide (I-160)

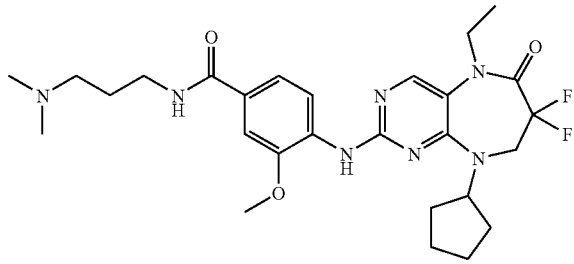

To a mixture of 0.06 g (0.13 mmole) of 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-benzoic acid (I-156), 0.06 g (0.17 mmole) of 1-[bis(dimethylamino)methylene]-1H-benzotriazolium-3-oxide hexafluorophosphate and 2 mL of dimethylformamide was added 0.06 mL (0.33 mmole) of diisopropylethylamine. After stirring at room temperature for 30 minutes 0.04 mL (0.33 mmole) of 3-(dimethylamino)-propylamine was added. The mixture was stirred for 18 hours, and then diluted with ethyl acetate and water. The aqueous phase was extracted twice with ethyl acetate. The combined organic layers were washed with water then brine, dried over anhydrous magnesium sulfate, filtered and concentrated under reduced pressure. The residue was purified by silica gel chromatography eluting with methanol-dichloromethane (gradient, 0:100-25:75) to give 0.030 g of 4-(9-cyclopentyl-5-ethyl-7,7-difluoro-6-oxo-6,7,8,9-tetra-hydro-5H-pyrimido[4,5-b][1,4]diazepin-2-ylamino)-N-(3-dimethylamino-propyl)-3-methoxy-benzamide (I-160).

Example 161

4-(9-cyclopentyl-5-ethyl-7,7-difluoro-6-oxo-6,7,8,9-tetrahydro-5H-pyrimido[4,5-b][1,4]diazepin-2-ylamino)-3-methoxy-N-(tetrahydro-pyran-4-yl)-benzamide (I-161)

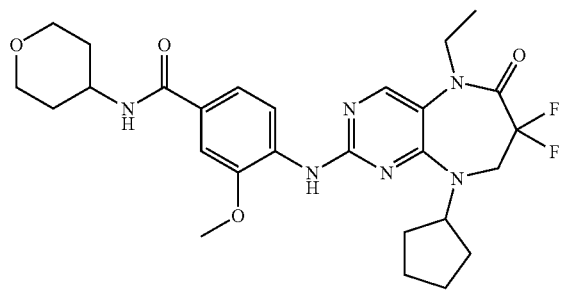

To a mixture of 0.05 g (0.11 mmole) of 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-benzoic acid (I-156), 0.06 g (0.17 mmole) of 1-[bis(dimethylamino)methylene]-1H-1,2,3-triazolo[4,5-b]pyridinium-3-oxide hexafluorophosphate and 2 mL of dimethylformamide was added 0.06 mL (0.33 mmole) of diisopropylethylamine. After stirring at room temperature for 30 minutes 0.033 g (0.33 mmole) of 4-aminotetrahydropyran was then added. The mixture was stirred at room temperature for 18 hours and then diluted with ethyl acetate and water. The aqueous phase was extracted twice with ethyl acetate. The combined organic layers were washed with water then brine, dried over anhydrous magnesium sulfate, filtered and concentrated under reduced pressure. The residue was purified by silica gel chromatography eluting with hexanes-ethyl acetate (30:70) to give 0.025 g of 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-N-(tetrahydro-pyran-4-yl)-benzamide (I-161).

Example 162

4-(9-cyclopentyl-5-ethyl-7,7-difluoro-6-oxo-5-propyl-6,7,8,9-tetrahydro-5H-pyrimido[4,5-b][1,4]diazepin-2-ylamino)-3-methoxy-benzoic acid (I-162)

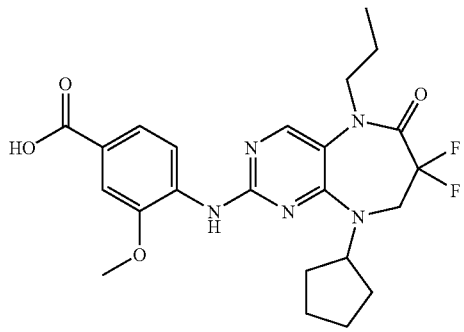

A mixture of 0.30 g (0.87 mmole) of 2-chloro-9-cyclopentyl-7,7-difluoro-5-propyl-5,7,8,9-tetrahydro-pyrimido[4,5-b][1,4]diazepin-6-one (VII-144) and 0.17 g (1.04 mmole) of 4-amino-3-methoxy-benzoic acid in a 5 mL 1:4 mixture of ethanol and 1M hydrochloric acid was heated at 100 degrees for 18 hours. After cooling, the precipitate was collected by filtration, washed with water and dried to give 0.27 g, 4-(9-cyclopentyl-5-ethyl-7,7-difluoro-6-oxo-5-propyl-6,7,8,9-tetrahydro-5H-pyrimido[4,5-b][1,4]diazepin-ylamino)-3-methoxy-benzoic acid (I-162).

Example 163

4-(9-cyclopentyl-7,7-difluoro-6-oxo-5-propyl-6,7,8, 9-tetrahydro-5H-pyrimido[4,5-b][1,4]diazepin-2-ylamino)-3-methoxy-benzamide (I-163)

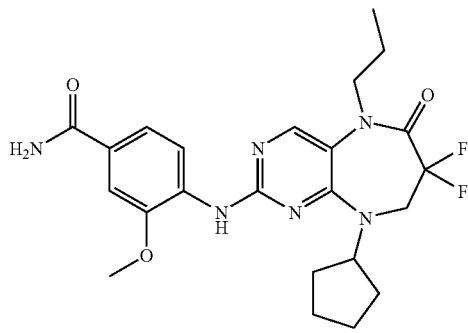

To a mixture of 0.05 g (0.11 mmole) of 4-(9-cyclopentyl-7,7-difluoro-6-oxo-5-propyl-6,7,8,9-tetrahydro-5H-pyrimido[4,5-b][1,4]diazepin-2-ylamino)-3-methoxy-benzoic acid (I-162), 0.05 g (0.13 mmole) of 1-[bis(dimethylamino)methylene]-1H-1,2,3-triazolo[4,5-b]pyridinium-3-oxide hexafluorophosphate and 2 mL of dimethylformamide was added 0.03 mL (0.16 mmole) of diisopropylethylamine. After stirring at room temperature for 30 minutes 0.010 g (0.16 mmole) of ammonium chloride was added. The mixture was stirred at room temperature for 18 hours and then diluted with ethyl acetate and water. The aqueous phase was extracted twice with ethyl acetate. The combined organic layers were washed with water then brine, dried over anhydrous magnesium sulfate, filtered and concentrated under reduced pressure. The residue was purified by silica gel chromatography eluting with ethyl acetate to give 0.029 g of 4-(9-cyclopentyl-7,7-difluoro-6-oxo-5-propyl-6,7,8,9-tetrahydro-5H-pyrimido[4,5-b][1,4]diazepin-2-ylamino)-3-methoxy-benzamide (I-163).

Example 164

4-(9-cyclopentyl-7,7-difluoro-6-oxo-5-propyl-6,7,8, 9-tetrahydro-5H-pyrimido[4,5-b][1,4]diazepin-2-ylamino)-3-methoxy-N-methyl-benzamide (I-164)

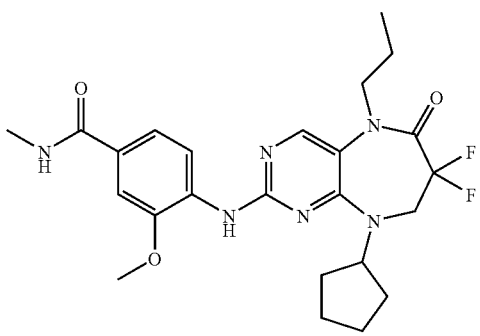

To a mixture of 0.05 g (0.11 mmole) of 4-(9-cyclopentyl-7,7-difluoro-6-oxo-5-propyl-6,7,8,9-tetrahydro-5H-pyrimido[4,5-b][1,4]diazepin-2-ylamino)-3-methoxy-benzoic acid (I-162), 0.06 g (0.16 mmole) of 1-[bis(dimethylamino)methylene]-1H-1,2,3-triazolo[4,5-b]pyridinium-3-oxide hexafluorophosphate and 2 mL of dimethylformamide was added 0.05 mL (0.32 mmole) of diisopropylethylamine. After stirring at room temperature for 30 minutes 0.16 mL (0.32 mmole) of 2M methylamine in tetrahydrofuran was then added. The mixture was stirred at room temperature for 18 hours and then diluted with ethyl acetate and water. The aqueous phase was extracted twice with ethyl acetate. The combined organic layers were washed with water then brine, dried over anhydrous magnesium sulfate, filtered and concentrated under reduced pressure. The residue was purified by silica gel chromatography eluting with ethyl acetate-hexanes (60:40) to give 0.036 g of 4-(9-cyclopentyl-7,7-difluoro-6-oxo-5-propyl-6,7,8,9-tetrahydro-5H-pyrimido[4,5-b][1,4]diazepin-2-ylamino)-3-methoxy-N-methyl-benzamide (I-164).

Example 165

4-(9-cyclopentyl-7,7-difluoro-6-oxo-5-propyl-6,7,8, 9-tetrahydro-5H-pyrimido[4,5-b][1,4]diazepin-2-ylamino)-3-methoxy-N-(1-methyl-piperidin-4-yl)-benzamide (I-165)

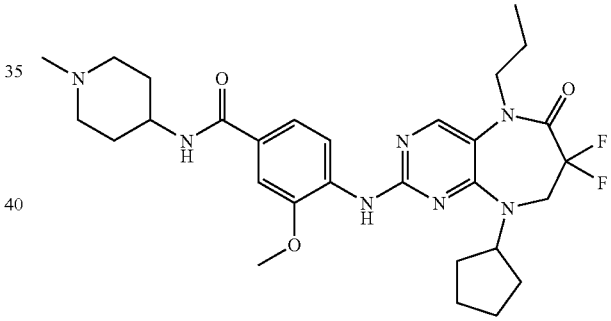

A mixture of 0.05 g (0.15 mmole) of 2-chloro-9-cyclopentyl-7,7-difluoro-5-propyl-5,7,8,9-tetrahydro-pyrimido[4,5-b][1,4]diazepin-6-one (VII-144), 0.05 g (0.17 mmole) of 4-amino-3-methoxy-N-(1-methyl-piperidin-4-yl)-benzamide, 0.04 g (0.22 mmole) of p-toluenesulfonic acid monohydrate and 4.0 mL of 2-propanol was heated at 160 degrees for 2 hours in a microwave reactor. The cooled reaction mixture was concentrated under reduced pressure. The residue was diluted with dichloromethane and washed twice with saturated aqueous sodium bicarbonate solution. The aqueous phase was extracted with dichloromethane). The combined organic layers were washed with brine, dried over anhydrous magnesium sulfate, filtered and concentrated under reduced pressure. The residue was purified by silica gel chromatography eluting with methanol-dichloromethane (gradient, 0:100-25:75) to give 0.051 g of 4-(9-cyclopentyl-7,7-difluoro-6-oxo-5-propyl-6,7,8,9-tetrahydro-5H-pyrimido[4,5-b][1,4]diazepin-2-ylamino)-3-methoxy-N-(1-methyl-piperidin-4-yl)-benzamide (I-165).

Example 166

4-(9-cyclopentyl-5-propyl-7,7-difluoro-6-oxo-6,7,8,9-tetra-hydro-5H-pyrimido[4,5-b][1,4]diazepin-2-ylamino)-N-(3-dimethylamino-propyl)-3-methoxy-benzamide (I-166)

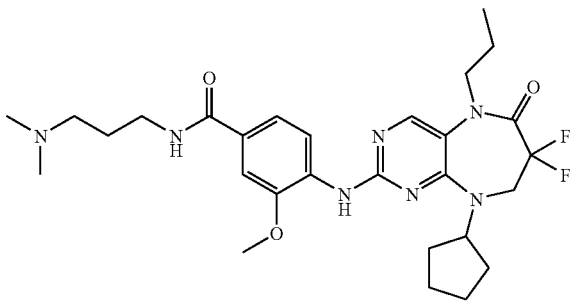

To a mixture of 0.05 g (0.11 mmole) of 4-(9-cyclopentyl-5-propyl-7,7-difluoro-6-oxo-6,7,8,9-tetrahydro-5H-pyrimido[4,5-b][1,4]diazepin-2-ylamino)-3-methoxy-benzoic acid (I-162), 0.06 g (0.16 mmole) of 1-[bis(dimethylamino)methylene]-1H-benzotriazolium-3-oxide hexafluorophosphate and 2 mL of dimethylformamide was added 0.05 mL (0.32 mmole) of diisopropylethylamine. After stirring at room temperature for 30 minutes 0.04 mL (0.32 mmole) of 3-(dimethylamino)-propylamine was then added. The mixture was stirred at room temperature for 18 hours and then diluted with ethyl acetate and water. The aqueous phase was extracted twice with ethyl acetate. The combined organic layers were washed with water then brine, dried over anhydrous magnesium sulfate, filtered and concentrated under reduced pressure. The residue was purified by silica gel chromatography eluting with methanol-dichloromethane (gradient, 0:100-25:75) to give 0.018 g of 4-(9-cyclopentyl-5-propyl-7,7-difluoro-6-oxo-6,7,8,9-tetra-hydro-5H-pyrimido[4,5-b][1,4]diazepin-2-ylamino)-N-(3-dimethylamino-propyl)-3-methoxy-benzamide (I-166).

Example 167

4-(9-cyclopentyl-7,7-difluoro-6-oxo-5-propyl-6,7,8,9-tetrahydro-5H-pyrimido[4,5-b][1,4]diazepin-2-ylamino)-3-methoxy-N-(tetrahydro-pyran-4-yl)-benzamide (I-167)

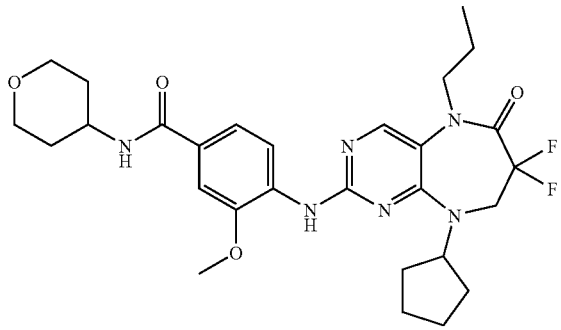

To a mixture of 0.05 g, 0.11 mmole) of 4-(9-cyclopentyl-7,7-difluoro-6-oxo-5-propyl-6,7,8,9-tetrahydro-5H-pyrimido[4,5-b][1,4]diazepin-2-ylamino)-3-methoxy-benzoic acid (I-162), 0.06 g (0.16 mmole) of 1-[bis(dimethylamino)methylene]-1H-1,2,3-triazolo[4,5-b]pyridinium-3-oxide hexafluorophosphate and 2 mL of dimethylformamide was added 0.05 mL of 0.32 mmole) of diisopropylethylamine. After stirring at room temperature for 30 minutes 0.032 g (0.32 mmole) of 4-aminotetrahydropyran was added. The mixture was stirred at room temperature for 18 hours and then diluted with ethyl acetate and water. The aqueous phase was extracted twice with ethyl acetate. The combined organic layers were washed with water then brine, dried over anhydrous magnesium sulfate, filtered and concentrated under reduced pressure. The residue was purified by silica gel chromatography eluting with hexanes-ethyl acetate (30:70) to give 0.046 g of 4-(9-cyclopentyl-7,7-difluoro-6-oxo-5-propyl-6,7,8,9-tetrahydro-5H-pyrimido[4,5-b][1,4]diazepin-2-ylamino)-3-methoxy-N-(tetrahydro-pyran-4-yl)-benzamide (I-167).

Example 168

4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid methyl ester (I-168)

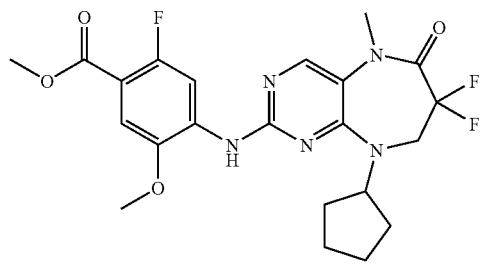

To a mixture of 0.67 g (0.0021 mole) of 2-chloro-9-cyclopentyl-7,7-difluoro-5-methyl-5,7,8,9-tetrahydro-pyrimido[4,5-b][1,4]diazepin-6-one (VII-20), 0.63 g (0.00317 mole) of 4-amino-2-fluoro-5-methoxy-benzoic acid methyl ester and 30 mL of dioxane was added 0.05 g (0.00021 mole) of palladium (II) acetate and 1.91 g (0.00588 mole) of cesium carbonate. The mixture was stirred at room temperature for 5 minutes and then heated to 100 degrees for 18 hours. The solid was removed by filtration and the filtrate was concentrated under reduced pressure. The residue was diluted with ethyl acetate, washed with water then brine, dried over anhydrous magnesium sulfate, filtered and concentrated under reduced pressure. The residue was purified by silica gel chromatography eluting with hexanes-ethyl acetate (60:40) to give 0.81 g of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid methyl ester (I-168).

Example 169

4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid (I-169)

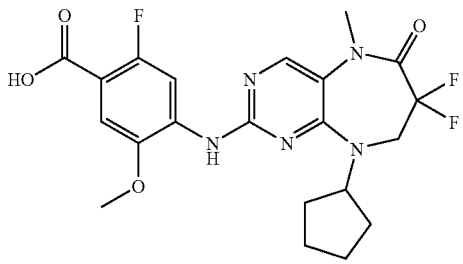

An aqueous solution of 5 mL of aqueous 2M (0.010 mole) of sodium hydroxide was added to a solution of 0.51 g (0.00106 mole) of 4-(9-cyclopentyl-7,7-difluoro-5-methyl-6-oxo-6,7,8,9-tetrahydro-5H-pyrimido[4,5-b][1,4]diazepin-2-yl amino)-2-fluoro-5-methoxy-benzoic acid methyl ester (I-168) in 20 mL of tetrahydrofuran-methanol (3:1). The mixture was heated at 50° C. for 18 hours and then concentrated under reduced pressure. The residue was dissolved in water and acidified to pH 2 with 2M hydrochloric acid. After stirring for 30 minutes, the solid was collected by filtration, washed with water and dried to give 0.50 g of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid (I-169).

Example 170

4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzamide (I-170)

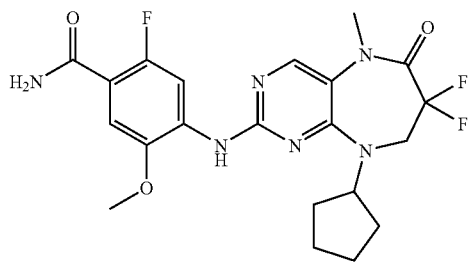

To a mixture of 0.05 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid (I-169), 0.06 g (0.16 mmole) of 1-[bis(dimethylamino)methylene]-1H-benzotriazolium-3-oxide hexafluorophosphate and 2 mL of dimethylformamide was added 0.06 mL (0.32 mmole) of diisopropylethylamine. After stirring at room temperature for 30 minutes 0.02 g (0.32 mmole) of ammonium chloride was then added. The mixture was stirred at room temperature for 18 hours and then diluted with ethyl acetate and water. The aqueous phase was extracted twice with ethyl acetate. The combined organic layers were washed with 1M sodium hydroxide solution then brine, dried over anhydrous magnesium sulfate, filtered and concentrated under reduced pressure. The residue was purified by silica gel chromatography eluting with ethyl acetate to give 0.029 g of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzamide (I-170).

Example 171

4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-methyl-benzamide (I-171)

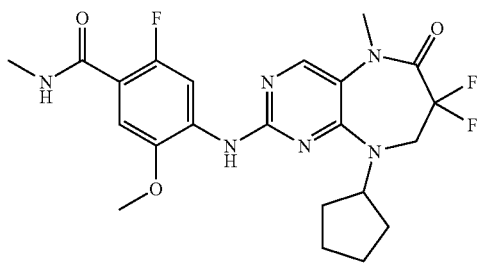

To a mixture of 0.05 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid (I-169), 0.06 g (0.16 mmole) of 1-[bis(dimethylamino)methylene]-1H-benzotriazolium-3-oxide hexafluorophosphate and 2 mL of dimethylformamide was added 0.06 mL (0.32 mmole) of diisopropylethylamine. After stirring at room temperature for 30 minutes 0.16 mL (0.32 mmole) of 2M methylamine in tetrahydrofuran was added. The mixture was stirred at room temperature for 18 hours and then diluted with ethyl acetate and water. The aqueous phase was extracted twice with ethyl acetate. The combined organic layers were washed with 1 M sodium hydroxide solution then brine, dried over anhydrous magnesium sulfate, filtered and concentrated under reduced pressure. The residue was purified by silica gel chromatography eluting with hexanes-ethyl acetate (60:40) to give 0.027 g of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-methyl-benzamide (I-171).

Example 172

4-(9-cyclopentyl-7,7-difluoro-5-methyl-6-oxo-6,7,8,9-tetra-hydro-5H-pyrimido[4,5-b][1,4]diazepin-2-ylamino)-N-(3-dimethylamino-propyl)-2-fluoro-5-methoxy-benzamide (I-172)

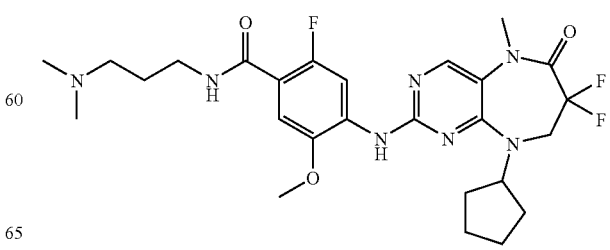

To a mixture of (0.05 g, 0.11 mmole) of 4-(9-cyclopentyl-7,7-difluoro-5-methyl-6-oxo-6,7,8,9-tetrahydro-5H-pyrimido[4,5-b][1,4]diazepin-2-yl amino)-2-fluoro-5-methoxy-benzoic acid (I-169), 0.06 g (0.16 mole) of 1-[bis(dimethylamino)methylene]-1H-benzotriazolium-3-oxide hexafluorophosphate and 2 mL of dimethylformamide was added 0.06 mL (0.32 mole) of diisopropylethylamine. After stirring at room temperature for 30 minutes 0.04 mL (0.32 mmole) of 3-(dimethylamino)-propylamine was added. The mixture was stirred at room temperature for 18 hours, then diluted with ethyl acetate and water. The aqueous phase was extracted twice with ethyl acetate. The combined organic layers were washed with 1M sodium hydroxide solution then brine, dried over anhydrous magnesium sulfate, filtered and concentrated. The residue was purified by silica gel chromatography eluting with methanol-dichloromethane (gradient, 0:100-20:80) to give 0.037 g of 4-(9-cyclopentyl-7,7-difluoro-5-methyl-6-oxo-6,7,8,9-tetra-hydro-5H-pyrimido[4,5-b][1,4]diazepin-2-ylamino)-N-(3-dimethylamino-propyl)-2-fluoro-5-methoxy-benzamide (I-172).

Example 173

4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(tetrahydropyran-4-yl)-benzamide (I-173)

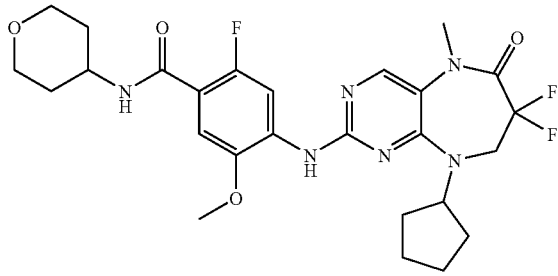

To a mixture of 0.05 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid (I-169), 0.06 g (0.16 mmole) of 1-[bis(dimethylamino)methylene]-1H-benzotriazolium-3-oxide hexafluorophosphate and 2 mL of dimethylformamide was added 0.06 mL (0.32 mmole) of diisopropylethylamine. After stirring at room temperature for 30 minutes 0.03 g (0.32 mmole) of 4-aminotetrahydropyran was added. The mixture was stirred at room temperature for 18 hours, then diluted with ethyl acetate and water. The aqueous phase was extracted twice with ethyl acetate. The combined organic layers were washed with 1M sodium hydroxide solution then brine, dried over anhydrous magnesium sulfate, filtered and concentrated under reduced pressure. The residue was purified by silica gel chromatography eluting with ethyl acetate to give 0.035 g of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(tetrahydropyran-4-yl)-benzamide (I-173).

Example 174

4-(9-cyclopentyl-7,7-difluoro-5-methyl-6-oxo-6,7,8,9-tetra-hydro-5H-pyrimido[4,5-b][1,4]diazepin-2-ylamino)-N-(3-dimethylamino-ethyl)-2-fluoro-5-methoxy-benzamide (I-174)

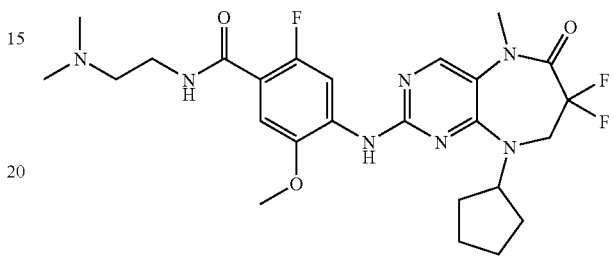

To a mixture of 0.05 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid (I-169), 0.06 g (0.16 mmole) of 1-[bis(dimethylamino)methylene]-1H-benzotriazolium-3-oxide hexafluorophosphate and 2 mL of dimethylformamide was added 0.06 mL (0.32 mmole) of diisopropylethylamine. After stirring at room temperature for 30 minutes 0.04 mL (0.32 mmole) of 3-(dimethylamino)-ethylamine was added. The mixture was stirred at room temperature for 18 hours, then diluted with ethyl acetate and water. The aqueous phase was extracted twice with ethyl acetate. The combined organic layers were washed with 1M sodium hydroxide solution then brine, dried over anhydrous magnesium sulfate, filtered and concentrated under reduced pressure. The residue was purified by silica gel chromatography eluting with methanol-dichloromethane (gradient, 0:100-20:80) to give 0.028 g of 4-(9-cyclopentyl-7,7-difluoro-5-methyl-6-oxo-6,7,8,9-tetra-hydro-5H-pyrimido[4,5-b][1,4]diazepin-2-ylamino)-N-(3-dimethylamino-ethyl)-2-fluoro-5-methoxy-benzamide (I-174).

Example 175

4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methyl-piperidin-4-yl)-benzamide (I-175)

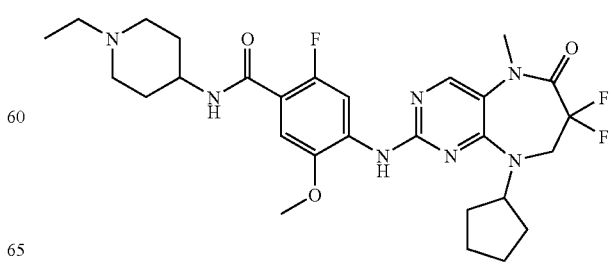

To a mixture of 0.05 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid (I-169), 0.06 g (0.16 mmole) of 1-[bis(dimethylamino)methylene]-1H-benzotriazolium-3-oxide hexafluorophosphate and 2 mL of dimethylformamide was added 0.06 mL (0.32 mmole) of diisopropylethylamine. After stirring at room temperature for 30 minutes 0.04 g (0.32 mmole) of 4-amino-1-ethylpiperidine was added. The mixture was stirred at room temperature for 18 hours, then diluted with ethyl acetate and water. The aqueous phase was extracted twice with ethyl acetate. The combined organic layers were washed with 1M sodium hydroxide solution then brine, dried over anhydrous magnesium sulfate, filtered and concentrated under reduced pressure. The residue was purified by silica gel chromatography eluting with methanol-dichloromethane (gradient, 0:100-20:80) to give 0.038 g of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methyl-piperidin-4-yl)-benzamide (I-175).

Example 176

4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methyl-piperidin-4-yl)-benzamide (I-176)

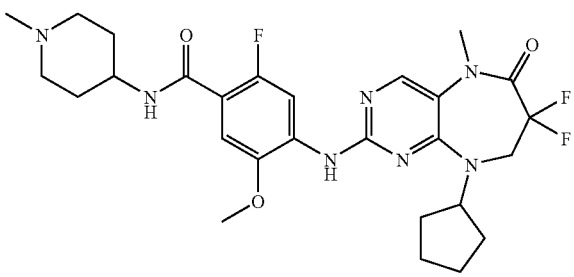

To a mixture of 0.05 g (0.11 mmole) of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid (I-169), 0.06 g (0.16 mmole) of 1-[bis(dimethylamino)methylene]-1H-benzotriazolium-3-oxide hexafluorophosphate and 2 mL of dimethylformamide was added 0.06 mL (0.32 mmole) of diisopropylethylamine. After stirring at room temperature for 30 minutes 0.04 g (0.32 mmole) of 4-amino-1-methylpiperidine was added. The mixture was stirred at room temperature for 18 hours, then diluted with ethyl acetate and water. The aqueous phase was extracted twice with ethyl acetate. The combined organic layers were washed with 1M sodium hydroxide solution then brine, dried over anhydrous magnesium sulfate, filtered and concentrated under reduced pressure. The residue was purified by silica gel chromatography eluting with methanol-dichloromethane (gradient, 0:100-20:80) to give 0.038 g of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methyl-piperidin-4-yl)-benzamide (I-176).

Example 177

4-[4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoyl-amino]-piperidin-1-carboxylic acid tert-butyl ester (I-177)

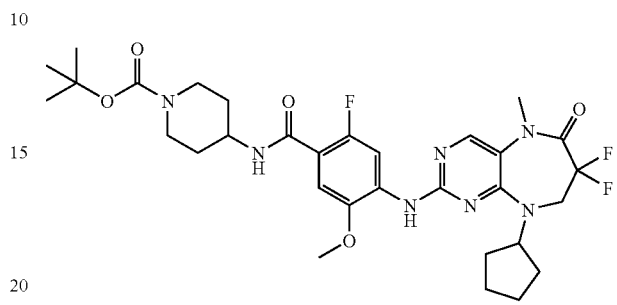

To a mixture of 0.075 g (0.16 mmole) of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid (I-169), 0.09 g (0.24 mmole) of 1-[bis(dimethylamino)methylene]-1H-benzotriazolium-3-oxide hexafluorophosphate and 2 mL of dimethylformamide was added 0.08 mL (0.48 mmole) of diisopropylethylamine. After stirring at room temperature for 30 minutes 0.10 g (0.48 mmole) of 4-amino-1-Boc-piperidine was added. The mixture was stirred at room temperature for 18 hours, then diluted with ethyl acetate and water. The aqueous phase was extracted twice with ethyl acetate. The combined organic layers were washed with 1M sodium hydroxide solution then brine, dried over anhydrous magnesium sulfate, filtered and concentrated under reduced pressure. The residue was purified by silica gel chromatography eluting with ethyl acetate to give 0.071 g of 4-[4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoyl-amino]-piperidin-1-carboxylic acid tert-butyl ester (I-177).

Example 178

4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-piperidin-4-yl-benzamide (I-178)

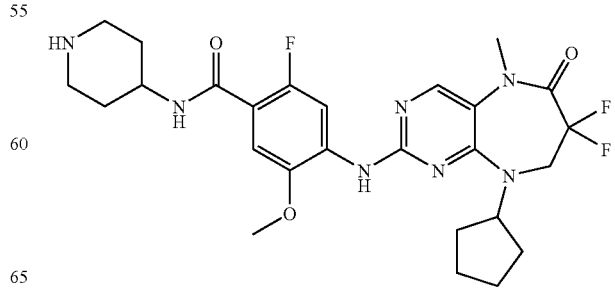

To a solution of 0.071 g (0.11 mmole) of 4-[4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoyl-amino]-piperidin-1-carboxylic acid tert-butyl ester (I-177) and 3 mL of dichloromethane was added 6 mL of trifluoroacetic acid-dichloromethane (1:1). The mixture was stirred at room temperature for 18 hours, and then concentrated under reduced pressure. The residue was diluted with ethyl acetate and washed with saturated aqueous sodium bicarbonate solution, then brine, dried over anhydrous magnesium sulfate, filtered and concentrated under reduced pressure. The residue was purified by silica gel chromatography eluting with methanol-dichloromethane (gradient, 0:100-25:75) to give 0.050 g of 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-piperidin-4-yl-benzamide (I-178).

Example 179

3-chloro-4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide (I-179)

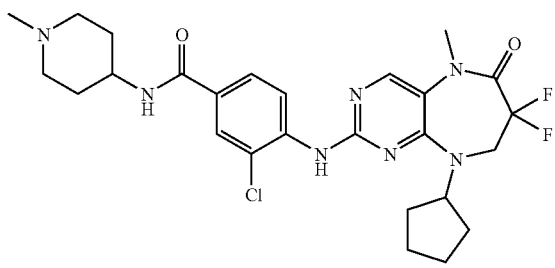

A mixture of 0.1 g (0.32 mmole) of 2-chloro-9-cyclopentyl-7,7-difluoro-5-methyl-5,7,8,9-tetrahydro-pyrimido[4,5-b][1,4]diazepin-6-one (VII-20) and 0.1 g (0.38 mmole) of 4-amino-3-chloro-N-(1-methyl-piperidin-4-yl)-benzamide in 10 mL of ethanol-water-hydrochloric acid (20:80:1) was refluxed for 18 hours, and then heated in a pressure tube at 130 degrees for 3 hours. After removal of the solvents under reduced pressure, dichloromethane and saturated sodium carbonate were added. The mixture was extracted with dichloromethane twice. The combined organic layers were washed three times with sodium carbonate, three times with water, dried over anhydrous sodium sulfate, filtered and concentrated under reduced pressure. Purification by silica gel chromatography, eluting with dichloromethane-methanol (gradient, 100:0-75:25) gave 0.028 g of 3-chloro-4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide (I-179) as a white solid.

Example 180

4-(9-cyclopentyl-7,7-difluoro-5-methyl-6-oxo-6,7,8,9-tetrahydro-5H-pyrimido[4,5-b][1,4]diazepin-2-ylamino)-3-isopropoxy-N-(1-methyl-piperidin-4-yl)-benzamide (I-180)

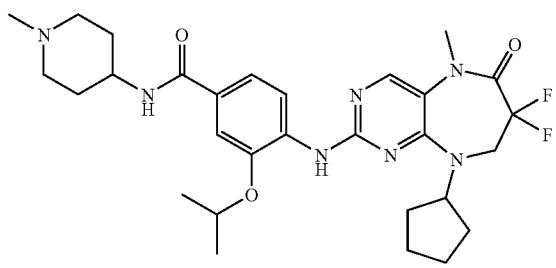

A mixture of 0.10 g (0.32 mmole) of 2-chloro-9-cyclopentyl-7,7-difluoro-5-methyl-5,7,8,9-tetrahydro-pyrimido[4,5-b][1,4]diazepin-6-one (VII-20), 0.11 g (0.38 mmole) of 4-amino-3-isopropoxy-N-(1-methyl-piperidin-4-yl)-benzamide, 0.090 g (0.48 mmole) of p-toluenesulfonic acid monohydrate and 4 mL of isopropanol was heated in a pressure tube at 140 degrees overnight, then cooled and diluted with dichloromethane and saturated sodium carbonate. The mixture was extracted twice with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-60:40) gave 0.13 g of 4-(9-cyclopentyl-7,7-difluoro-5-methyl-6-oxo-6,7,8,9-tetrahydro-5H-pyrimido[4,5-b][1,4]diazepin-2-ylamino)-3-isopropoxy-N-(1-methyl-piperidin-4-yl)-benzamide (I-180) as a white solid.

Example 181

4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-3-trifluoromethoxy-benzamide (I-181)

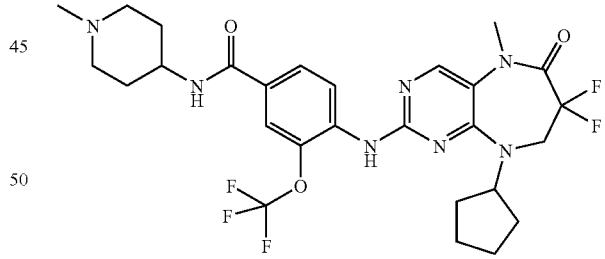

A mixture of 0.10 g (0.32 mmole) of 2-chloro-9-cyclopentyl-7,7-difluoro-5-methyl-5,7,8,9-tetrahydro-pyrimido[4,5-b][1,4]diazepin-6-one (VII-20), 0.11 g (0.35 mmole) of 4-amino-N-(1-methyl-piperidin-4-yl)-3-trifluoromethoxy-benzamide, 0.090 g (0.48 mmole) of p-toluenesulfonic acid monohydrate and 4 mL of isopropanol was heated in a pressure tube at 140 degrees overnight, then cooled and diluted with dichloromethane and saturated sodium carbonate. The mixture was extracted twice with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-60:40) gave 0.022 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-3-trifluoromethoxy-benzamide (I-181) as a white solid.

Example 182

4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182)

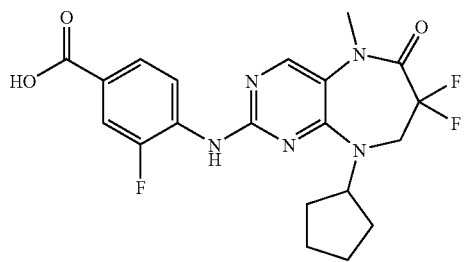

A mixture of 0.1 g (0.32 mmole) of 2-chloro-9-cyclopentyl-7,7-difluoro-5-methyl-5,7,8,9-tetrahydro-pyrimido[4,5-b][1,4]diazepin-6-one (VII-20), 0.059 g (0.57 mmole) of 4-amino-3-fluoro-benzoic acid and 0.7 mL of ethanol-water-hydrochloric acid (20:80:1) was refluxed for 18 hours, then cooled and partially concentrated under reduced pressure. The resulting solid was collected by filtration, washed with water and dried to give 0.11 g of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182).

Example 183

4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-(1-methyl-piperidin-4-yl)-benzamide (I-183)

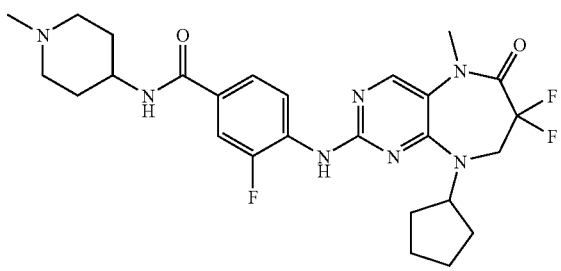

To a mixture of 0.11 g (0.24 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182), 0.17 mL (0.96 mmole) of ethyldiisopropyl amine, 0.030 g (0.26 mmole) of 4-amino-1-methyl-piperidine and 3.0 mL of dimethylformamide was added 0.11 g (0.26 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-80:20) gave 0.065 g of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-(1-methyl-piperidin-4-yl)-benzamide (I-183) as a white solid.

Example 184

4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184)

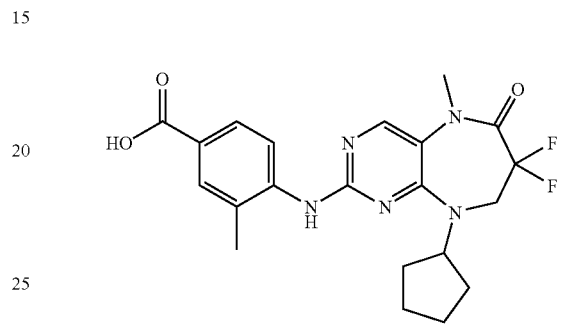

A mixture of 1.0 g (3.15 mmole) of 2-chloro-9-cyclopentyl-7,7-difluoro-5-methyl-5,7,8,9-tetrahydro-pyrimido[4,5-b][1,4]diazepin-6-one (VII-20), 0.572 g (3.78 mmole) of 4-amino-3-methylbenzoic acid, 10 mL of ethanol and 40 mL of 1M hydrochloric acid was heated at reflux for 14 hours. The mixture was cooled and the white precipitate was collected by filtratration, washed with cold water and dried in vacuum to give 0.3251 g of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184) as off-white solid.

Example 185

4-(9-cyclopentyl-7,7-difluoro-5-methyl-6-oxo-6,7,8,9-tetrahydro-5H-pyrimido[4,5-b][1,4]diazepin-2-ylamino)-3-methyl-N-(1-methyl-piperidin-4-yl)-benzamide (I-185)

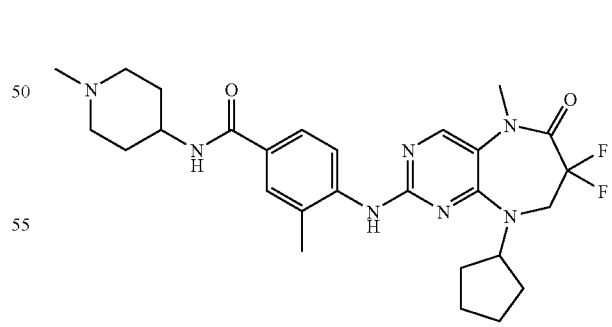

To a mixture of 0.050 g (0.116 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184) and 5 mL of dimethylformamide was added 0.0235 g (0.174 mmole) of 1-hydroxybenzotriazole, 0.0659 g (0.174 mmole) of 1-[bis(dimethylamino)methylene]-1H- benzotriazolium-3-oxide hexafluorophosphate and 0.060 g (0.463 mmole) of diisopropylethylamine. The mixture was stirred for 10 minutes, then 0.0198 g (0.174 mmole) of 4-amino-1-methylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0536 g) of 4-(9-cyclopentyl-7,7-difluoro-5-methyl-6-oxo-6,7,8,9-tetrahydro-5H-pyrimido[4,5-b][1,4]diazepin-2-ylamino)-3-methyl-N-(1-methyl-piperidin-4-yl)-benzamide (I-185) as a white solid.

Example 186

4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methyl-benzamide (I-186)

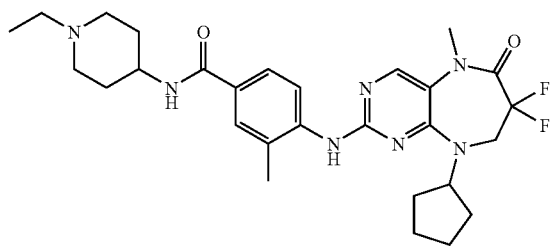

To a mixture of 0.050 g (0.116 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184) and 8 mL of dimethylformamide was added 0.0235 g (0.174 mmole) of 1-hydroxybenzotriazole, 0.0659 g (0.174 mmole) of 1-[bis(dimethylamino)methylene]-1H-benzotriazolium-3-oxide hexafluorophosphate and 0.060 g (0.463 mmole) of diisopropylethylamine. The mixture was stirred for 10 minutes, then 0.0227 g (0.177 mmole) of 4-amino-1-methylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0547 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methyl-benzamide (I-186) as a white solid.

Example 187

4-(9-cyclopentyl-7,7-difluoro-5-methyl-6-oxo-6,7,8,9-tetrahydro-5H-pyrimido[4,5-b][1,4]diazepin-2-ylamino)-3-methyl-N-(tetrahydro-pyran-4-yl)-benzamide (I-187)

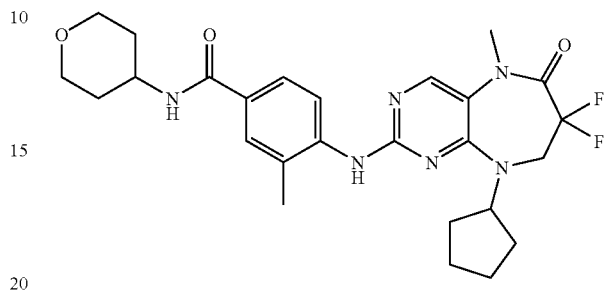

To a mixture of 0.060 g (0.139 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184) and 8 mL of dimethylformamide was added 0.0282 g (0.209 mmole) of 1-hydroxybenzotriazole, 0.079 g (0.208 mmole) of 1-[bis(dimethylamino)methylene]-1H-benzotriazolium-3-oxide hexafluorophosphate and 0.072 g (0.555 mmole) of diisopropylethylamine. The mixture was stirred for 10 minutes, then 0.0212 g (0.209 mmole) of 4-aminotetrahydropyran was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0532 g of 4-(9-cyclopentyl-7,7-difluoro-5-methyl-6-oxo-6,7,8,9-tetrahydro-5H-pyrimido[4,5-b][1,4]diazepin-2-ylamino)-3-methyl-N-(tetrahydro-pyran-4-yl)-benzamide (I-187) as a white solid.

Example 188

4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methyl-benzamide (I-188)

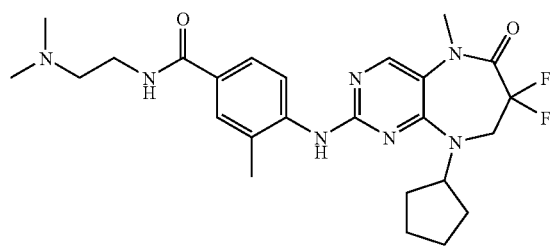

To a mixture of 0.0560 g (0.129 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184) and 6 mL of dimethylformamide was added 0.0282 g (0.209 mmole) of 1-hydroxybenzotriazole, 0.079 g (0.208 mmole) of 1-[bis(dimethylamino)methylene]-1H-benzotriazolium-3-oxide hexafluorophosphate and 0.072 g (0.555 mmole) of diisopropylethylamine. The mixture was stirred for 10 minutes, then 0.0212 g (0.209 mmole) of 4-aminotetrahydropyran was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0450 g of 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methyl-benzamide (I-188) as a white solid.

Example 189

4-(9-cyclopentyl-7,7-difluoro-5-methyl-6-oxo-6,7,8, 9-tetrahydro-5H-pyrimido[4,5-b][1,4]diazepin-2-ylamino)-N-(3-dimethylamino-propyl)-3-methyl-benzamide (I-189)

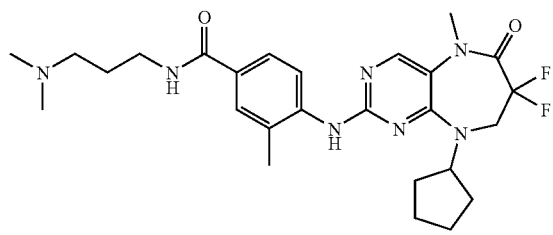

To a mixture of 0.060 g (0.139 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184) and 8 mL of dimethylformamide was added 0.0282 g (0.209 mmole) of 1-hydroxybenzotriazole, 0.079 g (0.208 mmole) of 1-[bis(dimethylamino)methylene]-1H-benzotriazolium-3-oxide hexafluorophosphate and 0.072 g (0.555 mmole) of diisopropylethylamine. The mixture was stirred for 10 minutes, then 0.0212 g (0.207 mmole) of 3-(dimethylamino)propylamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0651 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methyl-benzamide (I-189) as a white solid

Example 190

4-(9-cyclopentyl-7,7-difluoro-5-methyl-6-oxo-6,7,8, 9-tetrahydro-5H-pyrimido[4,5-b][1,4]diazepin-2-ylamino)-3,N-dimethyl-benzamide (I-190)

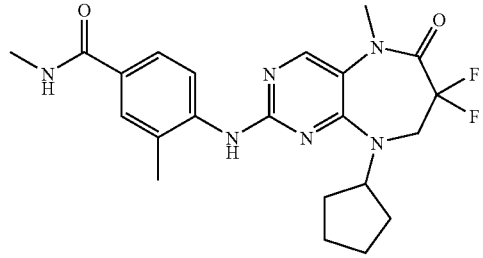

To a mixture of 0.060 g (0.139 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184) and 8 mL of dimethylformamide was added 0.0282 g (0.209 mmole) of 1-hydroxybenzotriazole, 0.079 g (0.208 mmole) of 1-[bis(dimethylamino)methylene]-1H-benzotriazolium-3-oxide hexafluorophosphate and 0.072 g (0.555 mmole) of diisopropylethylamine. The mixture was stirred for 10 minutes, then 0.0187 g (0.277 mmole) of methylamine hydrochloride was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0505 g of 4-(9-cyclopentyl-7,7-difluoro-5-methyl-6-oxo-6,7,8,9-tetrahydro-5H-pyrimido[4,5-b][1,4]diazepin-2-ylamino)-3,N-dimethyl-benzamide (I-190) as a white solid.

Example 191

4-[4-(9-cyclopentyl-7,7-difluoro-5-methyl-6-oxo-6, 7,8,9-tetrahydro-5H-pyrimido[4,5-b][1,4]diazepin-2-ylamino)-3-methyl-benzoylamino]-piperidine-1-carboxylic acid tert-butyl ester (I-191)

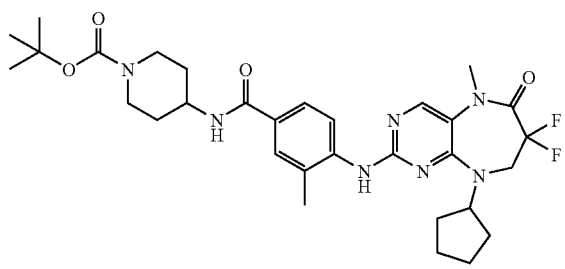

To a mixture of 0.060 g (0.139 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184) and 8 mL of dimethylformamide was added 0.0282 g (0.209 mmole) of 1-hydroxybenzotriazole, 0.079 g (0.208 mmole) of 1-[bis(dimethylamino)methylene]-1H-benzotriazolium-3-oxide hexafluorophosphate and 0.072 g (0.555 mmole) of diisopropylethylamine. The mixture was stirred for 10 minutes, then 0.0417 g (0.208 mmole) of 4-amino-1-Boc-piperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0772 g of 4-[4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoylamino]-piperidine-1-carboxylic acid tert-butyl ester (I-191) as a white solid.

Example 192

4-(9-cyclopentyl-7,7-difluoro-5-methyl-6-oxo-6,7,8,9-tetrahydro-5H-pyrimido[4,5-b][1,4]diazepin-2-ylamino)-3-methyl-N-piperidin-4-yl-benzamide (I-192)

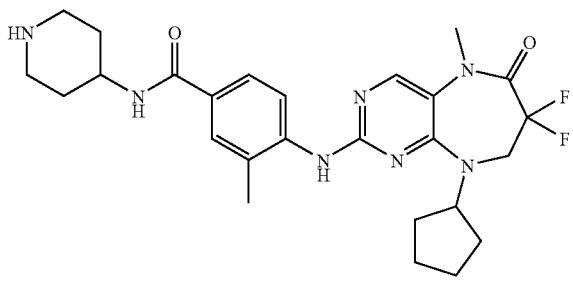

A solution of 0.071 g (0.115 mmole) of 4-[4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoylamino]-piperidine-1-carboxylic acid tert-butyl ester (I-191) in 4 mL of dichloromethane was stirred with 2 mL of trifluoroacetic acid for 2 hours and concentrated under reduced pressure. The residue was dissolved in 80 mL of dichloromethane, washed with 15 mL of sodium carbonate solution, twice with 15 mL of brine and concentrated under reduced pressure. The residue was purified by reverse phase silica gel chromatography, eluting with water-acetonitrile (gradient, 90:10-0:100) to give 0.0549 g of 4-(9-cyclopentyl-7,7-difluoro-5-methyl-6-oxo-6,7,8,9-tetrahydro-5H-pyrimido[4,5-b][1,4]diazepin-2-ylamino)-3-methyl-N-piperidin-4-yl-benzamide (I-192) as a white solid.

Example 193

4-(9-cyclopentyl-7,7-difluoro-5-methyl-6-oxo-6,7,8,9-tetrahydro-5H-pyrimido[4,5-b][1,4]diazepin-2-ylamino)-3-methyl-benzamide (I-193)

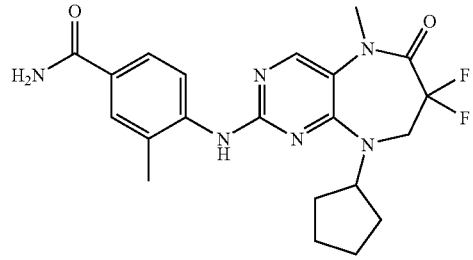

A mixture of 0.0755 g (0.175 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid (I-184), 4 mL of dimethylformamide, 0.0904 g (0.231 mmole) of 1-[bis(dimethylamino)methylene]-1H-1,2,3-triazolo[4,5-b]pyridinium-3-oxide hexafluorophosphate and 0.15 mL (0.859 mmole) of diisopropylethylamine was stirred for 20 minutes, then 0.0196 g (0.366 mmole) of ammonium chloride was added. The reaction mixture was stirred for 1.5 hours and then 150 mL of ethyl acetate and 25 mL of water was added. The organic layer was washed with 25 mL of ammonium chloride solution, 25 mL of water, 25 mL of brine, dried over anhydrous sodium sulfate, filtered and concentrated under reduced pressure. Purification by silica gel chromatography, eluting with dichloromethane-methanol (gradient, 95:5-80:20) gave 0.0521 g of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzamide (I-193).

Example 194

4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194)

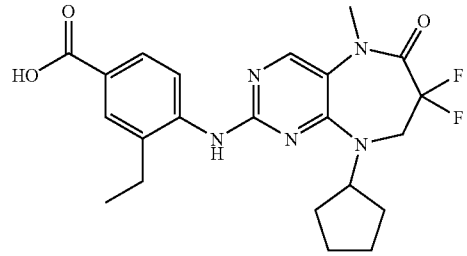

A mixture of 1.1 g (3.481 mmole) of 2-chloro-9-cyclopentyl-7,7-difluoro-5-methyl-5,7,8,9-tetrahydro-pyrimido[4,5-b][1,4]diazepin-6-one (VII-20), 0.746 g (4.525 mmole) of 4-amino-3-ethylbenzoic acid, 10 mL of ethanol and 40 mL of 1M hydrochloric acid was heated at reflux for 18 hours. The mixture was cooled and the white precipitate was collected by filtratration, washed with cold water and dried in vacuum to give 0.3421 g of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194) as off-white solid.

Example 195

4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-(1-methyl-piperidin-4-yl)-benzamide (I-195)

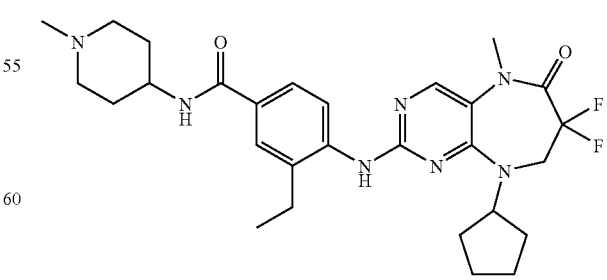

To a mixture of 0.040 g (0.0899 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194) and 6 mL of dimethylformamide was added 0.0182 g (0.135 mmole) of 1-hydroxybenzotriazole, 0.0520 g (0.135 mmole) of 1-[bis(dimethylamino)methylene]-1H-benzotriazolium-3-oxide hexafluorophosphate and 0.060 g (0.463 mmole) of diisopropylethylamine. The mixture was stirred for 10 minutes, then 0.0153 g (0.134 mmole) of 4-amino-1-methylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0231 g of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-(1-methyl-piperidin-4-yl)-benzamide (I-195) as a white solid.

Example 196

4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-(1-ethyl-piperidin-4-yl)-benzamide (I-196)

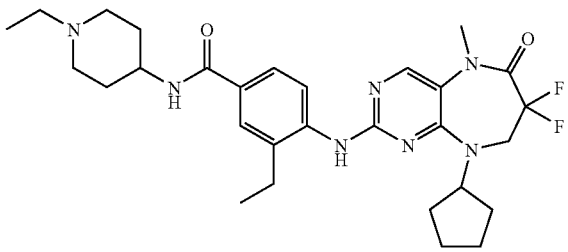

To a mixture of 0.040 g (0.0899 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194) and 6 mL of dimethylformamide was added 0.0182 g (0.135 mmole) of 1-hydroxybenzotriazole, 0.0520 g (0.135 mmole) of 1-[bis(dimethylamino)methylene]-1H-benzotriazolium-3-oxide hexafluorophosphate and 0.047 g (0.359 mmole) of diisopropylethylamine. The mixture was stirred for 10 minutes, then 0.0173 g (0.135 mmole) of 4-amino-1-ethylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0368 g of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-(1-ethyl-piperidin-4-yl)-benzamide (I-196) as a white solid.

Example 197

4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-(tetrahydro-pyran-4-yl)-benzamide (I-197)

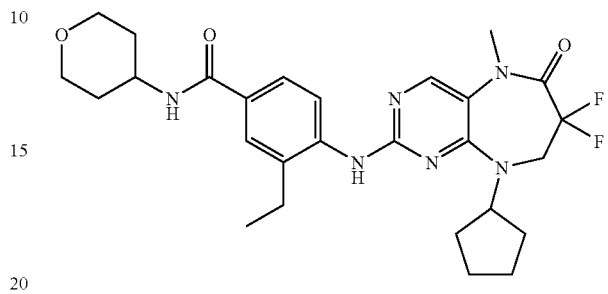

To a mixture of 0.040 g (0.0899 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194) and 6 mL of dimethylformamide was added 0.0182 g (0.135 mmole) of 1-hydroxybenzotriazole, 0.0520 g (0.135 mmole) of 1-[bis(dimethylamino)methylene]-1H-benzotriazolium-3-oxide hexafluorophosphate and 0.047 g (0.359 mmole) of diisopropylethylamine. The mixture was stirred for 10 minutes, then 0.0136 g (0.135 mmole) of 4-aminotetrahydropyran was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0349 g of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-(tetrahydro-pyran-4-yl)-benzamide (I-197).

Example 198

4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-ethyl-benzamide (I-198)

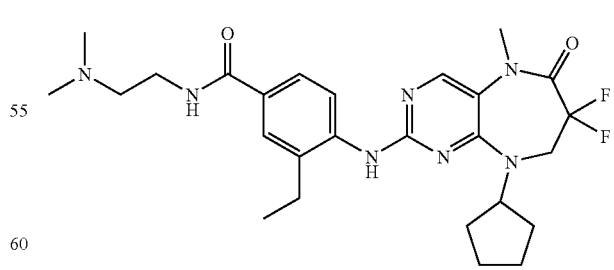

To a mixture of 0.040 g (0.0899 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194) and 6 mL of dimethylformamide was added 0.0182 g (0.135 mmole) of 1-hydroxybenzotriazole, 0.0520 g (0.135 mmole) of 1-[bis(dimethylamino)methylene]-1H-benzotriazolium-3-oxide hexafluorophosphate and 0.047 g (0.359 mmole) of diisopropylethylamine. The mixture was stirred for 10 minutes, then 0.0120 g (0.134 mmole) of N,N-dimethylethylenediamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0359 g of 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-ethyl-benzamide (I-198) as a white solid.

Example 199

4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-ethyl-benzamide (I-199)

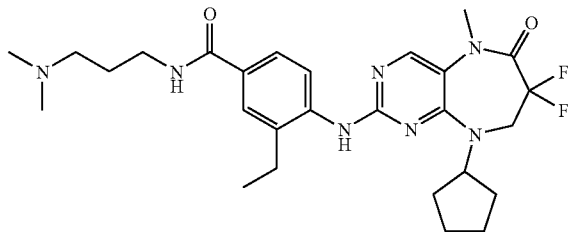

To a mixture of 0.040 g (0.0899 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194) and 6 mL of dimethylformamide was added 0.0182 g (0.135 mmole) of 1-hydroxybenzotriazole, 0.0520 g (0.135 mmole) of 1-[bis(dimethylamino)methylene]-1H-benzotriazolium-3-oxide hexafluorophosphate and 0.047 g (0.359 mmole) of diisopropylethylamine. The mixture was stirred for 10 minutes, then 0.0120 g (0.134 mmole) of N,N-dimethylethylenediamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0244 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-ethyl-benzamide (I-199) as a white solid.

Example 200

4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-methyl-benzamide (I-200)

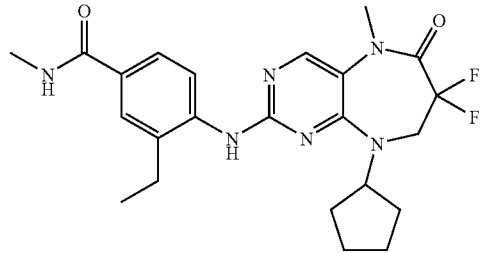

To a mixture of 0.040 g (0.0899 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194) and 6 mL of dimethylformamide was added 0.0182 g (0.135 mmole) of 1-hydroxybenzotriazole, 0.0520 g (0.135 mmole) of 1-[bis(dimethylamino)methylene]-1H-benzotriazolium-3-oxide hexafluorophosphate and 0.047 g (0.359 mmole) of diisopropylethylamine. The mixture was stirred for 10 minutes, then 0.0098 g (0.145 mmole) of methylamine hydrochloride was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0275 g of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-methyl-benzamide (I-200) as a white solid.

Example 201

4-[4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoylamino]-piperidine-1-carboxylic acid tert-butyl ester (I-201)

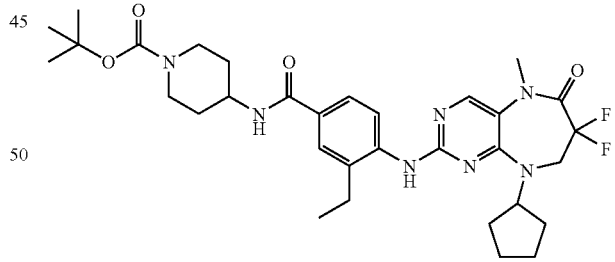

To a mixture of 0.040 g (0.0899 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194) and 6 mL of dimethylformamide was added 0.0182 g (0.135 mmole) of 1-hydroxybenzotriazole, 0.0520 g (0.135 mmole) of 1-[bis(dimethylamino)methylene]-1H-benzotriazolium-3-oxide hexafluorophosphate and 0.047 g (0.359 mmole) of diisopropylethylamine. The mixture was stirred for 10 minutes, then 0.0270 g (0.135 mmole) of 4-amino-1-Boc-piperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0527 g of 4-[4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoylamino]-piperidine-1-carboxylic acid tert-butyl ester (I-201) as a white solid.

Example 202

4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-piperidin-4-yl-benzamide (I-202)

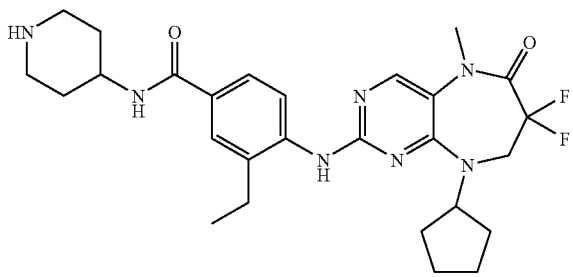

A solution of 0.0447 g (0.0712 mmole) 4-[4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoylamino]-piperidine-1-carboxylic acid tert-butyl ester (I-201) in 4 mL of dichloromethane was stirred with 2 mL of trifluoroacetic acid for 2 hours and concentrated under reduced pressure. The residue was dissolved in 80 mL of dichloromethane, washed with 15 mL of sodium carbonate solution, twice with 15 mL of brine and concentrated under reduced pressure. The residue was purified by reverse phase silica gel chromatography, eluting with water-acetonitrile (gradient, 90:10-0:100) to give 0.00269 g of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-piperidin-4-yl-benzamide (I-202) as a white solid.

Example 203

4-(9-cyclopentyl-7,7-difluoro-5-methyl-6-oxo-6,7,8,9-tetrahydro-5H-pyrimido[4,5-b][1,4]diazepin-2-ylamino)-3-methyl-benzamide (I-203)

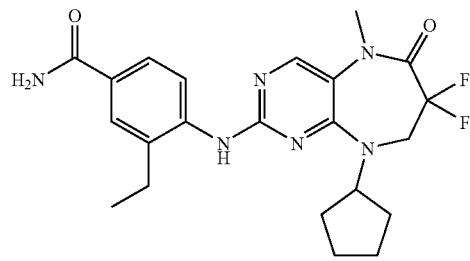

A mixture of 0.075 g (0.129 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid (I-194), 4 mL of dimethylformamide, 0.0654 g (0.167 mmole) of 1-[bis(dimethylamino)methylene]-1H-1,2,3-triazolo[4,5-b]pyridinium-3-oxide hexafluorophosphate and 0.12 mL (0.689 mmole) of diisopropylethylamine was stirred for 20 minutes, then 0.0159 g (0.297 mmole) of ammonium chloride was added. The reaction mixture was stirred for 1.5 hours and then 150 mL of ethyl acetate and 25 mL of water was added. The organic layer was washed with 25 mL of ammonium chloride solution, 25 mL of water, 25 mL of brine, dried over anhydrous sodium sulfate, filtered and concentrated under reduced pressure. Purification by silica gel chromatography, eluting with dichloromethane-methanol (gradient, 95:5-80:20) gave 0.0346 g of 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzamide (I-203).

Example 204

4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204)

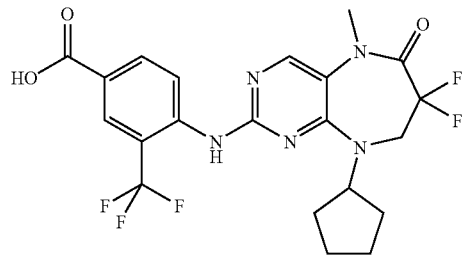

To a mixture of 1.00 g (3.16 mmole) of 2-chloro-9-cyclopentyl-7,7-difluoro-5-methyl-5,7,8,9-tetrahydro-pyrimido[4,5-b][1,4]diazepin-6-one (VII-20), 0.971 g (4.74 mmole) of 4-amino-3-trifluoromethyl)benzoic acid, and 50 mL of dioxane, was added 2.05 g (6.32 mmole) of cesium carbonate and 0.070 g (0.316 mmole) of palladium acetate. The mixture was deoxygenated with argon, 0.393 g (0.632 mmole) of 1,1'-[1,1'-binaphthalene]-2,2'-diylbis[1,1-diphenyl phosphine was added and the reaction mixture was heated at 100 degrees for 3 hrs. The cooled mixture was concentrated under reduced pressure, dissolved in ethyl acetate, made slightly acidic by the addition of 1M hydrochloric acid, washed with water, brine, filtered and concentrated under reduced pressure. Purification by silica gel chromatography, eluting with dichloromethane-methanol (gradient, 95:5-80:20) gave 1.36 g of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204) as an off-white solid.

Example 205

4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-3-trifluoromethyl-benzamide (I-205)

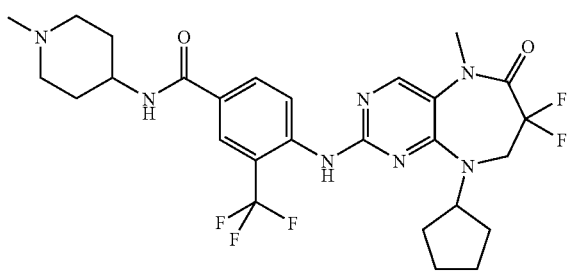

To a mixture of 0.075 g (0.155 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204) and 8 mL of dimethylformamide was added 0.0313 g (0.232 mmole) of 1-hydroxybenzotriazole, 0.0880 g (0.232 mmole) of 1-[bis(dimethylamino)methylene]-1H-benzotriazolium-3-oxide hexafluorophosphate and 0.080 g (0.617 mmole) of diisopropylethylamine. The mixture was stirred for 10 minutes, then 0.027 g (0.236 mmole) of 4-amino-1-methylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0392 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-3-trifluoromethyl-benzamide (I-205) as a white solid.

Example 206

4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-trifluoromethyl-benzamide (I-206)

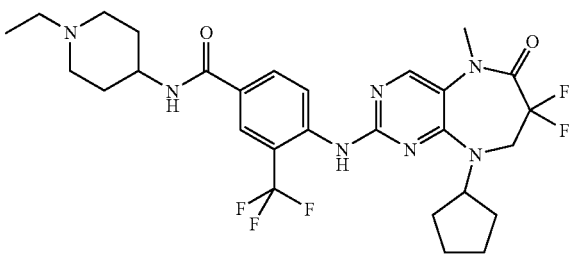

To a mixture of 0.075 g (0.155 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204) and 8 mL of dimethylformamide was added 0.0313 g (0.232 mmole) of 1-hydroxybenzotriazole, 0.0880 g (0.232 mmole) of 1-[bis(dimethylamino)methylene]-1H-benzotriazolium-3-oxide hexafluorophosphate and 0.080 g (0.617 mmole) of diisopropylethylamine. The mixture was stirred for 10 minutes, then 0.0299 g (0.233 mmole) of 4-amino-1-ethylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0459 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-trifluoromethyl-benzamide (I-206) as a white solid.

Example 207

4-(9-cyclopentyl-7,7-difluoro-5-methyl-6-oxo-6,7,8,9-tetrahydro-5H-pyrimido[4,5-b][1,4]diazepin-2-ylamino)-N-(tetrahydro-pyran-4-yl)-3-trifluoromethyl-benzamide (I-207)

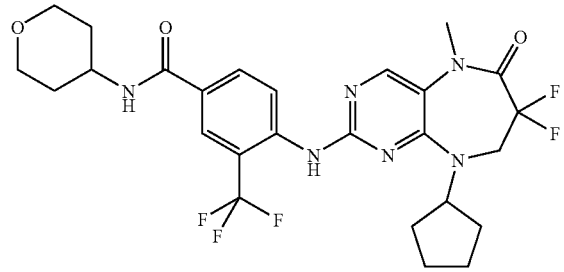

To a mixture of 0.075 g (0.155 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204) and 8 mL of dimethylformamide was added 0.0313 g (0.232 mmole) of 1-hydroxybenzotriazole, 0.0880 g (0.232 mmole) of 1-[bis(dimethylamino)methylene]-1H-benzotriazolium-3-oxide hexafluorophosphate and 0.080 g (0.617 mmole) of diisopropylethylamine. The mixture was stirred for 10 minutes, then 0.024 g (0.237 mmole) of 4-aminotetrahydropyran was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0439 g of 4-(9-cyclopentyl-7,7-difluoro-5-methyl-6-oxo-6,7,8,9-tetrahydro-5H-pyrimido[4,5-b][1,4]diazepin-2-ylamino)-N-(tetrahydro-pyran-4-yl)-3-trifluoromethyl-benzamide (I-207) as a white solid.

Example 208

4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-trifluoromethyl-benzamide (I-208)

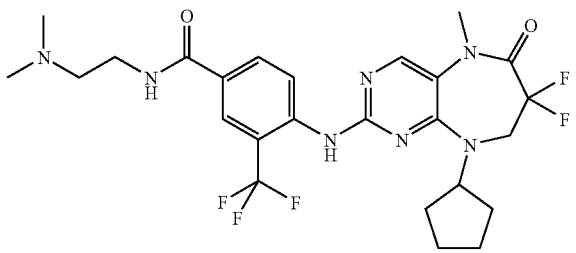

To a mixture of 0.125 g (0.257 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204) and 9 mL of dimethylformamide was added 0.0521 g (0.386 mmole) of 1-hydroxybenzotriazole, 0.146 g (0.385 mmole) of 1-[bis(dimethylamino)methylene]-1H-benzotriazolium-3-oxide hexafluorophosphate and 0.140 g (1.081 mmole) of diisopropylethylamine. The mixture was stirred for 10 minutes, then 0.034 g (0.385 mmole) of N,N-dimethylethylenediamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.1188 g of 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-trifluoromethyl-benzamide (I-208) as a white solid.

Example 209

4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-trifluoromethyl-benzamide (I-209)

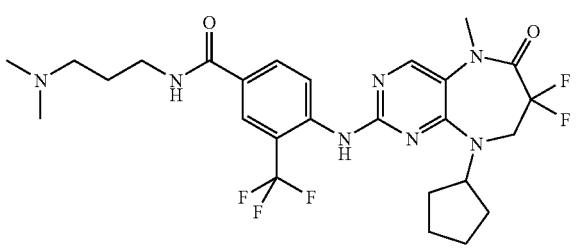

To a mixture of 0.125 g (0.257 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204) and 9 mL of dimethylformamide was added 0.0521 g (0.386 mmole) of 1-hydroxybenzotriazole, 0.146 g (0.385 mmole) of 1-[bis(dimethylamino)methylene]-1H-benzotriazolium-3-oxide hexafluorophosphate and 0.140 g (1.081 mmole) of diisopropylethylamine. The mixture was stirred for 10 minutes, then 0.0393 g (0.385 mmole) of 3-(dimethylamino)-propylamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.955 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-trifluoromethyl-benzamide (I-209) as a white solid.

Example 210

4-(9-cyclopentyl-7,7-difluoro-5-methyl-6-oxo-6,7,8,9-tetrahydro-5H-pyrimido[4,5-b][1,4]diazepin-2-ylamino)-N-methyl-3-trifluoromethyl-benzamide (I-210)

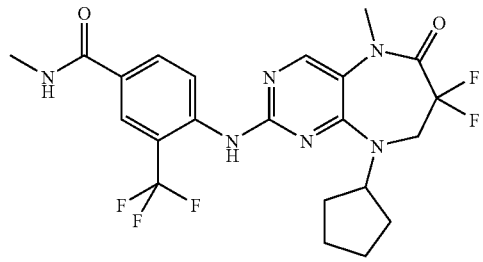

To a mixture of 0.125 g (0.257 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204) and 9 mL of dimethylformamide was added 0.0521 g (0.386 mmole) of 1-hydroxybenzotriazole, 0.146 g (0.385 mmole) of 1-[bis(dimethylamino)methylene]-1H-benzotriazolium-3-oxide hexafluorophosphate and 0.140 g (1.081 mmole) of diisopropylethylamine. The mixture was stirred for 10 minutes, then 0.0260 g (0.385 mmole) of methylamine hydrochloride was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0527 g of 4-(9-cyclopentyl-7,7-difluoro-5-methyl-6-oxo-6,7,8,9-tetrahydro-5H-pyrimido[4,5-b][1,4]diazepin-2-ylamino)-N-methyl-3-trifluoromethyl-benzamide (I-210) as a white solid.

Example 211

4-[4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoylamino]-piperidine-1-carboxylic acid tert-butyl ester (I-211)

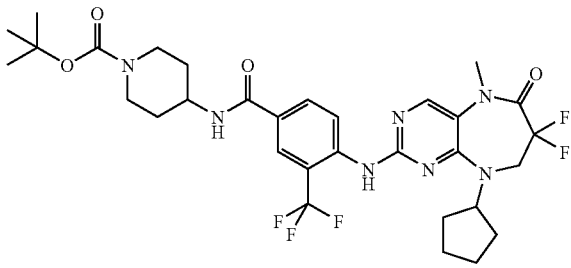

To a mixture of 0.075 g (0.155 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204) and 8 mL of dimethylformamide was added 0.0313 g (0.232 mmole) of 1-hydroxybenzotriazole, 0.088 g (0.232 mmole) of 1-[bis(dimethylamino)methylene]-1H-benzotriazolium-3-oxide hexafluorophosphate and 0.080 g (0.617 mmole) of diisopropylethylamine. The mixture was stirred for 10 minutes, then 0.0465 g (0.232 mmole) of 4-amino-1-Boc-piperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0354 g of 4-[4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoylamino]-piperidine-1-carboxylic acid tert-butyl ester (I-211) as a white solid.

Example 212

4-(9-cyclopentyl-7,7-difluoro-5-methyl-6-oxo-6,7,8,9-tetrahydro-5H-pyrimido[4,5-b][1,4]diazepin-2-ylamino)-N-piperidin-4-yl-3-trifluoromethyl-benzamide (I-212)

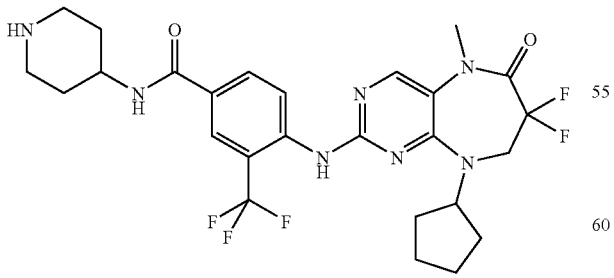

A solution of 0.0298 g (0.0446 mmole) 4-[4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoylamino]-piperidine-1-carboxylic acid tert-butyl ester (I-211) in 4 mL of dichloromethane was stirred with 2 mL of trifluoroacetic acid for 2 hours and then concentrated under reduced pressure. The residue was dissolved in 80 mL of dichloromethane, washed with 15 mL of sodium carbonate solution, twice with 15 mL of brine and concentrated under reduced pressure. The residue was purified by reverse phase silica gel chromatography, eluting with water-acetonitrile (gradient, 90:10-0:100) to give 0.0209 g of 4-(9-cyclopentyl-7,7-difluoro-5-methyl-6-oxo-6,7,8,9-tetrahydro-5H-pyrimido[4,5-b][1,4]diazepin-2-ylamino)-N-piperidin-4-yl-3-trifluoromethyl-benzamide (I-212) as a white solid.

Example 213

4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzamide (I-213)

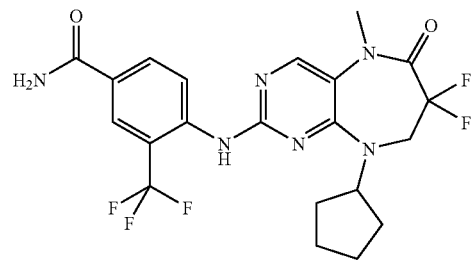

A mixture of 0.1013 g (0.208 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid (I-204), 5 mL of dimethylformamide, 0.107 g (0.208 mmole) of 1-[bis(dimethylamino)methylene]-1H-1,2,3-triazolo[4,5-b]pyridinium-3-oxide hexafluorophosphate and 0.25 mL (1.435 mmole) of diisopropylethylamine was stirred for 20 minutes, then 0.0444 g (0.830 mmole) of ammonium chloride was added. The reaction mixture was stirred for 1.5 hours and then 150 mL of ethyl acetate and 25 mL of water was added. The organic layer was washed with 25 mL of ammonium chloride solution, 25 mL of water, 25 mL of brine, dried over anhydrous sodium sulfate, filtered and concentrated under reduced pressure. Purification by silica gel chromatography, eluting with dichloromethane-methanol (gradient, 95:5-80:20) gave 0.048 g of 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzamide (I-213).

Example 214

4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214)

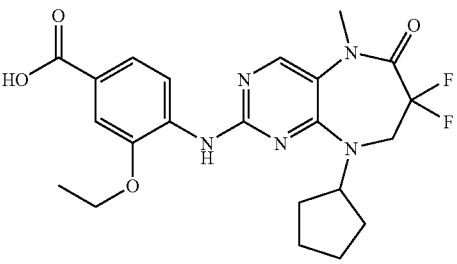

A mixture of 1.0 g (3.159 mmole) of 2-chloro-9-cyclopentyl-7,7-difluoro-5-methyl-5,7,8,9-tetrahydro-pyrimido[4,5-b][1,4]diazepin-6-one (VII-20), 0.740 g (3.79 mmole) of 4-amino-3-ethoxybenzoic acid, 10 mL of ethanol and 40 mL of 1M hydrochloric acid was heated at reflux for 18 hours. The mixture was cooled and the white precipitate was collected by filtratration, washed with cold water and dried in vacuum to give 0.6391 g of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214) as off-white solid.

Example 215

4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-(1-methyl-piperidin-4-yl)-benzamide (I-215)

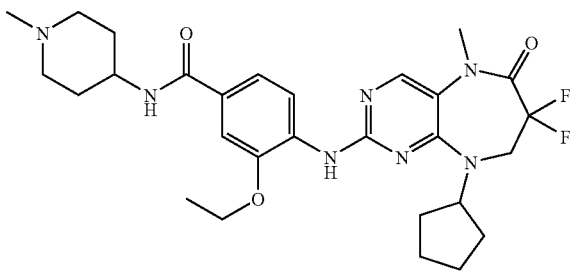

To a mixture of 0.0649 g (0.141 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214) and 4 mL of dimethylformamide was added 0.0309 g (0.229 mmole) of 1-hydroxybenzotriazole, 0.0825 g (0.229 mmole) of 1-[bis(dimethylamino)methylene]-1H-benzotriazolium-3-oxide hexafluorophosphate and 0.1113 g (0.862 mmole) of diisopropylethylamine. The mixture was stirred for 10 minutes, then 0.021 g (0.211 mmole) of 4-amino-1-methylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0231 g of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-(1-methyl-piperidin-4-yl)-benzamide (I-215) as a white solid.

Example 216

4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-(1-ethyl-piperidin-4-yl)-benzamide (I-216)

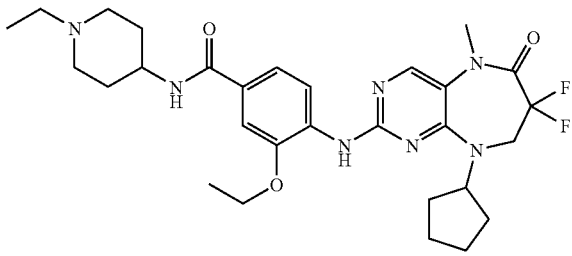

To a mixture of 0.0644 g (0.141 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214) and 4 mL of dimethylformamide was added 0.0309 g (0.229 mmole) of 1-hydroxybenzotriazole, 0.0825 g (0.229 mmole) of 1-[bis(dimethylamino)methylene]-1H-benzotriazolium-3-oxide hexafluorophosphate and 0.1113 g (0.862 mmole) of diisopropylethylamine. The mixture was stirred for 10 minutes, then 0.0273 g (0.211 mmole) of 4-amino-1-ethylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0596 g of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-(1-ethyl-piperidin-4-yl)-benzamide (I-216) as a white solid.

Example 217

4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-(tetrahydro-pyran-4-yl)-benzamide (I-217)

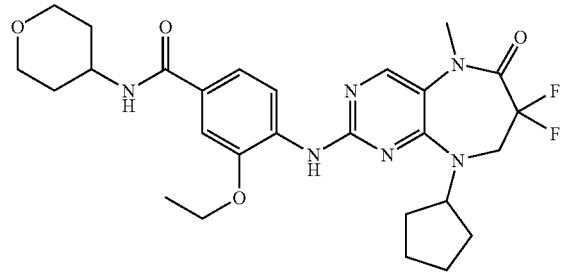

To a mixture of 0.0651 g (0.141 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214) and 4 mL of dimethylformamide was added 0.0309 g (0.229 mmole) of 1-hydroxybenzotriazole, 0.0825 g (0.229 mmole) of 1-[bis(dimethylamino)methylene]-1H-benzotriazolium-3-oxide hexafluorophosphate and 0.1113 g (0.862 mmole) of diisopropylethylamine. The mixture was stirred for 10 minutes, then 0.0213 g (0.211 mmole) of 4-aminotetrahydropyran was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0631 g of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-(tetrahydro-pyran-4-yl)-benzamide (I-217).

Example 218

4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-ethoxy-benzamide (I-219)

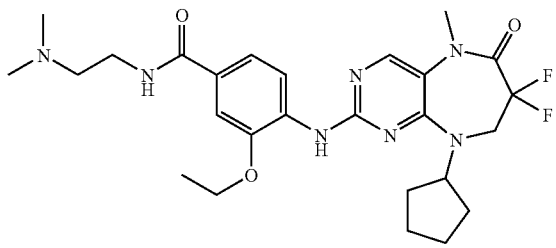

To a mixture of 0.0604 g (0.131 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214) and 4 mL of dimethylformamide was added 0.0309 g (0.229 mmole) of 1-hydroxybenzotriazole, 0.0825 g (0.229 mmole) of 1-[bis(dimethylamino)methylene]-1H-benzotriazolium-3-oxide hexafluorophosphate and 0.1113 g (0.862 mmole) of diisopropylethylamine. The mixture was stirred for 10 minutes, then 0.0172 g (0.197 mmole) of N,N-dimethylethylenediamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0631 g of 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-ethoxy-benzamide (I-219) as a white solid.

Example 219

4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-ethoxy-benzamide (I-219)

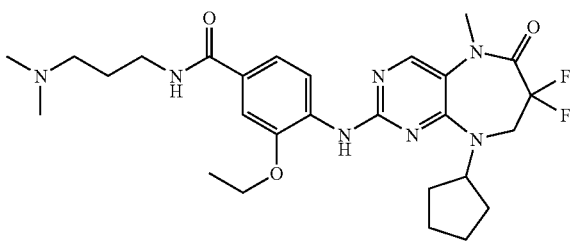

To a mixture of 0.0651 g (0.141 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214) and 4 mL of dimethylformamide was added 0.0309 g (0.229 mmole) of 1-hydroxybenzotriazole, 0.0825 g (0.229 mmole) of 1-[bis(dimethylamino)methylene]-1H-benzotriazolium-3-oxide hexafluorophosphate and 0.1113 g (0.862 mmole) of diisopropylethylamine. The mixture was stirred for 10 minutes, then 0.0216 g (0.211 mmole) of 3-(dimethylamino)-propylamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0477 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-ethoxy-benzamide (I-219) as a white solid.

Example 220

4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-methyl-benzamide (I-220)

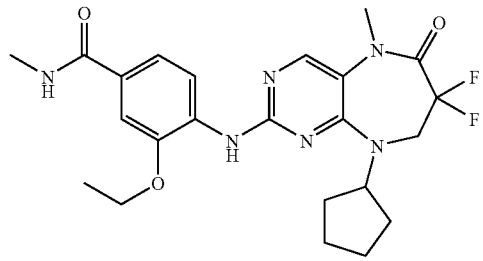

To a mixture of 0.0704 g (0.153 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214) and 4 mL of dimethylformamide was added 0.03338 g (0.250 mmole) of 1-hydroxybenzotriazole, 0.0904 g (0.238 mmole) of 1-[bis(dimethylamino)methylene]-1H-benzotriazolium-3-oxide hexafluorophosphate and 0.1632 g (1.265 mmole) of diisopropylethylamine. The mixture was stirred for 10 minutes, then 0.0229 g (0.337 mmole) of methylamine hydrochloride was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0562 g of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-methyl-benzamide (I-220) as a white solid.

Example 221

4-[4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoylamino]-piperidine-1-carboxylic acid tert-butyl ester (I-221)

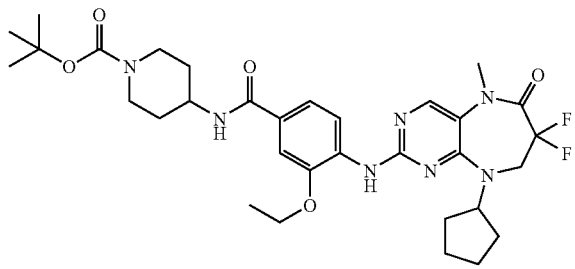

To a mixture of 0.0905 g (0.196 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214) and 6 mL of dimethylformamide was added 0.0418 g (0.310 mmole) of 1-hydroxybenzotriazole, 0.1146 g (0.302 mmole) of 1-[bis(dimethylamino)methylene]-1H-benzotriazolium-3-oxide hexafluorophosphate and 0.1484 g (1.148 mmole) of diisopropylethylamine. The mixture was stirred for 10 minutes, then 0.0624 g (0.299 mmole) of 4-amino-1-Boc-piperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.1081 g of 4-[4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoylamino]-piperidine-1-carboxylic acid tert-butyl ester (I-221) as a white solid.

Example 222

4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-piperidin-4-yl-benzamide (I-222)

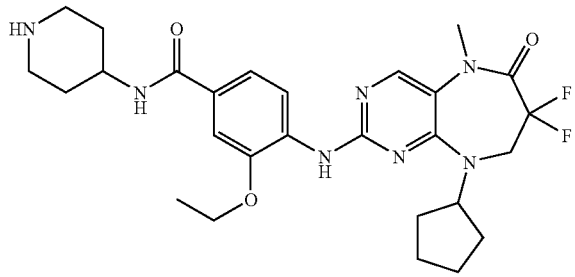

A solution of 0.0749 g (0.0712 mmole) 4-[4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoylamino]-piperidine-1-carboxylic acid tert-butyl ester (I-221) in 3 mL of dichloromethane was stirred with 3 mL of trifluoroacetic acid for 2 hours and then concentrated under reduced pressure. The residue was dissolved in 80 mL of dichloromethane, washed with 15 mL of sodium carbonate solution, twice with 15 mL of brine and concentrated under reduced pressure. The residue was purified by reverse phase silica gel chromatography, eluting with water-acetonitrile (gradient, 90:10-0:100) to give 0.060 g of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-piperidin-4-yl-benzamide (I-222) as a white solid.

Example 223

4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzamide (I-223)

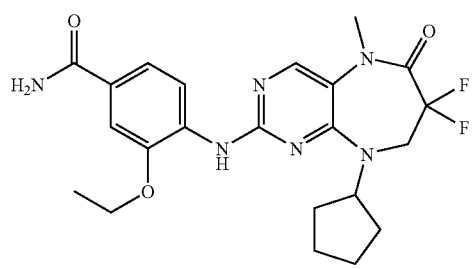

A mixture of 0.0704 g (0.153 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid (I-214), 4 mL of dimethylformamide, 0.0776 g (0.198 mmole) of 1-[bis(dimethylamino)methylene]-1H-1,2,3-triazolo[4,5-b]pyridinium-3-oxide hexafluorophosphate and 0.103 mg (0.804 mmole) of diisopropylethylamine was stirred for 20 minutes, then 0.0175 g (0.327 mmole) of ammonium chloride was added. The reaction mixture was stirred for 1.5 hours and then 150 mL of ethyl acetate and 25 mL of water was added. The organic layer was washed with 25 mL of ammonium chloride solution, 25 mL of water, 25 mL of brine, dried over anhydrous sodium sulfate, filtered and concentrated under reduced pressure. Purification by silica gel chromatography, eluting with dichloromethane-methanol (gradient, 95:5-80:20) gave 0.0554 g of 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzamide (I-223).

Example 224

4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-fluoro-benzamidemide (I-224)

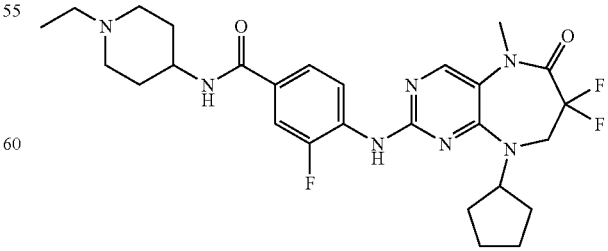

To a mixture of 0.070 g (0.161 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182) and 4 mL of dimethylformamide was added 0.0346 g (0.256 mmole) of 1-hydroxybenzotriazole, 0.0950 g (0.250 mmole) of 1-[bis(dimethylamino)methylene]-1H-benzotriazolium-3-oxide hexafluorophosphate and 0.1253 g (0.936 mmole) of diisopropylethylamine. The mixture was stirred for 10 minutes, then 0.0309 g (0.241 mmole) of 4-amino-1-ethylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0608 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-fluoro-benzamidemide (I-224) as a white solid.)

Example 225

4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-(tetrahydro-pyran-4-yl)-benzamide (I-225)

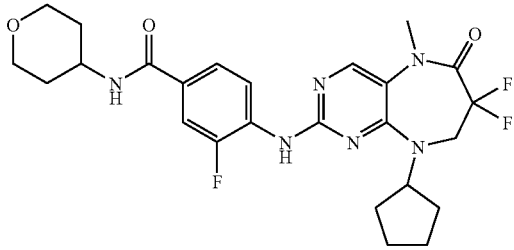

To a mixture of 0.070 g (0.161 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182) and 4 mL of dimethylformamide was added 0.0346 g (0.256 mmole) of 1-hydroxybenzotriazole, 0.0950 g (0.250 mmole) of 1-[bis(dimethylamino)methylene]-1H-benzotriazolium-3-oxide hexafluorophosphate and 0.1253 g (0.936 mmole) of diisopropylethylamine. The mixture was stirred for 10 minutes, then 0.0248 g (0.246 mmole) of 4-aminotetrahydropyran was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0504 g of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-(tetrahydro-pyran-4-yl)-benzamide (I-225).

Example 226

4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-fluoro-benzamide (I-226)

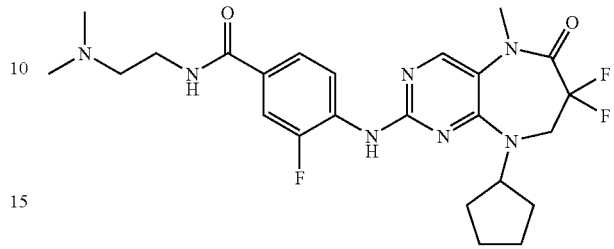

To a mixture of 0.070 g (0.161 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182) and 4 mL of dimethylformamide was added 0.0346 g (0.256 mmole) of 1-hydroxybenzotriazole, 0.0950 g (0.250 mmole) of 1-[bis(dimethylamino)methylene]-1H-benzotriazolium-3-oxide hexafluorophosphate and 0.1253 g (0.936 mmole) of diisopropylethylamine. The mixture was stirred for 10 minutes, then 0.0212 g (0.243 mmole) of N,N-dimethylethylenediamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0605 g of 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-fluoro-benzamide (I-226) as a white solid.

Example 227

4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-fluoro-benzamide (I-227)

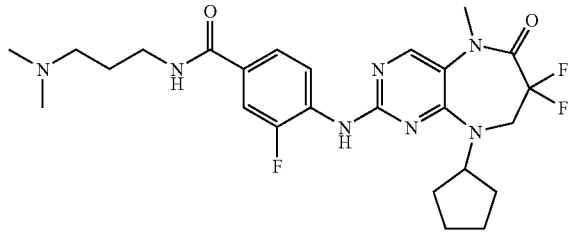

To a mixture of 0.070 g (0.161 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182) and 4 mL of dimethylformamide was added 0.0346 g (0.256 mmole) of 1-hydroxybenzotriazole, 0.0950 g (0.250 mmole) of 1-[bis(dimethylamino)methylene]-1H-benzotriazolium-3-oxide hexafluorophosphate and 0.1253 g (0.936 mmole) of diisopropylethylamine. The mixture was stirred for 10 minutes, then 0.0246 g (0.242 mmole) of 3-(dimethylamino)-propylamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.052 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-fluoro-benzamide (I-227) as a white solid.

Example 228

4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-methyl-benzamide (I-228)

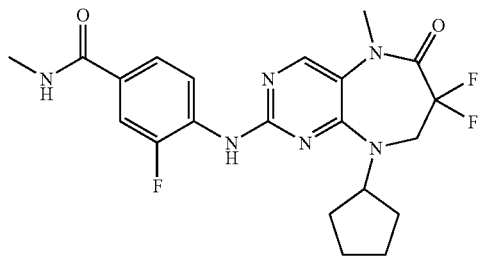

To a mixture of 0.070 g (0.161 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182) and 4 mL of dimethylformamide was added 0.0346 g (0.256 mmole) of 1-hydroxybenzotriazole, 0.0950 g (0.250 mmole) of 1-[bis(dimethylamino)methylene]-1H-benzotriazolium-3-oxide hexafluorophosphate and 0.1253 g (0.936 mmole) of diisopropylethylamine. The mixture was stirred for 10 minutes, then 0.0236 g (0.346 mmole) of methylamine hydrochloride was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0523 g of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-methyl-benzamide (I-228) as a white solid.

Example 229

4-[4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoylamino]-piperidine-1-carboxylic acid tert-butyl ester (I-229)

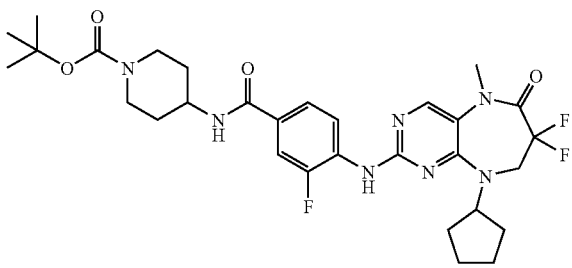

To a mixture of 0.10 g (0.23 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182) and 6 mL of dimethylformamide was added 0.0499 g (0.37 mmole) of 1-hydroxybenzotriazole, 0.1349 g (0.356 mmole) of 1-[bis(dimethylamino)methylene]-1H-benzotriazolium-3-oxide hexafluorophosphate and 0.0615 g (1.378 mmole) of diisopropylethylamine. The mixture was stirred for 10 minutes, then 0.0728 g (0.349 mmole) of 4-amino-1-Boc-piperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0906 g of 4-[4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoylamino]-piperidine-1-carboxylic acid tert-butyl ester (I-229) as a white solid.

Example 230

4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-piperidin-4-yl-benzamide (I-230)

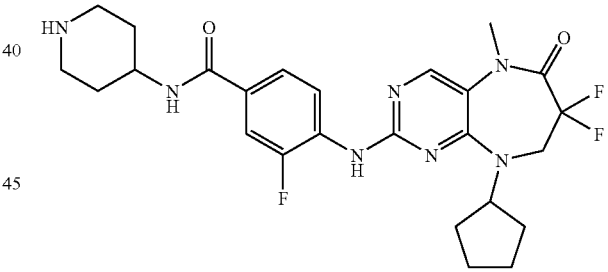

A solution of 0.067 g (0.109 mmole) 4-[4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoylamino]-piperidine-1-carboxylic acid tert-butyl ester (I-229) in 3 mL of dichloromethane was stirred with 3 mL of trifluoroacetic acid for 2 hours and then concentrated under reduced pressure. The residue was dissolved in 80 mL of dichloromethane, washed with 15 mL of sodium carbonate solution, twice with 15 mL of brine and concentrated under reduced pressure. The residue was purified by reverse phase silica gel chromatography, eluting with water-acetonitrile (gradient, 90:10-0:100) to give 0.0533 g of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-piperidin-4-yl-benzamide (I-230) as a white solid.

Example 231

4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzamide (I-231)

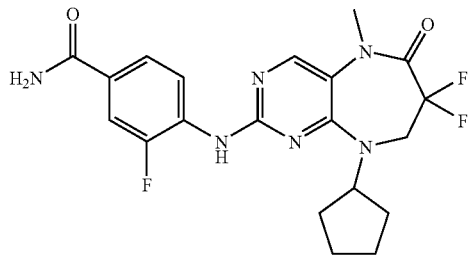

A mixture of 0.0703 g (0.161 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid (I-182), 4 mL of dimethylformamide, 0.0792 g (0.202 mmole) of 1-[bis(dimethylamino)methylene]-1H-1,2,3-triazolo[4,5-b]pyridinium-3-oxide hexafluorophosphate and 0.103 mg (0.804 mmole) of diisopropylethylamine was stirred for 20 minutes, then 0.0186 g (0.348 mmole) of ammonium chloride was added. The reaction mixture was stirred for 1.5 hours and then 150 mL of ethyl acetate and 25 mL of water was added. The organic layer was washed with 25 mL of ammonium chloride solution, 25 mL of water, 25 mL of brine, dried over anhydrous sodium sulfate, filtered and concentrated under reduced pressure. Purification by silica gel chromatography, eluting with dichloromethane-methanol (gradient, 95:5-80:20) gave 0.0531 g of 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzamide (I-231).

Example 232

4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232)

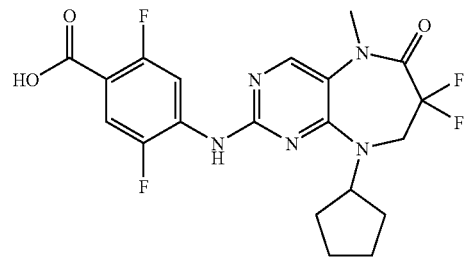

To a mixture of 0.9503 g (3.0 mmole) of 2-chloro-9-cyclopentyl-7,7-difluoro-5-methyl-5,7,8,9-tetrahydro-pyrimido[4,5-b][1,4]diazepin-6-one (VII-20), 0.6252 g (3.611 mmole) of 4-amino-2,5-difluorobenzoic acid, and 48 mL of dioxane, was added 1.96 g (6.01 mmole) of cesium carbonate and 0.0682 g (0.304 mmole) of palladium acetate. The mixture was deoxygenated with argon, 0.386 g (0.621 mmole) of 1,1'-[1,1'-binaphthalene]-2,2'-diylbis[1,1-diphenyl phosphine was added and the reaction mixture was heated at 100 degrees for 3 hrs. The cooled mixture was concentrated under reduced pressure, dissolved in ethyl acetate, made slightly acidic by the addition of 1M hydrochloric acid, washed with water, brine, filtered and concentrated under reduced pressure. Purification by silica gel chromatography, eluting with dichloromethane-methanol (gradient, 95:5-80:20) gave 0.5533 g of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232) as off-white solid.

Example 233

4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-(1-methyl-piperidin-4-yl)-benzamide (I-233)

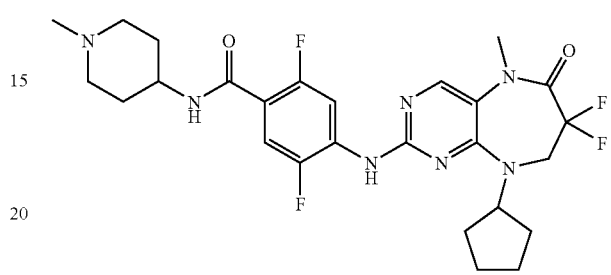

To a mixture of 0.0606 g (0.134 mmole) of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232) and 4 mL of dimethylformamide was added 0.0292 g (0.216 mmole) of 1-hydroxybenzotriazole, 0.0784 g (0.207 mmole) of 1-[bis(dimethylamino)methylene]-1H-benzotriazolium-3-oxide hexafluorophosphate and 0.1083 g (0.804 mmole) of diisopropylethylamine. The mixture was stirred for 10 minutes, then 0.0228 g (0.20 mmole) of 4-amino-1-methylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0628 g of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-(1-methyl-piperidin-4-yl)-benzamide (I-233) as a white solid.

Example 234

4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-2,5-difluoro-benzamide (I-234)

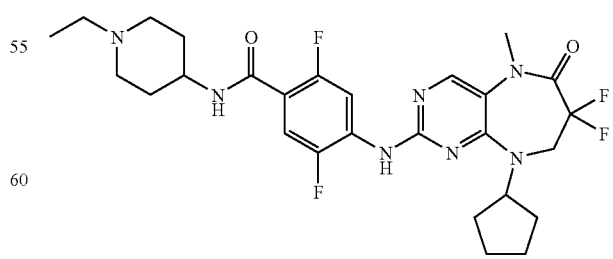

To a mixture of 0.0606 g (0.134 mmole) of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232) and 4 mL of dimethylformamide was added 0.0292 g (0.216 mmole) of 1-hydroxybenzotriazole, 0.0784 g (0.207 mmole) of 1-[bis(dimethylamino)methylene]-1H-benzotriazolium-3-oxide hexafluorophosphate and 0.1083 g (0.804 mmole) of diisopropylethylamine. The mixture was stirred for 10 minutes, then 0.0256 g (0.20 mmole) of 4-amino-1-ethylpiperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.053 g of 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-2,5-difluoro-benzamide (I-234) as a white solid.

Example 235

4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-(tetrahydro-pyran-4-yl)-benzamide (I-235)

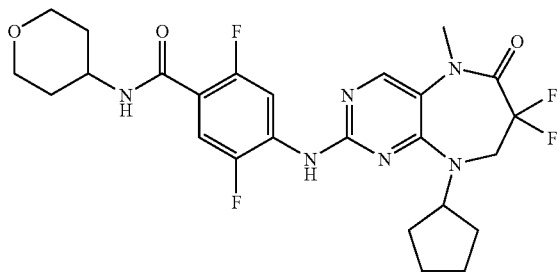

To a mixture of 0.0606 g (0.134 mmole) of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232) and 4 mL of dimethylformamide was added 0.0292 g (0.216 mmole) of 1-hydroxybenzotriazole, 0.0784 g (0.207 mmole) of 1-[bis(dimethylamino)methylene]-1H-benzotriazolium-3-oxide hexafluorophosphate and 0.1083 g (0.804 mmole) of diisopropylethylamine. The mixture was stirred for 10 minutes, then 0.0203 g (0.201 mmole) of 4-aminotetrahydropyran was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.0511 g of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-(tetrahydro-pyran-4-yl)-benzamide (I-235).

Example 236

4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-2,5-difluoro-benzamide (I-236)

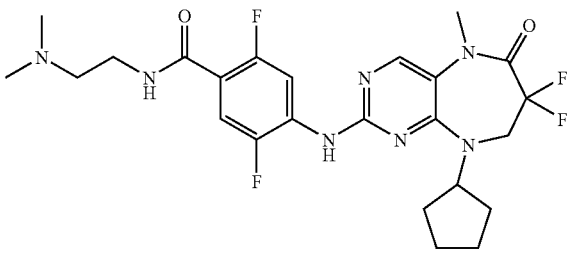

To a mixture of 0.0606 g (0.134 mmole) of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232) and 4 mL of dimethylformamide was added 0.0292 g (0.216 mmole) of 1-hydroxybenzotriazole, 0.0784 g (0.207 mmole) of 1-[bis(dimethylamino)methylene]-1H-benzotriazolium-3-oxide hexafluorophosphate and 0.1083 g (0.804 mmole) of diisopropylethylamine. The mixture was stirred for 10 minutes, then 0.0174 g (0.198 mmole) of N,N-dimethylethylenediamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0589 g of 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-2,5-difluoro-benzamide (I-236) as a white solid.

Example 237

4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-2,5-difluoro-benzamide (I-237)

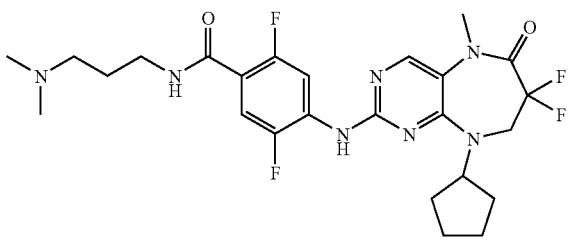

To a mixture of 0.0606 g (0.134 mmole) of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232) and 4 mL of dimethylformamide was added 0.0292 g (0.216 mmole) of 1-hydroxybenzotriazole, 0.0784 g (0.207 mmole) of 1-[bis(dimethylamino)methylene]-1H-benzotriazolium-3-oxide hexafluorophosphate and 0.1083 g (0.804 mmole) of diisopropylethylamine. The mixture was stirred for 10 minutes, then 0.0202 g (0.198 mmole) of 3-(dimethylamino)-propylamine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0576 g of 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-2,5-difluoro-benzamide (I-237) as a white solid.

Example 238

4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-methyl-benzamide (I-238)

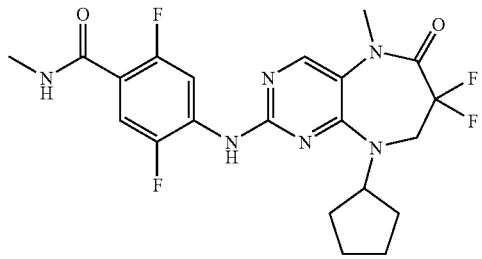

To a mixture of 0.0696 g (0.154 mmole) of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232) and 4 mL of dimethylformamide was added 0.0339 g (0.251 mmole) of 1-hydroxybenzotriazole, 0.0906 g (0.239 mmole) of 1-[bis(dimethylamino)methylene]-1H-benzotriazolium-3-oxide hexafluorophosphate and 0.1629 g (1.263 mmole) of diisopropylethylamine. The mixture was stirred for 10 minutes, then 0.0224 g (0.328 mmole) of methylamine hydrochloride was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-80:20) gave 0.0594 g of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-methyl-benzamide (I-238) as a white solid.

Example 239

4-[4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoylamino]-piperidine-1-carboxylic acid tert-butyl ester (I-239)

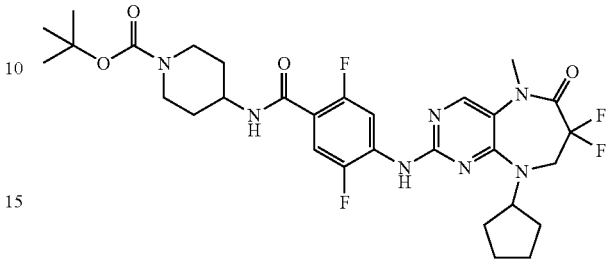

To a mixture of 0.1055 g (0.233 mmole) of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232) and 4 mL of dimethylformamide was added 0.0515 g (0.382 mmole) of 1-hydroxybenzotriazole, 0.1361 g (0.359 mmole) of 1-[bis(dimethylamino)methylene]-1H-benzotriazolium-3-oxide hexafluorophosphate and 0.1778 g (1.378 mmole) of diisopropylethylamine. The mixture was stirred for 10 minutes, then 0.0742 g (0.370 mmole) of 4-amino-1-Boc-piperidine was added. The reaction mixture was stirred for 2 hours and then concentrated under reduced pressure. The residue was dissolved in 80 mL of ethyl acetate and washed three times with 10 mL of 1M sodium hydroxide, twice with 15 mL of brine, dried, filtered and concentrated under reduced pressure. Purification by silica gel chromatography, eluting with dichloromethane-methanol (gradient, 95:5-90:10) gave 0.1183 g of 4-[4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoylamino]-piperidine-1-carboxylic acid tert-butyl ester (I-239) as a white solid.

Example 240

4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-piperidin-4-yl-benzamide (I-240)

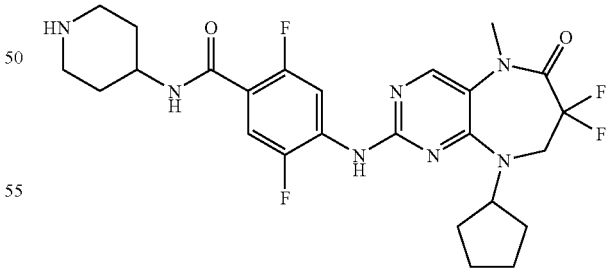

A solution of 0.0781 g (0.123 mmole) 4-[4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoylamino]-piperidine-1-carboxylic acid tert-butyl ester (I-239) in 3 mL of dichloromethane was stirred with 3 mL of trifluoroacetic acid for 2 hours and then concentrated under reduced pressure. The residue was dissolved in 80 mL of dichloromethane, washed with 15 mL of sodium carbonate solution, twice with 15 mL of brine and concentrated under reduced pressure. The residue was purified by reverse phase silica gel chromatography, eluting with water-acetonitrile (gradient, 90:10-0:100) to give 0.0637 g of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-piperidin-4-yl-benzamide (I-240) as a white solid.

Example 241

4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzamide (I-241)

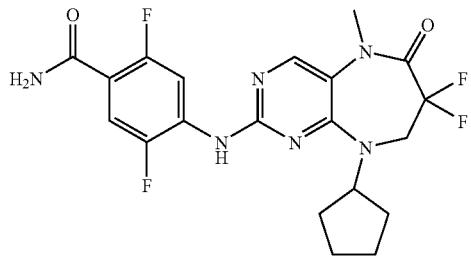

A mixture of 0.0697 g (0.154 mmole) of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid (I-232), 4 mL of dimethylformamide, 0.0783 g (0.20 mmole) of 1-[bis(dimethylamino)methylene]-1H-1,2,3-triazolo[4,5-b]pyridinium-3-oxide hexafluorophosphate and 0.103 mg (0.804 mmole) of diisopropylethylamine was stirred for 20 minutes, then 0.0166 g (0.31 mmole) of ammonium chloride was added. The reaction mixture was stirred for 1.5 hours and then 150 mL of ethyl acetate and 25 mL of water was added. The organic layer was washed with 25 mL of ammonium chloride solution, 25 mL of water, 25 mL of brine, dried over anhydrous sodium sulfate, filtered and concentrated under reduced pressure. Purification by silica gel chromatography, eluting with dichloromethane-methanol (gradient, 95:5-80:20) gave 0.040 g of 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzamide (I-241).

Example 242

4-(9-cyclopentyl-7,7-difluoro-5-methyl-6-oxo-6,7,8,9-tetrahydro-5H-pyrimido[4,5-b][1,4]diazepin-2-ylamino)-2,3-difluoro-benzoic acid methyl ester (I-242)

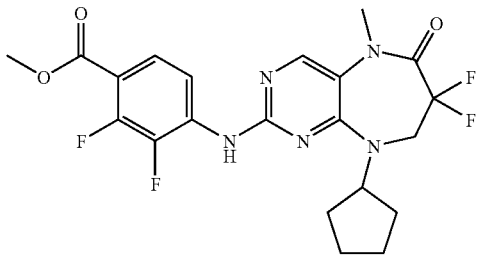

To a mixture of 0.4997 g (1.578 mmole) of 2-chloro-9-cyclopentyl-7,7-difluoro-5-methyl-5,7,8,9-tetrahydro-pyrimido[4,5-b][1,4]diazepin-6-one (VII-20), 0.3539 g (1.891 mmole) of 4-amino-2,3-difluorobenzoic acid, and 25 mL of dioxane, was added 1.028 g (3.152 mmole) of cesium carbonate and 0.0367 g (0.163 mmole) of palladium acetate. The mixture was deoxygenated with argon, 0.2044 g (0.318 mmole) of 1,1'-[1,1'-binaphthalene]-2,2'-diylbis[1,1-diphenyl phosphine was added and the reaction mixture was heated at 100 degrees for 4 hrs. The cooled mixture was concentrated under reduced pressure, dissolved in ethyl acetate, made slightly acidic by the addition of 1M hydrochloric acid, washed with water, brine, filtered and concentrated under reduced pressure. Purification by silica gel chromatography, eluting with dichloromethane-methanol (gradient, 95:5-80:20) gave 0.565 g of 4-(9-cyclopentyl-7,7-difluoro-5-methyl-6-oxo-6,7,8,9-tetrahydro-5H-pyrimido[4,5-b][1,4]diazepin-2-ylamino)-2,3-difluoro-benzoic acid methyl ester (I-242) as off-white solid.

Example 243

4-(9-cyclopentyl-7,7-difluoro-6-oxo-6,7,8,9-tetrahydro-5H-pyrimido[4,5-b][1,4]diazepin-2-ylamino)-2,3-difluoro-N-(1-methyl-piperidin-4-yl)-benzamide (I-243)

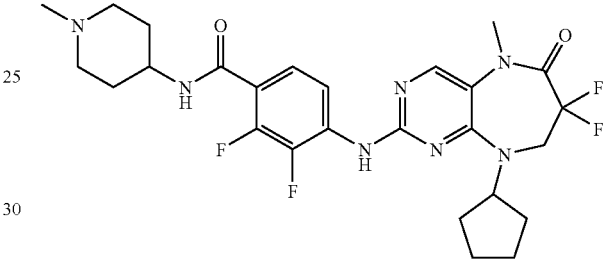

To a solution of 0.534 g (1.142 mmole) of 4-(9-cyclopentyl-7,7-difluoro-5-methyl-6-oxo-6,7,8,9-tetrahydro-5H-pyrimido[4,5-b][1,4]diazepin-2-ylamino)-2,3-difluoro-benzoic acid methyl ester (I-242) and 48 mL of tetrahydrofuran, was added 0.284 g (6.772 mmole) of lithium hydroxide monohydrate in 32 mL of water. The reaction mixture was stirred for 2 hours, then neutralized by the addition of 1M hydrochloric acid. The resulting solid was collected by filtration and dried to give a 2:1 mixture of 4-(9-cyclopentyl-7,7-difluoro-5-methyl-6-oxo-6,7,8,9-tetrahydro-5H-pyrimido[4,5-b][1,4]diazepin-2-ylamino)-2,3-difluoro-benzoic acid and 4-{4-[(2-Carboxy-2,2-difluoro-ethyl)-cyclopentyl-amino]-5-methylamino-pyrimidin-2-ylamino}-2,3-difluoro-benzoic acid, which was used without further purification.

A mixture of 0.0507 g of the 2:1 mixture of 4-(9-cyclopentyl-7,7-difluoro-5-methyl-6-oxo-6,7,8,9-tetrahydro-5H-pyrimido[4,5-b][1,4]diazepin-2-ylamino)-2,3-difluoro-benzoic acid and 4-{4-[(2-carboxy-2,2-difluoro-ethyl)-cyclopentyl-amino]-5-methylamino-pyrimidin-2-ylamino}-2,3-difluoro-benzoic acid in 4 mL of dimethylformamide was treated with 0.0971 g (0.248 mmole) of 1-[bis(dimethylamino)methylene]-1H-1,2,3-triazolo[4,5-b]pyridinium-3-oxide hexafluorophosphate and 0.0742 g (0.574 mmole) of diisopropylethylamine. After 15 minutes, 0.0186 g (0.162 mmole) of 4-amino-1-methylpiperidine in 1 mL of dimethylformamide was added. The reaction mixture stirred for 30 minutes and then diluted with 150 mL of ethyl acetate and 25 mL of water. The mixture was then washed successively with 20 mL of ammonium chloride, 20 mL of saturated aqueous sodium bicarbonate, dried over anhydrous sodium sulfate, filtered and concentrated under reduced pressure. Purification by silica gel chromatography, eluting with dichloromethane-methanol (gradient, 95:5-80:20) gave 0.0359 g of 4-(9-cyclopentyl-7,7-difluoro-6-oxo-6,7,8,9-tetrahydro-5H-pyrimido

[4,5-b][1,4]diazepin-2-ylamino)-2,3-difluoro-N-(1-methyl-piperidin-4-yl)-benzamide (I-243) as a white solid.

Example 244

4-(9-cyclopentyl-7,7-difluoro-6-oxo-6,7,8,9-tetrahydro-5H-pyrimido[4,5-b][1,4]diazepin-2-ylamino)-N-(1-ethyl-piperidin-4-yl)-2,3-difluoro-benzamide (I-244)

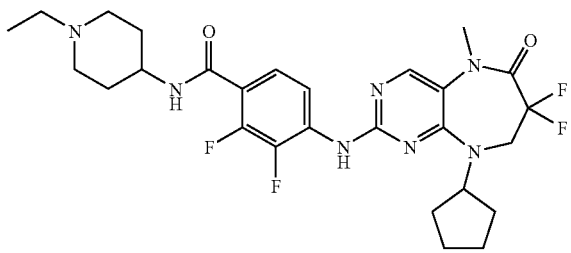

A mixture of 0.0801 g of the 2:1 mixture of 4-(9-cyclopentyl-7,7-difluoro-5-methyl-6-oxo-6,7,8,9-tetrahydro-5H-pyrimido[4,5-b][1,4]diazepin-2-ylamino)-2,3-difluoro-benzoic acid and 4-{4-[(2-carboxy-2,2-difluoro-ethyl)-cyclopentyl-amino]-5-methylamino-pyrimidin-2-ylamino}-2,3-difluoro-benzoic acid (from example 243) in 7 mL of dimethylformamide was treated with 0.154 g (0.393 mmole) of 1-[bis(dimethylamino)methylene]-1H-1,2,3-triazolo[4,5-b]pyridinium-3-oxide hexafluorophosphate and 0.1185 g (0.918 mmole) of diisopropylethylamine. After 15 minutes, 0.0328 g (0.256 mmole) of 4-amino-1-ethylpiperidine in 1 mL of dimethylformamide was added. The reaction mixture stirred for 30 minutes and then diluted with 150 mL of ethyl acetate and 25 mL of water. The mixture was then washed successively with 20 mL of ammonium chloride, 20 mL of saturated aqueous sodium bicarbonate, dried over anhydrous sodium sulfate, filtered and concentrated under reduced pressure. Purification by silica gel chromatography, eluting with dichloromethane-methanol (gradient, 95:5-80:20) gave 0.0651 g of 4-(9-cyclopentyl-7,7-difluoro-6-oxo-6,7,8,9-tetrahydro-5H-pyrimido[4,5-b][1,4]diazepin-2-ylamino)-N-(1-ethyl-piperidin-4-yl)-2,3-difluoro-benzamide (I-244) as a white solid.

Example 245

4-(9-cyclopentyl-7,7-difluoro-6-oxo-6,7,8,9-tetrahydro-5H-pyrimido[4,5-b][1,4]diazepin-2-ylamino)-2,3-difluoro-N-methyl-benzamide (I-245)

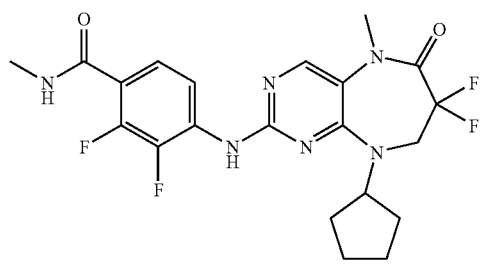

A mixture of 0.0804 g of the 2:1 mixture of 4-(9-cyclopentyl-7,7-difluoro-5-methyl-6-oxo-6,7,8,9-tetrahydro-5H-pyrimido[4,5-b][1,4]diazepin-2-ylamino)-2,3-difluoro-benzoic acid and 4-{4-[(2-carboxy-2,2-difluoro-ethyl)-cyclopentyl-amino]-5-methylamino-pyrimidin-2-ylamino}-2,3-difluoro-benzoic acid (from example 243) in 7 mL of dimethylformamide was treated with 0.1546 g (0.406 mmole) of 1-[bis(dimethylamino)methylene]-1H-1,2,3-triazolo[4,5-b]pyridinium-3-oxide hexafluorophosphate and 0.1558 g (1.206 mmole) of diisopropylethylamine. After 15 minutes, 0.0243 g (0.356 mmole) of methylamine hydrochloride in 1 mL of dimethylformamide was added. The reaction mixture stirred for 30 minutes and then diluted with 150 mL of ethyl acetate and 25 mL of water. The mixture was then washed successively with 20 mL of ammonium chloride, 20 mL of saturated aqueous sodium bicarbonate, dried over anhydrous sodium sulfate, filtered and concentrated under reduced pressure. Purification by silica gel chromatography, eluting with dichloromethane-methanol (gradient, 95:5-80:20) gave 0.0411 g of 4-(9-cyclopentyl-7,7-difluoro-6-oxo-6,7,8,9-tetrahydro-5H-pyrimido[4,5-b][1,4]diazepin-2-ylamino)-2,3-difluoro-N-methyl-benzamide (I-245) as a white solid.

Example 246

4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoic acid (I-246)

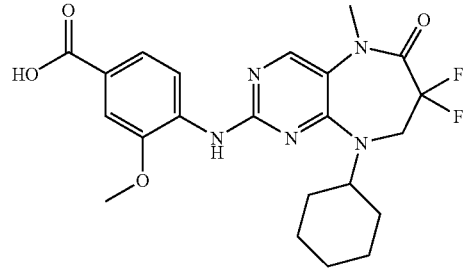

Step a

A solution of 16 g (0.068 mole) 3-cyclohexlamino-2,2-difluoropropionic acid ethyl ester in 10 mL of ethyl acetate was added dropwise to a mixture of 13.2 g (0.068 mole) of 2,4-dichloro-5-nitro-pyrimidine, 22.8 g (0.27 mole) of sodium bicarbonate and 100 mL of ethyl acetate at 0 degrees. The cooling bath was removed and the reaction was stirred at room temperature for 18 h. Activated charcoal was added, and the mixture was filtered through a pad of Celite, washing the filter pad with ethyl acetate. The filtrate was concentrated under reduced pressure, to give 18 g of 3-[(2-chloro-5-nitro-pyrimidin-4-yl)-cyclohexyl-amino]-2,2-difluoro-propionic acid ethyl ester (IV-246).

Step b

To a solution of 18 g (0.046 mole) of 3-[(2-chloro-5-nitro-pyrimidin-4-yl)-cyclohexyl-amino]-2,2-difluoro-propionic acid ethyl ester (IV-246) in 100 mL of acetic acid was added 15.5 g (0.191 g-atom) of iron powder. The mixture was heated to 80 degrees for 2 hours and then filtered while hot. Water and ethyl acetate were added to the filtrate and the mixture was stirred for 10 minutes. The organic layer was washed with ammonium hydroxide and water, dried over anhydrous sodium sulfate, filtered and concentrated under reduced pressure. The solid residue was washed with 50 mL of hexanes- EtOAc (90:10) and then air dried to give 10.5 g of 2-chloro-9-cyclohexyl-7,7-difluoro-5,7,8,9-tetrahydro-pyrimido[4,5-b][1,4]diazepin-6-one (VI-246).

Step c

To a mixture of 10.5 g (0.0332 mole) of 2-chloro-9-cyclohexyl-7,7-difluoro-5,7,8,9-tetrahydro-pyrimido[4,5-b][1,4]diazepin-6-one (VI-246), 25 mL of dimethylformamide and 16.2 g (0.0498 mole) of cesium carbonate was added 28.3 g (0.1992 mole) of iodomethane. The mixture was stirred for 3 hours, then 80 mL of water was added and the solid collected by suction filtration to give 10.0 g of 2-chloro-9-cyclohexyl-7,7-difluoro-5-methyl-5,7,8,9-tetrahydro-pyrimido[4,5-b][1,4]diazepin-6-one (VII-246).

Step d

A mixture of 3.30 g (0.010 mole) of 2-chloro-9-cyclohexyl-7,7-difluoro-5-methyl-5,7,8,9-tetrahydro-pyrimido[4,5-b][1,4]diazepin-6-one (VII-246), 2.006 g (0.012 mole) of 4-amino-3-methoxybenzoic acid and 200 mL of ethanol-water-hydrochloric acid (20:80:1) was refluxed for 18 hours, then concentrated under reduced pressure. The solid was washed with water and then purified by silica gel chromatography, eluting with dichloromethane-methanol-ammonium hydroxide (92:8:0.3) to give 1.400 g of 4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoic acid (I-246).

Example 247

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-247)

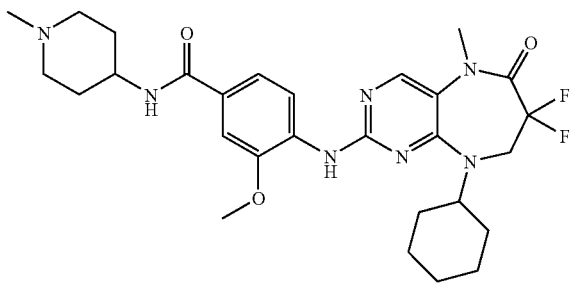

A mixture of 0.15 g (0.33 mmole) of 4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoic acid (I-246), 0.133 g (1.32 mmole) of triethylamine, 0.186 g (0.49 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes and then 0.056 g (0.49 mmole) of 4-amino-1-methyl-piperidine was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.140 g of 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-247).

Example 248

4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzamide (I-248)

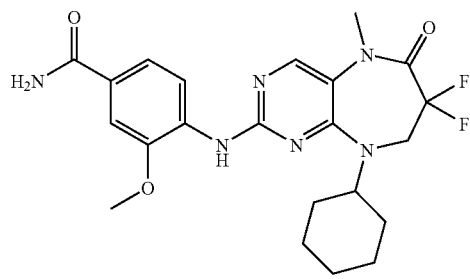

A mixture of 0.120 g (0.26 mmole) of 4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoic acid (I-246), 0.105 g (1.04 mmole) of triethylamine, 0.148 g (0.39 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes, then 0.045 g (0.84 mmole) of ammonium chloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.082 of 4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzamide (I-248).

Example 249

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-methyl-benzamide (I-249)

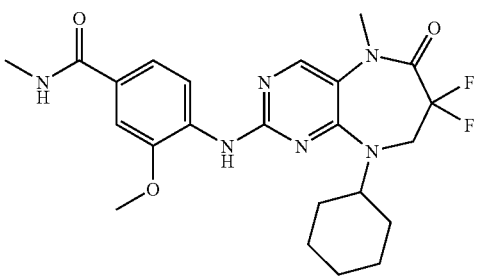

A mixture of 0.100 g (0.22 mmole) of 4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoic acid (I-246), 0.089 g (0.88 mmole) of triethylamine, 0.125 g (0.33 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes and then 0.023 g (0.35 mmole) of methylamine hydrochloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.046 g of 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-methyl-benzamide (I-249).

Example 250

4-[4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester (I-250)

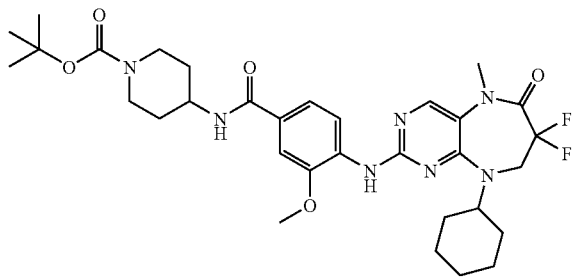

A mixture of 0.10 g (0.22 mmole) of 4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoic acid (I-246), 0.089 g (0.88 mmole) of triethylamine, 0.125 g (0.33 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes and then 0.066 g (0.33 mmole) of 4-amino-1-piperidinecarboxylic acid 1,1-dimethylethyl ester was added. The mixture was stirred for 3 hours, then taken up in 50 mL of dichloromethane and washed twice with 100 mL of water and then 100 mL of brine. The organic layer was dried over anhydrous sodium sulfate, filtered and concentrated under reduced pressure. The residue was purified by silica gel chromatography, eluting with hexane-ethyl acetate (gradient 50:50-0:100) to give 0.090 g of 4-[4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester (I-250).

Example 251

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-piperidin-4-yl-benzamide (I-251)

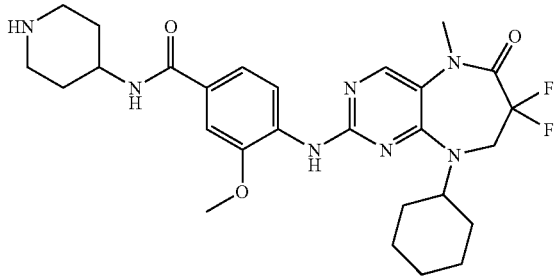

A mixture of 0.090 g (0.14 mmole) of 4-[4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester (I-250) 1 mL of trifluoroacetic acid and 5 mL of dichloromethane was stirred for 1 hour and then concentrated under reduced pressure. The residue was taken up in 30 mL of ethyl acetate, washed twice with 30 mL of saturated aqueous sodium bicarbonate and then brine. The organic layer was dried over anhydrous sodium sulfate, filtered and concentrated under reduced pressure. The residue was triturated with ether, to give 0.060 g of 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-piperidin-4-yl-benzamide (I-251).

Example 252

4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(tetrahydro-pyran-4-yl)-benzamide (I-252)

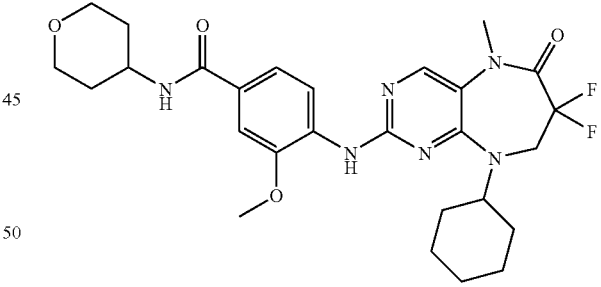

A mixture of 0.0562 g (0.18 mmole) 2-chloro-9-cyclohexyl-7,7-difluoro-5-methyl-5,7,8,9-tetrahydro-pyrimido[4,5-b][1,4]diazepin-6-one (VII-246), 0.0514 g (0.27 mmole) of toluenesulfonic acid monohydrate, 0.0451 g (0.18 mmole) of 4-amino-3-methoxy-N-(tetrahydro-2H-pyran-4-yl) benzamide and 1 mL of isopropanol was heated in a sealed vessel at 140 degrees for 16 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with ethyl acetate to give 0.0643 g of 4-(9-cyclohexyl-7,7-difluoro-5-methyl-6- oxo-6,7,8,9-tetrahydro-5H-pyrimido[4,5-b][1,4]diazepin-2-ylamino)-3-methoxy-N-(tetrahydro-pyran-4-yl)-benzamide (I-252) as a white solid.

Example 253

4-(9-cyclohexyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methoxy-benzamide (I-253)

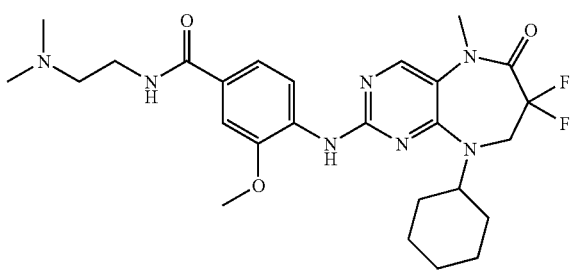

A mixture of 0.0642 g (0.194 mmole) 2-chloro-9-cyclohexyl-7,7-difluoro-5-methyl-5,7,8,9-tetrahydro-pyrimido[4,5-b][1,4]diazepin-6-one (VII-246), 0.0542 g (0.29 mmole) of toluenesulfonic acid monohydrate, 0.0451 g (0.194 mmole) of 4-amino-N-(2-dimethylamino-ethyl)-3-methoxy-benzamide and 1 mL of isopropanol was heated in a sealed vessel at 140 degrees for 16 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (85:15:1) to give 0.0743 g of 4-(9-cyclohexyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methoxy-benzamide (I-253) as a white solid.

Example 254

4-(9-cyclohexyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methoxy-benzamide (I-254)

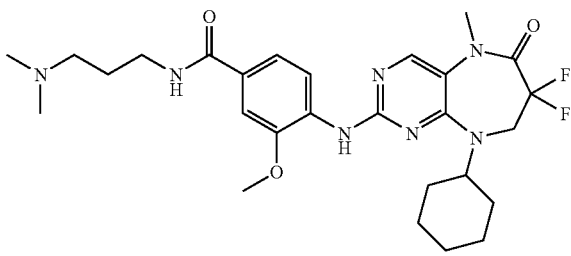

A mixture of 0.0562 g (0.18 mmole) 2-chloro-9-cyclohexyl-7,7-difluoro-5-methyl-5,7,8,9-tetrahydro-pyrimido[4,5-b][1,4]diazepin-6-one (VII-246), 0.0514 g (0.27 mmole) of toluenesulfonic acid monohydrate, 0.0398 g (0.18 mmole) of 4-amino-N-(3-dimethylamino-propyl)-benzamide and 1 mL of isopropanol was heated in a sealed vessel at 140 degrees for 20 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (80:20:2) to give 0.0645 g of 4-(9-cyclohexyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methoxy-benzamide (I-254) as a white solid.

Example 255

4-(9-cyclohexyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide (I-255)

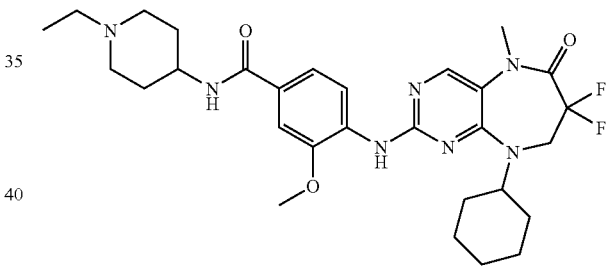

A mixture of 0.0628 g (0.19 mmole) 2-chloro-9-cyclohexyl-7,7-difluoro-5-methyl-5,7,8,9-tetrahydro-pyrimido[4,5-b][1,4]diazepin-6-one (VII-246), 0.0542 g (0.285 mmole) of toluenesulfonic acid monohydrate, 0.0527 g (0.19 mmole) of 4-amino-N-(1-ethyl-piperidin-4-yl)-3-methoxy-benzamide and 1 mL of isopropanol was heated in a sealed vessel at 140 degrees for 25 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (90:10:1) and then recrystallization from acetonitrile to give 0.0519 g of 4-(9-cyclohexyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide (I-255) as a white solid.

Example 256

4-(9-cyclohexyl-7,7-difluoro-5-methyl-6-oxo-6,7,8,9-tetrahydro-5H-pyrimido[4,5-b][1,4]diazepin-2-ylamin)-benzoic acid (I-256)

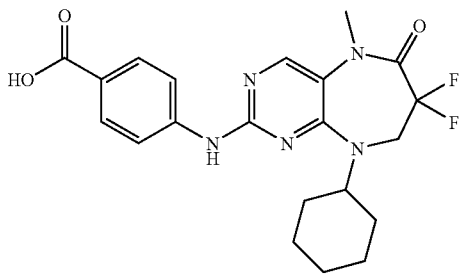

A mixture of 2.50 g (7.6 mmole) of 2-chloro-9-cyclohexyl-7,7-difluoro-5-methyl-5,7,8,9-tetrahydro-pyrimido[4,5-b][1,4]diazepin-6-one (VII-246), 1.25 g (9.1 mmole) of aminobenzoic acid and 200 mL of ethanol-water-hydrochloric acid (20:80:1) was refluxed for 18 hours, then concentrated under reduced pressure. The solid was washed with water and then purified by silica gel chromatography, eluting with dichloromethane-methanol-ammonium hydroxide (92:8:0.3) to give 1.600 g of 4-(9-cyclohexyl-7,7-difluoro-5-methyl-6-oxo-6,7,8,9-tetrahydro-5H-pyrimido[4,5-b][1,4]diazepin-2-ylamin)-benzoic acid (I-256).

Example 257

4-(9-cyclohexyl-7,7-difluoro-5-methyl-6-oxo-6,7,8,9-tetrahydro-5H-pyrimido[4,5-b][1,4]diazepin-2-ylamino)-benzamide (I-257)

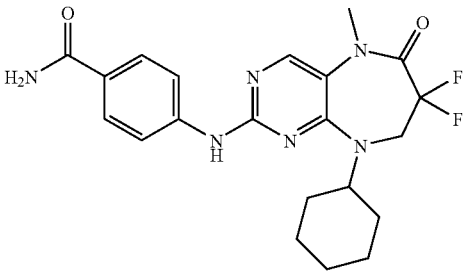

A mixture of 0.120 g (0.26 mmole) of 4-(9-cyclohexyl-7,7-difluoro-5-methyl-6-oxo-6,7,8,9-tetrahydro-5H-pyrimido[4,5-b][1,4]diazepin-2-ylamino)-benzoic acid (I-256), 0.105 g (1.04 mmole) of triethylamine, 0.148 g (0.39 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes, then 0.045 g (0.84 mmole) of ammonium chloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.096 g of 4-(9-cyclohexyl-7,7-difluoro-5-methyl-6-oxo-6,7,8,9-tetrahydro-5H-pyrimido[4,5-b][1,4]diazepin-2-ylamino)-benzamide (I-257).

Example 258

4-(9-cyclohexyl-7,7-difluoro-5-methyl-6-oxo-6,7,8,9-tetrahydro-5H-pyrimido[4,5-b][1,4]diazepin-2-ylamino)-N-methyl-benzamide (I-258)

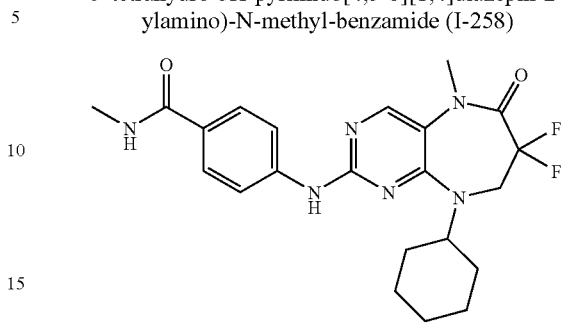

A mixture of 0.10 g (0.22 mmole) of 4-(9-cyclohexyl-7,7-difluoro-5-methyl-6-oxo-6,7,8,9-tetrahydro-5H-pyrimido[4,5-b][1,4]diazepin-2-ylamino)-benzoic acid (I-256), 0.089 g (0.88 mmole) of triethylamine, 0.125 g (0.33 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes, then 0.022 g (0.33 mmole) of methylamine hydrochloride was added. The mixture was stirred for 3 hours, then taken up in 100 mL of ethyl acetate and washed twice with 100 mL of water and then 100 mL of brine. The organic layer was dried over anhydrous sodium sulfate, filtered and concentrated under reduced pressure. The residue was purified by silica gel chromatography, eluting with dichloromethane-methanol-ammonium hydroxide (gradient 100:0:0-92:8:0.3) to give 0.089 g of 4-(9-cyclohexyl-7,7-difluoro-5-methyl-6-oxo-6,7,8,9-tetrahydro-5H-pyrimido[4,5-b][1,4]diazepin-2-ylamino)-N-methyl-benzamide (I-258)

Example 259

4-[4-(9-cyclohexyl-7,7-difluoro-5-methyl-6-oxo-6,7,8,9-tetrahydro-5H-pyrimido[4,5-b][1,4]diazepin-2-ylamino)-benzoylamino]-piperidine-1-carboxylic acid tert-butyl ester (I-259)

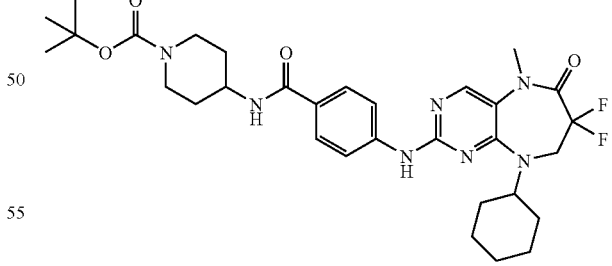

A mixture of 0.10 g (0.23 mmole) of 4-(9-cyclohexyl-7,7-difluoro-5-methyl-6-oxo-6,7,8,9-tetrahydro-5H-pyrimido[4,5-b][1,4]diazepin-2-ylamino)-benzoic acid (I-256), 0.093 g (0.92 mmole) of triethylamine, 0.133 g (0.35 mmole) of 1-[bis(dimethylamino)methylene]-1H-1,2,3-triazolo[4,5-b]pyridinium-3-oxide hexafluorophosphate and 5 mL of dimethylformamide was stirred for 15 minutes and then 0.070 g (0.35 mmole) of 4-amino-1-piperidinecarboxylic acid 1,1-dimethylethyl ester was added. The mixture was stirred for 3 hours, then taken up in 50 mL of dichloromethane and washed twice with 100 mL of water and then 100 mL of brine. The organic layer was dried over anhydrous sodium sulfate, filtered and concentrated under reduced pressure. The residue was purified by silica gel chromatography, eluting with hexane-ethyl acetate (gradient 50:50-0:100) to give 0.095 g of 4-[4-(9-cyclohexyl-7,7-difluoro-5-methyl-6-oxo-6,7,8,9-tetrahydro-5H-pyrimido[4,5-b][1,4]diazepin-2-ylamino)-benzoylamino]-piperidine-1-carboxylic acid tert-butyl ester (I-259).

Example 260

4-(9-cyclohexyl-7,7-difluoro-5-methyl-6-oxo-6,7,8,9-tetrahydro-5H-pyrimido[4,5-b][1,4]diazepin-2-ylamino)-N-piperidin-4-yl-benzamide (I-260)

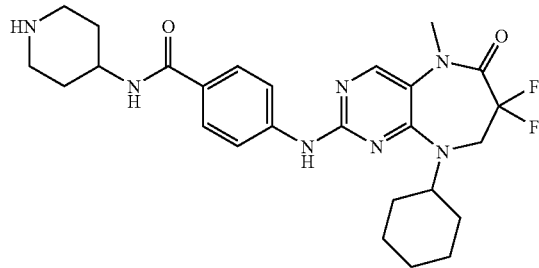

A mixture of 0.095 g (0.15 mmole) of 4-[4-(9-cyclohexyl-7,7-difluoro-5-methyl-6-oxo-6,7,8,9-tetrahydro-5H-pyrimido[4,5-b][1,4]diazepin-2-ylamino)-benzoylamino]-piperidine-1-carboxylic acid tert-butyl ester (I-259) 1 mL of trifluoroacetic acid and 5 mL of dichloromethane was stirred for 1 hour and then concentrated under reduced pressure. The residue was taken up in 30 mL of ethyl acetate, washed twice with 30 mL of saturated aqueous sodium bicarbonate and then brine. The organic layer was dried over anhydrous sodium sulfate, filtered and concentrated under reduced pressure. The residue was triturated with ether, to give 0.062 g of 4-(9-cyclohexyl-7,7-difluoro-5-methyl-6-oxo-6,7,8,9-tetrahydro-5H-pyrimido[4,5-b][1,4]diazepin-2-ylamino)-N-piperidin-4-yl-benzamide (I-260).

Example 261

4-(9-cyclohexyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-benzamide (I-261)

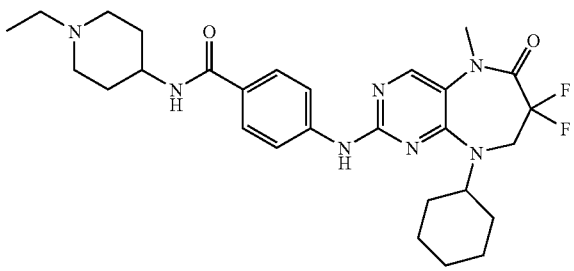

A mixture of 0.10 g (0.30 mmole) 2-chloro-9-cyclohexyl-7,7-difluoro-5-methyl-5,7,8,9-tetrahydro-pyrimido[4,5-b][1,4]diazepin-6-one (VII-246), 0.086 g (0.45 mmole) of toluenesulfonic acid monohydrate, 0.075 g (0.30 mmole) of 4-amino-N-(1-ethyl-piperidin-4-yl)-benzamide and 1 mL of isopropanol was heated in a sealed vessel at 170 degrees in a microwave reactor for 2 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was recrystallized from acetonitrile to give 0.115 g of 4-(9-cyclohexyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-benzamide (I-261).

Example 262

4-(9-cyclohexyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide (I-262)

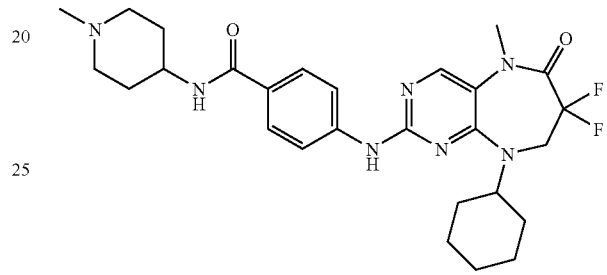

A mixture of 0.0562 g (0.17 mmole) 2-chloro-9-cyclohexyl-7,7-difluoro-5-methyl-5,7,8,9-tetrahydro-pyrimido[4,5-b][1,4]diazepin-6-one (VII-246), 0.0485 g (0.255 mmole) of toluenesulfonic acid monohydrate, 0.0397 g (0.17 mmole) of 4-amino-N-(1-methyl-piperidin-4-yl)-benzamide and 1 mL of isopropanol was heated in a sealed vessel at 140 degrees for 15 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was recrystallized from acetonitrile to give 0.0501 g of 4-(9-cyclohexyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide (I-262) as a white solid.

Example 263

4-(9-cyclohexyl-7,7-difluoro-5-methyl-6-oxo-6,7,8,9-tetrahydro-5H-pyrimido[4,5-b][1,4]diazepin-2-ylamino)-N-(tetrahydro-pyran-4-yl)-benzamide (I-263)

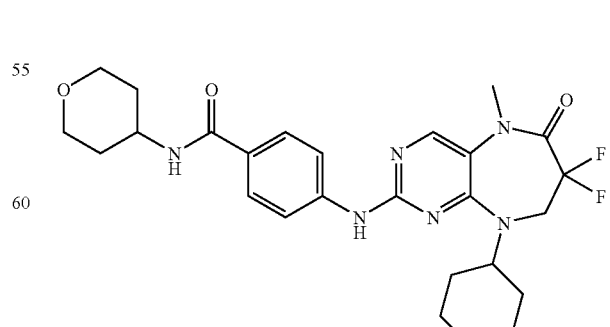

A mixture of 0.0562 g (0.18 mmole) 2-chloro-9-cyclohexyl-7,7-difluoro-5-methyl-5,7,8,9-tetrahydro-pyrimido[4,5-b][1,4]diazepin-6-one (VII-246), 0.0514 g (0.27 mmole) of toluenesulfonic acid monohydrate, 0.0396 g (0.18 mmole) of 4-amino-N-(tetrahydro-pyran-4-yl)-benzamide and 1 mL of isopropanol was heated in a sealed vessel at 140 degrees for 16.5 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was recrystallized from acetonitrile to give 0.0501 g of 4-(9-cyclohexyl-7,7-difluoro-5-methyl-6-oxo-6,7,8,9-tetrahydro-5H-pyrimido[4,5-b][1,4]diazepin-2-ylamino)-N-(tetrahydro-pyran-4-yl)-benzamide (I-263) as a white solid.

Example 264

4-(9-cyclohexyl-7,7-difluoro-5-methyl-6-oxo-6,7,8,9-tetrahydro-5H-pyrimido[4,5-b][1,4]diazepin-2-ylamino)-N-(2-dimethylamino-ethyl)-benzamide (I-264)

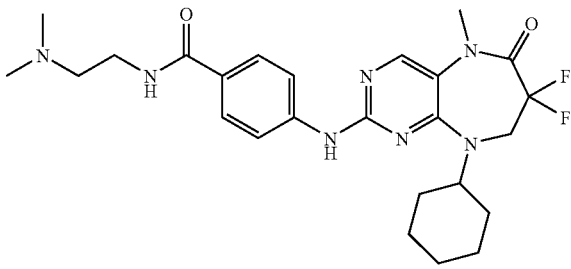

A mixture of 0.0562 g (0.18 mmole) 2-chloro-9-cyclohexyl-7,7-difluoro-5-methyl-5,7,8,9-tetrahydro-pyrimido[4,5-b][1,4]diazepin-6-one (VII-246), 0.0514 g (0.27 mmole) of toluenesulfonic acid monohydrate, 0.0373 g (0.18 mmole) of 4-amino-N-(2-dimethylamino-ethyl)-benzamide and 1 mL of isopropanol was heated in a sealed vessel at 140 degrees for 15.5 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (80:20:1) to give 0.0603 g of 4-(9-cyclohexyl-7,7-difluoro-5-methyl-6-oxo-6,7,8,9-tetrahydro-5H-pyrimido[4,5-b][1,4]diazepin-2-ylamino)-N-(2-dimethylamino-ethyl)-benzamide (I-264)

Example 265

4-(9-cyclohexyl-7,7-difluoro-5-methyl-6-oxo-6,7,8,9-tetrahydro-5H-pyrimido[4,5-b][1,4]diazepin-2-ylamino)-N-(3-dimethylamino-propyl)-benzamide (I-265)

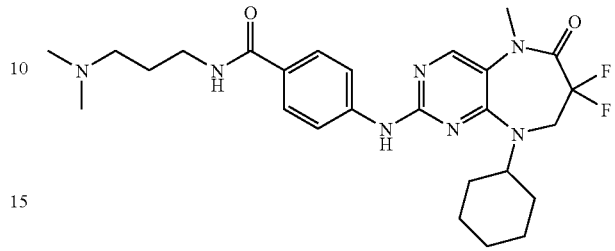

A mixture of 0.0562 g (0.18 mmole) 2-chloro-9-cyclohexyl-7,7-difluoro-5-methyl-5,7,8,9-tetrahydro-pyrimido[4,5-b][1,4]diazepin-6-one (VII-246), 0.0514 g (0.27 mmole) of toluenesulfonic acid monohydrate, 0.0398 g (0.18 mmole) of 4-amino-N-(3-dimethylamino-propyl)-benzamide and 1 mL of isopropanol was heated in a sealed vessel at 140 degrees for 16 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was purified by silica gel chromatography, eluting with acetonitrile-methanol-triethylamine (80:20:2) to give 0.0645 g of 4-(9-cyclohexyl-7,7-difluoro-5-methyl-6-oxo-6,7,8,9-tetrahydro-5H-pyrimido[4,5-b][1,4]diazepin-2-ylamino)-N-(3-dimethylamino-propyl)-benzamide (I-265).

Example 266

4-(9-cyclohexyl-7,7-difluoro-5-methyl-6-oxo-6,7,8,9-tetrahydro-5H-pyrimido[4,5-b][1,4]diazepin-2-ylamino)-N-[1-(2,2-difluoro-ethyl)-piperidin-4-yl]-3-methoxy-benzamide (I-266)

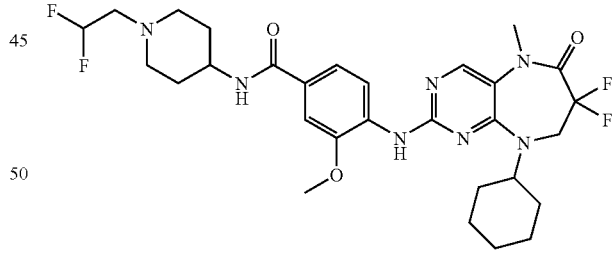

A mixture of 0.10 g (0.30 mmole) 2-chloro-9-cyclohexyl-7,7-difluoro-5-methyl-5,7,8,9-tetrahydro-pyrimido[4,5-b][1,4]diazepin-6-one (VII-246), 0.086 g (0.45 mmole) of toluenesulfonic acid monohydrate, 0.095 g (0.30 mmole) of 4-amino-N-[1-(2,2-difluoro-ethyl)-piperidin-4-yl]-3-methoxy-benzamide and 1 mL of isopropanol was heated in a sealed vessel at 170 degrees in a microwave reactor for 2 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was recrystallized from acetonitrile to give 0.110 g of 4-(9-cyclohexyl-7,7-difluoro-5-methyl-6-oxo-6,7,8,9-tetrahydro-5H-pyrimido[4,5-b][1,4]diazepin-2-ylamino)-N-[1-(2,2-difluoro-ethyl)-piperidin-4-yl]-3-methoxy-benzamide (I-266)

Example 267

4-(9-cyclohexyl-7,7-difluoro-5-methyl-6-oxo-6,7,8,9-tetrahydro-5H-pyrimido[4,5-b][1,4]diazepin-2-ylamino)-N-[1-(2-hydroxy-ethyl)-piperidin-4-yl]-3-methoxy-benzamide (I-267)

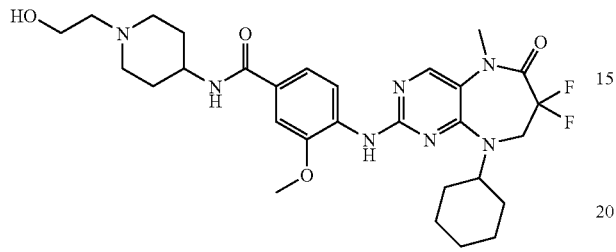

A mixture of 0.112 g (0.34 mmole) 2-chloro-9-cyclohexyl-7,7-difluoro-5-methyl-5,7,8,9-tetrahydro-pyrimido[4,5-b][1,4]diazepin-6-one (VII-246), 0.097 g (0.51 mmole) of toluenesulfonic acid monohydrate, 0.10 g (0.34 mmole) of 4-amino-N-[1-(2-hydroxy-ethyl)-piperidin-4-yl]-3-methoxy-benzamide and 1 mL of isopropanol was heated in a sealed vessel at 170 degrees in a microwave reactor for 2 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was by preparative thin layer chromatography, eluting with dichloromethane-methanol (90:10) to give 0.040 g of 4-(9-cyclohexyl-7,7-difluoro-5-methyl-6-oxo-6,7,8,9-tetrahydro-5H-pyrimido[4,5-b][1,4]diazepin-2-ylamino)-N-[1-(2-hydroxy-ethyl)-piperidin-4-yl]-3-methoxy-benzamide (I-267).

Example 268

4-(9-cyclohexyl-7,7-difluoro-5-methyl-6-oxo-6,7,8,9-tetrahydro-5H-pyrimido[4,5-b][1,4]diazepin-2-ylamino)-N-(1-methanesulfonyl-piperidin-4-yl)-3-methoxy-benzamide (I-268)

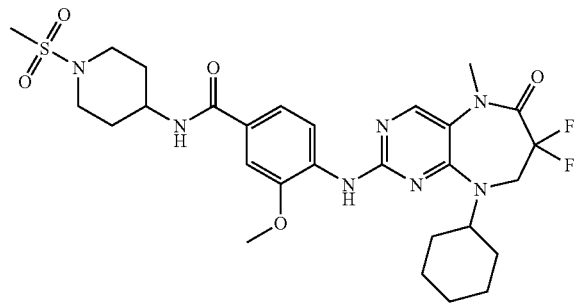

A mixture of 0.101 g (0.31 mmole) 2-chloro-9-cyclohexyl-7,7-difluoro-5-methyl-5,7,8,9-tetrahydro-pyrimido[4,5-b][1,4]diazepin-6-one (VII-246), 0.088 g (0.47 mmole) of toluenesulfonic acid monohydrate, 0.10 g (0.31 mmole) of 4-amino-N-(1-methanesulfonyl-piperidin-4-yl)-benzamide and 1 mL of isopropanol was heated in a sealed vessel at 170 degrees in a microwave reactor for 2 hours, cooled and concentrated under reduced pressure. The residue taken up in ethyl acetate and washed successively with 50 mL of saturated aqueous sodium bicarbonate, 50 mL of water, 50 mL of brine. The organic layer was dried over anhydrous sodium sulfate, filtered and concentrated under reduced pressure. The residue was recrystallized from acetonitrile to give 0.110 g of 4-(9-cyclohexyl-7,7-difluoro-5-methyl-6-oxo-6,7,8,9-tetrahydro-5H-pyrimido[4,5-b][1,4]diazepin-2-ylamino)-N-(1-methanesulfonyl-piperidin-4-yl)-3-methoxy-benzamide (I-268).

Example 269

4-[7,7-difluoro-5-methyl-6-oxo-9-(2-thiophen-2-yl-ethyl)-6,7,8,9-tetrahydro-5-pyrimido[4,5-b]diazepin-2-ylamino]-3-methoxy-benzoic acid (I-269)

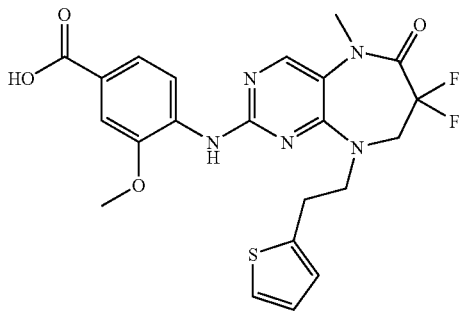

Step a

A solution of 0.98 g (0.0037 mole) of 2,2-difluoro-3-(2-thiophen-2-yl-ethylamino)-propionic acid ethyl ester in 1 mL of ethyl acetate was added over 5 minutes to a cooled (0 degrees) mixture of 0.72 g (0.0037 mole) of 2,4-dichloro-5-nitro-pyrimidine, 1.3 g (0.15 mole) of sodium bicarbonate and 10 mL of ethyl acetate. The cooling bath was removed and the mixture stirred for 17 hours at room temperature. Activated charcoal was added and after stirring briefly, the mixture was filtered through a pad of Celite, washing the filter pad with ethyl acetate. The filtrate was concentrated under reduced pressure to give 1.53 g of 3-[(2-chloro-5-nitro-pyrimidin-4-yl)-(2-thiophen-2-yl-ethyl)-amino]-2,2-difluoro-propionic acid ethyl ester (IV-269) as a yellow thick oil. This material was used directly in the next step without further purification.

Step b

To a solution of 1.48 g (0.0035 mole) of 3-[(2-chloro-5-nitro-pyrimidin-4-yl)-(2-thiophen-2-yl-ethyl)-amino]-2,2-difluoro-propionic acid ethyl ester (IV-269) in 20 mL of acetic acid was added 1.5 g (0.027 g-atom) of iron powder. The mixture was heated to 80 degrees for 2 hours and then filtered while hot. Water and ethyl acetate were added to the filtrate and the mixture was stirred for 10 minutes and then filtered. The layers were separated. The organic layer was washed successively with ammonium hydroxide and water, dried over anhydrous magnesium sulfate, filtered and concentrated under reduced pressure. Recrystallization of the residue from ethyl acetate and hexane gave 0.52 g of 2-chloro-7,7-difluoro-9-(2-thiophen-2-yl-ethyl)-5,7,8,9-tetrahydro-pyrimido[4,5-b][1,4]diazepin-6-one (VI-269).

Step c

To a solution of 0.51 g (0.0015 mole) of 2-chloro-7,7-difluoro-9-(2-thiophen-2-yl-ethyl)-5,7,8,9-tetrahydro-pyrimido[4,5-b][1,4]diazepin-6-one (VI-269) in 12 mL of dimethylformamide was added 0.58 g (0.0023 mole) of cesium carbonate, followed by 0.28 mL (0.0045 mole) of iodomethane. After stirring four hours, the mixture filtered and then concentrated under reduced pressure. Ice water and dichloromethane were added. The mixture was extracted with dichloromethane twice. The combined organic layers were washed three times with sodium carbonate, three times with brine, dried over anhydrous sodium sulfate, filtered and concentrated under reduced pressure to give 0.55 g of 2-chloro-7,7-difluoro-5-methyl-9-(2-thiophen-2-yl-ethyl)-5,7,8,9-tetrahydro-pyrimido[4,5-b][1,4]diazepin-6-one (VII-269) as a sticky solid.

Step d

A mixture of 0.4 g (1.1 mole) of 2-chloro-7,7-difluoro-5-methyl-9-(2-thiophen-2-yl-ethyl)-5,7,8,9-tetrahydro-pyrimido[4,5-b][1,4]diazepin-6-one (VII-269) and 0.22 g (1.2 mole) of 4-amino-3-methoxy-benzoic acid in 2.5 mL of ethanol-water-hydrochloric acid (20:80:1) was refluxed for 18 hours, then cooled and partially concentrated under reduced pressure. The resulting solid was collected by filtration, washed with water and dried to give 0.48 g of 4-[7,7-difluoro-5-methyl-6-oxo-9-(2-thiophen-2-yl-ethyl)-6,7,8,9-tetrahydro-5-pyrimido[4,5-b][1,4]diazepin-2-ylamino]-3-methoxy-benzoic acid (I-269).

Example 270

4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-(1-methyl-piperidin-4-yl)-benzamide (I-270)

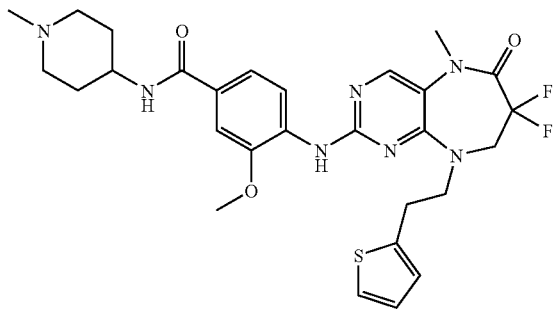

The mixture of 0.10 g (0.26 mmole) of 2-chloro-7,7-difluoro-5-methyl-9-(2-thiophen-2-yl-ethyl)-5,7,8,9-tetrahydro-pyrimido[4,5-b][1,4]diazepin-6-one (VII-269), 0.088 g (0.34 mmole) of 4-amino-3-methoxy-N-(1-methyl-piperidin-4-yl)-benzamide,d 0.080 g (0.42 mmole) of p-toluenesulfonic acid monohydrate and 4 mL of isopropanol was heated in a pressure tube at 140 degrees overnight. After cooling, dichloromethane and saturated sodium carbonate were added. The mixture was extracted with dichloromethane twice. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-80:20) gave 0.120 g of 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-(1-methyl-piperidin-4-yl)-benzamide (I-270) as a white solid.

Example 271

4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-benzamide (I-271)

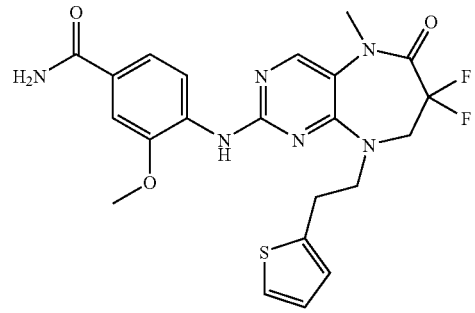

To a mixture of 0.08 g (0.16 mmole) of 4-[7,7-difluoro-5-methyl-6-oxo-9-(2-thiophen-2-yl-ethyl)-6,7,8,9-tetrahydro-5-pyrimido[4,5-b][1,4]diazepin-2-ylamino]-3-methoxy-benzoic acid (I-269), 0.12 mL (0.64 mmole) of ethyldiisopropyl amine and 0.018 g (0.32 mmole) of ammonium chloride in 2.0 mL of dimethylformamide was added 0.078 g (0.18 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-90:10) gave 0.057 g of 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-benzamide (I-271) as a white solid.

Example 272

4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-methyl-benzamide (I-272)

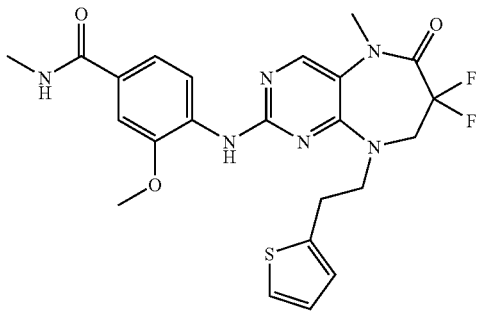

To a mixture of 0.08 g (0.16 mmole) of 4-[7,7-difluoro-5-methyl-6-oxo-9-(2-thiophen-2-yl-ethyl)-6,7,8,9-tetrahydro-5-pyrimido[4,5-b][1,4]diazepin-2-ylamino]-3-methoxy-benzoic acid (I-269), 0.12 mL (0.64 mmole) of ethyldiisopropyl amine and 0.012 g (0.18 mmole) of methylamine hydrochloride in 2.0 mL of dimethylformamide was added 0.078 g (0.18 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-90:10) gave 0.063 g of 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-methyl-benzamide (I-272) as a white solid.

Example 273

4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-N-(3-dimethylamino-propyl)-3-methoxy-benzamide (I-273)

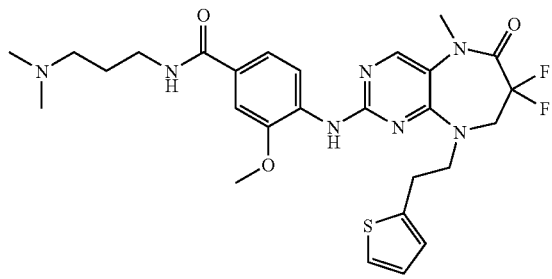

To a mixture of 0.08 g (0.16 mmole) of 4-[7,7-difluoro-5-methyl-6-oxo-9-(2-thiophen-2-yl-ethyl)-6,7,8,9-tetrahydro-5-pyrimido[4,5-b][1,4]diazepin-2-ylamino]-3-methoxy-benzoic acid (I-269), 0.12 mL (0.64 mmole) of ethyldiisopropyl amine and 0.018 g (0.18 mmole) of N,N-dimethyl-propane-1,3-diamine in 2.0 mL of dimethylformamide was added 0.078 g (0.18 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-60:40) gave 0.062 g of 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-N-(3-dimethylamino-propyl)-3-methoxy-benzamide (I-273) as a white solid.

Example 274

4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-(tetrahydro-pyran-4-yl)-benzamide (I-274)

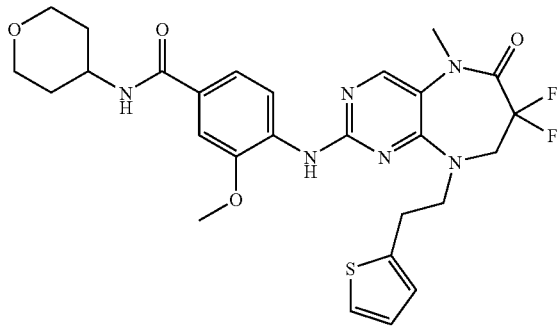

To a mixture of 0.08 g (0.16 mmole) of 4-[7,7-difluoro-5-methyl-6-oxo-9-(2-thiophen-2-yl-ethyl)-6,7,8,9-tetrahydro-5-pyrimido[4,5-b][1,4]diazepin-2-ylamino]-3-methoxy-benzoic acid (I-269), 0.12 mL (0.64 mmole) of ethyldiisopropyl amine and 0.018 g (0.18 mmole) of tetrahydro-pyran-4-ylamine in 2.0 mL of dimethylformamide was added 0.078 g (0.18 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-95:5) gave 0.076 g of 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-(tetrahydro-pyran-4-yl)-benzamide (I-274) as a white solid.

Example 275

4-(7,7-difluoro-5-methyl-6-oxo-9-phenethyl-6,7,8,9-tetrahydro-5H-pyrimido[4,5-b][1,4]diazepin-2-ylamino)-3-methoxy-benzoic acid (I-275)

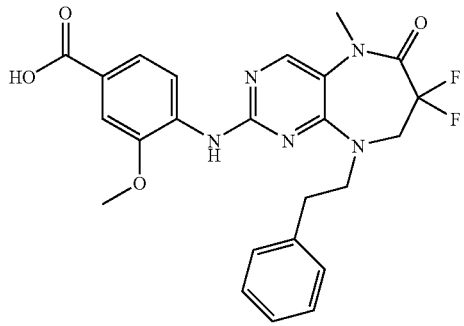

Step A

A solution of 0.57 g (0.0022 mole) of 2,2-difluoro-3-phenethylamino-propionic acid ethyl ester in 1 mL of ethyl acetate was added over 5 minutes to a cooled (0 degrees) mixture of 0.43 g (0.0022 mole) of 2,4-dichloro-5-nitro-pyrimidine, 0.75 g (0.0088 mole) of sodium bicarbonate and 6 mL of ethyl acetate. The cooling bath was removed and the mixture stirred for 17 hours at room temperature. Activated charcoal was added and after stirring briefly, the mixture was filtered through a pad of Celite, washing the filter pad with ethyl acetate. The filtrate was concentrated under reduced pressure to give 1.24 g of 3-[(2-chloro-5-nitro-pyrimidin-4-yl)-phenethyl-amino]-2,2-difluoro-propionic acid ethyl ester (IV-275) as a yellow thick oil. This material was used directly in the next step without further purification.

Step B

To a solution of 1.22 g (0.003 mole) of 3-[(2-chloro-5-nitro-pyrimidin-4-yl)-phenethyl-amino]-2,2-difluoro-propionic acid ethyl ester (IV-275) in 20 mL of acetic acid was added 1.3 g (0.023 g-atom) of iron powder. The mixture was heated to 80 degrees for 2 hours and then filtered while hot. Water and ethyl acetate were added to the filtrate and the mixture was stirred for 10 minutes and then filtered. The layers were separated. The organic layer was washed successively with ammonium hydroxide and water, dried over anhydrous magnesium sulfate, filtered and concentrated under reduced pressure. Recrystallization of the residue with ethyl acetate and hexane gave 0.65 g of 2-chloro-7,7-difluoro-9-phenethyl-5,7,8,9-tetrahydro-pyrimido[4,5-b][1,4]diazepin-6-one (VI-275).

Step C

To a solution of 0.64 g (0.0019 mole) of 2-chloro-7,7-difluoro-9-phenethyl-5,7,8,9-tetrahydro-pyrimido[4,5-b][1,4]diazepin-6-one (VI-275) in 15 mL of dimethylformamide was added 0.92 g (0.0029 mole) of cesium carbonate, followed by 0.35 mL (0.0057 mole) of iodomethane. After stirring four hours, the mixture filtered and then concentrated under reduced pressure. Ice water and dichloromethane were added. The mixture was extracted with dichloromethane twice. The combined organic layers were washed three times with sodium carbonate, three times with brine, dried over anhydrous sodium sulfate, filtered and concentrated under reduced pressure to give 0.41 g of 2-chloro-7,7-difluoro-5-methyl-9-phenethyl-5,7,8,9-tetrahydro-pyrimido[4,5-b][1,4]diazepin-6-one (VII-275) as a yellow solid.

Step D

A mixture of 0.31 g (8.8 mmole) of 2-chloro-7,7-difluoro-5-methyl-9-phenethyl-5,7,8,9-tetrahydro-pyrimido[4,5-b][1,4]diazepin-6-one (VII-275) and 0.18 g (11 mmole) of 4-amino-3-methoxy-benzoic acid in 2.0 mL of ethanol-water-hydrochloric acid (20:80:1) was refluxed for 18 hours, then cooled and partially concentrated under reduced pressure. The resulting solid was collected by filtration, washed with water and dried to give 0.48 g of 4-(7,7-difluoro-5-methyl-6-oxo-9-phenethyl-6,7,8,9-tetrahydro-5H-pyrimido[4,5b][1,4]diazepin-2-ylamino)-3-methoxy-benzoic acid (I-275).

Example 276

4-(7,7-difluoro-5-methyl-6-oxo-9-phenethyl-6,7,8,9-tetrahydro-5!-pyrimido[4,5-b][1,4]diazepin-2-ylamino)-3-methoxy-N-(1-methyl-piperidin-4-yl)-benzamide (I-276)

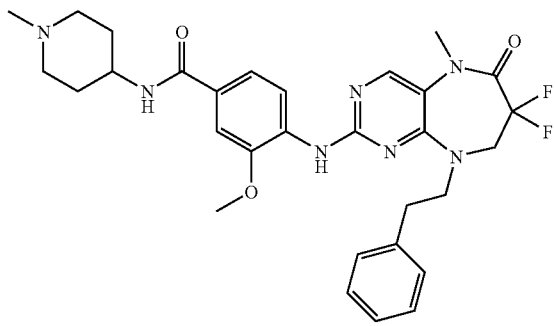

To a mixture of 0.08 g (0.17 mmole) of 4-(7,7-difluoro-5-methyl-6-oxo-9-phenethyl-6,7,8,9-tetrahydro-5H-pyrimido[4,5-b][1,4]diazepin-2-ylamino)-3-methoxy-benzoic acid (VII-275), 0.12 mL (0.64 mmole) of ethyldiisopropyl amine and 0.021 g (0.19 mmole) of 4-amino-1-methyl-piperidine in 3.0 mL of dimethylformamide was added 0.079 g (0.19 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-80:20) gave 0.054 g of 4-(7,7-difluoro-5-methyl-6-oxo-9-phenethyl-6,7,8,9-tetrahydro-5!-pyrimido[4,5-b][1,4]diazepin-2-ylamino)-3-methoxy-N-(1-methyl-piperidin-4-yl)-benzamide (I-276) as a white solid.

Example 277

4-(7,7-difluoro-5-methyl-6-oxo-9-phenethyl-6,7,8,9-tetrahydro-5H-pyrimido[4,5-b][1,4]diazepin-2-ylamino)-3-methoxy-benzamide (I-277)

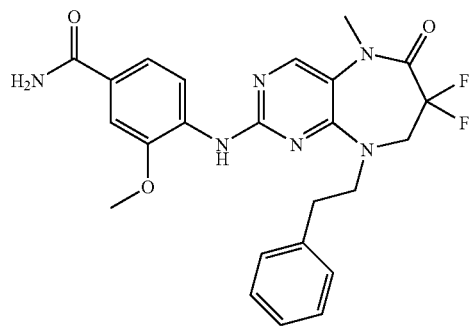

To a mixture of 0.08 g (0.17 mmole) of 4-(7,7-difluoro-5-methyl-6-oxo-9-phenethyl-6,7,8,9-tetrahydro-5H-pyrimido[4,5-b][1,4]diazepin-2-ylamino)-3-methoxy-benzoic acid (I-275), 0.12 mL (0.64 mmole) of ethyldiisopropyl amine and 0.018 g (0.34 mmole) of ammonium chloride in 2.0 mL of dimethylformamide was added 0.079 g (0.19 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted with dichloromethane 3 times. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-90:10) gave 0.052 g of 4-(7,7-difluoro-5-methyl-6-oxo-9-phenethyl-6,7,8,9-tetrahydro-5H-pyrimido[4,5-b][1,4]diazepin-2-ylamino)-3-methoxy-benzamide (I-277) as a white solid.

Example 278

4-(7,7-difluoro-5-methyl-6-oxo-9-phenethyl-6,7,8,9-tetrahydro-5H-pyrimido[4,5-b][1,4]diazepin-2-ylamino)-3-methoxy-N-methyl-benzamide (I-278)

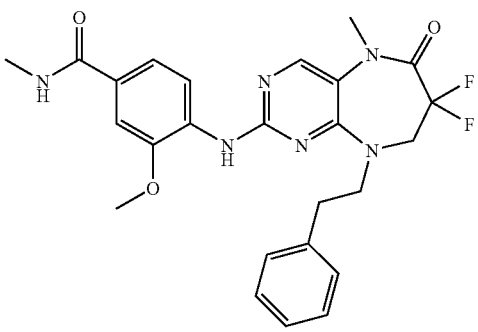

To a mixture of 0.08 g (0.17 mmole) of 4-(7,7-difluoro-5-methyl-6-oxo-9-phenethyl-6,7,8,9-tetrahydro-5H-pyrimido[4,5-b][1,4]diazepin-2-ylamino)-3-methoxy-benzoic acid (I-275), 0.12 mL (0.64 mmole) of ethyldiisopropyl amine and 0.012 g (0.19 mmole) of methylamine hydrochloride in 2.0 mL of dimethylformamide was added 0.079 g (0.19 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted with dichloromethane 3 times. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-90:10) gave 0.056 g of 4-(7,7-difluoro-5-methyl-6-oxo-9-phenethyl-6,7,8,9-tetrahydro-5H-pyrimido[4,5-b][1,4]diazepin-2-ylamino)-3-methoxy-N-methyl-benzamide (I-278) as a white solid.

Example 279

4-(7,7-difluoro-5-methyl-6-oxo-9-phenethyl-6,7,8,9-tetrahydro-5H-pyrimido[4,5-b][1,4]diazepin-2-ylamino)-N-(3-dimethylamino-propyl)-3-methoxy-benzamide (I-279)

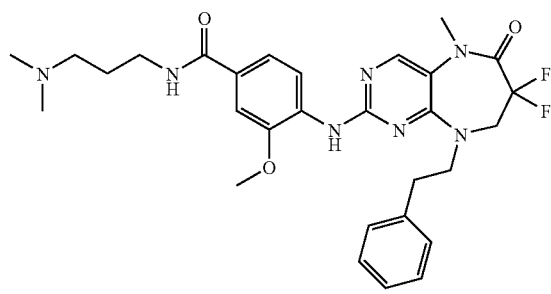

To a mixture of 0.08 g (0.17 mmole) of 4-(7,7-difluoro-5-methyl-6-oxo-9-phenethyl-6,7,8,9-tetrahydro-5H-pyrimido[4,5-b][1,4]diazepin-2-ylamino)-3-methoxy-benzoic acid (I-275), 0.12 mL (0.64 mmole) of ethyldiisopropyl amine and 0.019 g (0.19 mmole) of N,N-dimethyl-propane-1,3-diamine in 2.0 mL of dimethylformamide was added 0.079 g (0.19 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted with dichloromethane 3 times. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-70:30) gave 0.045 g of 4-(7,7-difluoro-5-methyl-6-oxo-9-phenethyl-6,7,8,9-tetrahydro-5H-pyrimido[4,5-b][1,4]diazepin-2-ylamino)-N-(3-dimethylamino-propyl)-3-methoxy-benzamide (I-279) as a white solid.

Example 280

4-(7,7-difluoro-5-methyl-6-oxo-9-phenethyl-6,7,8,9-tetrahydro-5H-pyrimido[4,5-b][1,4]diazepin-2-ylamino)-3-methoxy-N-(tetrahydro-pyran-4-yl)-benzamide (I-280)

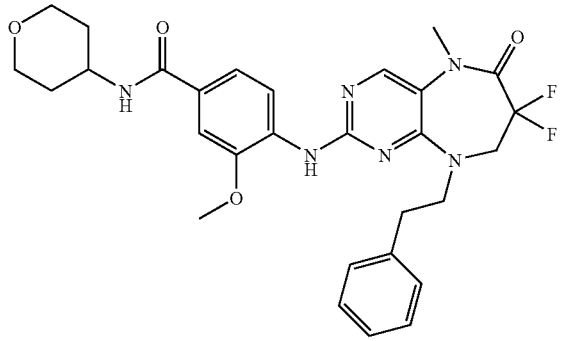

To a mixture of 0.08 g (0.17 mmole) of 4-(7,7-difluoro-5-methyl-6-oxo-9-phenethyl-6,7,8,9-tetrahydro-5H-pyrimido[4,5-b][1,4]diazepin-2-ylamino)-3-methoxy-benzoic acid (I-275), 0.12 mL (0.64 mmole) of ethyldiisopropyl amine and 0.018 g (0.19 mmole) of tetrahydro-pyran-4-ylamine in 2.0 mL of dimethylformamide was added 0.079 g (0.19 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted with dichloromethane 3 times. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-95:5) gave 0.070 g of 4-(7,7-difluoro-5-methyl-6-oxo-9-phenethyl-6,7,8,9-tetrahydro-5H-pyrimido[4,5-b][1,4]diazepin-2-ylamino)-3-methoxy-N-(tetrahydro-pyran-4-yl)-benzamide (I-280) as a white solid.

Example 281

4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzoic acid (I-281)

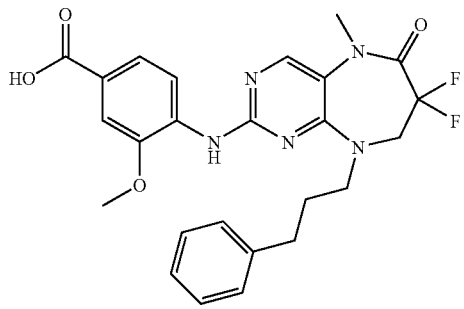

Step a

A solution of 1.08 g (0.004 mole) of 2,2-difluoro-3-(3-phenyl-propylamino)-propionic acid ethyl ester (method 10) in 4 mL of ethyl acetate was added over 5 minutes to a cooled (0 degrees) mixture of 0.77 g (0.004 mole) of 2,4-dichloro-5-nitro-pyrimidine, 1.34 g (0.016 mole) of sodium bicarbonate and 11 mL of ethyl acetate. The cooling bath was removed and the mixture stirred for 17 hours at room temperature. Activated charcoal was added and after stirring briefly, the mixture was filtered through a pad of Celite, washing the filter pad with ethyl acetate. The filtrate was concentrated under reduced pressure to give 1.63 g of 3-[(2-chloro-5-nitro-pyrimidin-4-yl)-(3-phenyl-propyl)-amino]-2,2-difluoro-propionic acid ethyl ester (IV-281) as a yellow thick oil. This material was used directly in the next step without further purification.

Step b

To a solution of 1.61 g (0.0038 mole) of 3-[(2-chloro-5-nitro-pyrimidin-4-yl)-(3-phenyl-propyl)-amino]-2,2-difluoro-propionic acid ethyl ester (IV-281) in 25 mL of acetic acid was added 1.6 g (0.029 g-atom) of iron powder. The mixture was heated to 80 degrees for 2 hours and then filtered while hot. Water and ethyl acetate were added to the filtrate and the mixture was stirred for 10 minutes and then filtered. The layers were separated. The organic layer was washed successively with ammonium hydroxide and water, dried over anhydrous magnesium sulfate, filtered and concentrated under reduced pressure to give 1.09 g of 2-chloro-7,7-difluoro-9-(3-phenyl-propyl)-5,7,8,9-tetrahydro-pyrimido[4,5-b][1,4]diazepin-6-one (VI-281) as a yellow foam.

Step c

To a solution of 1.0 g (0.0028 mole) of 2-chloro-7,7-difluoro-9-(3-phenyl-propyl)-5,7,8,9-tetrahydro-pyrimido[4,5-b][1,4]diazepin-6-one (VI-281) in 20 mL of dimethylformamide was added 1.4 g (0.0042 mole) of cesium carbonate, followed by 0.53 mL (0.0084 mole) of iodomethane. After stirring four hours, the mixture filtered and then concentrated under reduced pressure. Ice water and dichloromethane were added. The mixture was extracted with dichloromethane twice. The combined organic layers were washed three times with sodium carbonate, three times with brine, dried over anhydrous sodium sulfate, filtered and concentrated under reduced pressure to give 0.98 g of 2-chloro-7,7-difluoro-5-methyl-9-(3-phenyl-propyl)-5,7,8,9-tetrahydro-pyrimido[4,5-b][1,4]diazepin-6-one (VII-281) as a yellow oil.

Step d

A mixture of 0.50 g (0.0014 mole) of 2-chloro-7,7-difluoro-5-methyl-9-(3-phenyl-propyl)-5,7,8,9-tetrahydro-pyrimido[4,5-b][1,4]diazepin-6-one (VII-281) and 0.27 g (0.0017 mole) of 4-amino-3-methoxy-benzoic acid in 3.2 mL of ethanol-water-hydrochloric acid (20:80:1) was refluxed for 18 hours, then cooled and partially concentrated under reduced pressure. The resulting solid was collected by filtration, washed with water and dried to give 0.53 g of 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzoic acid (I-281).

Example 282

4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-(1-methyl-piperidin-4-yl)-benzamide (I-282)

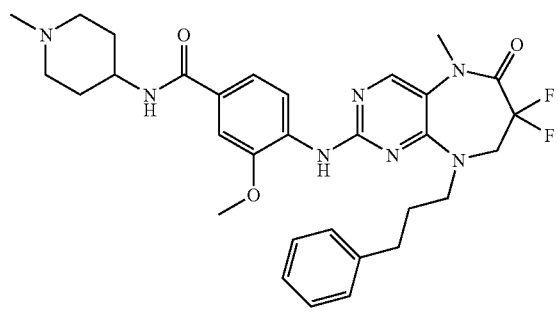

The mixture of 0.08 g (0.22 mmole) of 2-chloro-7,7-difluoro-5-methyl-9-(3-phenyl-propyl)-5,7,8,9-tetrahydro-pyrimido[4,5-b][1,4]diazepin-6-one (VII-281), 0.069 g (0.26 mmole) of 4-amino-3-methoxy-N-(1-methyl-piperidin-4-yl)-benzamide, 0.062 g (0.33 mmole) of p-toluenesulfonic acid monohydrate and 4 mL of isopropanol was heated in a pressure tube at 140 degrees overnight. After cooling, dichloromethane and saturated sodium carbonate were added. The mixture was extracted with dichloromethane twice. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-80:20) gave 0.40 g of 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-(1-methyl-piperidin-4-yl)-benzamide (I-282) as a white solid.

Example 283

4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzamide (I-283)

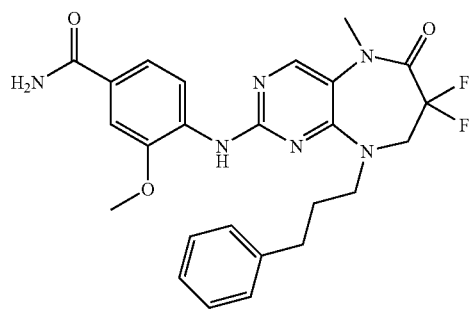

To a mixture of 0.05 g (0.10 mmole) of 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzoic acid (I-281), 0.07 mL (0.4 mmole) of ethyldiisopropyl amine and 0.011 g (0.20 mmole) of ammonium chloride in 2.0 mL of dimethylformamide was added 0.048 g (0.11 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-90:10) gave 0.011 g of 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzamide (I-283) as a white solid.

Example 284

4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-methyl-benzamide (I-284)

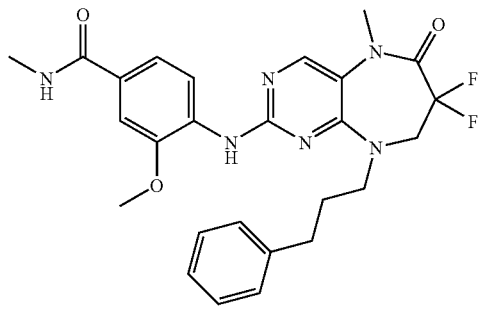

To a mixture of 0.05 g (0.10 mmole) of 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzoic acid (I-281), 0.07 mL (0.40 mmole) of ethyldiisopropyl amine and 0.0074 g (0.11 mmole) of methylamine hydrochloride in 2.0 mL of dimethylformamide was added 0.048 g (0.11 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted with dichloromethane 3 times. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-90:10) gave 0.025 g of 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-methyl-benzamide (I-284) as a white solid.

Example 285

4-[7,7-difluoro-5-methyl-6-oxo-9-(3-phenyl-propyl)-6,7,8,9-tetrahydro-5H-pyrimido[4,5-b][1,4]diazepin-2-ylamino]-N-(3-dimethylamino-propyl)-3-methoxy-benzamide (I-285)

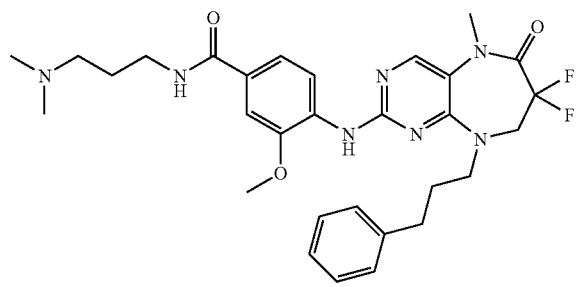

To a mixture of 0.05 g (0.10 mmole) of 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzoic acid (I-281), 0.07 mL (0.40 mmole) of ethyldiisopropyl amine and 0.0074 g (0.11 mmole) of N,N-dimethyl-propane-1,3-diamine in 2.0 mL of dimethylformamide was added 0.048 g (0.11 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-40:60) gave 0.020 g of 4-[7,7-difluoro-5-methyl-6-oxo-9-(3-phenyl-propyl)-6,7,8,9-tetrahydro-5H-pyrimido[4,5-b][1,4]diazepin-2-ylamino]-N-(3-dimethylamino-propyl)-3-methoxy-benzamide (I-285) as a white solid.

Example 286

4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-(tetrahydro-pyran-4-yl)-benzamide (I-286)

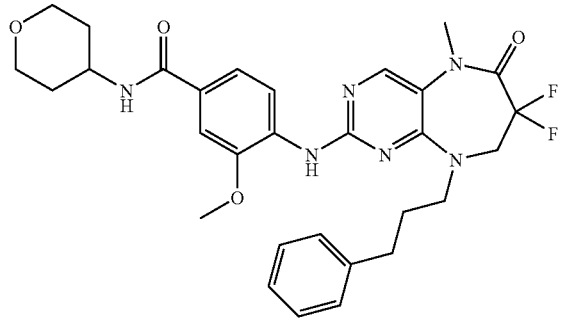

To a mixture of 0.05 g (0.10 mmole) of 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzoic acid (I-281), 0.07 mL (0.40 mmole) of ethyldiisopropyl amine and 0.011 g (0.11 mmole) of tetrahydro-pyran-4-ylamine in 2.0 mL of dimethylformamide was added 0.048 g (0.11 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-95:5) gave 0.030 g of 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-(tetrahydro-pyran-4-yl)-benzamide (I-286) as a white solid.

Example 287

4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-benzoic acid (I-287)

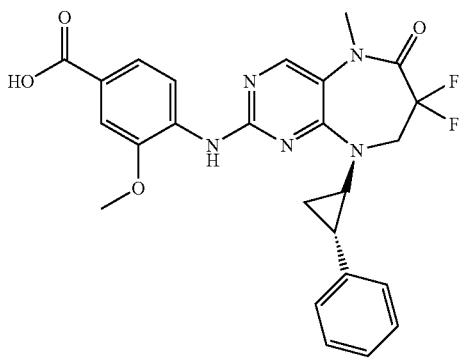

Step A

A solution of 7.8 g (0.029 mole) of 2,2-difluoro-3-(trans-2-phenyl-cyclopropylamino)-propionic acid ethyl ester in 20 mL of ethyl acetate was added over 5 minutes to a cooled (0 degrees) mixture of 5.6 g (0.029 mole) of 2,4-dichloro-5-nitro-pyrimidine, 9.7 g (0.12 mole) of sodium bicarbonate and 80 mL of ethyl acetate. The cooling bath was removed and the mixture stirred for 17 hours at room temperature. Activated charcoal was added and after stirring briefly, the mixture was filtered through a pad of Celite, washing the filter pad with ethyl acetate. The filtrate was concentrated under reduced pressure to give 11.8 g of 3-[(2-chloro-5-nitro-pyrimidin-4-yl)-(trans-2-phenyl-cyclopropyl)-amino]-2,2-difluoro-propionic acid ethyl ester (IV-287) as a yellow thick oil.

Step B

To a solution of 11.8 g (0.028 mole) of 3-[(2-chloro-5-nitro-pyrimidin-4-yl)-(trans-2-phenyl-cyclopropyl)-amino]-2,2-difluoro-propionic acid ethyl ester (IV-287) in 180 mL of acetic acid was added 11 g (0.20 g-atom) of iron powder. The mixture was heated to 80 degrees for 2 hours and then filtered while hot. Water and ethyl acetate were added to the filtrate and the mixture was stirred for 10 minutes and then filtered. The layers were separated. The organic layer was washed successively with ammonium hydroxide and water, dried over anhydrous magnesium sulfate, filtered and concentrated under reduced pressure to give 7.95 g of 2-chloro-7,7-difluoro-9-(trans-2-phenyl-cyclopropyl)-5,7,8,9-tetrahydro-pyrimido[4,5-b][1,4]diazepin-6-one (VI-287) as a yellow foam.

Step C

To a solution of 7.0 g (0.020 mole) of 2-chloro-7,7-difluoro-9-(trans-2-phenyl-cyclopropyl)-5,7,8,9-tetrahydro-pyrimido[4,5-b][1,4]diazepin-6-one (VI-287) in 140 mL of dimethylformamide was added 9.7 g (0.030 mole) of cesium carbonate, followed by 3.7 mL (0.060 mole) of iodomethane. After stirring four hours, the mixture filtered and then concentrated under reduced pressure. Ice water and dichloromethane were added. The mixture was extracted with dichloromethane twice. The combined organic layers were washed three times with sodium carbonate, three times with brine, dried over anhydrous sodium sulfate, filtered and concentrated under reduced pressure to give 6.5 g of 2-chloro-7,7-difluoro-5-methyl-9-(trans-2-phenyl-cyclopropyl)-5,7,8,9-tetrahydro-pyrimido[4,5-b][1,4]diazepin-6-one (VII-287) as a yellow oil.

Step D

A mixture of 1.0 g (0.0028 mole) of 2-chloro-7,7-difluoro-5-methyl-9-(2-phenyl-cyclopropyl)-5,7,8,9-tetrahydro-pyrimido[4,5-b][1,4]diazepin-6-one (VII-287) and 0.55 g (0.0034 mole) of 4-amino-3-methoxy-benzoic acid in 6.4 mL of ethanol-water-hydrochloric acid (20:80:1) was refluxed for 18 hours, then cooled and partially concentrated under reduced pressure. The resulting solid was collected by filtration, washed with water and dried to give 0.97 g of 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-benzoic acid (I-287).

Example 288

4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-N-(1-methyl-piperidin-4-yl)-benzamide (I-288)

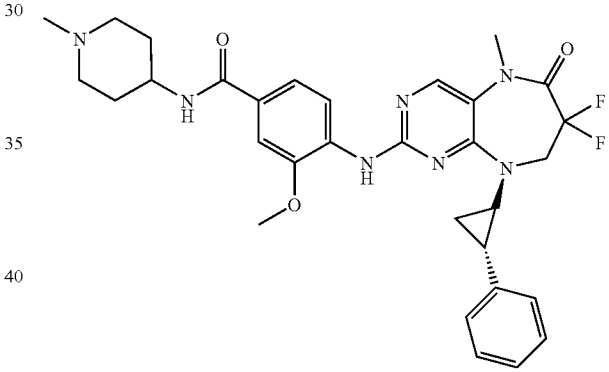

The mixture of 0.08 g (0.22 mmole) of 2-chloro-7,7-difluoro-5-methyl-9-(trans-2-phenyl-cyclopropyl)-5,7,8,9-tetrahydro-pyrimido[4,5-b][1,4]diazepin-6-one (VII-287), 0.069 g (0.26 mmole) of 4-amino-3-methoxy-N-(1-methyl-piperidin-4-yl)-benzamide, 0.062 g (0.33 mmole) of p-toluenesulfonic acid monohydrate and 4 mL of isopropanol was heated in a pressure tube at 140 degrees overnight. After cooling, dichloromethane and saturated sodium carbonate were added. The mixture was extracted with dichloromethane twice. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-65:35) gave 0.059 g of give 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-N-(1-methyl-piperidin-4-yl)-benzamide (I-288) as a white solid.

Example 289

4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-benzamide (I-289)

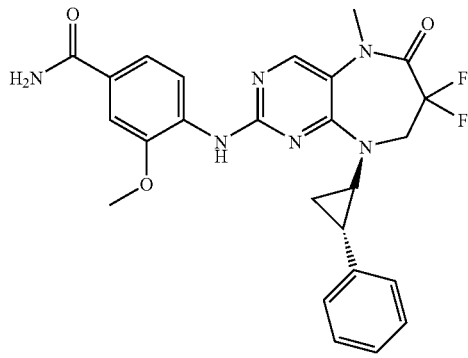

To a mixture of 0.074 g (0.15 mmole) of 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-benzoic acid (I-287), 0.11 mL (0.6 mmole) of ethyldiisopropyl amine and 0.016 g (0.30 mmole) of ammonium chloride in 2.0 mL of dimethylformamide was added 0.071 g (0.17 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-90:10) gave 0.072 g of 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-benzamide (I-289) as a white solid.

Example 290

4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-N-(3-dimethylamino-propyl)-3-methoxy-benzamide (I-290)

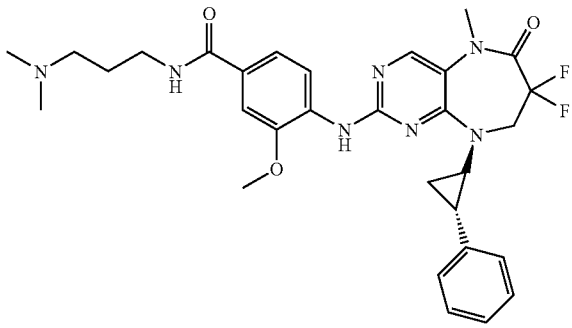

To a mixture of 0.074 g (0.15 mmole) of 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-benzoic acid (I-287), 0.11 mL (0.6 mmole) of ethyldiisopropyl amine and 0.016 g (0.30 mmole) of N,N-dimethyl-propane-1,3-diamine in 2.0 mL of dimethylformamide was added 0.071 g (0.17 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-0:100) gave 0.063 g of 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-N-(3-dimethylamino-propyl)-3-methoxy-benzamide (I-290) as a white solid.

Example 291

4-[7,7-difluoro-9-(4-methoxy-benzyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide (I-291)

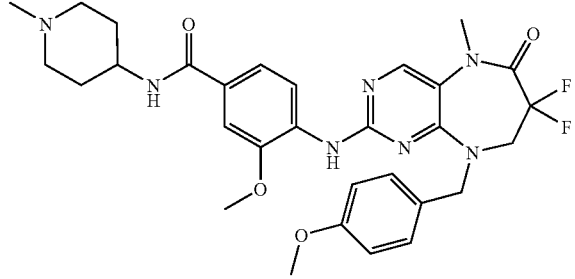

Step A

A solution of 1.2 g (0.0044 mole) of 2,2-difluoro-3-(4-methoxy-benzylamino)-propionic acid ethyl ester) in 4 mL of ethyl acetate was added over 5 minutes to a cooled (0 degrees) mixture of 0.85 g (0.0044 mole) of 2,4-dichloro-5-nitro-pyrimidine, 1.5 g (0.018 mole) of sodium bicarbonate and 10 mL of ethyl acetate. The cooling bath was removed and the mixture stirred for 17 hours at room temperature. Activated charcoal was added and after stirring briefly, the mixture was filtered through a pad of Celite, washing the filter pad with ethyl acetate. The filtrate was concentrated under reduced pressure to give 1.9 g of 3-[(2-chloro-5-nitro-pyrimidin-4-yl)-(4-methoxy-benzyl)-amino]-2,2-difluoro-propionic acid ethyl ester (IV-291) as a yellow thick oil. This material was used directly in the next step without further purification.

Step B

To a solution of 1.9 g (0.0044 mole) of 3-[(2-chloro-5-nitro-pyrimidin-4-yl)-(4-methoxy-benzyl)-amino]-2,2-difluoro-propionic acid ethyl ester (IV-291) in 40 mL of acetic acid was added 1.9 g (0.034 g-atom) of iron powder. The mixture was heated to 80 degrees for 2 hours and then filtered while hot. Water and ethyl acetate were added to the filtrate and the mixture was stirred for 10 minutes and then filtered. The layers were separated. The organic layer was washed successively with ammonium hydroxide and water, dried over anhydrous magnesium sulfate, filtered and concentrated under reduced pressure and recrystallized from ethyl acetate to give 0.65 g of 2-chloro-7,7-difluoro-9-(4-methoxy-benzyl)-5,7,8,9-tetrahydro-pyrimido[4,5-b][1,4]diazepin-6-one (VI-291) as a white solid.

Step C

To a solution of 0.60 g (0.0017 mole) of 2-chloro-7,7-difluoro-9-(4-methoxy-benzyl)-5,7,8,9-tetrahydro-pyrimido[4,5-b][1,4]diazepin-6-one (VI-291) in 8 mL of dimethylformamide was added 0.83 g (0.0026 mole) of cesium carbonate, followed by 0.32 mL (0.0051 mole) of iodomethane. After stirring four hours, the mixture filtered and then concentrated under reduced pressure. Ice water was added to the residue to give a precipitate. The solid was collected by filtration, washed with water and dried under vacuum to give 0.56 g of 2-chloro-7,7-difluoro-9-(4-methoxy-benzyl)-5-methyl-5,7,8,9-tetrahydro-pyrimido[4,5-b][1,4]diazepin-6-one (VII-291) as a white solid.

Step D

A mixture of 0.11 g (0.30 mmole) of 2-chloro-7,7-difluoro-9-(4-methoxy-benzyl)-5-methyl-5,7,8,9-tetrahydro-pyrimido[4,5-b][1,4]diazepin-6-one (VII-291), 0.088 g (0.22 mmole) of 4-amino-3-methoxy-N-(1-methyl-piperidin-4-yl)-benzamide, 0.062 g (0.33 mmole) of p-toluenesulfonic acid monohydrate and 4 mL of isopropanol was heated in pressure tube at 140 degrees overnight. After cooling, dichloromethane and saturated sodium carbonate were added. The mixture was extracted with dichloromethane twice. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-60:40) gave 0.13 g of 4-[7,7-difluoro-9-(4-methoxy-benzyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide (I-291) as a white solid.

Example 292

4-(7,7-difluoro-9-isopropyl-5-methyl-6-oxo-6,7,8,9-tetrahydro-5H-pyrimido[4,5-b][1,4]diazepin-2-ylamino)-3-methoxy-benzoic acid (I-292)

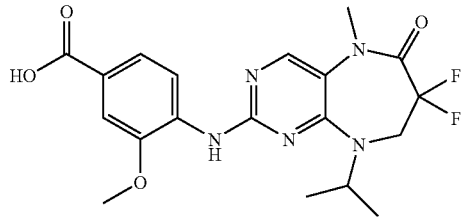

Step a

A solution of 0.3 g (0.0082 mole) of 2-chloro-7,7-difluoro-9-(4-methoxy-benzyl)-5-methyl-5,7,8,9-tetrahydro-pyrimido[4,5-b][1,4]diazepin-6-one (VII-291) and 0.3 mL of anisole in 10 mL of trifluoroacetic acid was heated at 85 degrees in a pressure tube for 24 hours. The mixture was concentrated under reduced pressure, a small amount of methanol was added followed by ether. The resulting solid was collected by filtration and washed with ether to give 0.26 g of 2-chloro-7,7-difluoro-5-methyl-5,7,8,9-tetrahydro-pyrimido[4,5-b][1,4]diazepin-6-one (VII-292). as a lightly yellow solid.

Step b

To a solution of 0.6 g (0.0017 mole) of 2-chloro-7,7-difluoro-5-methyl-5,7,8,9-tetrahydro-pyrimido[4,5-b][1,4]diazepin-6-one(VII-292a) in 6 mL of dimethylformamide was added 1.57 g (0.0048 mole) of cesium carbonate, followed by 0.97 mL (0.0097 mole) of isopropyl iodide. The mixture was stirred at 50 degrees overnight, then mixture filtered and concentrated under reduced pressure. Ice water was added to the residue, and the solid was collected by filtration, washed with ice-water and dried under vacuum to give 0.47 g of 2-chloro-7,7-difluoro-9-isopropyl-5-methyl-5,7,8,9-tetrahydro-pyrimido[4,5-b][1,4]diazepin-6-one (VII-292b) as a lightly yellow, sticky foam.

Step c

A mixture of 0.5 g (0.0017 mole) of 2-chloro-7,7-difluoro-9-isopropyl-5-methyl-5,7,8,9-tetrahydro-pyrimido[4,5-b][1,4]diazepin-6-one (VII-292b) and 0.35 g (0.002 mole) of 4-amino-3-methoxy-benzoic acid in 20 mL of ethanol-water-hydrochloric acid (20:80:1) was refluxed for 18 hours, then cooled and partially concentrated under reduced pressure. The resulting solid was collected by filtration, washed with 0.5M hydrochloric acid and water and dried to give 0.40 g of 4-(7,7-difluoro-9-isopropyl-5-methyl-6-oxo-6,7,8,9-tetrahydro-5H-pyrimido[4,5-b][1,4]diazepin-2-ylamino)-3-methoxy-benzoic acid (I-292).

Example 293

4-(7,7-difluoro-9-isopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-293)

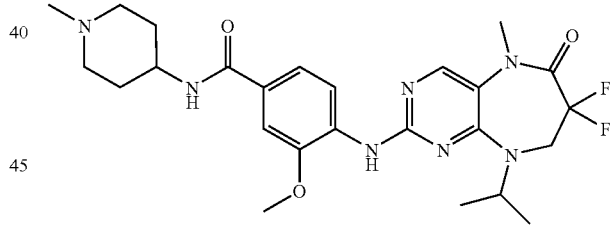

A mixture of 0.07 g (0.24 mmole) of 2-chloro-7,7-difluoro-9-isopropyl-5-methyl-5,7,8,9-tetrahydro-pyrimido[4,5-b][1,4]diazepin-6-one (VII-292b), 0.070 g (0.26 mmole) of 4-amino-3-methoxy-N-(1-methyl-piperidin-4-yl)-benzamide, 0.069 g (0.36 mmole) of p-toluenesulfonic acid monohydrate and 4 mL of isopropanol was heated in a pressure tube at 140 degrees overnight. After cooling, dichloromethane and saturated sodium carbonate were added. The mixture was extracted with dichloromethane twice. The combined organic layers were washed three times with sodium carbonate, times with brine, dried over anhydrous sodium sulfate, filtered and concentrated under reduced pressure. Purification by silica gel chromatography, eluting with dichloromethane-methanol (gradient, 100:0-40:60) gave 0.038 g of 4-(7,7-difluoro-9-isopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-293) as a white solid.

Example 294

4-(7,7-difluoro-9-isopropyl-5-methyl-6-oxo-6,7,8,9-tetrahydro-5H-pyrimido[4,5-b][1,4]diazepin-2-ylamino)-3-methoxy-benzamide (I-294)

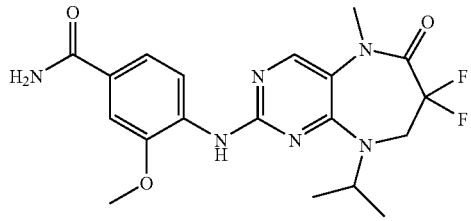

To a mixture of 0.08 g (0.19 mmole) of 4-(7,7-difluoro-9-isopropyl-5-methyl-6-oxo-6,7,8,9-tetrahydro-5H-pyrimido[4,5-b][1,4]diazepin-2-ylamino)-3-methoxy-benzoic acid (I-292), 0.13 mL (0.76 mmole) of ethyldiisopropyl amine and 0.020 g (0.38 mmole) of ammonium chloride in 2.0 mL of dimethylformamide was added 0.082 g (0.21 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-90:10) gave 0.074 g of 4-(7,7-difluoro-9-isopropyl-5-methyl-6-oxo-6,7,8,9-tetrahydro-5H-pyrimido[4,5-b][1,4]diazepin-2-ylamino)-3-methoxy-benzamide (I-294) as a white solid.

Example 295

4-(7,7-difluoro-9-isopropyl-5-methyl-6-oxo-6,7,8,9-tetrahydro-5H-pyrimido[4,5-b][1,4]diazepin-2-ylamino)-3-methoxy-N-methyl-benzamide (I-295)

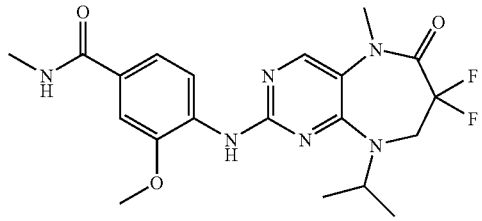

To a mixture of 0.08 g (0.19 mmole) of 4-(7,7-difluoro-9-isopropyl-5-methyl-6-oxo-6,7,8,9-tetrahydro-5H-pyrimido[4,5-b][1,4]diazepin-2-ylamino)-3-methoxy-benzoic acid (I-292), 0.13 mL (0.76 mmole) of ethyldiisopropyl amine and 0.014 g (0.21 mmole) of methylamine hydrochloride in 2.0 mL of dimethylformamide was added 0.082 g (0.21 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-90:10) gave 0.082 g of 4-(7,7-difluoro-9-isopropyl-5-methyl-6-oxo-6,7,8,9-tetrahydro-5H-pyrimido[4,5-b][1,4]diazepin-2-ylamino)-3-methoxy-N-methyl-benzamide (I-295) as a white solid.

Example 296

4-(7,7-difluoro-9-isopropyl-5-methyl-6-oxo-6,7,8,9-tetrahydro-5H-pyrimido[4,5-b][1,4]diazepin-2-ylamino)-N-(3-dimethylamino-propyl)-3-methoxy-benzamide (I-296)

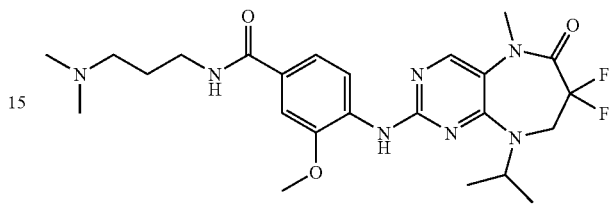

A mixture of 0.07 g (0.24 mmole) of 2-chloro-7,7-difluoro-9-isopropyl-5-methyl-5,7,8,9-tetrahydro-pyrimido[4,5-b][1,4]diazepin-6-one (VII-292), 0.067 g (0.26 mmole) of 4-amino-N-(3-dimethylamino-propyl)-3-methoxy-benzamide, 0.069 g (0.36 mmole) of p-toluenesulfonic acid monohydrate and 4 mL of isopropanol was heated in a pressure tube at 140 degrees overnight. After cooling, dichloromethane and saturated sodium carbonate were added. The mixture was extracted with dichloromethane twice. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-0:100) gave 0.065 g of give 4-(7,7-difluoro-9-isopropyl-5-methyl-6-oxo-6,7,8,9-tetrahydro-5H-pyrimido[4,5-b][1,4]diazepin-2-ylamino)-N-(3-dimethylamino-propyl)-3-methoxy-benzamide (I-296) as a white solid.

Example 297

4-(7,7-difluoro-9-isopropyl-5-methyl-6-oxo-6,7,8,9-tetrahydro-5H-pyrimido[4,5-b][1,4]diazepin-2-ylamino)-3-methoxy-N-(tetrahydro-pyran-4-yl)-benzamide (I-297)

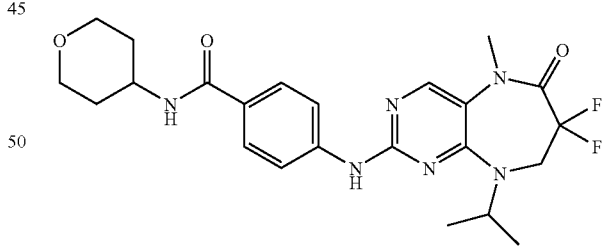

To a mixture of 0.08 g (0.19 mmole) of 4-(7,7-difluoro-9-isopropyl-5-methyl-6-oxo-6,7,8,9-tetrahydro-5H-pyrimido[4,5-b][1,4]diazepin-2-ylamino)-3-methoxy-benzoic acid (I-292), 0.13 mL (0.76 mmole) of ethyldiisopropyl amine and 0.021 g (0.21 mmole) of tetrahydro-pyran-4-ylamine in 2.0 mL of dimethylformamide was added 0.082 g (0.21 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The mixture was extracted three times with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-90:10) gave 0.086 g of give 4-(7,7-difluoro-9-isopropyl-5-methyl-6-oxo-6,7,8,9-tetrahydro-5H-pyrimido[4,5-b][1,4]diazepin-2-ylamino)-3-methoxy-N-(tetrahydro-pyran-4-yl)-benzamide (I-297) as a white solid.

Example 298

4-(7,7-dichloro-9-cyclopentyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-298)

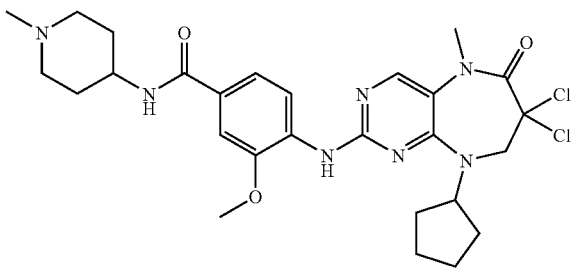

Step a

A solution of 1.5 g (0.0063 mole) of 2,2-dichloro-3-cyclopentylamino-propionic acid methyl ester in 3 mL of ethyl acetate was added over 5 minutes to a cooled (0 degrees) mixture of 0.81 g (0.0042 mole) of 2,4-dichloro-5-nitro-pyrimidine, 1.76 g (0.02 mole) of sodium bicarbonate and 15 mL of ethyl acetate. The cooling bath was removed and the mixture stirred for 24 hours at room temperature and then 24 hours at 75 degrees. Activated charcoal was added and after stirring briefly, the mixture was filtered through a pad of Celite, washing the filter pad with ethyl acetate. The filtrate was concentrated under reduced pressure to give 2.4 g of 3-[(2-chloro-5-nitro-pyrimidin-4-yl)-cyclopentyl-amino]-2,2-dichloro-propanoic acid methyl ester (IV-298) as a yellow thick oil. This material was used directly in the next step without further purification.

Step b

To a solution of 2.2 g (0.0056 mole) of 3-[(2-chloro-5-nitro-pyrimidin-4-yl)-cyclopentyl-amino]-2,2-dichloro-propanoic acid methyl ester (IV-298) in 40 mL of acetic acid was added 2.2 g (0.039 g-atom) of iron powder. The mixture was heated to 80 degrees for 2 hours and then filtered while hot. Water and ethyl acetate were added to the filtrate and the mixture was stirred for 10 minutes and then filtered. The layers were separated. The organic layer was washed successively with ammonium hydroxide and water, dried over anhydrous magnesium sulfate, filtered and concentrated under reduced pressure. The combined organic layers were washed three times with sodium carbonate, three times with brine, dried over anhydrous sodium sulfate, filtered and concentrated under reduced pressure. Purification by silica gel chromatography, eluting with hexane-ethyl acetate (gradient, 95:5-50:50) gave 0.66 g of 2-chloro-9-cyclopentyl-7,7-dichloro-5,7,8,9-tetrahydro-pyrimido[4,5-b][1,4]diazepin-6-one (VI-298).

Step c

To a solution of 0.60 g (0.0018 mole) of 2-chloro-9-cyclopentyl-7,7-dichloro-5,7,8,9-tetrahydro-pyrimido[4,5-b][1,4]diazepin-6-one (VI-298) in 12 mL of dimethylformamide was added 0.88 g (0.0027 mole) of cesium carbonate, followed by 0.34 mL (0.0054 mole) of iodomethane. After stirring four hours, the mixture was filtered and then concentrated under reduced pressure. Ice water was added to the residue and the resulting solid was collected by filtration, washed with water and dried under vacuum to give 0.47 g of 2-chloro-9-cyclopentyl-7,7-dichloro-5-methyl-5,7,8,9-tetrahydro-pyrimido[4,5-b][1,4]diazepin-6-one (VII-298) as a white solid.

Step d

A mixture of 0.1 g (0.29 mmole) of 2-chloro-9-cyclopentyl-7,7-dichloro-5-methyl-5,7,8,9-tetrahydro-pyrimido[4,5-b][1,4]diazepin-6-one (VII-298), 0.090 g (0.34 mmole) of 4-amino-3-methoxy-N-(1-methyl-piperidin-4-yl)-benzamide, 0.082 g (0.43 mmole) of p-toluenesulfonic acid monohydrate and 4 mL of isopropanol was heated in a pressure tube at 120 degrees overnight. After cooling, dichloromethane and saturated sodium carbonate were added. The mixture was extracted with dichloromethane twice. The combined organic layers were washed three times with sodium carbonate, three times with water, dried over anhydrous sodium sulfate, filtered and concentrated under reduced pressure. Purification by silica gel chromatography, eluting with dichloromethane-methanol (gradient, 100:0-80:20) gave 0.082 g of 4-(9-cyclopentyl-7,7-dichloro-5-methyl-6-oxo-6,7,8,9-tetrahydro-5H-pyrimido[4,5-b][1,4]diazepin-2-ylamino)-N-[1-(2-fluoro-ethyl)-piperidin-4-yl]-3-methoxy-benzamide (I-298).

Example 299

4-(9-cyclopentyl-7,7-difluoro-5-methyl-6-oxo-6,7,8,9-tetrahydro-5H-pyrimido[4,5-b][1,4]diazepin-2-ylamino)-N-[cis-4-(4-cyclopropylmethyl-piperazin-1-yl)-cyclohexyl]-3-methoxy-benzamide (I-299)

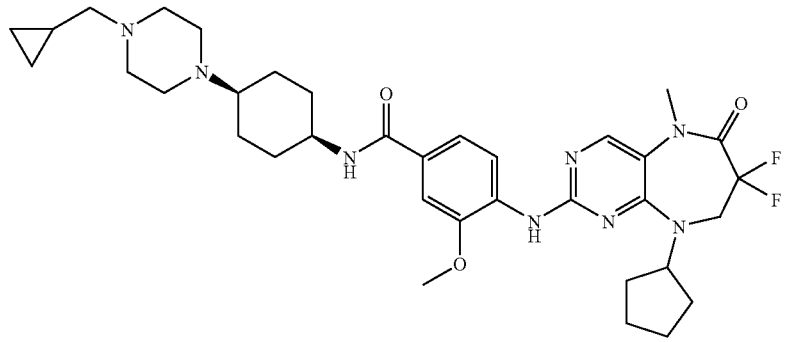

Example 300

4-(9-cyclopentyl-7,7-difluoro-5-methyl-6-oxo-6,7,8,9-tetrahydro-5H-pyrimido[4,5-b][1,4]diazepin-2-ylamino)-N-[trans-4-(4-cyclopropylmethyl-piperazin-1-yl)-cyclohexyl]-3-methoxy-benzamide (I-300)

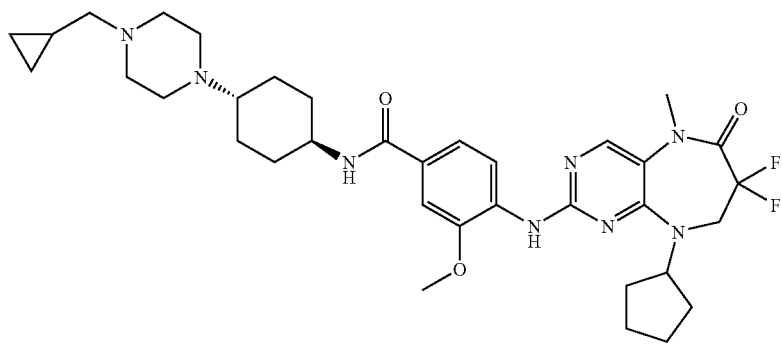

A mixture of 1.1 g (7.0 mmole) of 4-acetamido-cyclohexanone, 2.0 g (14 mmole) of N-cyclopropylmethylpiperazine and 0.036 mL of methanesulphonic acid in 16 mL of toluene are refluxed using water separator until no more water is formed. After cooling to 50 degrees, 16 mL of ethanol was added. The mixture was cooled to room temperature, and 0.27 g (7.0 mmole) of sodium borohydride was added portionwise. The mixture was stirred at room temperature for 16 hours, then quenched by the dropwise addition of 10 mL of 4M hydrochloric acid. After removal of the solvent under reduced pressure, 5 mL of potassium carbonate solution and 10 mL of methylisobutylketone are added to the residue. The mixture was extracted six times with dichloromethane. The combined organic layers were dried over anhydrous sodium sulfate. Activated charcoal was added, the mixture was stirred for 5 minutes and then filtered and concentrated under reduced pressure. Ether was added, and the resulting solid was collected by filtration, washed with hexane dried to give 0.66 g of a cis/trans mixture of N-[4-(4-cyclopropylmethyl-piperazin-1-yl)-cyclohexyl]-acetamide as a yellow solid.

A solution of 0.65 (2.3 mmole) of the cis/trans N-[4-(4-cyclopropylmethyl-piperazin-1-yl)-cyclohexyl]-acetamide in 24% hydrochloric acid was refluxed for 10 hours. The mixture was concentrated under reduced pressure and the residue was crystallized from isopropanol. The solid was collected by filtration and washed with tert-butylmethylether and dried to give 0.74 g of a cis/rans mixture of 4-(4-cyclopropylmethyl-piperazin-1-yl)-cyclohexylamine with trihydrochloride as a gray solid.

To a mixture of 0.08 g (0.18 mmole) of 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid (I-22), 0.19 mL (1.1 mmole) of ethyldiisopropyl amine and 0.068 mg (0.20 mmole) of the cis/trans mixture of 4-(4-cyclopropylmethyl-piperazin-1-yl)-cyclohexylamine with trihydrochloride in 2.0 mL of dimethylformamide was added 0.085 g (0.20 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-70:30) gave 0.026 g of 4-(9-cyclopentyl-7,7-difluoro-5-methyl-6-oxo-6,7,8,9-tetrahydro-5H-pyrimido[4,5-b][1,4]diazepin-2-ylamino)-N-[cis-4-(4-cyclopropylmethyl-piperazin-1-yl)-cyclohexyl]-3-methoxy-benzamide (I-299) (Rf: 0.56 in dichloromethane:methanol 7:3) as a white solid, and 0.063 g of 4-(9-cyclopentyl-7,7-difluoro-5-methyl-6-oxo-6,7,8,9-tetrahydro-5H-pyrimido[4,5-b][1,4]diazepin-2-ylamino)-N-[trans-4-(4-cyclopropylmethyl-piperazin-1-yl)-cyclohexyl]-3-methoxy-benzamide (I-300) (Rf: 0.44 in dichloromethane:methanol 7:3) as a white solid.

Example 301

N-[cis-4-(4-cyclopropylmethyl-piperazin-1-yl)-cyclohexyl]-4-(7,7-difluoro-9-isopropyl-5-methyl-6-oxo-6,7,8,9-tetrahydro-5H-pyrimido[4,5-b][1,4]diazepin-2-ylamino)-3-methoxy-benzamide (I-301)

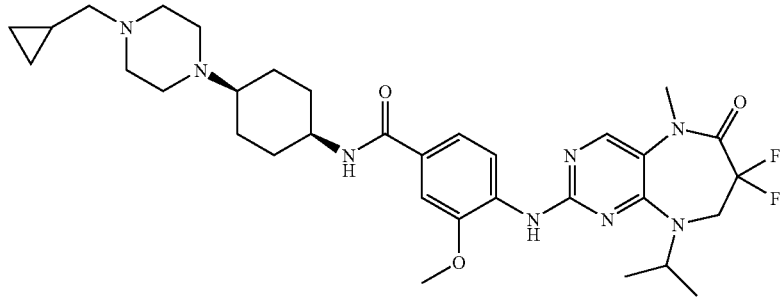

and

Example 302

N-[trans-4-(4-cyclopropylmethyl-piperazin-1-yl)-cyclohexyl]-4-(7,7-difluoro-9-isopropyl-5-methyl-6-oxo-6,7,8,9-tetrahydro-5H-pyrimido[4,5-b][1,4]diazepin-2-ylamino)-3-methoxy-benzamide (I-302)

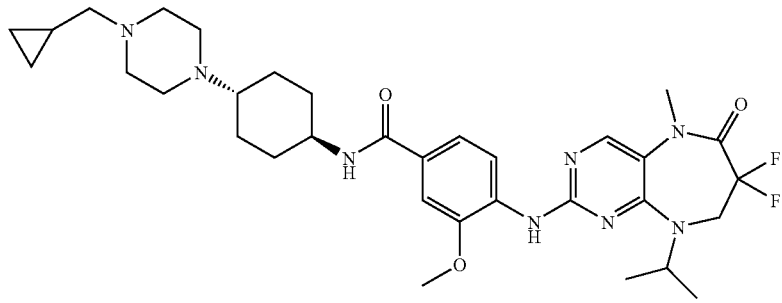

To a mixture of 0.08 g (0.19 mmole) of 4-(7,7-difluoro-9-isopropyl-5-methyl-6-oxo-6,7,8,9-tetrahydro-5H-pyrimido[4,5-b][1,4]diazepin-2-ylamino)-3-methoxy-benzoic acid (I-292), 0.20 mL (1.2 mmole) of ethyldiisopropyl amine and 0.072 mg (0.21 mmole) of a cis/trans mixture of 4-(4-cyclopropylmethyl-piperazin-1-yl)-cyclohexylamine with trihydrochloride in 2.0 mL of dimethylformamide was added 0.090 g (0.21 mmole) of 1-(di-1-pyrrolidinylmethylene)-1H-benzotriazolium 3-oxide hexafluorophosphate. The mixture was stirred at room temperature for 1 hour, then diluted with 10 mL of ice water. The resulting solid was collected by filtration, washed with saturated sodium carbonate and water, and dried under vacuum. Purification by silica gel chromatography, eluting with dichloromethane-methanol (gradient, 100:0-70:30) gave 0.024 g of N-[cis-4-(4-cyclopropylmethyl-piperazin-1-yl)-cyclohexyl]-4-(7,7-difluoro-9-isopropyl-5-methyl-6-oxo-6,7,8,9-tetrahydro-5H-pyrimido[4,5-b][1,4]diazepin-2-ylamino)-3-methoxy-benzamide (I-301) (Rf: 0.58 in dichloromethane:methanol 7:3) as a white solid and 0.061 g of N-[trans-4-(4-cyclopropylmethyl-piperazin-1-yl)-cyclohexyl]-4-(7,7-difluoro-9-isopropyl-5-methyl-6-oxo-6,7,8,9-tetrahydro-5H-pyrimido[4,5-b][1,4]diazepin-2-ylamino)-3-methoxy-benzamide (I-302) (Rf: 0.46 in dichloromethane:methanol 7:3) as a white solid.

Example 303

4-(7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-303)

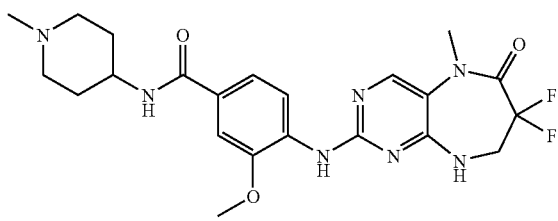

A mixture of 0.08 g (0.32 mmole) of 2-chloro-7,7-difluoro-5-methyl-5,7,8,9-tetrahydro-pyrimido[4,5-b][1,4]diazepin-6-one (VII-292), 0.093 g (0.35 mmole) of 4-amino-3-methoxy-N-(1-methyl-piperidin-4-yl)-benzamide, 0.092 g (0.48 mmole) of p-toluenesulfonic acid monohydrate and 4 mL of isopropanol was heated in pressure tube at 120 degrees overnight. After cooling, dichloromethane and saturated sodium carbonate were added. The mixture was extracted twice with dichloromethane. The combined organic layers were washed three times with sodium carbonate, times with brine, dried over anhydrous sodium sulfate, filtered and concentrated under reduced pressure. The residue was purified by C18 reverse phase silica gel chromatography, eluting with acetonitrile-water (gradient, 10:90-100:0) to gave 0.051 g of give 4-(7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide (I-303) as a white solid.

Example 304

4-[7,7-difluoro-5-methyl-6-oxo-9-(2-phenoxyethyl)-6,7,8,9-tetrahydro-5H-pyrimido[4,5-b][1,4]diazepin-2-ylamino]-3-methoxy-N-(1-methyl-piperidin-4-yl)-benzamide (I-304)

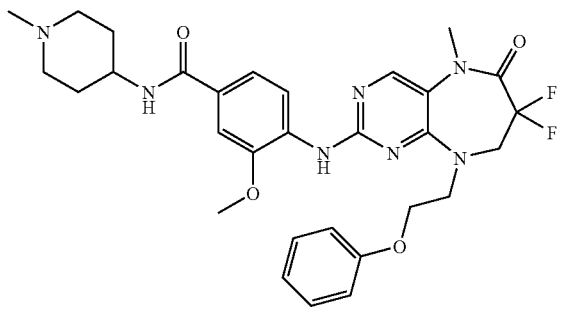

To a solution of 0.20 g (0.8 mmole) of 2-chloro-7,7-difluoro-5-methyl-5,7,8,9-tetrahydro-pyrimido[4,5-b][1,4]diazepin-6-one (VII-292) in 2 mL of dimethylformamide was added 0.53 g (1.6 mmole) of cesium carbonate, followed by 0.8 g (3.2 mole) of (2-iodo-ethoxy)-benzene. After stirring at 50 degrees overnight, the mixture was filtered and then concentrated under reduced pressure. Dichloromethane and saturated sodium carbonate were added. The mixture was extracted twice with dichloromethane. The combined organic layers were washed three times with sodium carbonate, three times with water, dried over anhydrous sodium sulfate, filtered and concentrated under reduced pressure to give 0.28 g of 2-chloro-7,7-difluoro-5-methyl-9-(2-phenoxy-ethyl)-5,7,8,9-tetrahydro-pyrimido[4,5-b][1,4]diazepin-6-one (VII-304) as an oil.

The mixture of 0.08 g (0.22 mole) of 2-chloro-7,7-difluoro-5-methyl-9-(2-phenoxy-ethyl)-5,7,8,9-tetrahydro-pyrimido[4,5-b][1,4]diazepin-6-one (VII-304), 0.070 g (0.26 mole) of 4-amino-3-methoxy-N-(1-methyl-piperidin-4-yl)-benzamide, 0.062 g (0.33 mole) of p-toluenesulfonic acid monohydrate and 4 mL of isopropanol was heated in a pressure tube at 140 degrees overnight. After cooling, dichloromethane and saturated sodium carbonate were added. The mixture was extracted twice with dichloromethane. The combined organic layers were washed three times with sodium carbonate, three times with brine, dried over anhydrous sodium sulfate, filtered and concentrated under reduced pressure. Purification by silica gel chromatography, eluting with dichloromethane-methanol (gradient, 100:0-20:80) gave 0.051 g of give 4-[7,7-difluoro-5-methyl-6-oxo-9-(2-phenoxy-ethyl)-6,7,8,9-tetrahydro-5H-pyrimido[4,5-b][1,4]diazepin-2-ylamino]-3-methoxy-N-(1-methyl-piperidin-4-yl)-benzamide as a white solid (I-304).

Biochemical Characterization Assay

Full-length, active GST-PLK1 is purified from Sf9 insect cells, and full-length GST-p53 is purified from *E. coli*. Anti-phospho p53 antibody is from Cell Signaling Technology. Europium-conjugated anti-rabbit antibody is from PerkinElmer Life and Analytical Sciences. APC-conjugated anti-GST antibody is from Prozyme.

To assay compounds of the invention, two microliters of test compound (0.6 nM-4 mM) in DMSO or plain DMSO for control wells, 38 microliters of 20 mM HEPES pH 7, 50 mM NaCl, 10 mM $MgCl_2$, 0.5 mM TCEP, 0.1 mM sodium orthovanadate, 0.1 mg/mL BSA, and 0.05% Triton X-100 (Kinase Assay Buffer) are added. Eight microliters of the compound solution are added to a 384-well black microtiter plate, followed by six microliters of GST-p53 (17 ug/mL) and ATP (333 uM) in Kinase Assay Buffer. Six microliters of GST-PLK1 (3 ug/mL) in Kinase Assay Buffer are then added and the solution incubated at 37° C. for 35 minutes. Six microliters of solution containing 43 mM EDTA to stop the reaction and a 1:600 dilution of anti-phospho-p53 antibody in 20 mM HEPES pH 7, 50 mM NaCl, and 0.5 mg/mL BSA (Antibody Binding Buffer) are added and the solution incubated at 37° C. for 30 minutes. Six microliters of solution containing 9 nM europium-conjugated anti-rabbit antibody and 120 nM APC-conjugated anti-GST antibody in Antibody Binding Buffer are then added and the mixture incubated at room temperature for 1.5 hours. The HTRF signal is read on an Envision reader from PerkinElmer Life and Analytical Sciences.

PLK1 $IC_{50}$ values A=1-50 nM, B=51-500 nM, C=0.5 uM-5 uM, D=>5 uM, ND=not determined.

TABLE 1

| Ex | cpd | MW | MH+/z | $IC_{50}$ | Name |
|---|---|---|---|---|---|
| 1 | I-1 | 433.32 | 434 | A | 4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzoic acid |
| 2 | I-2 | 432.43 | 433 | A | 4-(9-cyclobutyl-7,7-difluoro-5-methyl-6-oxo-6,7,8,9-tetrahydro-5H-pyrimido[4,5-b][1,4]diazepin-2-ylamino)-3-methoxy-benzamide |
| 3 | I-3 | 446.46 | 447 | A | 4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-methyl-benzamide |
| 4 | I-4 | 529.59 | 530 | A | 4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 5 | I-5 | 515.57 | 516 | A | 4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-piperidin-4-yl-benzamide |
| 6 | I-6 | 515.57 | 516 | B | 2-[4-(4-amino-piperidine-1-carbonyl)-2-methoxy-phenylamino]-9-cyclobutyl-7,7-difluoro-5-methyl-5,7,8,9-tetrahydro-pyrimido[4,5-b][1,4]diazepin-6-one |
| 7 | I-7 | 516.55 | 517 | A | 4-(9-cyclobutyl-7,7-difluoro-5-methyl-6-oxo-6,7,8,9-tetrahydro-5H-pyrimido[4,5-b][1,4]diazepin-2-ylamino)-3-methoxy-N-(tetrahydro-pyran-4-yl)-benzamide |
| 8 | I-8 | 503.56 | 504 | A | 4-(9-cyclobutyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methoxy-benzamide |
| 9 | I-9 | 517.58 | 518 | A | 4-(9-cyclobutyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methoxy-benzamide |
| 10 | I-10 | 543.62 | 544 | A | 4-(9-cyclobutyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide |
| 11 | I-11 | 403.39 | 404 | B | 4-(9-cyclobutyl-7,7-difluoro-5-methyl-6-oxo-6,7,8,9-tetrahydro-5H-pyrimido[4,5-b][1,4]diazepin-2-ylamino)-benzoic acid |
| 12 | I-12 | 402.41 | 403 | B | 4-(9-cyclobutyl-7,7-difluoro-5-methyl-6-oxo-6,7,8,9-tetrahydro-5H-pyrimido[4,5-b][1,4]diazepin-2-ylamino)-benzamide |
| 13 | I-13 | 416.43 | 417 | B | 4-(9-cyclobutyl-7,7-difluoro-5-methyl-6-oxo-6,7,8,9-tetrahydro-5H-pyrimido[4,5-b][1,4]diazepin-2-ylamino)-N-methyl-benzamide |
| 14 | I-14 | 485.54 | 486 | A | 4-(9-cyclobutyl-7,7-difluoro-5-methyl-6-oxo-6,7,8,9-tetrahydro-5H-pyrimido[4,5-b][1,4]diazepin-2-ylamino)-N-piperidin-4-yl-benzamide |
| 15 | I-15 | 485.54 | 486 | B | 2-[4-(4-amino-piperidine-1-carbonyl)-phenylamino]-9-cyclobutyl-7,7-difluoro-5-methyl-5,7,8,9-tetrahydro-pyrimido[4,5-b][1,4]diazepin-6-one |
| 16 | I-16 | 499.57 | 500 | A | 4-(9-cyclobutyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide |
| 17 | I-17 | 486.53 | 487 | A | 4-(9-cyclobutyl-7,7-difluoro-5-methyl-6-oxo-6,7,8,9-tetrahydro-5H-pyrimido[4,5-b][1,4]diazepin-2-ylamino)-N-(tetrahydro-pyran-4-yl)-benzamide |
| 18 | I-18 | 473.53 | 474 | A | 4-(9-cyclobutyl-7,7-difluoro-5-methyl-6-oxo-6,7,8,9-tetrahydro-5H-pyrimido[4,5-b][1,4]diazepin-2- |

TABLE 1-continued

| Ex | cpd | MW | MH+/z | IC$_{50}$ | Name |
|---|---|---|---|---|---|
| 19 | I-19 | 487.56 | 488 | A | ylamino)-N-(2-dimethylamino-ethyl)-benzamide 4-(9-cyclobutyl-7,7-difluoro-5-methyl-6-oxo-6,7,8,9-tetrahydro-5H-pyrimido[4,5-b][1,4]diazepin-2-ylamino)-N-(3-dimethylamino-propyl)-benzamide |
| 20 | I-20 | 417.42 | 418 | ND | 4-(9-cyclopentyl-7,7-difluoro-5-methyl-6-oxo-6,7,8,9-tetrahydro-5H-pyrimido[4,5-b][1,4]diazepin-2-ylamino)-benzoic acid |
| 21 | I-21 | 513.60 | 514 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide |
| 22 | I-22 | 447.45 | 448 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoic acid |
| 23 | I-23 | 446.46 | 447 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 24 | I-24 | 460.49 | 461 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-methyl-benzamide |
| 25 | I-25 | 488.54 | 489 | A | 4-(9-cyclopentyl-7,7-difluoro-5-methyl-6-oxo-6,7,8,9-tetrahydro-5H-pyrimido[4,5-b][1,4]diazepin-2-ylamino)-N-isopropyl-3-methoxy-benzamide |
| 26 | I-26 | 486.52 | 487 | A | 4-(9-cyclopentyl-7,7-difluoro-5-methyl-6-oxo-6,7,8,9-tetrahydro-5H-pyrimido[4,5-b][1,4]diazepin-2-ylamino)-N-cyclopropyl-3-methoxy-benzamide |
| 27 | I-27 | 528.61 | 529 | A | N-cyclohexyl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 28 | I-28 | 504.54 | 505 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-methoxy-ethyl)-benzamide |
| 29 | I-29 | 518.57 | 519 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-methoxy-propyl)-benzamide |
| 30 | I-30 | 490.51 | 491 | A | 4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxy-ethyl)-3-methoxy-benzamide |
| 31 | I-31 | 528.49 | 529 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2,2,2-trifluoro-ethyl)-benzamide |
| 32 | I-32 | 542.63 | 543 | B | N-cyclohexylmethyl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 33 | I-33 | 542.61 | 543 | B | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-thiophen-3-ylmethyl-benzamide |
| 34 | I-34 | 526.55 | 527 | A | 4-(9-cyclopentyl-7,7-difluoro-5-methyl-6-oxo-6,7,8,9-tetrahydro-5H-pyrimido[4,5-b][1,4]diazepin-2-ylamino)-N-furan-3-ylmethyl-3-methoxy-benzamide |
| 35 | I-35 | 536.59 | 536 | B | N-benzyl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 36 | I-36 | 604.58 | 605 | C | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(4-trifluoromethyl-benzyl)-benzamide |
| 37 | I-37 | 550.61 | 551 | B | rac-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-phenyl-ethyl)-benzamide |
| 38 | I-38 | 522.56 | 523 | B | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-phenyl-benzamide |
| 39 | I-39 | 518.57 | 519 | A | 4-(9-cyclopentyl-7,7-difluoro-5-methyl-6-oxo-6,7,8,9-tetrahydro-5H-pyrimido[4,5-b][1,4]diazepin-2-ylamino)-N-(4-hydroxy-butyl)-3-methoxy-benzamide |
| 40 | I-40 | 518.57 | 519 | A | 4-(9-cyclopentyl-7,7-difluoro-5-methyl-6-oxo-6,7,8,9-tetrahydro-5H-pyrimido[4,5-b][1,4]diazepin-2-ylamino)-N-(2-ethoxy-ethyl)-3-methoxy-benzamide |
| 41 | I-41 | 504.54 | 505 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-hydroxy-propyl)-3-methoxy-benzamide |
| 42 | I-42 | 605.48 | 605 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3,5-dichloro-benzyl)-3-methoxy-benzamide |
| 43 | I-43 | 594.62 | 595 | B | N-(2-benzo[1,3]dioxol-5-yl-ethyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 44 | I-44 | 557.61 | 558 | A | N-[(1S,2R)-(2-carbamoyl-cyclopentyl)]-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 45 | I-45 | 543.62 | 544 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-pyrrolidin-1-yl-ethyl)-benzamide |
| 46 | I-46 | 545.64 | 546 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-isopropylamino-propyl)-3-methoxy-benzamide |
| 47 | I-47 | 572.66 | 573 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[2-(4-methyl-piperazin-1-yl)-ethyl]-benzamide |
| 48 | I-48 | 489.53 | 490 | A | N-(2-amino-ethyl)-4-(9-cyclopentyl-7,7-difluoro-5-methyl-6-oxo-6,7,8,9-tetrahydro-5H-pyrimido[4,5- |

TABLE 1-continued

| Ex | cpd | MW | MH+/z | IC50 | Name |
|---|---|---|---|---|---|
| 49 | I-49 | 558.64 | 559 | A | b][1,4]diazepin-2-ylamino)-3-methoxy-benzamide 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-piperazin-1-yl-ethyl)-benzamide |
| 50 | I-50 | 569.66 | 570 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(8-methyl-8-aza-bicyclo[3.2.1]oct-3-yl)-benzamide |
| 51 | I-51 | 589.65 | 590 | B | 4-(9-cyclopentyl-7,7-difluoro-5-methyl-6-oxo-6,7,8,9-tetrahydro-5H-pyrimido[4,5-b][1,4]diazepin-2-ylamino)-N-[2-(1H-indol-3-yl)-ethyl]-3-methoxy-benzamide |
| 52 | I-52 | 517.58 | 518 | A | 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methoxy-benzamide |
| 53 | I-53 | 585.70 | 586 | A | N-(3-cyclohexylamino-propyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 54 | I-54 | 679.73 | 680 | B | rac-(3R,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-hydroxy-piperidine-1-carboxylic acid benzyl ester |
| 55 | I-55 | 693.76 | 694 | B | rac-(3R,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-methoxy-piperidine-1-carboxylic acid benzyl ester |
| 56 | I-56 | 659.74 | 660 | A | rac-(3S,4R)-4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-3-methoxy-piperidine-1-carboxylic acid tert-butyl ester |
| 57 | I-57 | 559.62 | 560 | A | rac-(3S,4R)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-methoxy-piperidin-4-yl)-benzamide |
| 58 | I-58 | 693.76 | 694 | B | rac-(3S,4S)-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-4-methoxy-piperidine-1-carboxylic acid benzyl ester |
| 59 | I-59 | 543.62 | 544 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 60 | I-60 | 559.66 | 560 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-2,2-dimethyl-propyl)-3-methoxy-benzamide |
| 61 | I-61 | 554.60 | 555 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-imidazol-1-yl-propyl)-3-methoxy-benzamide |
| 62 | I-62 | 606.68 | 607 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3,4,5,6-tetrahydro-2H-[1,4']bipyridinyl-4-yl)-benzamide |
| 63 | I-63 | 597.71 | 598 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-cyclopentyl-piperidin-4-yl)-3-methoxy-benzamide |
| 64 | I-64 | 571.68 | 572 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-isopropyl-piperidin-4-yl)-3-methoxy-benzamide (I-64) |
| 65 | I-65 | 585.70 | 586 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2,2,6,6-tetramethyl-piperidin-4-yl)-benzamide |
| 66 | I-66 | 569.66 | 570 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-cyclopropyl-piperidin-4-yl)-3-methoxy-benzamide |
| 67 | I-67 | 557.65 | 558 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide |
| 68 | I-68 | 544.61 | 545 | A | cis-4-(9-cyclopentyl-7,7-difluoro-5-methyl-6-oxo-6,7,8,9-tetrahydro-5H-pyrimido[4,5-b][1,4]diazepin-2-ylamino)-N-(4-hydroxy-cyclohexyl)-3-methoxy-benzamide |
| 69 | I-69 | 544.61 | 545 | A | trans-4-(9-cyclopentyl-7,7-difluoro-5-methyl-6-oxo-6,7,8,9-tetrahydro-5H-pyrimido[4,5-b][1,4]diazepin-2-ylamino)-N-(4-hydroxy-cyclohexyl)-3-methoxy-benzamide |
| 70 | I-70 | 751.84 | 752 | A | 4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid 9H-fluoren-9-ylmethyl ester |
| 71 | I-71 | 629.71 | 630 | B | 4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester |
| 72 | I-72 | 529.59 | 530 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-piperidin-4-yl-benzamide |
| 73 | I-73 | 725.80 | 726 | B | {3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]- |

TABLE 1-continued

| Ex | cpd | MW | MH+/z | IC$_{50}$ | Name |
|---|---|---|---|---|---|
| 74 | I-74 | 503.56 | 504 | A | propyl}-carbamic acid 9H-fluoren-9-ylmethyl ester N-(3-amino-propyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 75 | I-75 | 575.64 | 576 | A | 4-(9-cyclopentyl-7,7-difluoro-5-methyl-6-oxo-6,7,8,9-tetrahydro-5H-pyrimido[4,5-b][1,4]diazepin-2-ylamino)-N-[1-(2-fluoro-ethyl)-piperidin-4-yl]-3-methoxy-benzamide |
| 76 | I-76 | 649.77 | 650 | A | 4-(9-cyclopentyl-7,7-difluoro-5-methyl-6-oxo-6,7,8,9-tetrahydro-5H-pyrimido[4,5-b][1,4]diazepin-2-ylamino)-N-[1-(3-methanesulfonyl-propyl)-piperidin-4-yl]-3-methoxy-benzamide |
| 77 | I-77 | 611.62 | 612 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[1-(2,2,2-trifluoro-ethyl)-piperidin-4-yl]-benzamide |
| 78 | I-78 | 531.61 | 532 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methoxy-benzamide (I-78) |
| 79 | I-79 | 573.65 | 574 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-morpholin-4-yl-propyl)-benzamide |
| 80 | I-80 | 557.65 | 558 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-pyrrolidin-1-yl-propyl)-benzamide |
| 81 | I-81 | 615.69 | 616 | B | R-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-pyrrolidine-1-carboxylic acid tert-butyl ester |
| 82 | I-82 | 615.69 | 616 | A | S-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-pyrrolidine-1-carboxylic acid tert-butyl ester |
| 83 | I-83 | 515.57 | 516 | A | S-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N—(S)-pyrrolidin-3-yl-benzamide |
| 84 | I-84 | 571.68 | 572 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-piperidin-1-yl-propyl)-benzamide |
| 85 | I-85 | 599.73 | 600 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1,2,2,6,6-pentamethyl-piperidin-4-yl)-benzamide |
| 86 | I-86 | 601.66 | 602 | ND | 3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-azetidine-1-carboxylic acid tert-butyl ester |
| 87 | I-87 | 586.70 | 587 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[3-(4-methyl-piperazin-1-yl)-propyl]-benzamide |
| 88 | I-88 | 614.70 | 615 | A | N-[1-(2-amino-2-methyl-propionyl)-piperidin-4-yl]-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 89 | I-89 | 543.58 | 544 | A | R-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-oxo-piperidin-4-yl)-benzamide |
| 90 | I-90 | 543.58 | 544 | A | S-4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-oxo-piperidin-4-yl)-benzamide |
| 91 | I-91 | 615.67 | 616 | A | 3-{[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-methyl}-azetidine-1-carboxylic acid tert-butyl ester |
| 92 | I-92 | 629.71 | 630 | B | 3-{[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-methyl}-pyrrolidine-1-carboxylic acid tert-butyl ester |
| 93 | I-93 | 529.59 | 530 | A | 4-(9-cyclopentyl-7,7-difluoro-5-methyl-6-oxo-6,7,8,9-tetrahydro-5H-pyrimido[4,5b][1,4]diazepin-2-ylamino)-3-methoxy-N-pyrrolidin-3-ylmethyl-benzamide (I-93) |
| 94 | I-94 | 672.78 | 673 | A | 4-{3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-propyl}-piperazine-1-carboxylic acid tert-butyl ester |
| 95 | I-95 | 572.66 | 573 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3-piperazin-1-yl-propyl)-benzamide |
| 96 | I-96 | 616.72 | 617 | A | 4-(9-cyclopentyl-7,7-difluoro-5-methyl-6-oxo-6,7,8,9-tetrahydro-5H-pyrimido[4,5-b][1,4]diazepin-2-ylamino)-N-{3-[4-(2-hydroxy-ethyl)-piperazin-1-yl]-propyl}-3-methoxy-benzamide |
| 97 | I-97 | 643.74 | 644 | B | cis-{4-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-cyclohexyl}-carbamic acid tert-butyl ester |
| 98 | I-98 | 543.62 | 544 | A | cis-N-(4-amino-cyclohexyl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 99 | I-99 | 515.57 | 516 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(1-methyl-azetidin-3-yl)-benzamide |
| 100 | I-100 | 605.69 | 606 | A | N-((S)-1-benzyl-pyrrolidin-3-yl)-4-(9- |

TABLE 1-continued

| Ex | cpd | MW | MH+/z | IC50 | Name |
|---|---|---|---|---|---|
| 101 | I-101 | 605.69 | 606 | A | cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 102 | I-102 | 571.63 | 572 | A | N-((R)-1-benzyl-pyrrolidin-3-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 103 | I-103 | 631.69 | 632 | A | N-(1-acetyl-piperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 104 | I-104 | 531.57 | 532 | A | (3R,4R)-3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-4-hydroxy-pyrrolidine-1-carboxylic acid tert-butyl ester |
| 105 | I-105 | 587.68 | 588 | A | 4-(9-cyclopentyl-7,7-difluoro-5-methyl-6-oxo-6,7,8,9-tetrahydro-5H-pyrimido[4,5-b][1,4]diazepin-2-ylamino)-N-((3R,4R)-4-hydroxy-pyrrolidin-3-yl)-3-methoxy-benzamide |
| 106 | I-106 | 555.63 | 556 | A | 4-(9-cyclopentyl-7,7-difluoro-5-methyl-6-oxo-6,7,8,9-tetrahydro-5H-pyrimido[4,5-b][1,4]diazepin-2-ylamino)-N-[3-(4-hydroxy-piperidin-1-yl)-propyl]-3-methoxy-benzamide |
| 107 | I-107 | 555.63 | 556 | A | N—(R)-1-aza-bicyclo[2.2.2]oct-3-yl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 108 | I-108 | 606.68 | 607 | A | N—(S)-1-aza-bicyclo[2.2.2]oct-3-yl-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 109 | I-109 | 537.57 | 538 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(3,4,5,6-tetrahydro-2H-[1,2']bipyridinyl-4-yl)-benzamide |
| 110 | I-110 | 585.70 | 586 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-2-ylmethyl-benzamide |
| 111 | I-111 | 537.57 | 538 | A | 4-(9-Cyclopentyl-7,7-difluoro-5-methyl-6-oxo-6,7,8,9-tetrahydro-5H-pyrimido[4,5-b][1,4]diazepin-2-ylamino)-3-methoxy-N-[3-(2-methyl-piperidin-1-yl)-propyl]-benzamide |
| 112 | I-112 | 557.65 | 558 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-3-yl-methyl benzamide |
| 113 | I-113 | 571.63 | 572 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[2-(1-methyl-pyrrolidin-2-yl)-ethyl]-benzamide |
| 114 | I-114 | 557.65 | 558 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-[3-(2-oxo-pyrrolidin-1-yl)-propyl]-benzamide |
| 115 | I-115 | 529.59 | 530 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-piperidin-1-yl-ethyl)-benzamide |
| 116 | I-116 | 551.60 | 552 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-piperidin-1-yl-benzamide |
| 117 | I-117 | 559.62 | 560 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-pyridin-2-yl-ethyl)-benzamide |
| 118 | I-118 | 544.61 | 545 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-morpholin-4-yl-ethyl)-benzamide |
| 119 | I-119 | 565.63 | 566 | B | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(4-methyl-piperazin-1-yl) benzamide |
| 120 | I-120 | 688.78 | 689 | B | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-(2-phenylamino-ethyl)-benzamide |
| 121 | I-121 | 588.66 | 589 | A | 4-{3-[4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzoylamino]-2-hydroxy-propyl}-piperazine-1-carboxylic acid tert-butyl ester |
| 122 | I-122 | 619.73 | 620 | A | 4-(9-cyclopentyl-7,7-difluoro-5-methyl-6-oxo-6,7,8,9-tetrahydro-5H-pyrimido[4,5-b][1,4]diazepin-2-ylamino)-N-(2-hydroxy-3-piperazin-1-yl-propyl)-3-methoxy-benzamide |
| 123 | I-123 | 559.66 | 560 | A | N-(1-benzyl-piperidin-4-yl)-4-(9-cyclopentyl-7,7-difluoro-5-methyl-6-oxo-6,7,8,9-tetrahydro-5H-pyrimido[4,5-b][1,4]diazepin-2-ylamino)-3-methoxy-benzamide |
| 124 | I-124 | 530.58 | 531 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-diethylamino-propyl)-3-methoxy-benzamide |
| 125 | I-125 | 474.51 | 475 | A | 4-(9-cyclopentyl-7,7-difluoro-5-methyl-6-oxo-3,5,6,7,8,9-hexahydro-2H-pyrimido[4,5-b][1,4]diazepin-2-ylamino)-3-methoxy-N-(tetrahydro-pyran-4-yl)-benzamide |
| 126 | I-126 | 514.58 | 515 | B | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N,N-dimethyl-benzamide |
| 127 | I-127 | 516.55 | 517 | A | 9-cyclopentyl-7,7-difluoro-2-[2-methoxy-4-(piperidine-1-carbonyl)-phenylamino]-5-methyl-5,7,8,9-tetrahydro-pyrimido[4,5-b][1,4]diazepin-6-one |
| | | | | | 9-cyclopentyl-7,7-difluoro-2-[2-methoxy-4-(morpholine-4-carbonyl)-phenylamino]-5-methyl-5,7,8,9-tetrahydro-pyrimido[4,5-b][1,4]diazepin-6-one |

TABLE 1-continued

| Ex | cpd | MW | MH+/z | IC$_{50}$ | Name |
|---|---|---|---|---|---|
| 128 | I-128 | 529.59 | 530 | A | 9-cyclopentyl-7,7-difluoro-2-[2-methoxy-4-(4-methyl-piperazine-1-carbonyl)-phenylamino]-5-methyl-5,7,8,9-tetrahydro-pyrimido[4,5-b][1,4]diazepin-6-one |
| 129 | I-129 | 523.55 | 524 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-4-yl-benzamide |
| 130 | I-130 | 523.55 | 524 | A | 4-(9-cyclopentyl-7,7-difluoro-5-methyl-6-oxo-6,7,8,9-tetrahydro-5H-pyrimido[4,5-b][1,4]diazepin-2-ylamino)-3-methoxy-N-pyridin-3-yl-benzamide |
| 131 | I-131 | 403.39 | 404 | ND | 4-(9-cyclopentyl-7,7-difluoro-6-oxo-6,7,8,9-tetrahydro-5H-pyrimido[4,5-b][1,4]diazepin-2-ylamino)-benzoic acid |
| 132 | I-132 | 402.41 | 403 | D | 4-(9-cyclopentyl-7,7-difluoro-6-oxo-6,7,8,9-tetrahydro-5H-pyrimido[4,5-b][1,4]diazepin-2-ylamino)-benzamide |
| 133 | I-133 | 416.43 | 417 | C | 4-(9-cyclopentyl-7,7-difluoro-6-oxo-6,7,8,9-tetrahydro-5H-pyrimido[4,5-b][1,4]diazepin-2-ylamino)-N-methyl-benzamide |
| 134 | I-134 | 499.57 | 500 | B | 4-(9-cyclopentyl-7,7-difluoro-6-oxo-6,7,8,9-tetrahydro-5H-pyrimido[4,5-b][1,4]diazepin-2-ylamino)-N-(1-methyl-piperidin-4-yl)-benzamide |
| 135 | I-135 | 487.56 | 488 | C | 4-(9-cyclopentyl-7,7-difluoro-6-oxo-6,7,8,9-tetrahydro-5H-pyrimido[4,5-b][1,4]diazepin-2-yl-amino)-N-(3-dimethyl-amino-propyl)-benzamide |
| 136 | I-136 | 486.53 | 487 | C | 4-(9-cyclopentyl-7,7-difluoro-6-oxo-6,7,8,9-tetrahydro-5H-pyrimido[4,5-b][1,4]diazepin-2-ylamino)-N-(tetrahydro-pyran-4-yl)-benzamide |
| 137 | I-137 | 529.59 | 530 | B | 4-(9-cyclopentyl-7,7-difluoro-6-oxo-6,7,8,9-tetrahydro-5H-pyrimido[4,5-b][1,4]diazepin-2-ylamino)-3-methoxy-N-(1-methyl-piperidin-4-yl)-benzamide |
| 138 | I-138 | 431.45 | 432 | ND | 4-(9-cyclopentyl-5-ethyl-7,7-difluoro-6-oxo-6,7,8,9-tetrahydro-5H-pyrimido[4,5-b][1,4]diazepin-2-ylamino)-benzoic acid |
| 139 | I-139 | 430.46 | 431 | C | 4-(9-cyclopentyl-5-ethyl-7,7-difluoro-6-oxo-6,7,8,9-tetrahydro-5H-pyrimido[4,5-b][1,4]diazepin-2-ylamino)-benzamide |
| 140 | I-140 | 444.49 | 445 | C | 4-(9-cyclopentyl-5-ethyl-7,7-difluoro-6-oxo-6,7,8,9-tetrahydro-5H-pyrimido[4,5-b][1,4]diazepin-2-ylamino)-N-methyl-benzamide |
| 141 | I-141 | 527.62 | | B | 4-(9-cyclopentyl-5-ethyl-7,7-difluoro-6-oxo-6,7,8,9-tetrahydro-5H-pyrimido[4,5-b][1,4]diazepin-2-ylamino)-N-(1-methyl-piperidin-4-yl)-benzamide |
| 142 | I-142 | 515.61 | 516 | C | 4-(9-cyclopentyl-5-ethyl-7,7-difluoro-6-oxo-6,7,8,9-tetrahydro-5H-pyrimido[4,5-b][1,4]diazepin-2-yl-amino)-N-(3-dimethyl-amino-propyl)-benzamide |
| 143 | I-143 | 514.58 | 515 | C | 4-(9-cyclopentyl-5-ethyl-7,7-difluoro-6-oxo-6,7,8,9-tetrahydro-5H-pyrimido[4,5-b][1,4]diazepin-2-ylamino)-N-(tetrahydro-pyran-4-yl)-benzamide |
| 144 | I-144 | 445.47 | 446 | ND | 4-(9-cyclopentyl-7,7-difluoro-6-oxo-5-propyl-6,7,8,9-tetrahydro-5H-pyrimido[4,5-b][1,4]diazepin-2-ylamino)-benzoic acid |
| 145 | I-145 | 444.49 | 445 | C | 4-(9-cyclopentyl-7,7-difluoro-6-oxo-5-propyl-6,7,8,9-tetrahydro-5H-pyrimido[4,5-b][1,4]diazepin-2-ylamino)-benzamide |
| 146 | I-146 | 458.52 | 459 | C | 4-(9-cyclopentyl-7,7-difluoro-6-oxo-5-propyl-6,7,8,9-tetrahydro-5H-pyrimido[4,5-b][1,4]diazepin-2-ylamino)-N-methyl-benzamide |
| 147 | I-147 | 541.65 | 542 | B | 4-(9-cyclopentyl-7,7-difluoro-6-oxo-5-propyl-6,7,8,9-tetrahydro-5H-pyrimido[4,5-b][1,4]diazepin-2-ylamino)-N-(1-methyl-piperidin-4-yl)-benzamide |
| 148 | I-148 | 529.64 | 530 | C | 4-(9-cyclopentyl-7,7-difluoro-6-oxo-5-propyl-6,7,8,9-tetrahydro-5H-pyrimido[4,5-b][1,4]diazepin-2-yl-amino)-N-(3-dimethyl-amino-propyl)-benzamide |
| 149 | I-149 | 528.61 | 529 | C | 4-(9-cyclopentyl-7,7-difluoro-6-oxo-5-propyl-6,7,8,9-tetrahydro-5H-pyrimido[4,5-b][1,4]diazepin-2-ylamino)-N-(tetrahydro-pyran-4-yl)-benzamide |
| 150 | I-150 | 611.62 | 612 | C | 4-[9-cyclopentyl-7,7-difluoro-6-oxo-5-(2,2,2-trifluoro-ethyl)-6,7,8,9-tetrahydro-5H-pyrimido[4,5-b][1,4]diazepin-2-ylamino]-3-methoxy-N-(1-methyl-piperidin-4-yl)-benzamide |
| 151 | I-151 | 433.42 | 434 | ND | 4-(9-cyclopentyl-7,7-difluoro-6-oxo-6,7,8,9-tetrahydro-5H-pyrimido[4,5-b][1,4]diazepin-2-ylamino)-3-methoxy-benzoic acid |
| 152 | I-152 | 432.43 | 433 | C | 4-(9-cyclopentyl-7,7-difluoro-6-oxo-6,7,8,9-tetrahydro-5H-pyrimido[4,5-b][1,4]diazepin-2-ylamino)-3-methoxy-benzamide |
| 153 | I-153 | 446.46 | 447 | C | 4-(9-cyclopentyl-7,7-difluoro-6-oxo-6,7,8,9-tetrahydro-5H-pyrimido[4,5-b][1,4]diazepin-2-ylamino)-3-methoxy-N-methyl-benzamide |
| 154 | I-154 | 517.58 | 518 | C | 4-(9-cyclopentyl-7,7-difluoro-6-oxo-6,7,8,9-tetrahydro-5H-pyrimido[4,5-b][1,4]diazepin-2-ylamino)-N-(3-dimethylamino-propyl)-3-methoxy-benzamide |
| 155 | I-155 | 516.55 | 517 | D | 4-(9-cyclopentyl-7,7-difluoro-6-oxo-6,7,8,9-tetrahydro-5H-pyrimido[4,5-b][1,4]diazepin-2-ylamino)-3-methoxy-N-(tetrahydro-pyran-4-yl)-benzamide |
| 156 | I-156 | 461.47 | 462 | ND | 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-benzoic acid |
| 157 | I-157 | 460.49 | 461 | C | 4-(9-cyclopentyl-5-ethyl-7,7-difluoro-6-oxo-6,7,8,9-tetrahydro-5H-pyrimido[4,5-b][1,4]diazepin-2-yl-amino)-3-methoxy-benzamide |
| 158 | I-158 | 474.51 | 475 | C | 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-N-methyl-benzamide |
| 159 | I-159 | 557.65 | 558 | B | 4-(9-cyclopentyl-5-ethyl-7,7-difluoro- |

TABLE 1-continued

| Ex | cpd | MW | MH+/z | IC$_{50}$ | Name |
|---|---|---|---|---|---|
| 160 | I-160 | 545.64 | 546 | B | 6-oxo-6,7,8,9-tetrahydro-5H-pyrimido[4,5-b][1,4]diazepin-2-ylamino)-3-methoxy-N-(1-methyl-piperidin-4-yl)-benzamide |
| 161 | I-161 | 544.61 | 542 | C | 4-(9-cyclopentyl-5-ethyl-7,7-difluoro-6-oxo-6,7,8,9-tetra-hydro-5H-pyrimido[4,5-b][1,4]diazepin-2-ylamino)-N-(3-dimethylamino-propyl)-3-methoxy-benzamide |
| 162 | I-162 | 475.50 | 476 | ND | 4-(9-cyclopentyl-5-ethyl-7,7-difluoro-6-oxo-6,7,8,9-tetrahydro-5H-pyrimido[4,5-b][1,4]diazepin-2-ylamino)-3-methoxy-N-(tetrahydro-pyran-4-yl)-benzamide |
| 163 | I-163 | 474.51 | 475 | C | 4-(9-cyclopentyl-5-ethyl-7,7-difluoro-6-oxo-5-propyl-6,7,8,9-tetrahydro-5H-pyrimido[4,5-b][1,4]diazepin-2-ylamino)-3-methoxy-benzoic acid |
| 164 | I-164 | 488.54 | 489 | C | 4-(9-cyclopentyl-7,7-difluoro-6-oxo-5-propyl-6,7,8,9-tetrahydro-5H-pyrimido[4,5-b][1,4]diazepin-2-ylamino)-3-methoxy-N-methyl-benzamide |
| 165 | I-165 | 571.68 | 572 | B | 4-(9-cyclopentyl-7,7-difluoro-6-oxo-5-propyl-6,7,8,9-tetrahydro-5H-pyrimido[4,5-b][1,4]diazepin-2-ylamino)-3-methoxy-N-(1-methyl-piperidin-4-yl)-benzamide |
| 166 | I-166 | 559.66 | 560 | B | 4-(9-cyclopentyl-5-propyl-7,7-difluoro-6-oxo-6,7,8,9-tetra-hydro-5H-pyrimido[4,5-b][1,4]diazepin-2-ylamino)-N-(3-dimethylamino-propyl)-3-methoxy-benzamide |
| 167 | I-167 | 558.63 | 559 | C | 4-(9-cyclopentyl-7,7-difluoro-6-oxo-5-propyl-6,7,8,9-tetrahydro-5H-pyrimido[4,5-b][1,4]diazepin-2-ylamino)-3-methoxy-N-(tetrahydro-pyran-4-yl)-benzamide |
| 168 | I-168 | 479.46 | 480 | ND | 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid methyl ester |
| 169 | I-169 | 465.44 | 466 | ND | 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoic acid |
| 170 | I-170 | 464.45 | 465 | A | 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzamide |
| 171 | I-171 | 478.48 | 479 | A | 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-methyl-benzamide |
| 172 | I-172 | 549.60 | 550 | A | 4-(9-cyclopentyl-7,7-difluoro-5-methyl-6-oxo-6,7,8,9-tetra-hydro-5H-pyrimido[4,5-b][1,4]diazepin-2-ylamino)-N-(3-dimethylamino-propyl)-2-fluoro-5-methoxy-benzamide |
| 173 | I-173 | 548.57 | 549 | A | 4-(9-cyclopentyl-7,7-difluoro-5-6methyl-oxo-6,7,8,9-tetrahydro-5H-pyrimido[4,5-b][1,4]diazepin-2-ylamino)-2-fluoro-5-methoxy-N-(tetrahydropyran-4-yl)-benzamide |
| 174 | I-174 | 535.74 | 536 | A | 4-(9-cyclopentyl-7,7-difluoro-5-methyl-6-oxo-6,7,8,9-tetra-hydro-5H-pyrimido[4,5-b][1,4]diazepin-2-ylamino)-N-(3-dimethylamino-ethyl)-2-fluoro-5-methoxy-benzamide |
| 175 | I-175 | 575.64 | 576 | A | 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methyl-piperidin-4-yl)-benzamide |
| 176 | I-176 | 561.61 | 562 | A | 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-(1-methyl-piperidin-4-yl)-benzamide |
| 177 | I-177 | 647.70 | 648 | ND | 4-[4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-benzoyl-amino]-piperidin-1-carboxylic acid tert-butyl ester |
| 178 | I-178 | 547.59 | 548 | A | 4-(9-cyclopentyl-7,7-difluoro-5-methyl-6-oxo-6,7,8,9-tetrahydro-5H-pyrimido[4,5-b][1,4]diazepin-2-ylamino)-2-fluoro-5-methoxy-N-piperidin-4-yl-benzamide |
| 179 | I-179 | 548.04 | 548 | A | 3-chloro-4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide |
| 180 | I-180 | 571.68 | 572 | A | 4-(9-cyclopentyl-7,7-difluoro-5-methyl-6-oxo-6,7,8,9-tetrahydro-5H-pyrimido[4,5-b][1,4]diazepin-2-ylamino)-3-isopropoxy-N-(1-methyl-piperidin-4-yl)-benzamide |
| 181 | I-181 | 597.59 | 598 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-3-trifluoromethoxy-benzamide |
| 182 | I-182 | 435.41 | 436 | ND | 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoic acid |
| 183 | I-183 | 531.59 | 532 | A | 4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-(1-methyl-piperidin-4-yl)-benzamide |
| 184 | I-184 | 431.45 | 432 | ND | 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoic acid |
| 185 | I-185 | 527.62 | 523 | A | 4-(9-cyclopentyl-7,7-difluoro-5-methyl-6-oxo-6,7,8,9-tetrahydro-5H-pyrimido[4,5-b][1,4]diazepin-2-ylamino)-3-methyl-N-(1-methyl-piperidin-4-yl)-benzamide |
| 186 | I-186 | 541.65 | 542 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methyl-benzamide |
| 187 | I-187 | 514.58 | 515 | A | 4-(9-cyclopentyl-7,7-difluoro-5-methyl-6-oxo-6,7,8,9-tetrahydro-5H-pyrimido[4,5-b][1,4]diazepin-2-ylamino)-3-methyl-N-(tetrahydro-pyran-4-yl)-benzamide |
| 188 | I-188 | 501.58 | 502 | A | 4-(9-cyclopentyl-7,7-difluoro-5-methyl-6-oxo-6,7,8,9-tetrahydro-5H- |

TABLE 1-continued

| Ex | cpd | MW | MH+/z | IC$_{50}$ | Name |
|---|---|---|---|---|---|
| 189 | I-189 | 515.61 | 516 | A | pyrimido[4,5-b][1,4]diazepin-2-ylamino)-N-(2-dimethylamino-ethyl)-3-methyl-benzamide |
| 190 | I-190 | 444.49 | 445 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methyl-benzamide |
| 191 | I-191 | 613.71 | 614 | A | 4-(9-cyclopentyl-7,7-difluoro-5-methyl-6-oxo-6,7,8,9-tetrahydro-5H-pyrimido[4,5-b][1,4]diazepin-2-ylamino)-3,N-dimethyl-benzamide |
| 192 | I-192 | 513.60 | 514 | A | 4-[4-(9-cyclopentyl-7,7-difluoro-5-methyl-6-oxo-6,7,8,9-tetrahydro-5H-pyrimido[4,5-b][1,4]diazepin-2-ylamino)-3-methyl-benzoylamino]-piperidine-1-carboxylic acid tert-butyl ester |
| 193 | I-193 | 430.46 | 431 | A | 4-(9-cyclopentyl-7,7-difluoro-5-methyl-6-oxo-6,7,8,9-tetrahydro-5H-pyrimido[4,5-b][1,4]diazepin-2-ylamino)-3-methyl-N-piperidin-4-yl-benzamide |
| 194 | I-194 | 445.47 | 446 | ND | 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzamide |
| 195 | I-195 | 541.65 | 546 | A | 4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoic acid |
| 196 | I-196 | 555.68 | 556 | A | 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-(1-methyl-piperidin-4-yl)-benzamide |
| 197 | I-197 | 528.61 | 529 | A | 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-(1-ethyl-piperidin-4-yl)-benzamide |
| 198 | I-198 | 515.61 | 516 | A | 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-(tetrahydro-pyran-4-yl)-benzamide |
| 199 | I-199 | 529.64 | 530 | A | 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-ethyl-benzamide |
| 200 | I-200 | 458.52 | 459 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-ethyl-benzamide |
| 201 | I-201 | 627.74 | 628 | B | 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-methyl-benzamide |
| 202 | I-202 | 527.62 | 528 | A | 4-[4-(9-cyclopentyl-7,7-difluoro-5-methyl-6-oxo-6,7,8,9-tetrahydro-5H-pyrimido[4,5-b][1,4]diazepin-2-ylamino)-3-ethyl-benzoylamino]-piperidine-1-carboxylic acid tert-butyl ester |
| | | | | | 4-(9-cyclopentyl-7,7-difluoro-5-methyl-6-oxo-6,7,8,9-tetrahydro-5H-pyrimido[4,5-b][1,4]diazepin-2-ylamino)-3-ethyl-N-piperidin-4-yl-benzamide |
| 203 | I-203 | 444.45 | 445 | A | 4-(9-cyclopentyl-7,7-difluoro-5-methyl-6-oxo-6,7,8,9-tetrahydro-5H-pyrimido[4,5-b][1,4]diazepin-2-ylamino)-3-methyl-benzamide |
| 204 | I-204 | 485.42 | 486 | ND | 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoic acid |
| 205 | I-205 | 589.59 | 590 | | 4-(9-cyclopentyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-3-trifluoromethyl-benzamide |
| 206 | I-206 | 595.62 | 596 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-trifluoromethyl-benzamide |
| 207 | I-207 | 568.55 | 569 | B | 4-(9-cyclopentyl-7,7-difluoro-5-methyl-6-oxo-6,7,8,9-tetrahydro-5H-pyrimido[4,5-b][1,4]diazepin-2-ylamino)-N-(tetrahydro-pyran-4-yl)-3-trifluoromethyl-benzamide |
| 208 | I-208 | 555.56 | 556 | B | 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-trifluoromethyl-benzamide |
| 209 | I-209 | 569.58 | 570 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-trifluoromethyl-benzamide |
| 210 | I-210 | 498.46 | 499 | B | 4-(9-cyclopentyl-7,7-difluoro-5-methyl-6-oxo-6,7,8,9-tetrahydro-5H-pyrimido[4,5-b][1,4]diazepin-2-ylamino)-N-methyl-3-trifluoromethyl-benzamide |
| 211 | I-211 | 667.69 | 668 | B | 4-[4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzoylamino]-piperidine-1-carboxylic acid tert-butyl ester |
| 212 | I-212 | 567.57 | 568 | A | 4-(9-cyclopentyl-7,7-difluoro-5-methyl-6-oxo-6,7,8,9-tetrahydro-5H-pyrimido[4,5-b][1,4]diazepin-2-ylamino)-N-piperidin-4-yl-3-trifluoromethyl-benzamide |
| 213 | I-213 | 484.43 | 485 | B | 4-(9-cyclopentyl-7,7-difluoro-5-methyl-6-oxo-6,7,8,9-tetrahydro-5H-pyrimido[4,5-b][1,4]diazepin-2-ylamino)-3-trifluoromethyl-benzamide |
| 214 | I-214 | 461.47 | 462 | ND | 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoic acid |
| 215 | I-215 | 557.65 | 558 | A | 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-(1-methyl-piperidin-4-yl)-benzamide |
| 216 | I-216 | 571.68 | 572 | A | 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-(1-ethyl-piperidin-4-yl)-benzamide |
| 217 | I-217 | 544.61 | 545 | A | 4-(9-cyclopentyl-7,7-difluoro-5-methyl-6-oxo-6,7,8,9-tetrahydro-5H-pyrimido[4,5-b][1,4]diazepin-2- |

TABLE 1-continued

| Ex | cpd | MW | MH+/z | IC50 | Name |
|---|---|---|---|---|---|
| 218 | I-218 | 531.61 | 532 | A | ylamino)-3-ethoxy-N-(tetrahydro-pyran-4-yl)-benzamide |
| 219 | I-219 | 545.64 | 546 | A | 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-ethoxy-benzamide |
| 220 | I-220 | 474.51 | 475 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-ethoxy-benzamide |
| 221 | I-221 | 643.74 | 644 | B | 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-methyl-benzamide |
| 222 | I-222 | 543.62 | 544 | A | 4-[4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzoylamino]-piperidine-1-carboxylic acid tert-butyl ester |
| 223 | I-223 | 460.49 | 461 | A | 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-N-piperidin-4-yl-benzamide |
| 224 | I-224 | 545.61 | 546 | A | 4-(9-cyclopentyl-7,7-difluoro-5-methyl-6-oxo-6,7,8,9-tetrahydro-5H-pyrimido[4,5-b][1,4]diazepin-2-ylamino)-3-ethoxy-benzamide |
| 225 | I-225 | 518.54 | 519 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-fluoro-benzamidemide |
| 226 | I-226 | 505.55 | 506 | A | 4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-(tetrahydro-pyran-4-yl)-benzamide |
| 227 | I-227 | 519.57 | 520 | A | 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-fluoro-benzamide |
| 228 | I-228 | 448.45 | 449 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-fluoro-benzamide |
| 229 | I-229 | 617.68 | 618 | A | 4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-methyl-benzamide |
| 230 | I-230 | 517.56 | 518 | A | 4-[4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzoylamino]-piperidine-1-carboxylic acid tert-butyl ester |
| 231 | I-231 | 434.43 | 435 | A | 4-(9-cyclopentyl-7,7-difluoro-5-methyl-6-oxo-6,7,8,9-tetrahydro-5H-pyrimido[4,5-b][1,4]diazepin-2-ylamino)-3-fluoro-N-piperidin-4-yl-benzamide |
| | | | | | 4-(9-cyclopentyl-7,7-difluoro-5-methyl-6-oxo-6,7,8,9-tetrahydro-5H-pyrimido[4,5-b][1,4]diazepin-2-ylamino)-3-fluoro-benzamide |
| 232 | I-232 | 553.40 | 554 | ND | 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoic acid |
| 233 | I-233 | 549.58 | 550 | A | 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-(1-methyl-piperidin-4-yl)-benzamide |
| 234 | I-234 | 563.60 | 564 | A | 4-(9-cyclopentyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-2,5-difluoro-benzamid |
| 235 | I-235 | 536.53 | 537 | A | 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-(tetrahydro-pyran-4-yl)-benzamide |
| 236 | I-236 | 523.54 | 524 | A | 4-(9-cyclopentyl-7,7-difluoro-5-methyl-6-oxo-6,7,8,9-tetrahydro-5H-pyrimido[4,5-b][1,4]diazepin-2-ylamino)-N-(2-dimethylamino-ethyl)-2,5-difluoro-benzamide |
| 237 | I-237 | 537.57 | 538 | A | 4-(9-cyclopentyl-7,7-difluoro-5-methyl-6-oxo-6,7,8,9-tetrahydro-5H-pyrimido[4,5-b][1,4]diazepin-2-ylamino)-N-(3-dimethylamino-propyl)-2,5-difluoro-benzamide |
| 238 | I-238 | 466.44 | 467 | A | 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-methyl-benzamide |
| 239 | I-239 | 635.67 | 636 | B | 4-[4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzoylamino]-piperidine-1-carboxylic acid tert-butyl ester |
| 240 | I-240 | 535.55 | 536 | A | 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-N-piperidin-4-yl-benzamide |
| 241 | I-241 | 452.42 | 453 | A | 4-(9-cyclopentyl-7,7-difluoro-5-methyl-6-oxo-6,7,8,9-tetrahydro-5H-pyrimido[4,5-b][1,4]diazepin-2-ylamino)-2,5-difluoro-benzamide |
| 242 | I-242 | 467.43 | 468 | ND | 4-(9-cyclopentyl-7,7-difluoro-5-methyl-6-oxo-6,7,8,9-tetrahydro-5H-pyrimido[4,5-b][1,4]diazepin-2-ylamino)-2,3-difluoro-benzoic acid methyl ester |
| 243 | I-243 | 549.58 | 550 | A | 4-(9-cyclopentyl-7,7-difluoro-6-oxo-6,7,8,9-tetrahydro-5H-pyrimido[4,5-b][1,4]diazepin-2-ylamino)-2,3-difluoro-N-(1-methyl-piperidin-4-yl)-benzamide |
| 244 | I-244 | 563.60 | 564 | A | 4-(9-cyclopentyl-7,7-difluoro-6-oxo-6,7,8,9-tetrahydro-5H-pyrimido[4,5-b][1,4]diazepin-2-ylamino)-N-(1-ethyl-piperidin-4-yl)-2,3-difluoro-benzamide |
| 245 | I-245 | 466.44 | 467 | A | 4-(9-cyclopentyl-7,7-difluoro-6-oxo-6,7,8,9-tetrahydro-5H-pyrimido[4,5-yb][1,4]diazepin-2-lamino)-2,3-difluoro-N-methyl-benzamide |
| 246 | I-246 | 461.47 | 462 | A | 4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoic acid |

TABLE 1-continued

| Ex | cpd | MW | MH+/z | IC50 | Name |
|---|---|---|---|---|---|
| 247 | I-247 | 557.65 | 558 | A | 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 248 | I-248 | 460.49 | 461 | A | 4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzamide |
| 249 | I-249 | 474.51 | 475 | A | 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-methyl-benzamide |
| 250 | I-250 | 643.74 | 644 | ND | 4-[4-(9-cyclohexyl-7,7-difluoro-5-methyl-6-oxo-6,7,8,9-tetrahydro-5H-pyrimido[4,5-b][1,4]diazepin-2-ylamino)-3-methoxy-benzoylamino]-piperidine-1-carboxylic acid tert-butyl ester |
| 251 | I-251 | 543.62 | 544 | A | 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-piperidin-4-yl-benzamide |
| 252 | I-252 | 544.61 | 545 | A | 4-(9-cyclohexyl-7,7-difluoro-5-methyl-6-oxo-6,7,8,9-tetrahydro-5H-pyrimido[4,5-b][1,4]diazepin-2-ylamino)-3-methoxy-N-(tetrahydro-pyran-4-yl)-benzamide |
| 253 | I-253 | 531.61 | 532 | A | 4-(9-cyclohexyl-7,7-difluoro-5-methyl-6-oxo-6,7,8,9-tetrahydro-5H-pyrimido[4,5-b][1,4]diazepin-2-ylamino)-N-(2-dimethylamino-ethyl)-3-methoxy-benzamide |
| 254 | I-254 | 545.64 | 546 | A | 4-(9-cyclohexyl-7,7-difluoro-5-methyl-6-oxo-6,7,8,9-tetrahydro-5H-pyrimido[4,5-b][1,4]diazepin-2-ylamino)-N-(3-dimethylamino-propyl)-3-methoxy-benzamide |
| 255 | I-255 | 571.68 | 572 | A | 4-(9-cyclohexyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-3-methoxy-benzamide |
| 256 | I-256 | 431.45 | 432 | A | 4-(9-cyclohexyl-7,7-difluoro-5-methyl-6-oxo-6,7,8,9-tetrahydro-5H-pyrimido[4,5-b][1,4]diazepin-2-ylamin)-benzoic acid |
| 257 | I-257 | 430.46 | 431 | A | 4-(9-cyclohexyl-7,7-difluoro-5-methyl-6-oxo-6,7,8,9-tetrahydro-5H-pyrimido[4,5-b][1,4]diazepin-2-ylamino)-benzamide |
| 258 | I-258 | 444.49 | 445 | A | 4-(9-cyclohexyl-7,7-difluoro-5-methyl-6-oxo-6,7,8,9-tetrahydro-5H-pyrimido[4,5-b][1,4]diazepin-2-ylamino)-N-methyl-benzamide |
| 259 | I-259 | 613.71 | 614 | ND | 4-[4-(9-cyclohexyl-7,7-difluoro-5-methyl-6-oxo-6,7,8,9-tetrahydro-5H-pyrimido[4,5-b][1,4]diazepin-2-ylamino)-benzoylamino]-piperidine-1-carboxylic acid tert-butyl ester |
| 260 | I-260 | 513.60 | 514 | A | 4-(9-cyclohexyl-7,7-difluoro-5-methyl-6-oxo-6,7,8,9-tetrahydro-5H-pyrimido[4,5-b][1,4]diazepin-2-ylamino)-N-piperidin-4-yl-benzamide |
| 261 | I-261 | 541.65 | 542 | A | 4-(9-cyclohexyl-7,7-difluoro-5-methyl-6-oxo-6,7,8,9-tetrahydro-5H-pyrimido[4,5-b][1,4]diazepin-2-ylamino)-N-(1-ethyl-piperidin-4-yl)-benzamide |
| 262 | I-262 | 527.62 | 528 | A | 4-(9-cyclohexyl-7,7-difluoro-5-methyl-6-oxo-6,7,8,9-tetrahydro-5H-pyrimido[4,5-b][1,4]diazepin-2-ylamino)-N-(1-methyl-piperidin-4-yl)-benzamide |
| 263 | I-263 | 514.58 | 515 | A | 4-(9-cyclohexyl-7,7-difluoro-5-methyl-6-oxo-6,7,8,9-tetrahydro-5H-pyrimido[4,5-b][1,4]diazepin-2-ylamino)-N-(tetrahydro-pyran-4-yl)-benzamide |
| 264 | I-264 | 501.58 | 502 | A | 4-(9-cyclohexyl-7,7-difluoro-5-methyl-6-oxo-6,7,8,9-tetrahydro-5H-pyrimido[4,5-b][1,4]diazepin-2-ylamino)-N-(2-dimethylamino-ethyl)-benzamide |
| 265 | I-265 | 515.61 | 516 | A | 4-(9-cyclohexyl-7,7-difluoro-5-methyl-6-oxo-6,7,8,9-tetrahydro-5H-pyrimido[4,5-b][1,4]diazepin-2-ylamino)-N-(3-dimethylamino-propyl)-benzamide |
| 266 | I-266 | 607.66 | 608 | A | 4-(9-cyclohexyl-7,7-difluoro-5-methyl-6-oxo-6,7,8,9-tetrahydro-5H-pyrimido[4,5-b][1,4]diazepin-2-ylamino)-N-[1-(2,2-difluoro-ethyl)-piperidin-4-yl]-3-methoxy-benzamide |
| 267 | I-267 | 587.68 | 588 | A | 4-(9-cyclohexyl-7,7-difluoro-5-methyl-6-oxo-6,7,8,9-tetrahydro-5H-pyrimido[4,5-b][1,4]diazepin-2-ylamino)-N-[1-(2-hydroxy-ethyl)-piperidin-4-yl]-3-methoxy-benzamide |
| 268 | I-268 | 621.71 | 622 | B | 4-(9-cyclohexyl-7,7-difluoro-5-methyl-6-oxo-6,7,8,9-tetrahydro-5H-pyrimido[4,5-b][1,4]diazepin-2-ylamino)-N-(1-methanesulfonyl-piperidin-4-yl)-3-methoxy-benzamide |
| 269 | I-269 | 489.50 | 490 | B | 4-[7,7-difluoro-5-methyl-6-oxo-9-(2-thiophen-2-yl-ethyl)-6,7,8,9-tetrahydro-5-pyrimido[4,5-b][1,4]diazepin-2-ylamino]-3-methoxy-benzoic acid |
| 270 | I-270 | 585.68 | 586 | A | 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-(1-methyl-piperidin-4-yl)-benzamide |
| 271 | I-271 | 488.52 | 489 | B | 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-benzamide |
| 272 | I-272 | 502.55 | 503 | A | 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-methyl-benzamide |
| 273 | I-273 | 573.67 | 574 | A | 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-N-(3-dimethylamino-propyl)-3-methoxy-benzamide |
| 274 | I-274 | 572.64 | 573 | B | 4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-(tetrahydro-pyran-4-yl)-benzamide |
| 275 | I-275 | 483.48 | 484 | B | 4-(7,7-difluoro-5-methyl-6-oxo-9-phenethyl-6,7,8,9-tetrahydro-5H-pyrimido[4,5-b][1,4]diazepin-2-ylamino)-3-methoxy-benzoic acid |
| 276 | I-276 | 579.66 | 580 | A | 4-(7,7-difluoro-5-methyl-6-oxo-9-phenethyl-6,7,8,9-tetrahydro-5!-pyrimido[4,5-b][1,4]diazepin-2- |

TABLE 1-continued

| Ex | cpd | MW | MH+/z | IC$_{50}$ | Name |
|---|---|---|---|---|---|
| 277 | I-277 | 482.49 | 483 | B | ylamino)-3-methoxy-N-(1-methyl-piperidin-4-yl)-benzamide |
| 278 | I-278 | 496.52 | 497 | B | 4-(7,7-difluoro-5-methyl-6-oxo-9-phenethyl-6,7,8,9-tetrahydro-5H-pyrimido[4,5-b][1,4]diazepin-2-ylamino)-3-methoxy-benzamide |
| 279 | I-279 | 567.64 | 568 | B | 4-(7,7-difluoro-5-methyl-6-oxo-9-phenethyl-6,7,8,9-tetrahydro-5H-pyrimido[4,5-b][1,4]diazepin-2-ylamino)-3-methoxy-N-methyl-benzamide |
| 280 | I-280 | 566.61 | 567 | B | 4-(7,7-difluoro-5-methyl-6-oxo-9-phenethyl-6,7,8,9-tetrahydro-5H-pyrimido[4,5-b][1,4]diazepin-2-ylamino)-N-(3-dimethylamino-propyl)-3-methoxy-benzamide |
| 281 | I-281 | 497.51 | 498 | B | 4-(7,7-difluoro-5-methyl-6-oxo-9-phenethyl-6,7,8,9-tetrahydro-5H-pyrimido[4,5-b][1,4]diazepin-2-ylamino)-3-methoxy-N-(tetrahydro-pyran-4-yl)-benzamide |
| 282 | I-282 | 593.68 | 594 | A | 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzoic acid |
| 283 | I-283 | 496.52 | 497 | B | 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-(1-methyl-piperidin-4-yl)-benzamide |
| 284 | I-284 | 510.55 | 511 | B | 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzamide |
| 285 | I-285 | 581.67 | 582 | A | 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-methyl-benzamide |
| 286 | I-286 | 580.64 | 581 | B | 4-[7,7-difluoro-5-methyl-6-oxo-9-(3-phenyl-propyl)-6,7,8,9-tetrahydro-5H-pyrimido[4,5-b][1,4]diazepin-2-ylamino]-N-(3-dimethylamino-propyl)-3-methoxy-benzamide |
| 287 | I-287 | 495.49 | 496 | D | 4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-(tetrahydro-pyran-4-yl)-benzamide |
| 288 | I-288 | 591.67 | 592 | B | 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-benzoic acid |
| 289 | I-289 | 494.51 | 495 | D | 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-N-(1-methyl-piperidin-4-yl)-benzamide |
| 290 | I-290 | 579.66 | 580 | B | 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-N-(3-dimethylamino-propyl)-3-methoxy-benzamide |
| 291 | I-291 | 595.65 | 596 | B | 4-[7,7-difluoro-9-(4-methoxy-benzyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide |
| 292 | I-292 | 421.41 | 422 | B | 4-(7,7-difluoro-9-isopropyl-5-methyl-6-oxo-6,7,8,9-tetrahydro-5H-pyrimido[4,5-b][1,4]diazepin-2-ylamino)-3-methoxy-benzoic acid |
| 293 | I-293 | 517.58 | 518 | A | 4-(7,7-difluoro-9-isopropyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 294 | I-294 | 420.42 | 421 | A | 4-(7,7-difluoro-9-isopropyl-5-methyl-6-oxo-6,7,8,9-tetrahydro-5H-pyrimido[4,5-b][1,4]diazepin-2-ylamino)-3-methoxy-benzamide |
| 295 | I-295 | 434.45 | 435 | A | 4-(7,7-difluoro-9-isopropyl-5-methyl-6-oxo-6,7,8,9-tetrahydro-5H-pyrimido[4,5-b][1,4]diazepin-2-ylamino)-3-methoxy-N-methyl-benzamide |
| 296 | I-296 | 505.57 | 506 | A | 4-(7,7-difluoro-9-isopropyl-5-methyl-6-oxo-6,7,8,9-tetrahydro-5H-pyrimido[4,5-b][1,4]diazepin-2-ylamino)-N-(3-dimethylamino-propyl)-3-methoxy-benzamide |
| 297 | I-297 | 504.54 | 505 | A | 4-(7,7-difluoro-9-isopropyl-5-methyl-6-oxo-6,7,8,9-tetrahydro-5H-pyrimido[4,5-b][1,4]diazepin-2-ylamino)-3-methoxy-N-(tetrahydro-pyran-4-yl)-benzamide |
| 298 | I-298 | 576.53 | 576 | A | 4-(7,7-dichloro-9-cyclopentyl-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |
| 299 | I-299 | 666.82 | 667 | A | 4-(9-cyclopentyl-7,7-difluoro-5-methyl-6-oxo-6,7,8,9-tetrahydro-5H-pyrimido[4,5-b][1,4]diazepin-2-ylamino)-N-[cis-4-(4-cyclopropylmethyl-piperazin-1-yl)-cyclohexyl]-3-methoxy-benzamide |
| 300 | I-300 | 666.82 | 667 | A | 4-(9-cyclopentyl-7,7-difluoro-5-methyl-6-oxo-6,7,8,9-tetrahydro-5H-pyrimido[4,5-b][1,4]diazepin-2-ylamino)-N-[trans-4-(4-cyclopropylmethyl-piperazin-1-yl)-cyclohexyl]-3-methoxy-benzamide |
| 301 | I-301 | 640.78 | 641 | A | N-[cis-4-(4-cyclopropylmethyl-piperazin-1-yl)-cyclohexyl]-4-(7,7-difluoro-9-isopropyl-5-methyl-6-oxo-6,7,8,9-tetrahydro-5H-pyrimido[4,5-b][1,4]diazepin-2-ylamino)-3-methoxy-benzamide |
| 302 | I-302 | 640.78 | 641 | A | N-[trans-4-(4-cyclopropylmethyl-piperazin-1-yl)-cyclohexyl]-4-(7,7-difluoro-9-isopropyl-5-methyl-6-oxo-6,7,8,9-tetrahydro-5H-pyrimido[4,5-b][1,4]diazepin-2-ylamino)-3-methoxy-benzamide |
| 303 | I-303 | 475.50 | 476 | B | 4-(7,7-difluoro-5-methyl-6-oxo-6,7,8,9-tetrahydro-5H-pyrimido[4,5-b][1,4]diazepin-2-ylamino)-3-methoxy-N-(1-methyl-piperidin-4-yl)-benzamide |

TABLE 1-continued

| Ex | cpd | MW | MH+/z | IC$_{50}$ | Name |
|---|---|---|---|---|---|
| 304 | I-304 | 595.65 | 596 | B | 4-[7,7-difluoro-5-methyl-6-oxo-9-(2-phenoxy-ethyl)-6,7,8,9-tetrahydro-5H-pyrimido[4,5-b][1,4]diazepin-2-ylamino]-3-methoxy-N-(1-methyl-piperidin-4-yl)-benzamide |

What is claimed is:

1. A compound of formula I:

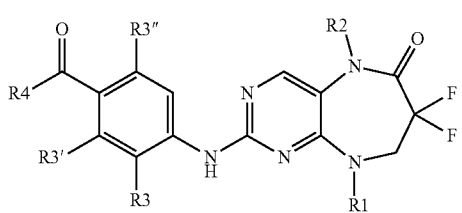

(I)

wherein
R1 is —(CH$_2$)$_n$-phenyl, —(CH$_2$)$_n$-thiophenyl or phenylcyclopropyl;
R2 is hydrogen, methyl, ethyl, or propyl;
each of R3, R3', and R3" is independently hydrogen, chloro, fluoro, C1 to C5 straight or branched alkyl, trifluoromethyl, methoxy, ethoxy, trifluoromethoxy, or trifluoromethoxy;
R4 is hydroxyl, amino, methoxy, R5-NH—, or

where X is CH$_2$, O, or NH, where if X is CH$_2$ or NH, X may be optionally substituted by amino or C1 to C5 straight or branched chain alkyl;
R5 is

R13-(CH$_2$)$_n$—, methyl
n is an integer from 0 to 4,
R7 is hydrogen or C1 to C5 straight or branched chain alkyl,
R13 is R14R15N—,
R14 and R15 are independently hydrogen, C1 to C5 straight or branched chain alkyl, C3 to C6 cycloalkyl, or phenyl;
or a pharmaceutically acceptable salt thereof.

2. A compound of claim 1 selected from the group consisting of:
4-[7,7-difluoro-5-methyl-6-oxo-9-(2-thiophen-2-yl-ethyl)-6,7,8,9-tetrahydro-5-pyrimido[4,5-b][1,4]diazepin-2-ylamino]-3-methoxy-benzoic acid;
4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-(1-methyl-piperidin-4-yl)-benzamide;
4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-benzamide;
4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-methyl-benzamide;
4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-N-(3-dimethylamino-propyl)-3-methoxy-benzamide;
4-[7,7-difluoro-5-methyl-6-oxo-9-(2-thiophen-2-yl-ethyl)-6,7,8,9-tetrahydro-5H-pyrimido[4,5-b][1,4]diazepin-2-ylamino]-3-methoxy-N-(tetrahydro-pyran-4-yl)-benzamide;
4-(7,7-difluoro-5-methyl-6-oxo-9-phenethyl-6,7,8,9-tetrahydro-5H-pyrimido[4,5-b][1,4]diazepin-2-ylamino)-3-methoxy-benzoic acid;
4-(7,7-difluoro-5-methyl-6-oxo-9-phenethyl-6,7,8,9-tetrahydro-5H-pyrimido[4,5-b][1,4]diazepin-2-ylamino)-3-methoxy-N-(1-methyl-piperidin-4-yl)-benzamide;
4-(7,7-difluoro-5-methyl-6-oxo-9-phenethyl-6,7,8,9-tetrahydro-5H-pyrimido[4,5-b][1,4]diazepin-2-ylamino)-3-methoxy-benzamide;
4-(7,7-difluoro-5-methyl-6-oxo-9-phenethyl-6,7,8,9-tetrahydro-5H-pyrimido[4,5-b][1,4]diazepin-2-ylamino)-3-methoxy-N-methyl-benzamide;
4-(7,7-difluoro-5-methyl-6-oxo-9-phenethyl-6,7,8,9-tetrahydro-5H-pyrimido[4,5-b][1,4]diazepin-2-ylamino)-N-(3-dimethylamino-propyl)-3-methoxy-benzamide;
4-(7,7-difluoro-5-methyl-6-oxo-9-phenethyl-6,7,8,9-tetrahydro-5H-pyrimido[4,5-b][1,4]diazepin-2-ylamino)-3-methoxy-N-(tetrahydro-pyran-4-yl)-benzamide;
4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzoic acid;
4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-(1-methyl-piperidin-4-yl)-benzamide;
4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-benzamide;
4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-methyl-benzamide;
4-[7,7-difluoro-5-methyl-6-oxo-9-(3-phenyl-propyl)-6,7,8,9-tetrahydro-5H-pyrimido[4,5-b][1,4]diazepin-2-ylamino]-N-(3-dimethylamino-propyl)-3-methoxy-benzamide;
4-[7,7-difluoro-5-methyl-6-oxo-9-(3-phenyl-propyl)-6,7,8,9-tetrahydro-5H-pyrimido[4,5-b][1,4]diazepin-2-ylamino]-3-methoxy-N-(tetrahydro-pyran-4-yl)-benzamide; and
4-[7,7-difluoro-9-(4-methoxy-benzyl)-5-methyl-6-oxo-6,7,8,9-tetrahydro-5H-pyrimido[4,5-b][1,4]diazepin-2-ylamino]-3-methoxy-N-(1-methyl-piperidin-4-yl)-benzamide; or a pharmaceutically acceptable salt of each of the above-mentioned compounds.

3. A compound of claim 1 selected from the group consisting of:
4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-benzoic acid;
4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-N-(1-methyl-piperidin-4-yl)-benzamide;

4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-3-methoxy-benzamide; and 4-[7,7-difluoro-5-methyl-6-oxo-9-(trans-2-phenyl-cyclopropyl)-6,7,8,9-tetrahydro-5H-pyrimido[4,5-b][1,4]diazepin-2-ylamino]-N-(3-dimethylamino-propyl)-3-methoxy-benzamide; or a pharmaceutically acceptable salt of each of the above-mentioned compounds.

* * * * *